(12) United States Patent
Quattropani et al.

(10) Patent No.: US 10,696,690 B2
(45) Date of Patent: Jun. 30, 2020

(54) IMIDAZO-OXADIAZOLE AND IMIDAZO-THIADIAZOLE DERIVATIVES

(71) Applicant: Ares Trading S.A., Aubonne (CH)

(72) Inventors: Anna Quattropani, Rolle (CH); Dominique Swinnen, Braine l'Alleud (BE)

(73) Assignee: Ares Trading S.A., Aubonne (CH)

( * ) Notice: Subject to any disclaimer, the term of this patent is extended or adjusted under 35 U.S.C. 154(b) by 0 days.

(21) Appl. No.: 15/829,030

(22) Filed: Dec. 1, 2017

(65) Prior Publication Data

US 2018/0215770 A1    Aug. 2, 2018

Related U.S. Application Data

(63) Continuation of application No. 14/402,395, filed as application No. PCT/EP2013/001521 on May 23, 2013, now Pat. No. 9,932,354.

(60) Provisional application No. 61/655,544, filed on Jun. 5, 2012.

(30) Foreign Application Priority Data

Jun. 5, 2012   (EP) .................................. 12170840

(51) Int. Cl.
| | |
|---|---|
| *C07D 513/04* | (2006.01) |
| *A61K 31/4245* | (2006.01) |
| *A61K 31/433* | (2006.01) |
| *A61K 31/4427* | (2006.01) |
| *A61K 31/4439* | (2006.01) |
| *A61K 31/506* | (2006.01) |
| *A61K 45/06* | (2006.01) |
| *C07D 498/04* | (2006.01) |
| *A61K 31/437* | (2006.01) |
| *A61K 31/454* | (2006.01) |
| *C07D 519/00* | (2006.01) |

(52) U.S. Cl.
CPC ........ *C07D 513/04* (2013.01); *A61K 31/4245* (2013.01); *A61K 31/433* (2013.01); *A61K 31/437* (2013.01); *A61K 31/4427* (2013.01); *A61K 31/4439* (2013.01); *A61K 31/454* (2013.01); *A61K 31/506* (2013.01); *A61K 45/06* (2013.01); *C07D 498/04* (2013.01); *C07D 519/00* (2013.01)

(58) Field of Classification Search
CPC .................................................. C07D 513/04
USPC .......................................... 548/126; 514/363
See application file for complete search history.

(56) References Cited

FOREIGN PATENT DOCUMENTS

| WO | 9425029 | 11/1994 |
|---|---|---|
| WO | 02066480 A2 | 8/2002 |
| WO | 02102800 A1 | 12/2002 |
| WO | 03068754 A1 | 8/2003 |
| WO | 04013140 A1 | 2/2004 |

OTHER PUBLICATIONS

Czodrowski et al., "Structure-Based, etc.," J. Med. Chem., 59, 9337-9349. (Year: 2016).*
Albert J.S., Prog Med Chem., 2009, 48: 133-61.
Beher D., Curr Topics Med Chem, 2008, 8: 34-37.
Bernstein J., Polymorphism in Molecular Crystals, 2002, p. 115-118, 272.
Braga et al., J. Royal Soc. Chem. Commun., 2005, p. 3635-3645.
Davidovich et al., Am. Pharm. Rev. v.&(1) p. 10, 12, 14, 16, 100 (2004).
Dean "Analytical Chem . . . " 1995, p. 10.24-10.26.
Ettmayer et al., J. Med. Chem., 2004, 47(10): 2393-2404.
Guillory (in Brittain ed.), "Polymorphism in Pharmaceutical Solids.," NY: Marcel Dekker, Inc., 1999, 1-2, 125-181, 183-226.
Hardy J., Current Alzheimer Research, 2006, 3: 71-73.
Hussain et al., Mol. Cell Neurosci., 1999, 14(6): 419-427.
Invanisevic et al., Pharm. Sci. Encycl., 2010, p. 1-42.
Jain et al., "Polymorphism in Pharmacy", Indian Drugs, 1986, 23(6): 315-329.
Jordan V. C., Nature Rev., 2003, 2: 205-213.
Kirk-Othmer Encyclopedia of Chemical Technology, 2002, 8: 95-147.
Panza et al., Curr Med Chem., 2011, 18(35): 5430-5447.
Schor N. F., Ann Neurol, 2011, 69: 237-239.
Seddon, "Pseudopolymorph . . . " Crystal Growth & design v.4(6) p. 1087 (2004) (2 pages from internet).
Stella V., Expert Opin. Ther. Patents, 2004, 14(3): 277-280.
Tanzi et al., Cell, 2005, 120: 545-555.
Testa B., Biochemical Pharmacology, 2004, 68: 2097-2106.
Tyle P., Pharmaceutical Research, 1986, 3(6): 318-319.
Vippagunta et al., Advanced Drug Delivery Reviews, 2001, 48: 3-26.
Yoshida et al., Int. J. Pharm., 1995, 115: 61-67.
Yu et al., PSTT, 1998, 1(3): 118-127.

* cited by examiner

*Primary Examiner* — Patricia L Morris
(74) *Attorney, Agent, or Firm* — Thomas W. Brown; Ares Trading S.A.

(57) ABSTRACT

The present invention provides compounds of Formula (I) used as Amyloid beta lowering agent for the treatment of neurodegenerative diseases.

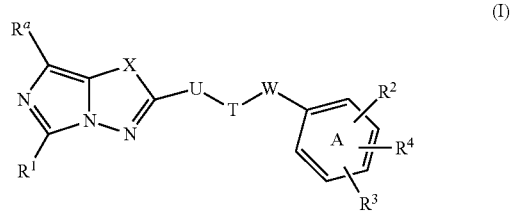

4 Claims, No Drawings

IMIDAZO-OXADIAZOLE AND IMIDAZO-THIADIAZOLE DERIVATIVES

RELATED APPLICATIONS

This application is a continuation application of U.S. Ser. No. 14/402,395, which is a 371 US national stage of PCT/EP2013/001521, filed on May 23, 2013, which claims the benefit of U.S. provisional application U.S. Ser. No. 61/655,544, filed on Jun. 5, 2012, and EP application 12170840.8, filed on Jun. 5, 2012. The entire contents of the aforementioned applications are incorporated herein by reference.

The present invention provides imidazo-oxadiazole and imidazo-thiadiazole derivatives useful as amyloid-beta lowering agents. The invention further relates to processes for preparing such compounds, pharmaceutical compositions comprising said compounds and their use in the treatment of amyloidosis and neurodegenerative diseases that include but are not limited to Alzheimer's disease and Down's Syndrome.

BACKGROUND OF THE INVENTION

Alzheimer's disease (AD) is a progressive neurodegenerative disorder marked by loss of memory, cognition, and behavioral stability. AD afflicts 6-10% of the population over age 65 and up to 50% over age 85. It is the leading cause of dementia and the third leading cause of death after cardiovascular disease and cancer. At present, there are no effective treatments for AD and treatment is limited to the use of symptomatic agents such as the cholinesterase inhibitor, donepezil (Aricept®, Pfizer). The total net cost related to AD in the U.S. exceeds $100 billion annually.

AD is characterised pathologically by the presence of specific lesions in the limbic and cortical regions of the brain. These include intracellular neurofibrillary tangles consisting of hyperphosphorylated tau protein and the extracellular deposition of fibrillar aggregates of amyloid-beta peptides in the form of amyloid plaques (senile plaques). The major components of amyloid plaques are amyloid-beta (A-beta, Abeta or Aβ) peptides of various lengths (39-42 amino acids). A variant thereof, which is the Aβ1-42 (Abeta1-42, Aβ42) peptide, is believed to be the major pathogenic species in AD brain and can act as a seed for amyloid plaque formation. Another variant is the Aβ1-40 (Abeta1-40, Aβ40) peptide.

The identification of mutations in the beta-Amyloid Precursor Protein (beta-APP, β-APP or APP), Presenilin-1 (PS-1) and Presenilin-2 (PS-2) genes that increase Aβ production and lead to early-onset familial forms of AD have given strong support to the "amyloid cascade hypothesis" of AD (Hardy, 2006 Curr Alzheimer Res. 3(1):71-73; Tanzi and Bertram, 2005 Cell 120, 545-555) and therapeutic approaches targeting Aβ production.

There is emerging data on the role of Aβ peptides in other diseases including, but not limited to Down's syndrome (DS), mild cognitive impairment (MCI), cerebral amyloid angiopathy (CAA), inclusion body myositis (IBM) and age-related macular degeneration. Hence, Aβ lowering agents could be beneficial for the treatment of diverse pathologies in which Aβ peptides are implicated. Aβ peptides are generated following proteolytic processing of APP. The generation of Aβ peptides is regulated by at least two proteolytic activities referred to as β-site APP cleaving enzyme 1 (BACE-1) and γ-secretase. APP is initially cleaved by BACE-1 at the N-terminus (Met-Asp bond) of the Aβ domain leading to the secretion of soluble APPβ (sAPPβ) and the retention of a 12 kDa membrane-bound carboxy terminal fragment (CTF3). The latter is subsequently cleaved by γ-secretase to generate Aβ peptides of varying length and an APP intracellular domain (AICD).

BACE-1 is a type I transmembrane aspartic protease that comprises a large extracellular domain containing the catalytic active site, a single transmembrane domain and a short cytoplasmic tail [Hussain et al. 1999 Mol. Cell Neurosci. 14(6):419-427]. The γ-secretase activity resides within a multiprotein complex containing at least four components: a presenilin (PS) heterodimer, nicastrin, anterior pharynx-defective 1 (Aph-1) and presenilin enhancer 2 (Pen-2). The PS heterodimer consists of the amino- and carboxy terminal fragments generated by endoproteolysis of PS and the two aspartates in the catalytic site are at the interface of this heterodimer.

Therapeutic approaches to lower Aβ production include but are not restricted to inhibition or modulation of BACE-1 and γ-secretase activity (Albert, 2009 Prog Med Chem. 48: 133-61; Beher, 2008 Curr Top Med Chem. 8: 34-37; Panza et al. 2011 Curr Med Chem. 18(35): 5430-5447). However, due to the fundamental role γ-secretase plays in the intramembrane proteolysis of other proteins, the clinical development of γ-secretase inhibitors was hindered by mechanism-based toxicities (Schor, 2011 Ann Neurol. 69: 237-239).

There is a strong need for novel compounds which decrease Aβ production thereby opening new avenues for the treatment of AD. It is an object of the present invention to provide such novel compounds.

SUMMARY OF THE INVENTION

The present invention provides compounds of Formula (I)

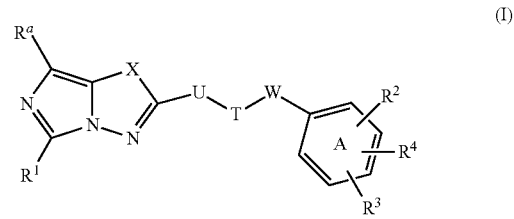

(I)

Wherein
X denotes O or S,
U is selected from
(i) a phenyl ring which may be substituted by 1 or 2 groups independently selected from $C_1$-$C_6$-alkoxy, $C_1$-$C_6$-alkyl, halogen, CN
(ii) a 5- or 6-membered unsaturated or aromatic heterocyclic system comprising 1 nitrogen atom and optionally up to 2 additional heteroatoms independently selected from N, O or S, which may be substituted by 1 or 2 groups independently selected from $C_1$-$C_6$-alkoxy, $C_1$-$C_6$-alkyl, halogen, CN,
(iii) a single bond.
T denotes —$NR^5$—, —$NR^5CO$—, —$CONR^5$, —$NR^5$—CO—$NR^5$, —CO—
W is selected from
(i) a linear or branched $C_1$-$C_6$-alkylene wherein 1 to 2 H atoms may be replaced by a phenyl ring, halogen, CN, $CF_3$, (ii) a linear or branched $C_1$-$C_6$-alkylene wherein 1 $CH_2$ group is replaced by a 3- to 7-membered saturated carbocyclic ring,
(iii) a linear or branched $C_1$-$C_6$-alkylene wherein 1 $CH_2$ group is replaced by
a phenyl ring optionally fused with the phenyl ring A,
a 5- or 6-membered saturated heterocyclic system containing 1 or 2 nitrogen atoms, or
a 5-membered aromatic heterocyclic system containing 1 to 3 heteroatoms independently selected from N, O and S, and optionally fused with a saturated 6-membered carbocyclic ring, or optionally fused with the phenyl ring A,
and wherein another $CH_2$ group which is not linked to T is optionally replaced by —O— or $NR^5$.
(iv) a single bond,
$R^5$ is H or a linear or branched $C_1$-$C_6$-alkyl,
$R^1$ denotes a linear or branched alkyl having 1 to 6 carbon atoms.
$R^a$ denotes H, CN, halogen, a linear or branched alkyl having 1 to 6 carbon atoms, wherein 1 to 3 H atoms may be replaced by halogens, linear or branched alkoxy having 1 to 6 carbon atoms, wherein 1 to 3 H atoms may be replaced by halogens,
$R^2$, $R^3$, $R^4$ are independently from one another selected from CN, halogen, a linear or branched alkyl having 1 to 6 carbon atoms, wherein 1 to 3 H atoms may be replaced by halogens, linear or branched alkoxy having 1 to 6 carbon atoms, wherein 1 to 3 H atoms may be replaced by halogens,
As well as pharmaceutically acceptable derivatives, solvates, tautomers, salts, hydrates and stereoisomers thereof, including mixtures thereof in all ratios.

When a substituent is mentioned several times in a group, like $R^5$ in T, each of the substitutent independently takes the meaning given above.

The present invention further relates to a set or a kit consisting of separate packs of
(a) an effective amount of a compound according to Formula (I) or related Formulae and/or pharmaceutically usable derivatives, tautomers, salts, solvates and stereoisomers thereof, including mixtures thereof in all ratios,
and
(b) an effective amount of a further medicament active ingredient.

In a preferred embodiment, U in the compounds of Formula (I) is selected from the following groups:

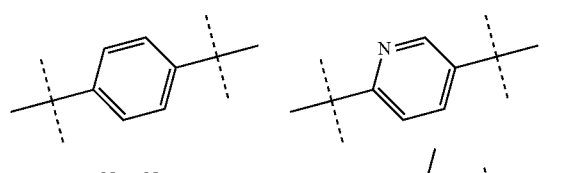

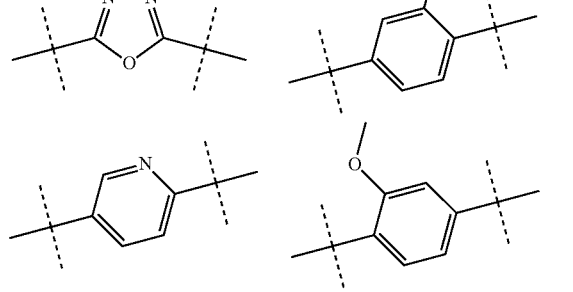

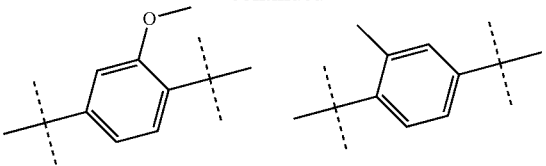

In another embodiment, U is single bond.

In another embodiment, W in Formula (I) denotes one of the following groups:

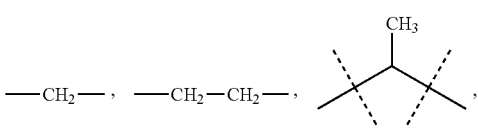

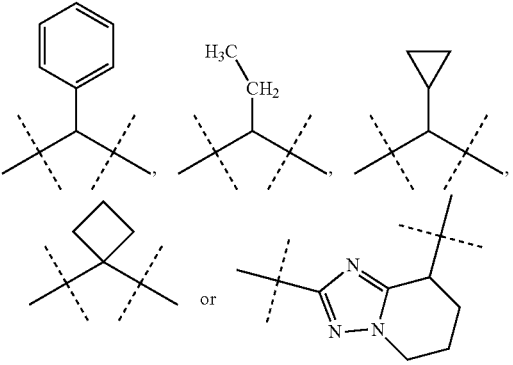

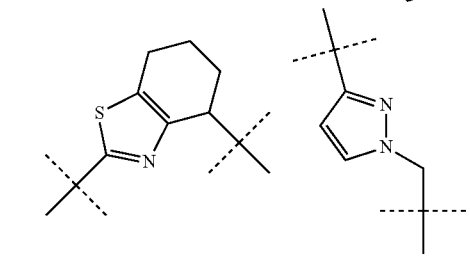

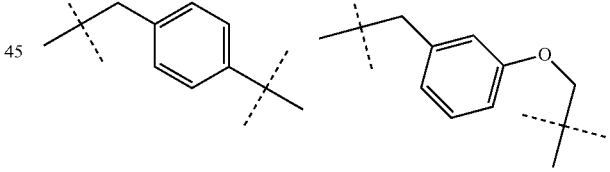

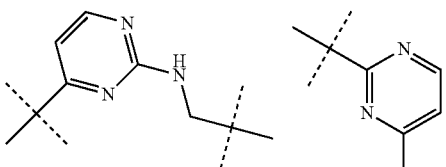

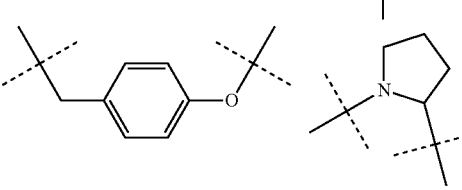

-continued
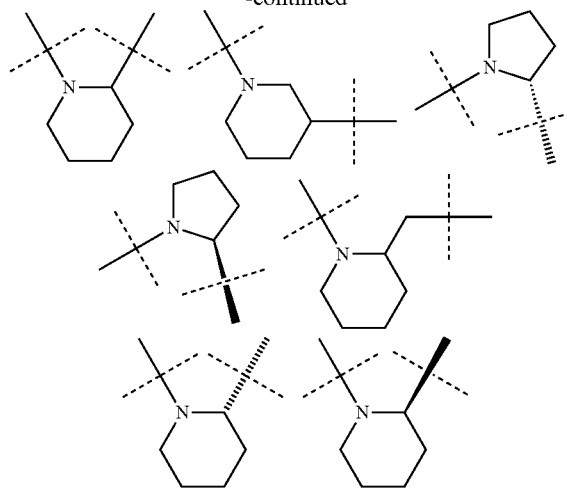
Alternatively, the group W-A denotes one of the following groups:
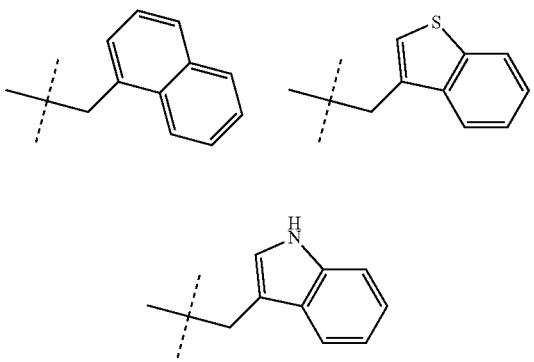
The preferred compounds of the present invention are the following:
| Ex. No | Structure |
|---|---|
| 1 | 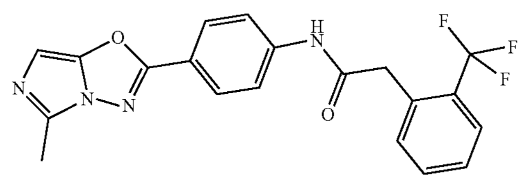 [SMILES: Cc1ncc2oc(-c3ccc(NC(=O)Cc4ccccc4C(F)(F)F)cc3)nn12] |
| 2 | 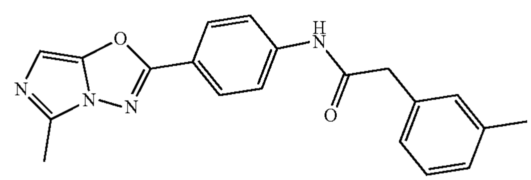 [SMILES: Cc1cccc(CC(=O)Nc2ccc(-c3nn4c(C)ncc4o3)cc2)c1] |
| 3 | 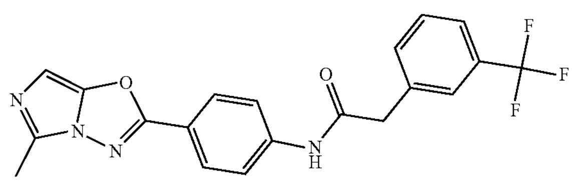 [SMILES: Cc1ncc2oc(-c3ccc(NC(=O)Cc4cccc(C(F)(F)F)c4)cc3)nn12] |
| 4 | 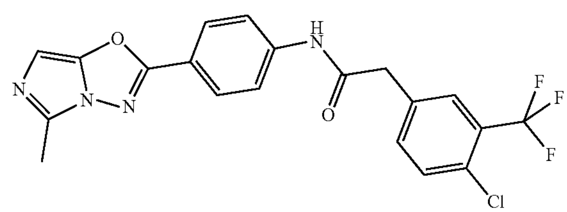 [SMILES: Cc1ncc2oc(-c3ccc(NC(=O)Cc4ccc(Cl)c(C(F)(F)F)c4)cc3)nn12] |
| 5 | 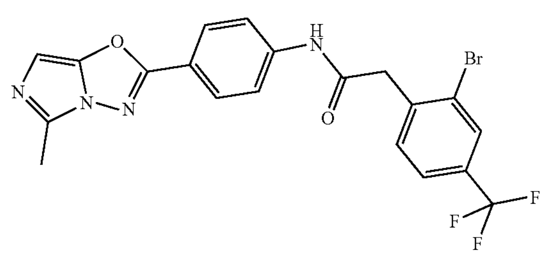 [SMILES: Cc1ncc2oc(-c3ccc(NC(=O)Cc4ccc(C(F)(F)F)cc4Br)cc3)nn12] |

-continued
| Ex. No | Structure |
|---|---|
| 6 | 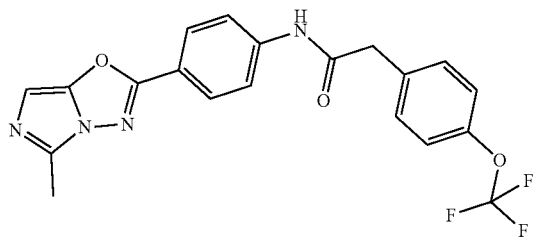 [SMILES: Cc1ncc2oc(-c3ccc(NC(=O)Cc4ccc(OC(F)(F)F)cc4)cc3)nn12] |
| 7 | 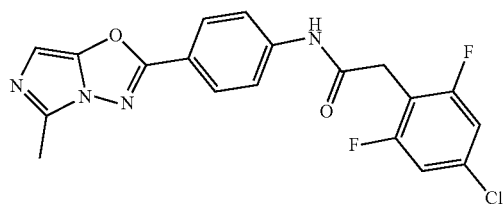 [SMILES: Cc1ncc2oc(-c3ccc(NC(=O)Cc4c(F)cc(Cl)cc4F)cc3)nn12] |
| 8 | 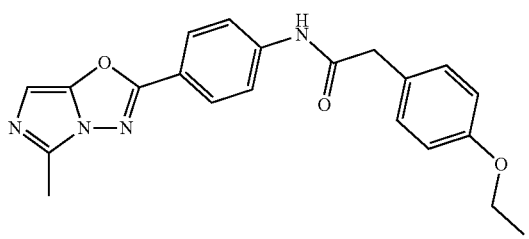 [SMILES: CCOc1ccc(CC(=O)Nc2ccc(-c3nn4c(C)ncc4o3)cc2)cc1] |
| 9 | 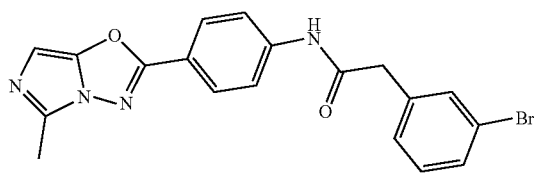 [SMILES: Cc1ncc2oc(-c3ccc(NC(=O)Cc4cccc(Br)c4)cc3)nn12] |
| 10 | 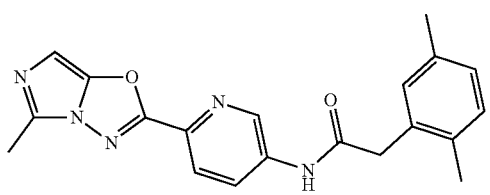 [SMILES: Cc1ccc(C)c(CC(=O)Nc2ccc(-c3nn4c(C)ncc4o3)nc2)c1] |
| 11 | 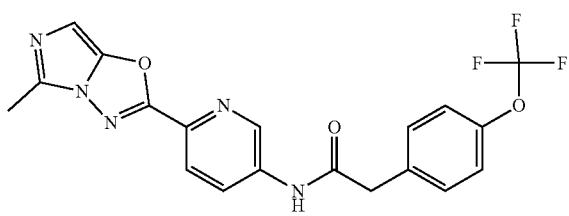 [SMILES: Cc1ncc2oc(-c3ccc(NC(=O)Cc4ccc(OC(F)(F)F)cc4)cn3)nn12] |
| 12 | 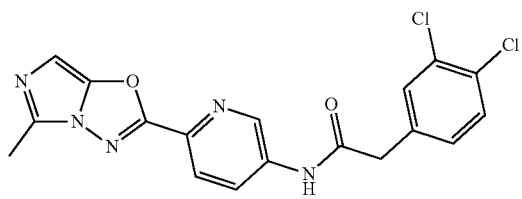 [SMILES: Cc1ncc2oc(-c3ccc(NC(=O)Cc4ccc(Cl)c(Cl)c4)cn3)nn12] |

-continued
| Ex. No | Structure |
|---|---|
| 13 | 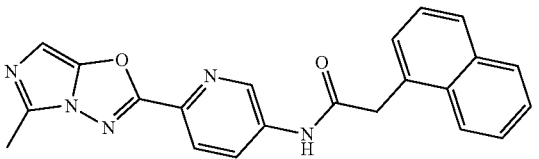 [SMILES: Cc1ncc2oc(-c3ccc(NC(=O)Cc4cccc5ccccc45)cn3)nn12] |
| 14 | 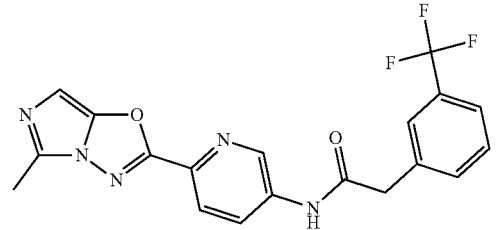 [SMILES: Cc1ncc2oc(-c3ccc(NC(=O)Cc4cccc(C(F)(F)F)c4)cn3)nn12] |
| 15 | 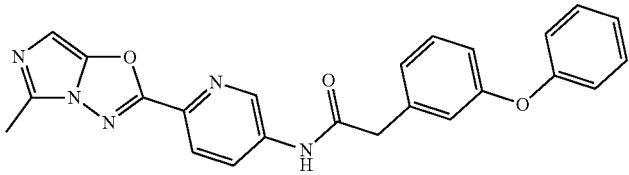 [SMILES: Cc1ncc2oc(-c3ccc(NC(=O)Cc4cccc(Oc5ccccc5)c4)cn3)nn12] |
| 16 | 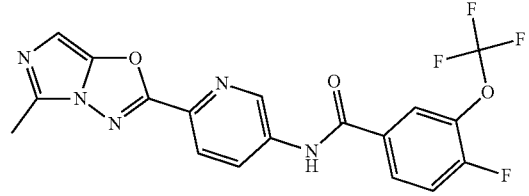 [SMILES: Cc1ncc2oc(-c3ccc(NC(=O)c4ccc(F)c(OC(F)(F)F)c4)cn3)nn12] |
| 18 | 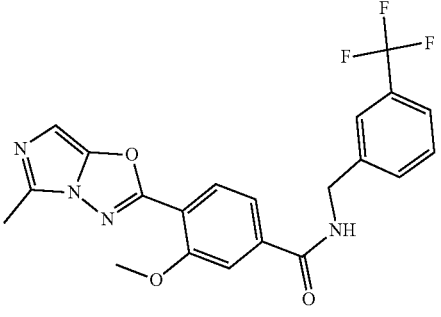 [SMILES: COc1cc(C(=O)NCc2cccc(C(F)(F)F)c2)ccc1-c1nn2c(C)ncc2o1] |
| 19 | 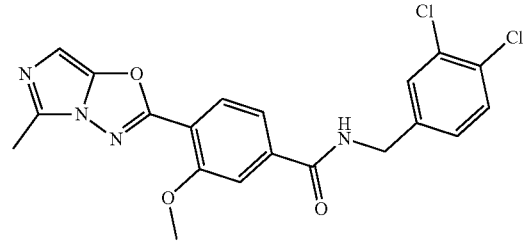 [SMILES: COc1cc(C(=O)NCc2ccc(Cl)c(Cl)c2)ccc1-c1nn2c(C)ncc2o1] |
| 20 | 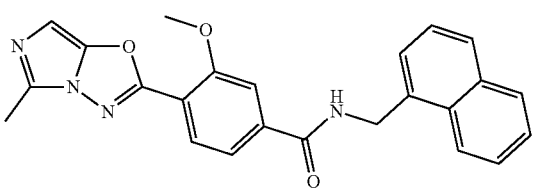 [SMILES: COc1cc(C(=O)NCc2cccc3ccccc23)ccc1-c1nn2c(C)ncc2o1] |

| Ex. No | Structure |
|---|---|
| 21 | 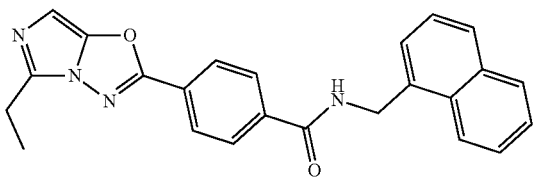 [SMILES: CCc1ncc2oc(-c3ccc(C(=O)NCc4cccc5ccccc45)cc3)nn12] |
| 22 | 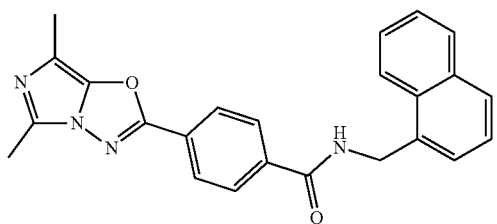 [SMILES: Cc1nc(C)n2nc(-c3ccc(C(=O)NCc4cccc5ccccc45)cc3)oc12] |
| 23 | 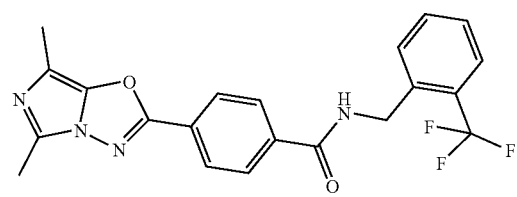 [SMILES: Cc1nc(C)n2nc(-c3ccc(C(=O)NCc4ccccc4C(F)(F)F)cc3)oc12] |
| 24 | 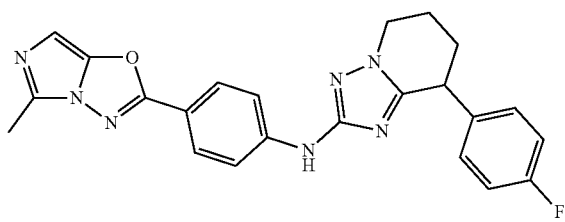 [SMILES: Cc1ncc2oc(-c3ccc(Nc4nc5n(n4)CCCC5c4ccc(F)cc4)cc3)nn12] |
| 25 | 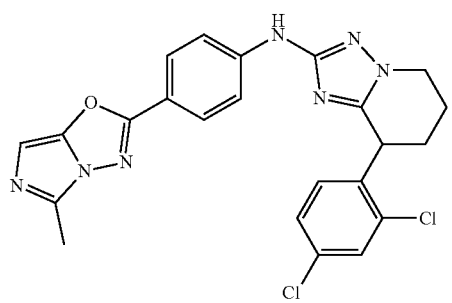 [SMILES: Cc1ncc2oc(-c3ccc(Nc4nc5n(n4)CCCC5c4ccc(Cl)cc4Cl)cc3)nn12] |
| 26 | 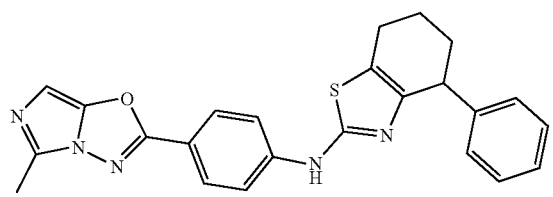 [SMILES: Cc1ncc2oc(-c3ccc(Nc4nc5c(s4)CCCC5c4ccccc4)cc3)nn12] |
| 27 | 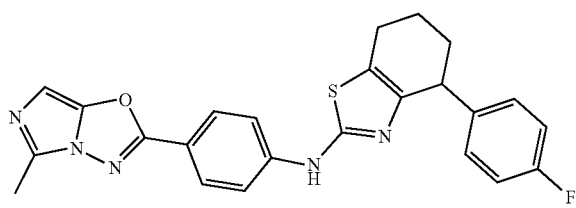 [SMILES: Cc1ncc2oc(-c3ccc(Nc4nc5c(s4)CCCC5c4ccc(F)cc4)cc3)nn12] |

-continued
| Ex. No | Structure |
|---|---|
| 28 | 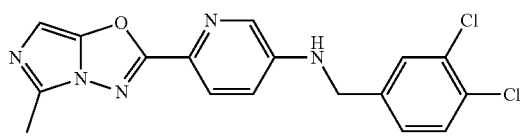 [SMILES: Cc1ncc2oc(-c3ccc(NCc4ccc(Cl)c(Cl)c4)cn3)nn12] |
| 29 | 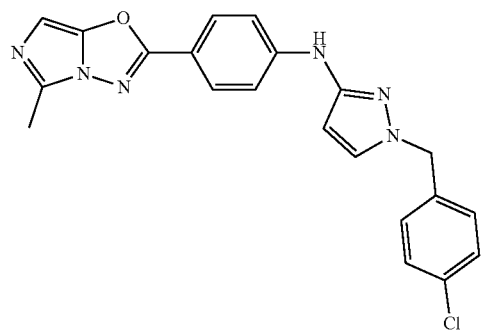 [SMILES: Cc1ncc2oc(-c3ccc(Nc4ccn(Cc5ccc(Cl)cc5)n4)cc3)nn12] |
| 30 | 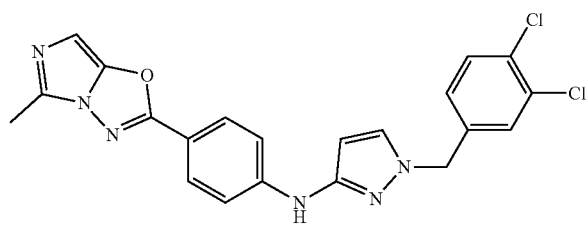 [SMILES: Cc1ncc2oc(-c3ccc(Nc4ccn(Cc5ccc(Cl)c(Cl)c5)n4)cc3)nn12] |
| 31 | 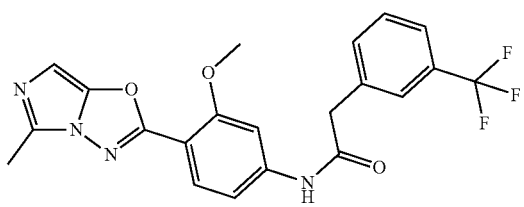 [SMILES: COc1cc(NC(=O)Cc2cccc(C(F)(F)F)c2)ccc1-c1nn2c(C)ncc2o1] |
| 32 | 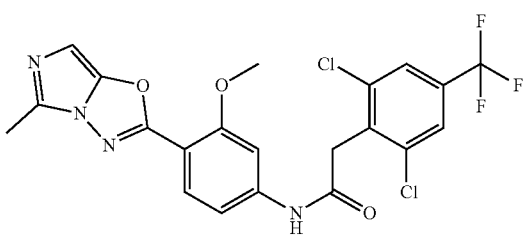 [SMILES: COc1cc(NC(=O)Cc2c(Cl)cc(C(F)(F)F)cc2Cl)ccc1-c1nn2c(C)ncc2o1] |
| 33 | 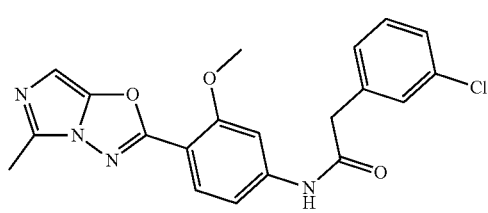 [SMILES: COc1cc(NC(=O)Cc2cccc(Cl)c2)ccc1-c1nn2c(C)ncc2o1] |

-continued
| Ex. No | Structure |
|---|---|
| 34 | 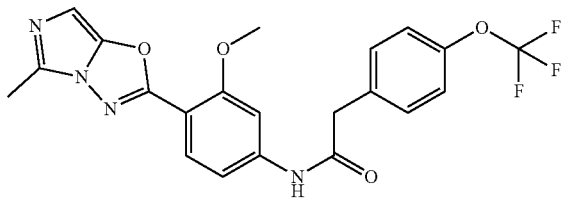 [SMILES: COc1cc(NC(=O)Cc2ccc(OC(F)(F)F)cc2)ccc1-c1nn2c(C)ncc2o1] |
| 35 | 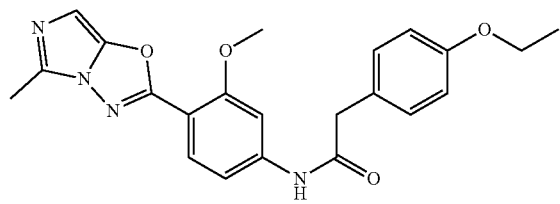 [SMILES: CCOc1ccc(CC(=O)Nc2ccc(-c3nn4c(C)ncc4o3)c(OC)c2)cc1] |
| 36 | 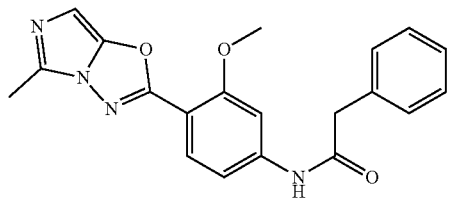 [SMILES: COc1cc(NC(=O)Cc2ccccc2)ccc1-c1nn2c(C)ncc2o1] |
| 37 | 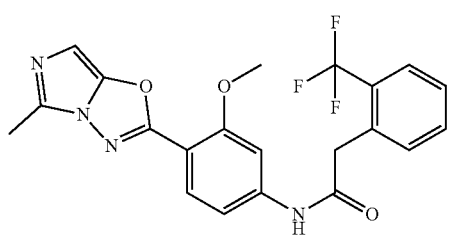 [SMILES: COc1cc(NC(=O)Cc2ccccc2C(F)(F)F)ccc1-c1nn2c(C)ncc2o1] |
| 38 | 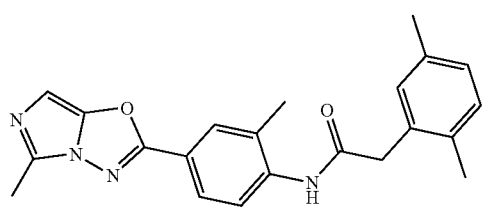 [SMILES: Cc1ccc(C)c(CC(=O)Nc2ccc(-c3nn4c(C)ncc4o3)cc2C)c1] |
| 39 | 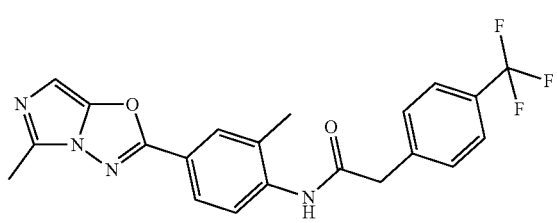 [SMILES: Cc1cc(-c2nn3c(C)ncc3o2)ccc1NC(=O)Cc1ccc(C(F)(F)F)cc1] |
| 40 | 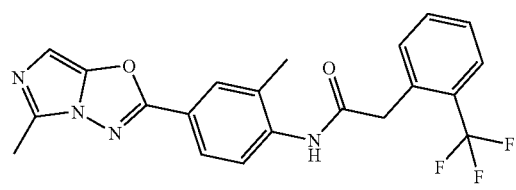 [SMILES: Cc1cc(-c2nn3c(C)ncc3o2)ccc1NC(=O)Cc1ccccc1C(F)(F)F] |

-continued
| Ex. No | Structure |
|---|---|
| 41 | 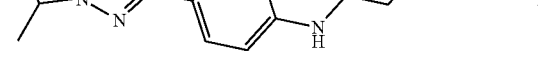 |
| 42 | 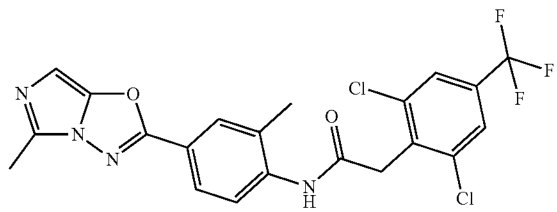 [SMILES: Cc1cc(-c2nn3c(C)ncc3o2)ccc1NC(=O)Cc1c(Cl)cc(C(F)(F)F)cc1Cl] |
| 43 | 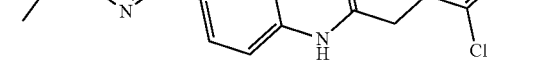 |
| 44 | 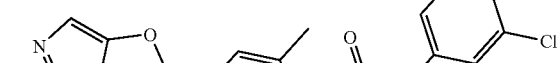 |
| 45 | 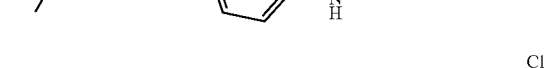 |
| 46 | 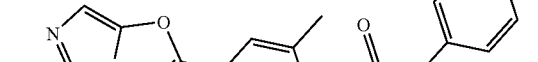 |
| 47 | 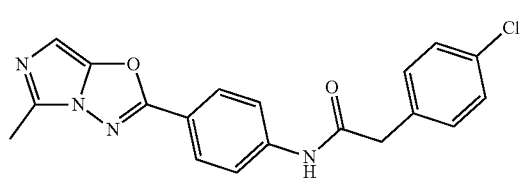 [SMILES: Cc1ncc2oc(-c3ccc(NC(=O)Cc4ccc(Cl)cc4)cc3)nn12] |
| 48 | 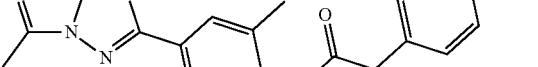 |

-continued
| Ex. No | Structure |
|---|---|
| 49 | 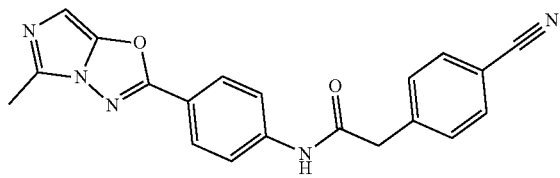 [SMILES: Cc1ncc2oc(-c3ccc(NC(=O)Cc4ccc(C#N)cc4)cc3)nn12] |
| 50 | 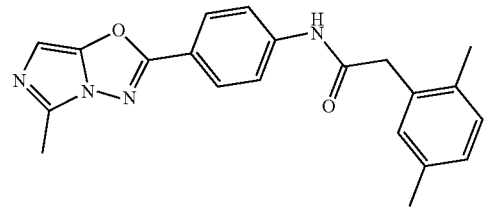 [SMILES: Cc1ccc(C)c(CC(=O)Nc2ccc(-c3nn4c(C)ncc4o3)cc2)c1] |
| 51 | 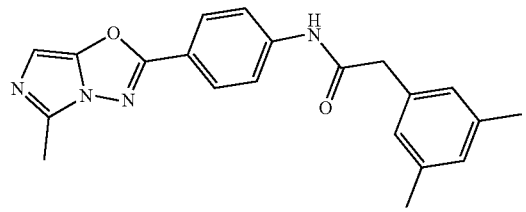 [SMILES: Cc1cc(C)cc(CC(=O)Nc2ccc(-c3nn4c(C)ncc4o3)cc2)c1] |
| 52 | 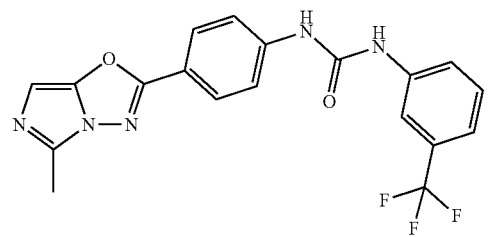 [SMILES: Cc1ncc2oc(-c3ccc(NC(=O)Nc4cccc(C(F)(F)F)c4)cc3)nn12] |
| 53 | 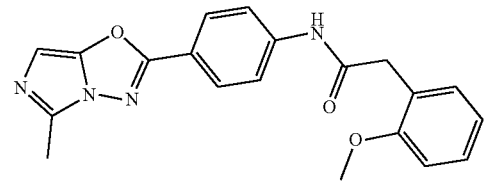 [SMILES: COc1ccccc1CC(=O)Nc1ccc(-c2nn3c(C)ncc3o2)cc1] |
| 54 | 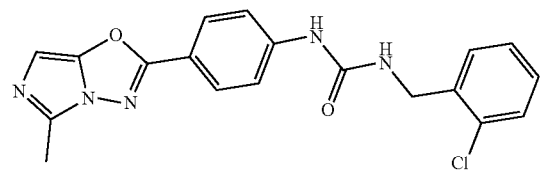 [SMILES: Cc1ncc2oc(-c3ccc(NC(=O)NCc4ccccc4Cl)cc3)nn12] |
| 55 | 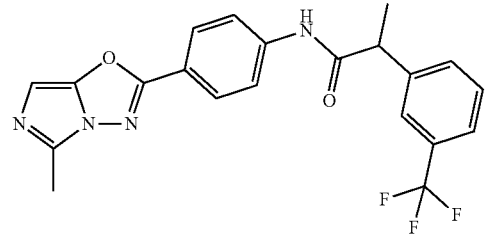 [SMILES: Cc1ncc2oc(-c3ccc(NC(=O)C(C)c4cccc(C(F)(F)F)c4)cc3)nn12] |

-continued
| Ex. No | Structure |
|---|---|
| 56 | 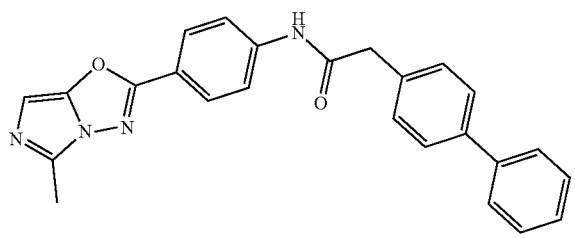 [SMILES: Cc1ncc2oc(-c3ccc(NC(=O)Cc4ccc(-c5ccccc5)cc4)cc3)nn12] |
| 57 | 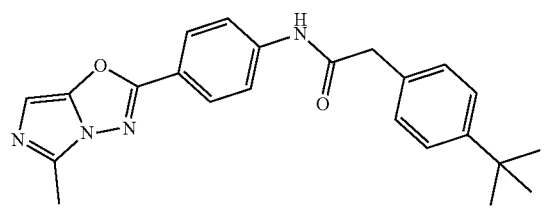 [SMILES: Cc1ncc2oc(-c3ccc(NC(=O)Cc4ccc(C(C)(C)C)cc4)cc3)nn12] |
| 58 | 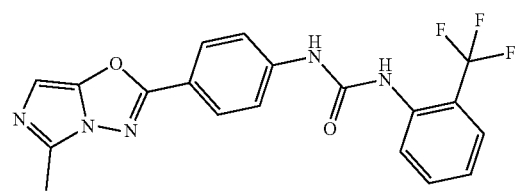 [SMILES: Cc1ncc2oc(-c3ccc(NC(=O)Nc4ccccc4C(F)(F)F)cc3)nn12] |
| 59 | 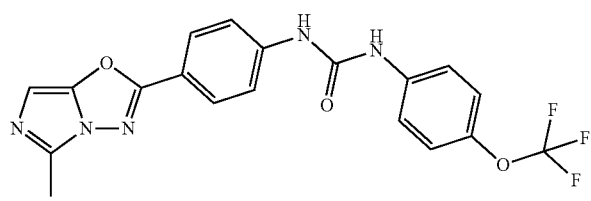 [SMILES: Cc1ncc2oc(-c3ccc(NC(=O)Nc4ccc(OC(F)(F)F)cc4)cc3)nn12] |
| 60 | 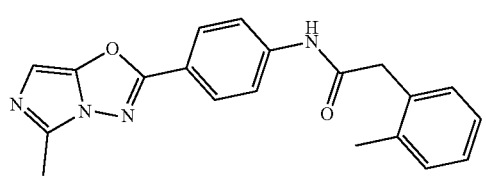 [SMILES: Cc1ccccc1CC(=O)Nc1ccc(-c2nn3c(C)ncc3o2)cc1] |
| 61 | 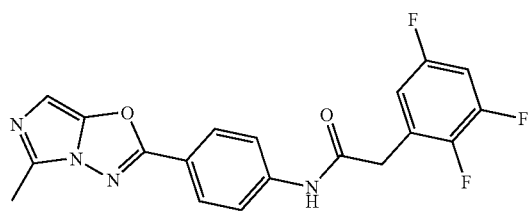 [SMILES: Cc1ncc2oc(-c3ccc(NC(=O)Cc4cc(F)cc(F)c4F)cc3)nn12] |
| 62 | 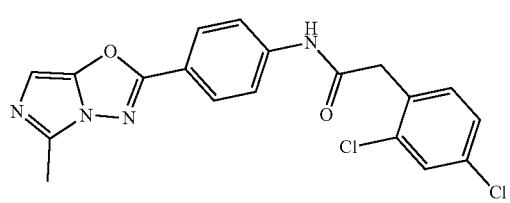 [SMILES: Cc1ncc2oc(-c3ccc(NC(=O)Cc4ccc(Cl)cc4Cl)cc3)nn12] |

-continued
| Ex. No | Structure |
|---|---|
| 63 | 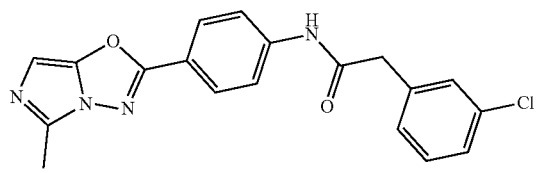 [SMILES: Cc1ncc2oc(-c3ccc(NC(=O)Cc4cccc(Cl)c4)cc3)nn12] |
| 64 | 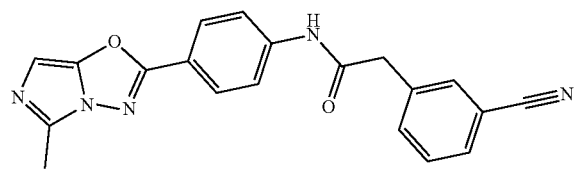 [SMILES: Cc1ncc2oc(-c3ccc(NC(=O)Cc4cccc(C#N)c4)cc3)nn12] |
| 65 | 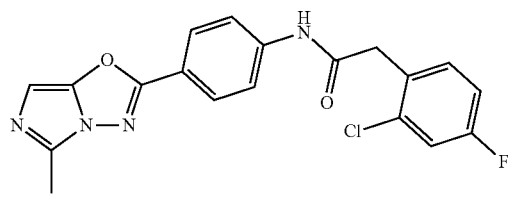 [SMILES: Cc1ncc2oc(-c3ccc(NC(=O)Cc4ccc(F)cc4Cl)cc3)nn12] |
| 66 | 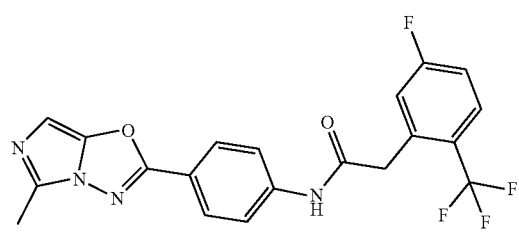 [SMILES: Cc1ncc2oc(-c3ccc(NC(=O)Cc4cc(F)ccc4C(F)(F)F)cc3)nn12] |
| 67 | 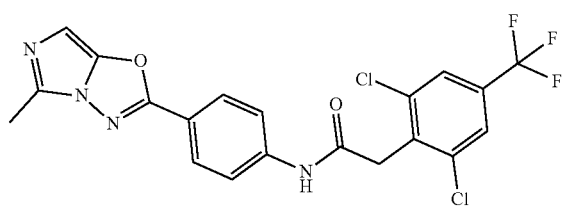 [SMILES: Cc1ncc2oc(-c3ccc(NC(=O)Cc4c(Cl)cc(C(F)(F)F)cc4Cl)cc3)nn12] |
| 68 | 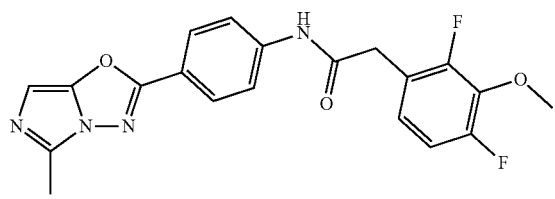 [SMILES: COc1c(F)ccc(CC(=O)Nc2ccc(-c3nn4c(C)ncc4o3)cc2)c1F] |
| 69 | 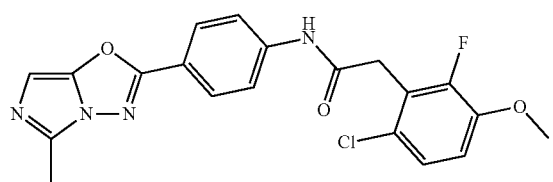 [SMILES: COc1ccc(Cl)c(CC(=O)Nc2ccc(-c3nn4c(C)ncc4o3)cc2)c1F] |

-continued
| Ex. No | Structure |
|---|---|
| 70 | 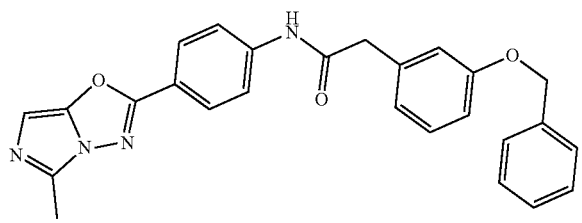 [SMILES: Cc1ncc2oc(-c3ccc(NC(=O)Cc4cccc(OCc5ccccc5)c4)cc3)nn12] |
| 71 | 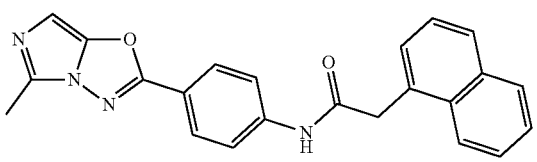 [SMILES: Cc1ncc2oc(-c3ccc(NC(=O)Cc4cccc5ccccc45)cc3)nn12] |
| 72 | 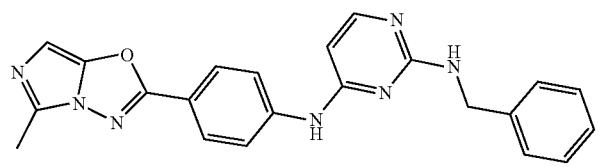 [SMILES: Cc1ncc2oc(-c3ccc(Nc4ccnc(NCc5ccccc5)n4)cc3)nn12] |
| 73 | 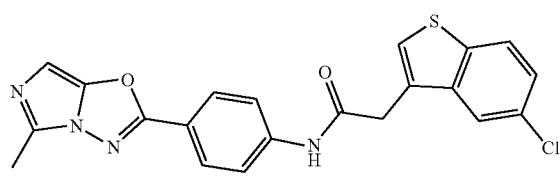 [SMILES: Cc1ncc2oc(-c3ccc(NC(=O)Cc4csc5ccc(Cl)cc45)cc3)nn12] |
| 74 | 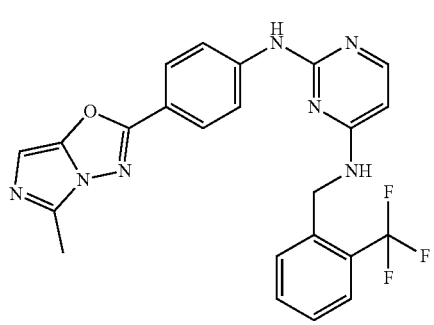 [SMILES: Cc1ncc2oc(-c3ccc(Nc4nccc(NCc5ccccc5C(F)(F)F)n4)cc3)nn12] |
| 75 | 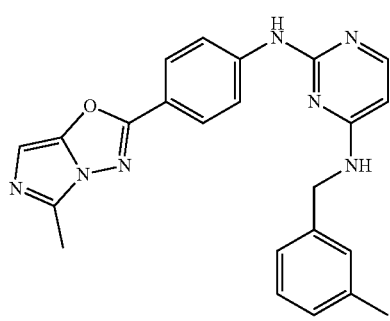 [SMILES: Cc1cccc(CNc2ccnc(Nc3ccc(-c4nn5c(C)ncc5o4)cc3)n2)c1] |

| Ex. No | Structure |
|---|---|
| 76 | 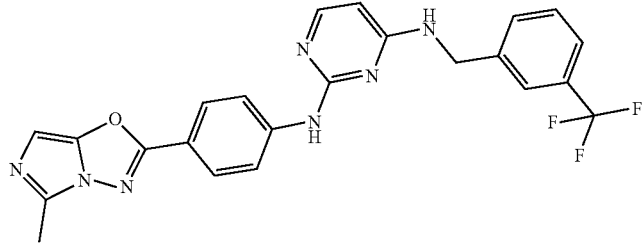 [SMILES: Cc1ncc2oc(-c3ccc(Nc4nccc(NCc5cccc(C(F)(F)F)c5)n4)cc3)nn12] |
| 77 | 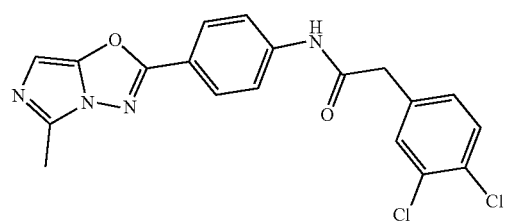 [SMILES: Cc1ncc2oc(-c3ccc(NC(=O)Cc4ccc(Cl)c(Cl)c4)cc3)nn12] |
| 78 | 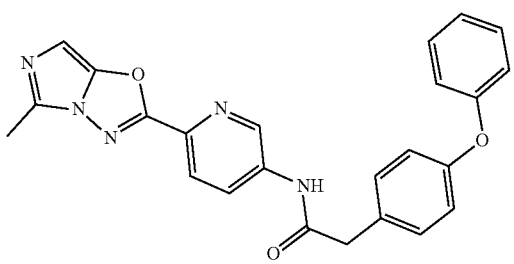 [SMILES: Cc1ncc2oc(-c3ccc(NC(=O)Cc4ccc(Oc5ccccc5)cc4)cn3)nn12] |
| 79 | 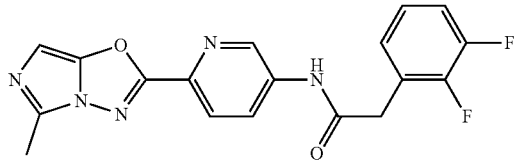 [SMILES: Cc1ncc2oc(-c3ccc(NC(=O)Cc4cccc(F)c4F)cn3)nn12] |
| 80 | 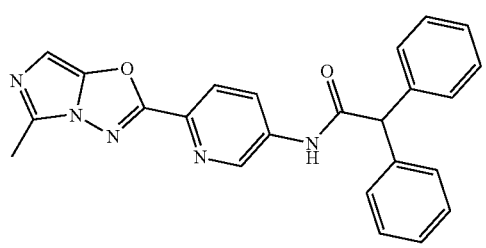 [SMILES: Cc1ncc2oc(-c3ccc(NC(=O)C(c4ccccc4)c4ccccc4)cn3)nn12] |
| 81 | 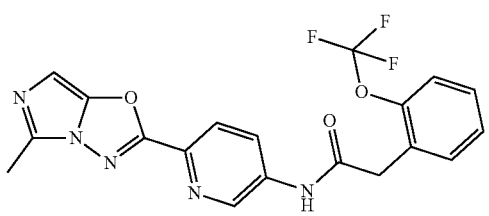 [SMILES: Cc1ncc2oc(-c3ccc(NC(=O)Cc4ccccc4OC(F)(F)F)cn3)nn12] |
| 82 | 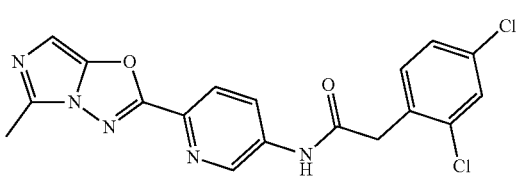 [SMILES: Cc1ncc2oc(-c3ccc(NC(=O)Cc4ccc(Cl)cc4Cl)cn3)nn12] |

-continued

| Ex. No | Structure |
|---|---|
| 83 | 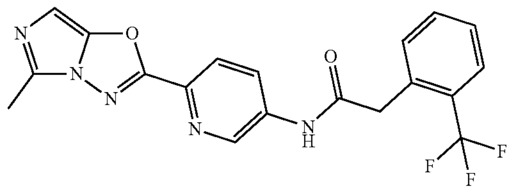 [SMILES: Cc1ncc2oc(-c3ccc(NC(=O)Cc4ccccc4C(F)(F)F)cn3)nn12] |
| 84 | 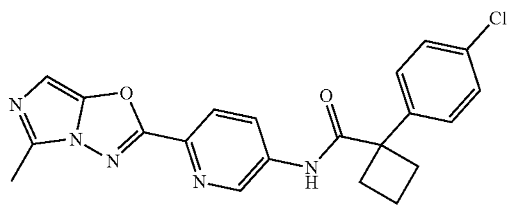 [SMILES: Cc1ncc2oc(-c3ccc(NC(=O)C4(c5ccc(Cl)cc5)CCC4)cn3)nn12] |
| 85 | 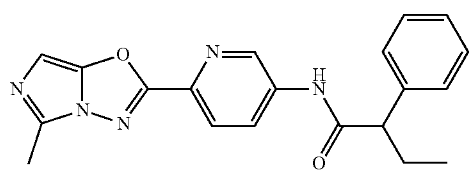 [SMILES: CCC(C(=O)Nc1ccc(-c2nn3c(C)ncc3o2)nc1)c1ccccc1] |
| 86 | 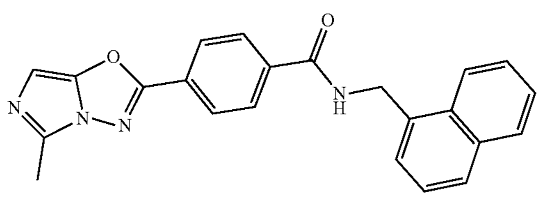 [SMILES: Cc1ncc2oc(-c3ccc(C(=O)NCc4cccc5ccccc45)cc3)nn12] |
| 87 | 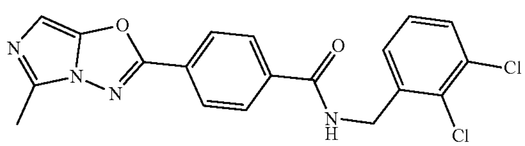 [SMILES: Cc1ncc2oc(-c3ccc(C(=O)NCc4cccc(Cl)c4Cl)cc3)nn12] |
| 88 | 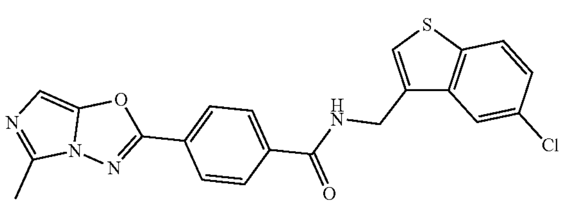 [SMILES: Cc1ncc2oc(-c3ccc(C(=O)NCc4csc5ccc(Cl)cc45)cc3)nn12] |
| 89 | 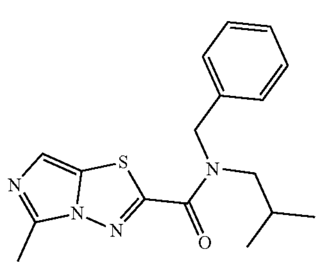 [SMILES: Cc1ncc2sc(C(=O)N(Cc3ccccc3)CC(C)C)nn12] |

-continued

| Ex. No | Structure |
|---|---|
| 90 | 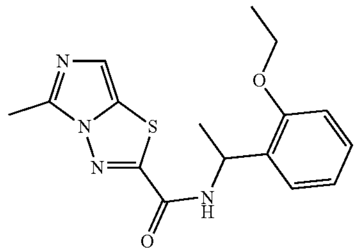 [SMILES: CCOc1ccccc1C(C)NC(=O)c1nn2c(C)ncc2s1] |
| 91 | 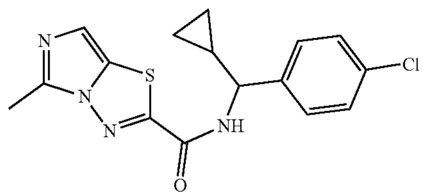 [SMILES: Cc1ncc2sc(C(=O)NC(c3ccc(Cl)cc3)C3CC3)nn12] |
| 92 | 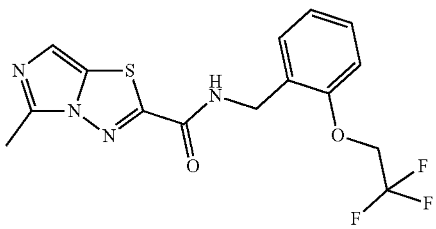 [SMILES: Cc1ncc2sc(C(=O)NCc3ccccc3OCC(F)(F)F)nn12] |
| 93 | 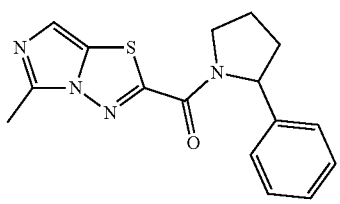 [SMILES: Cc1ncc2sc(C(=O)N3CCCC3c3ccccc3)nn12] |
| 94 | 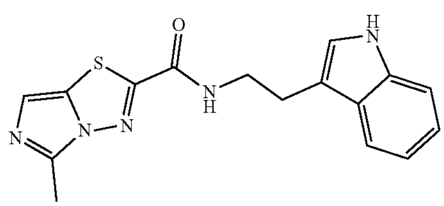 [SMILES: Cc1ncc2sc(C(=O)NCCc3c[nH]c4ccccc34)nn12] |
| 95 | 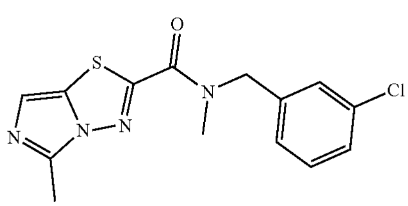 [SMILES: Cc1ncc2sc(C(=O)N(C)Cc3cccc(Cl)c3)nn12] |
| 96 | 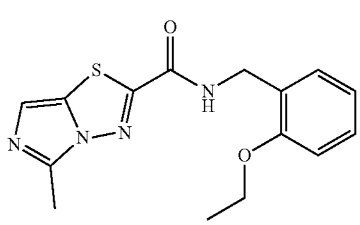 [SMILES: CCOc1ccccc1CNC(=O)c1nn2c(C)ncc2s1] |

-continued

| Ex. No | Structure |
|---|---|
| 97 | 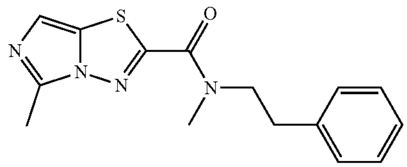 [SMILES: Cc1ncc2sc(C(=O)N(C)CCc3ccccc3)nn12] |
| 98 | 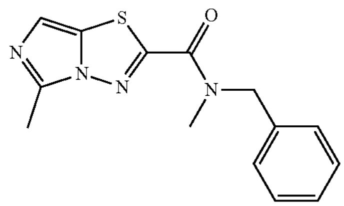 [SMILES: Cc1ncc2sc(C(=O)N(C)Cc3ccccc3)nn12] |
| 99 | 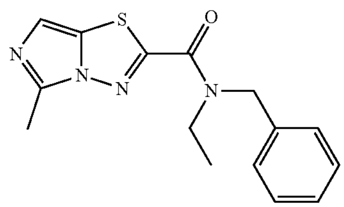 [SMILES: CCN(Cc1ccccc1)C(=O)c1nn2c(C)ncc2s1] |
| 100 | 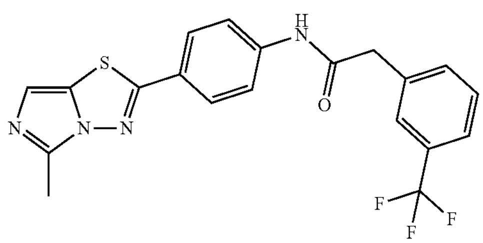 [SMILES: Cc1ncc2sc(-c3ccc(NC(=O)Cc4cccc(C(F)(F)F)c4)cc3)nn12] |
| 101 | 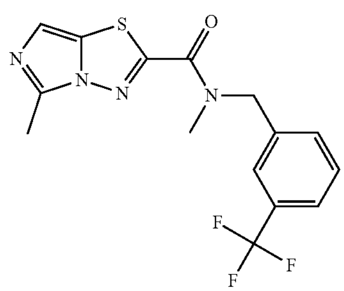 [SMILES: Cc1ncc2sc(C(=O)N(C)Cc3cccc(C(F)(F)F)c3)nn12] |
| 102 | 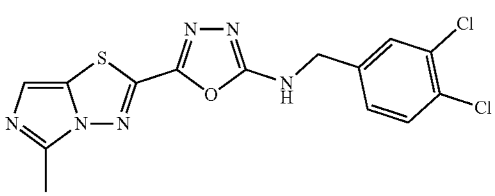 [SMILES: Cc1ncc2sc(-c3nnc(NCc4ccc(Cl)c(Cl)c4)o3)nn12] |
| 103 | 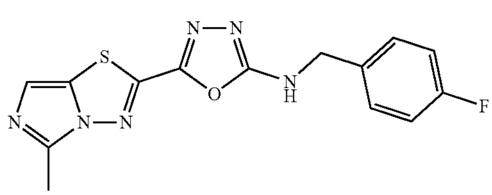 [SMILES: Cc1ncc2sc(-c3nnc(NCc4ccc(F)cc4)o3)nn12] |

| Ex. No | Structure |
|---|---|
| 104 | 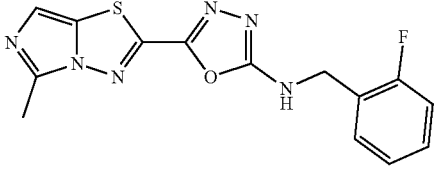 [SMILES: Cc1ncc2sc(-c3nnc(NCc4ccccc4F)o3)nn12] |
| 105 | 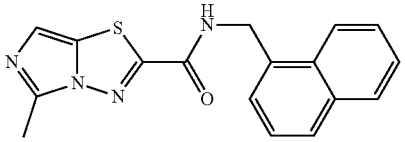 [SMILES: Cc1ncc2sc(C(=O)NCc3cccc4ccccc34)nn12] |
| 106 | 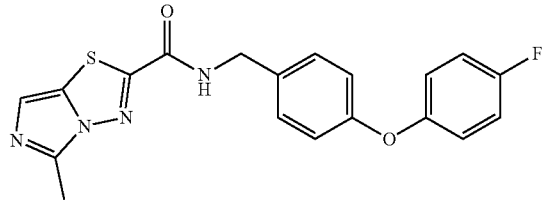 [SMILES: Cc1ncc2sc(C(=O)NCc3ccc(Oc4ccc(F)cc4)cc3)nn12] |
| 107 | 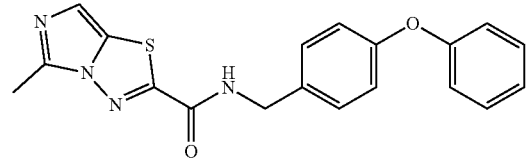 [SMILES: Cc1ncc2sc(C(=O)NCc3ccc(Oc4ccccc4)cc3)nn12] |
| 108 | 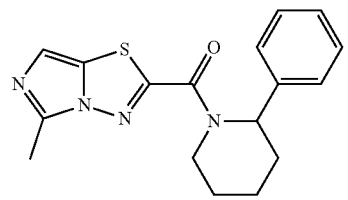 [SMILES: Cc1ncc2sc(C(=O)N3CCCCC3c3ccccc3)nn12] |
| 109 | 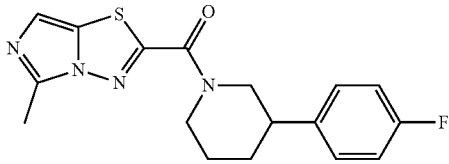 [SMILES: Cc1ncc2sc(C(=O)N3CCCC(c4ccc(F)cc4)C3)nn12] |
| 110 | 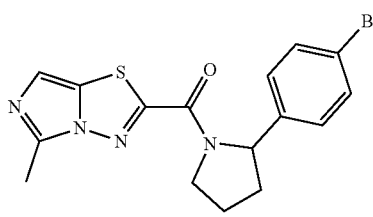 |
| 111 | 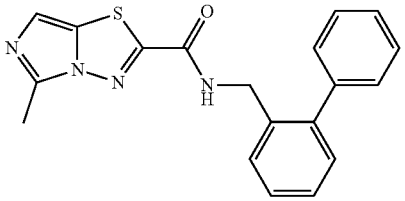 [SMILES: Cc1ncc2sc(C(=O)NCc3ccccc3-c3ccccc3)nn12] |

-continued
| Ex. No | Structure |
|---|---|
| 112 | 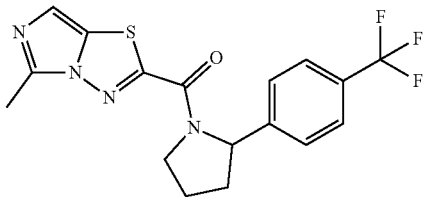 [SMILES: Cc1ncc2sc(C(=O)N3CCCC3c3ccc(C(F)(F)F)cc3)nn12] |
| 113 | 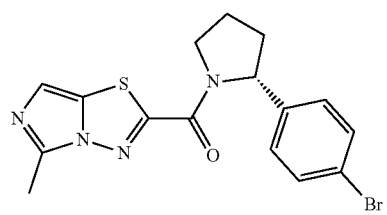 [SMILES: Cc1ncc2sc(C(=O)N3CCC[C@@H]3c3ccc(Br)cc3)nn12] |
| 114 | 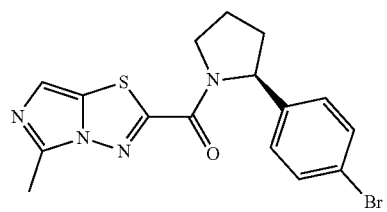 [SMILES: Cc1ncc2sc(C(=O)N3CCC[C@H]3c3ccc(Br)cc3)nn12] |
| 115 | 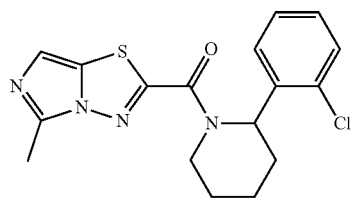 [SMILES: Cc1ncc2sc(C(=O)N3CCCCC3c3ccccc3Cl)nn12] |
| 116 | 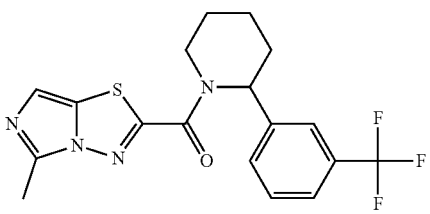 [SMILES: Cc1ncc2sc(C(=O)N3CCCCC3c3cccc(C(F)(F)F)c3)nn12] |
| 117 | 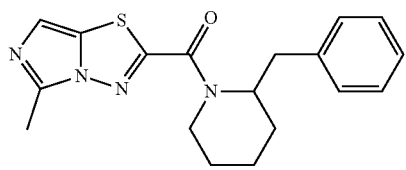 |
| 118 | 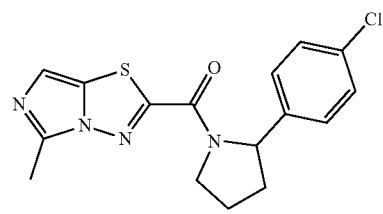 [SMILES: Cc1ncc2sc(C(=O)N3CCCC3c3ccc(Cl)cc3)nn12] |

-continued
| Ex. No | Structure |
|---|---|
| 119 | 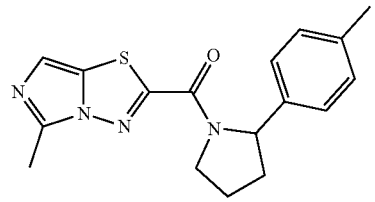 [SMILES: Cc1ccc(C2CCCN2C(=O)c2nn3c(C)ncc3s2)cc1] |
| 120 | 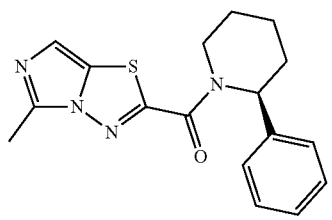 [SMILES: Cc1ncc2sc(C(=O)N3CCCC[C@H]3c3ccccc3)nn12] |
| 121 | 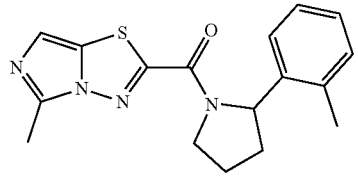 [SMILES: Cc1ccccc1C1CCCN1C(=O)c1nn2c(C)ncc2s1] |
| 122 | 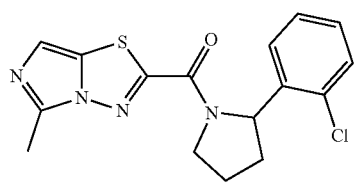 [SMILES: Cc1ncc2sc(C(=O)N3CCCC3c3ccccc3Cl)nn12] |
| 123 | 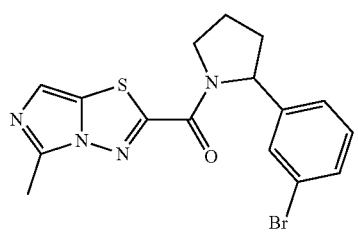 [SMILES: Cc1ncc2sc(C(=O)N3CCCC3c3cccc(Br)c3)nn12] |
| 124 | 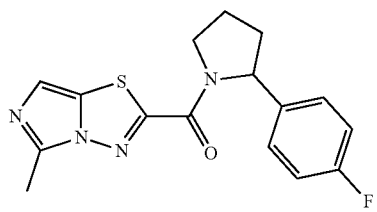 [SMILES: Cc1ncc2sc(C(=O)N3CCCC3c3ccc(F)cc3)nn12] |
| 125 | 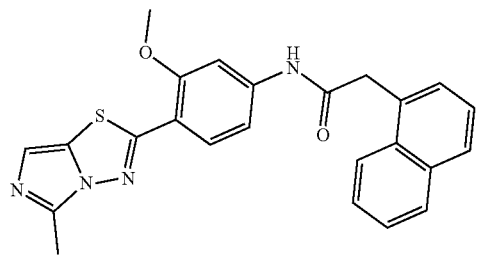 [SMILES: COc1cc(NC(=O)Cc2cccc3ccccc23)ccc1-c1nn2c(C)ncc2s1] |

| Ex. No | Structure |
|---|---|
| 126 | 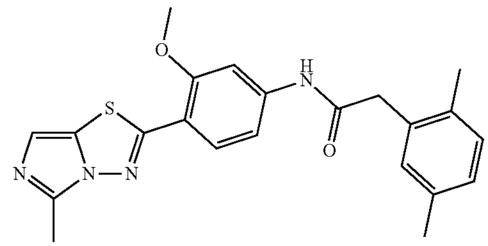 [SMILES: COc1cc(NC(=O)Cc2cc(C)ccc2C)ccc1-c1nn2c(C)ncc2s1] |
| 127 | 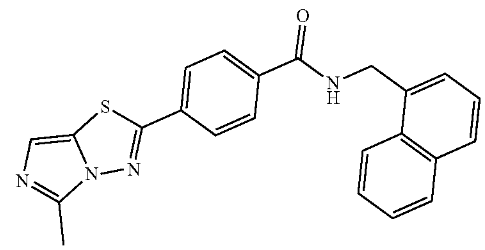 [SMILES: Cc1ncc2sc(-c3ccc(C(=O)NCc4cccc5ccccc45)cc3)nn12] |
| 128 | 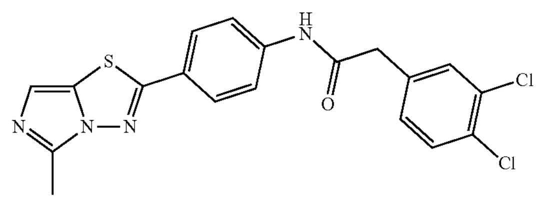 [SMILES: Cc1ncc2sc(-c3ccc(NC(=O)Cc4ccc(Cl)c(Cl)c4)cc3)nn12] |

The following abbreviations refer respectively to the definitions below:

aq (aqueous), h (hour), g (gram), L (litre), mg (milligram), MHz (Megahertz), μM (micromolar), min (minute), mm (millimeter), mmol (millimole), mM (millimolar), m.p. (melting point), eq (equivalent), mL (millilitre), μL (microlitre), ACN (acetonitrile), BINAP (2,2'-bis(disphenylphosphino)-1,1'-binaphthalene), BOC (tert-butoxy-carbonyl), CBZ (carbobenzoxy), CDCl3 (deuterated chloroform), CD$_3$OD (deuterated methanol), CH$_3$CN (acetonitrile), c-hex (cyclohexane), DABAL-Me$_3$ (Bis(trimethylaluminum)-1,4-diazabicyclo(2.2.2)octane adduct), DCC (dicyclohexyl carbodiimide), DCM (dichloromethane), dppf (1,1'-bis(diphenylphosphino)ferrocene), DIC (diisopropyl carbodiimide), DIEA (diisopropylethyl-amine), DMF (dimethylformamide), DMSO (dimethylsulfoxide), DMSO-d$_6$ (deuterated dimethylsulfoxide), EDC (1-(3-dimethyl-amino-propyl)-3-ethylcarbodiimide), ESI (Electro-spray ionization), EtOAc (Ethyl acetate), Et$_2$O (diethyl ether), EtOH (ethanol), FMOC (fluorenylmethyloxycarbonyl), HATU (dimethylamino-([1,2,3]triazolo[4,5-b]pyridin-3-yloxy)-methylene]-dimethyl-ammonium hexafluorophosphate), HPLC (High Performance Liquid Chromatography), i-PrOH (2-propanol), K$_2$CO$_3$ (potassium carbonate), LC (Liquid Chromatography), MD Autoprep (Mass directed preparative HPLC), MeOH (methanol), MgSO$_4$ (magnesium sulfate), NMI (N-methyl imidazole), MS (mass spectrometry), MTBE (Methyl tert-butyl ether), Mtr. (4-Methoxy-2, 3, 6-trimethylbenzensulfonyl), MW (microwave), NBS (N-bromo succinimide), NaHCO$_3$ (sodium bicarbonate), NaBH$_4$ (sodium borohydride), NMM (N-methyl morpholine), NMR (Nuclear Magnetic Resonance), POA (phenoxyacetate), Py (pyridine), PyBOP® (benzotriazole-1-yl-oxy-tris-pyrrolidino-phosphonium hexafluorophosphate), RT (room temperature), Rt (retention time), SFC (supercritical fluid chromatography), SPE (solid phase extraction), T3P (propylphosphonic anhydride), TBAF (tetra-n-butylammonium fluoride), TBTU (2-(1-H-benzotriazole-1-yl)-1,1,3,3-tetramethyluromium tetrafluoro borate), TEA (triethylamine), TFA (trifluoroacetic acid), THF (tetrahydrofuran), TLC (Thin Layer Chromatography), UV (Ultraviolet).

In general, the imidazo-oxadiazole and imidazo-thiadiazole compounds according to Formula (I) and related formulae of this invention may be prepared from readily available starting materials. If such starting materials are not commercially available, they may be prepared by standard synthetic techniques. In general, the synthesis pathways for any individual compound of Formula (I) and related formulae will depend on the specific substituents of each molecule, such factors being appreciated by those of ordinary skill in the art. The following general methods and procedures described hereinafter in the examples may be employed to prepare compounds of Formula (I) and related formulae. Reaction conditions depicted in the following schemes, such as temperatures, solvents, or co-reagents, are given as examples only and are not restrictive. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3$^{rd}$ Edition 1999.

Depending on the nature of $R^1$, $R^2$, $R^3$, $R^4$, $R^a$, A, T, U, W and X, different synthetic strategies may be selected for the synthesis of compounds of Formula (I). In the process illustrated in the following schemes $R^1$, $R^2$, $R^3$, $R^4$, $R^a$, A, T, U, W and X, are as above-defined in the description unless otherwise mentioned.

Compounds of Formula (Ia), wherein $R^1$, $R^2$, $R^3$, $R^4$, $R^a$, A, U, W and X are defined as above and T is —$CONR^5$—, can be prepared from a carboxylic acid of Formula (II), wherein $R^1$, $R^a$, U and X are defined as above and an amine (III), wherein $R^2$, $R^3$, $R^4$, $R^5$, A and W are defined as above, using coupling conditions well known to those skilled in the art. Alternatively, compounds of Formula (Ib), wherein $R^1$, $R^2$, $R^3$, $R^4$, $R^5$, $R^a$, A, U, W and X are defined as above and T is —$NR^5CO$—, can be prepared from an amine of Formula (IV), wherein $R^1$, $R^a$, U and X are defined as above and a carboxylic acid (V), wherein $R^2$, $R^3$, $R^4$, A and W are defined as above, using coupling conditions well known to those skilled in the art (Scheme 1).

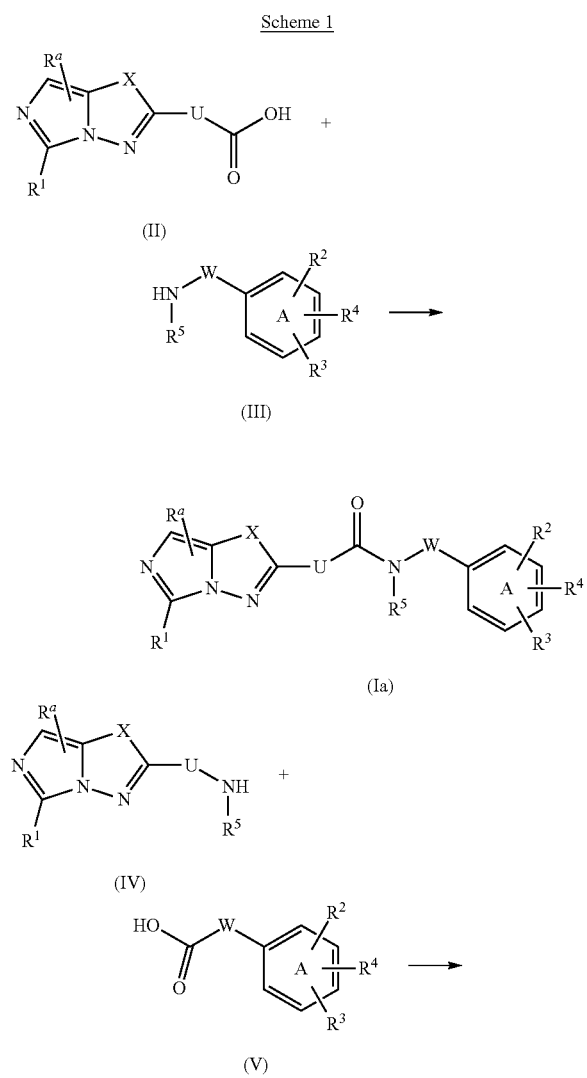

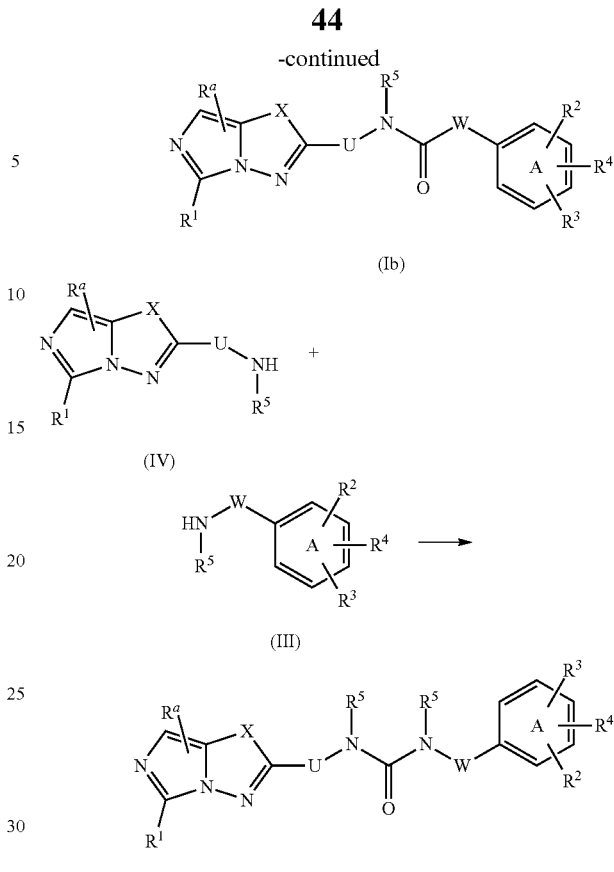

Standard coupling agents, such as HATU, EDC, T3P or isobutyl chloroformate can be used in the presence or not of a base such as DIEA, TEA or NMM in a suitable solvent such as DCM, DCE, THF or DMF at a temperature rising from about 0° C. to 100° C., for a time of 30 minutes to a few hours. Alternatively, carboxylic acid derivative (II) or (V) can be transformed into the corresponding acyl chloride and be coupled with amine (III) or (IV) respectively, using conditions and methods well known to those skilled in the art, in the presence of a base such as pyridine, TEA or DIEA in a suitable solvent such as DCM, THF or DMF, at a temperature rising from about 0° C. to RT, preferably at RT, for a few hours, affording compounds of Formula (Ia) and (Ib) respectively. On the other hand, carboxylic acid derivative (II) or (V) can be transformed into the corresponding alkyl ester, such as methyl ester, and coupled with amine derivatives (III) or (IV) respectively, in the presence or not of AlMe$_3$ in DCE or bis(trimethylaluminum)-1,4-diazabicyclo(2.2.2)octane adduct in THF, at a temperature rising from about 0° C. to 100° C. for a few hours, affording compounds of Formula (Ia) and (Ib) respectively.

Alternatively, compounds of Formula (Ic), wherein $R^1$, $R^2$, $R^3$, $R^4$, $R^5$, $R^a$, A, U, W and X are defined as above and T is —$NR^5CONR^5$—, can be prepared from an amine of Formula (IV), wherein $R^1$, $R^a$, U and X are defined as above and an amine (III), wherein $R^2$, $R^3$, $R^4$, $R^5$, A and W are defined as above, using coupling conditions well known to those skilled in the art (Scheme 1). In a typical reaction conditions, but not limited to it, amine (III) is reacted with CDI, followed by addition of amine (IV). Alternatively, isocyanate derived from amine (III) can be commercially available and directly used in the reaction with amine (IV).

Compounds of Formula (Id), wherein $R^1$, $R^2$, $R^3$, $R^4$, $R^a$, A, U, W and X are defined as above and T is $-NR^5-$, can be prepared from intermediate (VI), wherein $R^1$, $R^a$, U and X are defined as above and Hal is a halogen such as I, Br, Cl or sulfonate ester, and an amine (III), wherein $R^2$, $R^3$, $R^4$, $R^5$, $R^a$, A and W are defined as above, via metal catalyzed cross coupling reaction, such as Buchwald cross coupling reaction (Scheme 2). In a typical procedure, but not limited to it, intermediate (VI) and amine (III) are heated in a suitable solvent, such as dioxane, in the presence of a base, such as $Cs_2CO_3$, and a catalytic amount of a palladium catalyst, such as $Pd_2dba_3$, with Xantphos as ligand.

Scheme 2

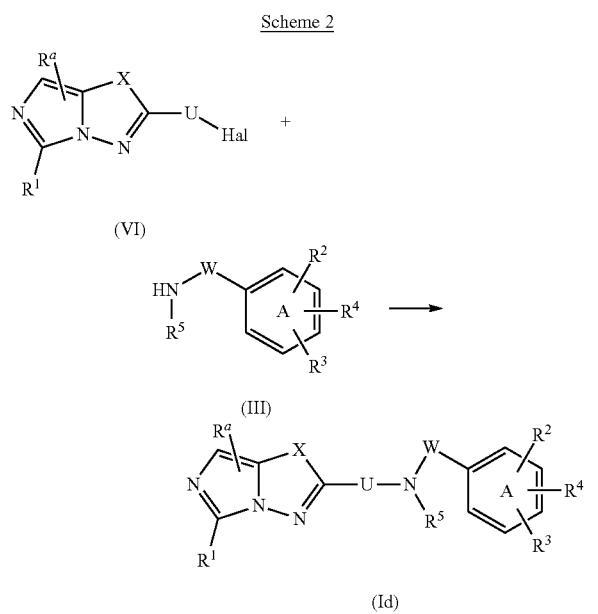

(Id)

Compounds of Formula (Ie), wherein $R^1$, $R^2$, $R^3$, $R^4$, $R^a$, A, U and X are defined as above and T is $-NR^5-$, W is a thiazole-containing bicycle and n=0-2, can be prepared from thiourea (VII), wherein $R^1$, $R^5$, $R^a$, U and X are defined as above, and α-halo ketone (VIII), wherein $R^2$, $R^3$, $R^4$, A and n are defined as above (Scheme 3). Thiourea (VII) is prepared from amine (IV), using condition well known by one skilled in the art, such as but not limited to reaction with 1,1'-thiocarbonyldi-2-(1H)-pyridone followed by addition of methanolic ammonia. α-Halo ketone (VIII) can be readily made by a number of methods known to one skilled in the art, such as but not limited to a three step process, nucleophilic addition to epoxide (IX), alcohol (X) oxidation followed by α-bromination of the resulting ketone (XI), affording α-bromoketone (VIII). Alternatively, α-bromoketone (VIII) can be transformed into 2-aminothiazole-containing bicycle (IIIa) that can be coupled with intermediate (VI), as previously depicted in Scheme 2.

Scheme 3

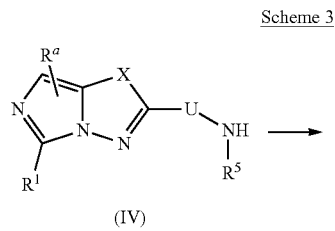

(IV)

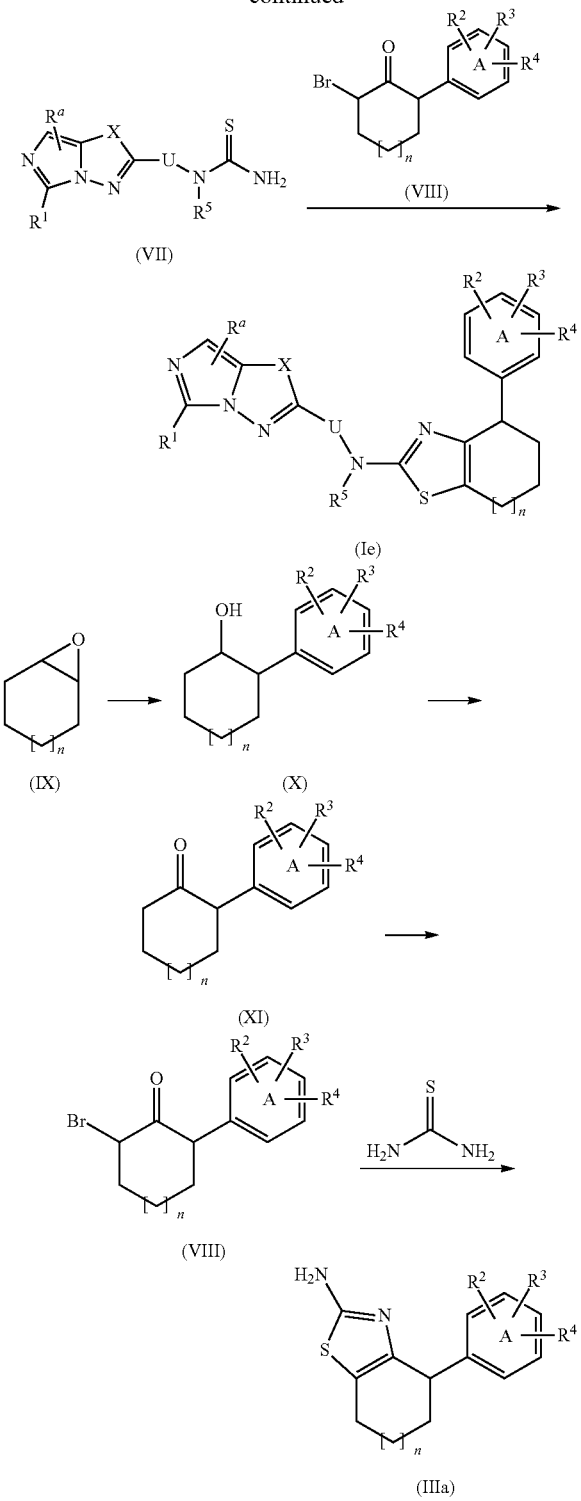

Compounds of Formula (If), wherein $R^1$, $R^2$, $R^3$, $R^4$, $R^a$, A, U and X are defined as above and T is $-NR^5-$, W is a triazole-containing bicycle and n=0-2, can be prepared as depicted in Scheme 4. Alkylation of thiourea (VII) with methyl iodide then provides the methyl isothioureas (VIII). The intermediates (VIII), wherein $R^1$, $R^5$, $R^a$, U and X are defined as above, are coupled using standard methods, to functionalized carboxylic acids, such as acids (XII), wherein $R^2$, $R^3$, $R^4$, A and n are defined as above, to afford the acylthioureas (XIII). Treatment of intermediate (XIII) with hydrazine provides triazole of formula (XIV). Triazole (XIV) undergo intramolecular alkylation using Hünig's base and sodium iodide in a solvent such as acetone or using and inorganic base, such as potassium or cesium carbonate, and potassium iodide in DMF to afford the bicyclic triazole of formula (If).

Functionalized carboxylic acid (XII) required for the synthesis of the compounds of formula (Ie) can be obtained using standard literature methods to those skilled in the art. In one variation, readily available phenylacetic acid (XV) can be mono alkylated under basic conditions with chlor-oiodoalkanes to provide functionalized acid (XII) (Scheme 4).

Scheme 4

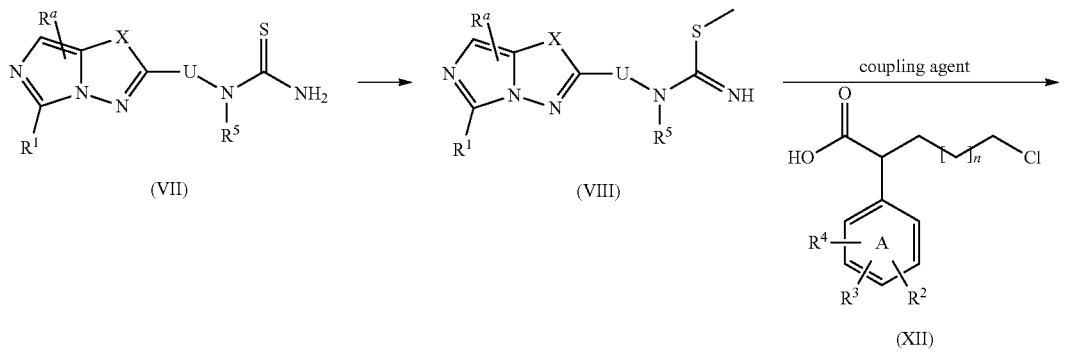

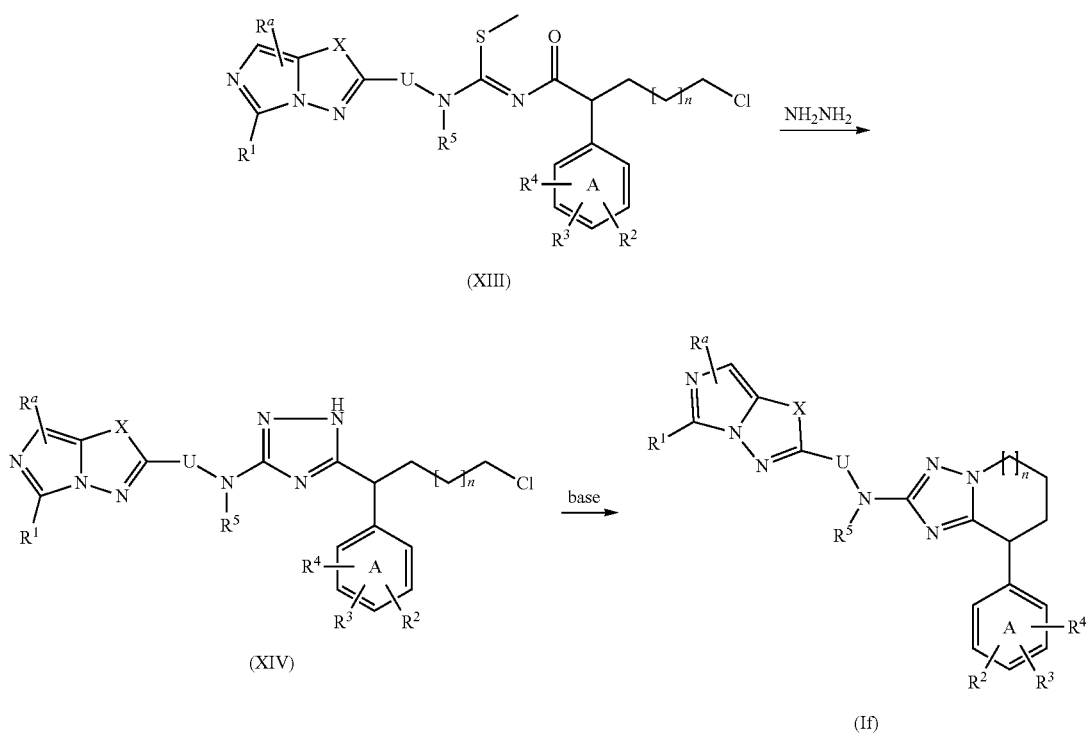

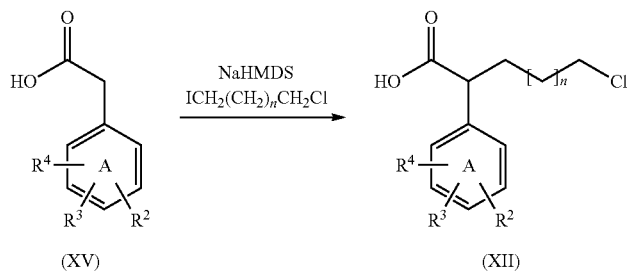

Compounds of Formula (Ig) and (Ih), wherein $R^1$, $R^2$, $R^3$, $R^4$, $R^a$, A, U and X are defined as above, T is —$NR^5$—, W is a substituted pyrimidine and n=0-2, can be prepared as depicted in Scheme 5. Amination of 2,4-dichloropyrimidine with compounds of Formula (XVI), wherein $R^2$, $R^3$, $R^4$, $R^a$, A and n are defined as above, yields intermediate (XVII) that can further react with amines of Formula (IV), either using $S_NAr$ reaction conditions or metal catalyzed coupling conditions, yielding compounds of Formula (Ig). Alternatively, addition of amines of Formula (IV) to 2,4-dichloropyrimidine provides intermediates (XVIII) that can further react with an amine of Formula (XVI), yielding compounds of Formula (Ih).

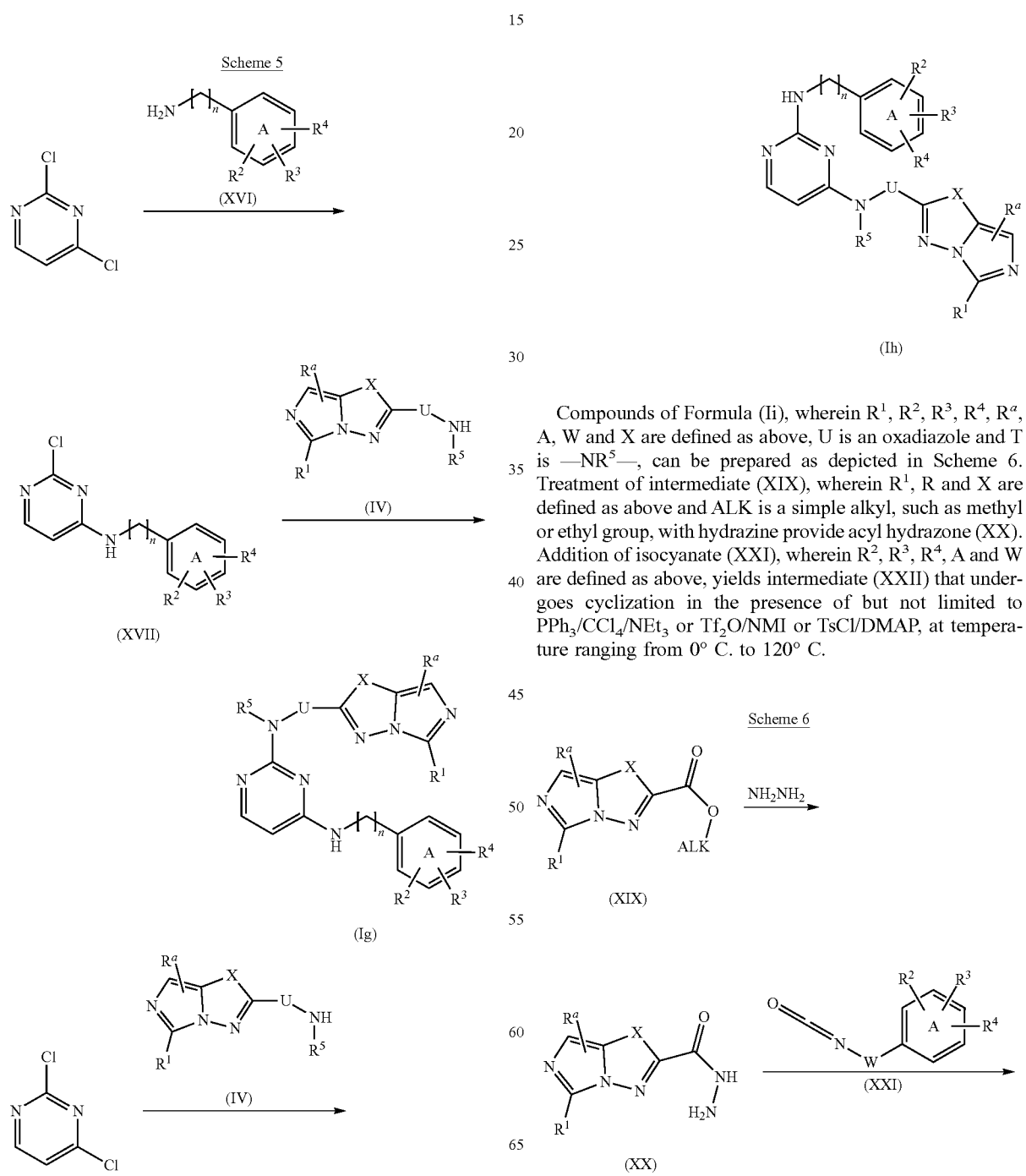

Compounds of Formula (Ii), wherein $R^1$, $R^2$, $R^3$, $R^4$, $R^a$, A, W and X are defined as above, U is an oxadiazole and T is —$NR^5$—, can be prepared as depicted in Scheme 6. Treatment of intermediate (XIX), wherein $R^1$, R and X are defined as above and ALK is a simple alkyl, such as methyl or ethyl group, with hydrazine provide acyl hydrazone (XX). Addition of isocyanate (XXI), wherein $R^2$, $R^3$, $R^4$, A and W are defined as above, yields intermediate (XXII) that undergoes cyclization in the presence of but not limited to $PPh_3/CCl_4/NEt_3$ or $Tf_2O/NMI$ or TsCl/DMAP, at temperature ranging from 0° C. to 120° C.

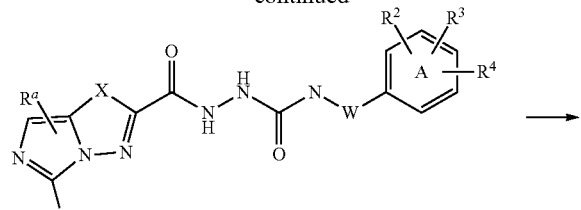

(XXII)

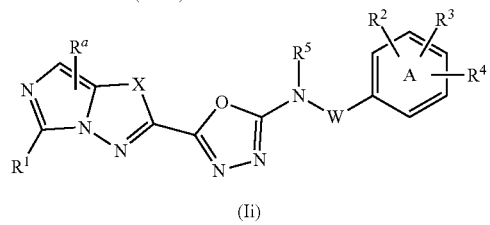

(Ii)

Alternatively, compounds of Formula (Ii), wherein $R^1$, $R^2$, $R^3$, $R^4$, $R^a$, A, W and X are defined as above, U is an oxadiazole and T is —$NR^5$—, can be prepared as depicted in Scheme 7. Cyclization of acyl hydrazone (XX) with CS2 yields [1,3,4]oxadiazole-2-thiols (XXIII). Addition of amine (III) provides compounds of Formula (Ii).

Scheme 7

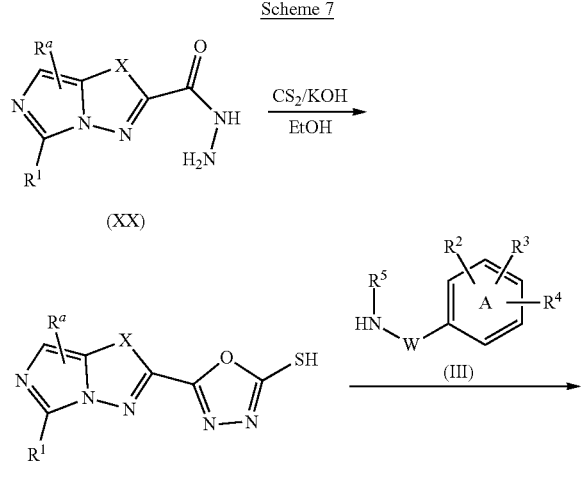

(XXIII)

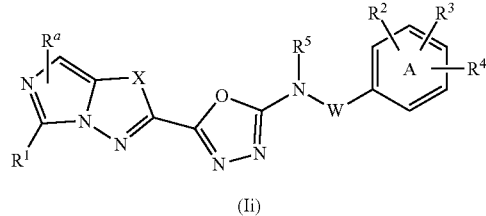

(Ii)

ment of ester (XXIV), wherein U and Y are defined as above, with hydrazine, provides acyl hydrazone (XXV) (Scheme 8). The coupling of the resulting acyl hydrazone (XXV) with N-protected amino acid, such as but not limited to N-acetyl glycine, affords intermediate (XXVI). Intermediate (XXVI) undergoes cyclization in the presence of an excess of $POCl_3$ in MeCN as solvent, affording intermediates (XXVIIa).

Scheme 8

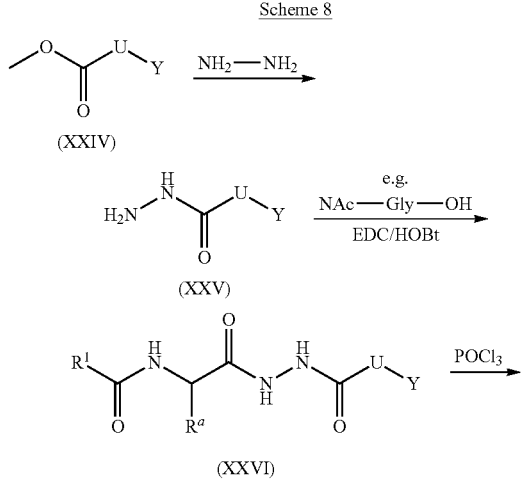

(XXVIIa)

As alternative method, carboxylic acid of formula (XXVII), wherein U and Y are defined as above, can be coupled with acyl hydrazone (XXVIII), using conditions well known to those skilled in the art, such as but not limited to T3P, affording intermediate (XXIX). Intermediate (XXIX) undergoes cyclization with an excess of $POCl_3$ in MeCN as solvent, affording intermediates (XXVIIa).

Scheme 9

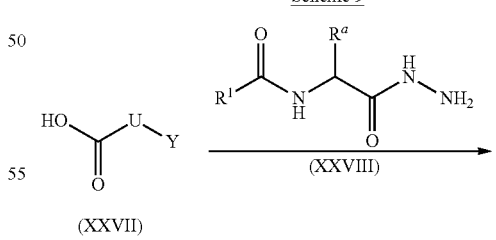

(XXVII)    (XXVIII)

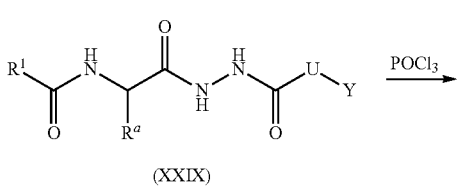

(XXIX)

Imidazooxadiazole intermediate (XXVIIa), wherein $R^1$, $R^a$ and U are defined as above, X=O and Y is an halogen such as Cl, Br or I, —COOALK or a protected amino group, such as but not limited to —NHCOOCH$_2$Ph, can be prepared following methods known to the one skill in the art. When Y is an halogen, such as Cl, Br or I, U is not a single bond. Typical synthetic pathways and conditions are depicted in Schemes 8 to 10 and described hereinafter in the examples. One alternative is presented in Scheme 8. Treat-

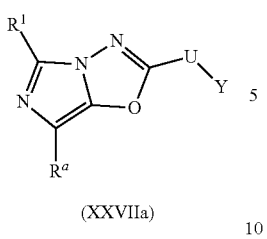

(XXVIIa)

On the other hand, treatment of N-protected amino ester (XXX), such as but not limited to N-(tert-butoxycarbonyl) glycine methyl ester, with hydrazine provides acyl hydrazone (XXXI). Its coupling with carboxylic acid (XXVII), wherein U and Y are defined as above, affords intermediate (XXXII) that yields oxadiazole (XXXIII) upon treatment with Tf$_2$O/NMI or APTS/TEA, at temperature ranging from 0° C. to 120° C. Amine deprotection on (XXXIII), followed by coupling with a carboxylic acid such as R$^1$COOH gives intermediate (XXXIV). Final cyclization is achieved with an excess of POCl$_3$ in MeCN as solvent, affording intermediates (XXVIIa), wherein R$^1$, R$^a$ and U are defined as above, X=O and Y is an halogen such as Cl, Br or I, —COOH, —COOAlk or a protected amino group, such as but not limited to —NHCOOCH$_2$Ph.

Alternatively, treatment of intermediate (XXXII) with Lawesson reagent yield formation of thiadiazole (XXXV). Amine deprotection on (XXXV), followed by coupling with a carboxylic acid such as R$^1$COOH gives intermediate (XXXVI). Final cyclization is achieved with an excess of POCl$_3$ in MeCN as solvent, affording intermediates (XXVIIb), wherein R$^1$, R$^a$ and U are defined as above, X=S and Y is an halogen such as Cl, Br or I, —COOH, —COOAlk or a protected amino group, such as but not limited to —NHCOOCH$_2$Ph.

Scheme 10

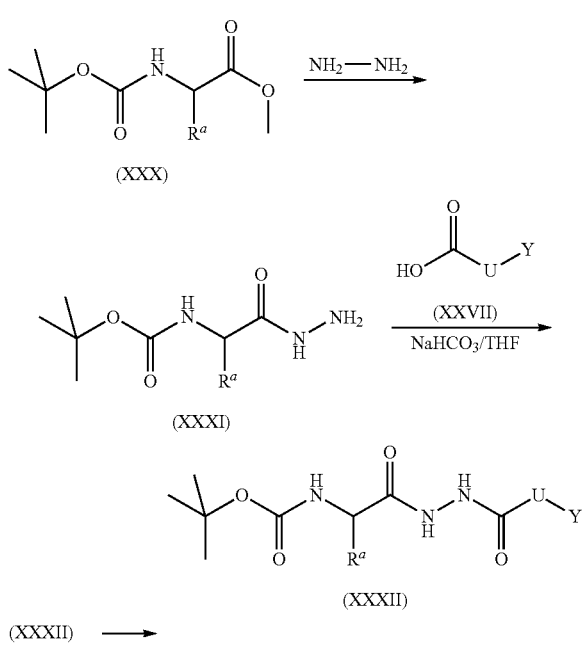

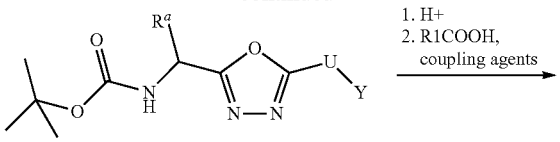

The method for preparing amide derivatives of Formula (XXVIIa) selected below:
2-(5-Bromo-pyridin-2-yl)-5-methyl-imidazo[5,1-b][1,2,4]oxadiazole, hydrochloride salt
3-methoxy-4-(5-methyl-imidazo[5,1-b][1,2,4]oxadiazol-2-yl)-phenylamine
2-Methyl-4-(5-methyl-imidazo[5,1-b][1,2,4]oxadiazol-2-yl)-phenylamine
4-(5-Methyl-imidazo[5,1-b][1,2,4]oxadiazol-2-yl)-phenylamine
6-(5-Methyl-imidazo[5,1-b][1,2,4]oxadiazol-2-yl)-pyridin-3-ylamine
4-(5-Methyl-imidazo[5,1-b][1,2,4]oxadiazol-2-yl)-benzoic acid methyl ester
3-Methoxy-4-(5-methyl-imidazo[5,1-b][1,2,4]oxadiazol-2-yl)-benzoic acid methyl ester
4-(5-Ethyl-imidazo[5,1-b][1,2,4]oxadiazol-2-yl)-benzoic acid methyl ester
4-(5,7-Dimethyl-imidazo[5,1-b][1,2,4]oxadiazol-2-yl)-benzoic acid methyl ester 2-(4-Bromo-phenyl)-5-methyl-imidazo[5,1-b][1,2,4]oxadiazole is more particularly described in the examples.

The method for preparing amide derivatives of Formula (XXVIIb) selected below:

5-Methylimidazo[5,1-b][1,3,4]thiadiazole-2-carboxylic acid ethyl ester 5-methylimidazo[5,1-b][1,3,4]thiadiazole-2-carboxylic acid 3-Methoxy-4-(5-methyl-imidazo[5,1-b][1,3,4]thiadiazol-2-yl)-phenylamine 4-(5-Methyl-imidazo[5,1-b][1,3,4]thiadiazol-2-yl)-benzoic acid methyl ester 4-(5-Methyl-imidazo[5,1-b][1,3,4]thiadiazol-2-yl)-phenylamine is more particularly described in the examples.

Compounds of Formulae (II) to (XXXVI) may be obtained either from commercial sources or they may be prepared from known compounds using procedures such as those described hereinafter in the examples, or conventional procedures, well known by one skilled in the art.

Compounds of Formulae (II) to (XXXVI), wherein $R^1$, $R^2$, $R^3$, $R^4$, $R^a$, A, T, U, W, X and Y are defined as above, may be converted to alternative compounds of Formulae (II) to (XXXVI), respectively, using suitable interconversion procedures such as those described hereinafter in the examples, or conventional interconversion procedures well known by one skilled in the art.

If the above set of general synthetic methods is not applicable to obtain compounds according to Formula (I) and/or necessary intermediates for the synthesis of compounds of Formula (I), suitable methods of preparation known by a person skilled in the art should be used.

Compounds of this invention can be isolated in association with solvent molecules by crystallization from evaporation of an appropriate solvent. The pharmaceutically acceptable acid addition salts of the compounds of formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compounds of formula (I), which contain an acid center, with a suitable base. Both types of salts may be formed or interconverted using ion-exchange resin techniques.

Depending on the conditions used, the reaction times are generally between a few minutes and 14 days, and the reaction temperature is between about −30° C. and 140° C., normally between −10° C. and 90° C., in particular between about 0° C. and about 70° C.

Compounds of the formula (I) can furthermore be obtained by liberating compounds of the formula (I) from one of their functional derivatives by treatment with a solvolysing or hydrogenolysing agent.

Preferred starting materials for the solvolysis or hydrogenolysis are those which conform to the formula (I), but contain corresponding protected amino and/or hydroxyl groups instead of one or more free amino and/or hydroxyl groups, preferably those which carry an amino-protecting group instead of an H atom bound to an N atom, in particular those which carry an R'—N group, in which R' denotes an amino-protecting group, instead of an HN group, and/or those which carry a hydroxyl-protecting group instead of the H atom of a hydroxyl group, for example those which conform to the formula (I), but carry a —COOR" group, in which R" denotes a hydroxyl protecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxy-carbonyl, ethoxycarbonyl, 2,2,2-trichloroethoxycarbonyl, BOC (tert-butoxy-carbonyl) and 2-iodoethoxycarbonyl; aralkoxycarbonyl, such as CBZ ("carbo-benz-oxy"), 4-methoxybenzyloxycarbonyl and FMOC; and aryl-sulfonyl, such as Mtr. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitro-benzoyl, p-toluenesulfonyl, tert-butyl and acetyl, where benzyl and tert-butyl are particu-larly preferred.

The term "solvates of the compounds" is taken to mean adductions of inert solvent molecules onto the compounds which form owing to their mutual attractive force. Solvates are, for example, mono- or dihydrates or alcoholates.

The compounds of the formula (I) are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as THF or dioxane, amides, such as DMF, halogenated hydrocarbons, such as DCM, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (RT).

The BOC, OBut and Mtr groups can, for example, preferably be cleaved off using TFA in DCM or using approximately 3 to 5N HCl in dioxane at 15-30° C., and the FMOC group can be cleaved off using an approximately 5 to 50% solution of dimethylamine, diethylamine or piperidine in DMF at 15-30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, tri-fluoro-methylbenzene, chloroform or DCM; alcohols, such as methanol, ethanol, isopropanol, n-propanol, n-butanol or tert-butanol; ethers, such as diethyl ether, diisopropyl ether, tetrahydrofurane (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethyl-formamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as EtOAc, or mixtures of the said solvents.

Esters can be saponified, for example, using LiOH, NaOH or KOH in water, water/THF, water/THF/ethanol or water/dioxane, at temperatures between 0 and 100° C. Furthermore, ester can be hydrolysed, for example, using acetic acid, TFA or HCL.

Free amino groups can furthermore be acylated in a conventional manner using an acyl chloride or anhydride or alkylated using an unsubstituted or substituted alkyl halide or reacted with CH3-C(=NH)—OEt, advantageously in an inert solvent, such as DCM or THF and/or in the presence of a base, such as triethylamine or pyridine, at temperatures between −60° C. and +30° C.

Throughout the specification, the term leaving group preferably denotes Cl, Br, I or a reactively modified OH group, such as, for example, an activated ester, an imidazolide or alkylsulfonyloxy having 1-6 carbon atoms (preferably methylsulfonyloxy or trifluoromethylsulfonyloxy) or arylsulfonyloxy having 6-10 carbon atoms (preferably phenyl- or p-tolylsulfonyloxy). Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart). Activated esters are advantageously formed in situ, for example through addition of HOBt or N-hydroxysuccinimide.

The term "pharmaceutically usable derivatives" is taken to mean, for example, the salts of the compounds of the formula I and so-called prodrug compounds.

The term "prodrug derivatives" is taken to mean compounds of the formula I which have been modified with, for example, alkyl or acyl groups, sugars like glucuronide or oligopeptides and which are rapidly cleaved in the organism to form the active compounds.

These also include biodegradable polymer derivatives of the compounds according to the invention, as described, for example, in Int. J. Pharm. 115, 61-67 (1995).

The formula (I) also encompasses the optically active forms (stereoisomers), the enantiomers, the racemates, the diastereomers and the hydrates, salts and solvates of these compounds.

In a specific embodiment, when 2 chiral centers or more are present, compounds of Formula (I) are obtained as one diastereoisomer.

A "diastereoisomer" means that each of the chiral centers present in the compound of Formula (I) is defined relatively to the others.

For all radicals and indices which occur more than once within the same chemical structure, their meanings are independent of one another.

The reactions are preferably carried out in an inert solvent.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or DCM; alcohols, such as methanol, ethanol, isopropanol, n-propanol, n-butanol or tert-butanol; ethers, such as diethyl ether, diisopropyl ether, THF (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as EtOAc, or mixtures of the said solvents.

Pharmaceutical Salts and Other Forms

The said compounds of the formula (I) can be used in their final non-salt form. On the other hand, the present invention also relates to the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains an acidic center, such as a carboxyl group, one of its suitable salts can be formed by reacting the compound with a suitable base to give the corresponding base-addition salt. Such bases are, for example, alkali metal hydroxides, including potassium hydroxide and sodium hydroxide; alkaline earth metal hydroxides, such as magnesium hydroxide and calcium hydroxide; and various organic bases, such as piperidine, diethanolamine and N-methylglucamine (meglumine), benzathine, choline, diethanolamine, ethylenediamine, benethamine, diethylamine, piperazine, lysine, L-arginine, ammonia, triethanolamine, betaine, ethanolamine, morpholine and tromethamine. In the case of certain compounds of the formula I, which contain a basic center, acid-addition salts can be formed by treating these compounds with pharmaceutically acceptable organic and inorganic acids, for example hydrogen halides, such as hydrogen chloride or hydrogen bromide, other mineral acids and corresponding salts thereof, such as sulfate, nitrate or phosphate and the like, and alkyl- and monoaryl-sulfonates, such as methanesulfonate, ethanesulfonate, toluenesulfonate and benzene-sulfonate, and other organic acids and corresponding salts thereof, such as carbonate, acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, aspartate, benzoate, benzene-sulfonate (besylate), bisulfate, bisulfite, bromide, camphorate, camphor-sulfonate, caprate, caprylate, chloride, chlorobenzoate, citrate, cyclamate, cinnamate, digluconate, dihydrogen-phosphate, dinitrobenzoate, dodecyl-sulfate, ethanesulfonate, formate, glycolate, fumarate, galacterate (from mucic acid), galacturonate, glucoheptanoate, gluco-nate, glutamate, glycerophosphate, hemi-succinate, hemisulfate, heptanoate, hexanoate, hippurate, hydro-chloride, hydrobromide, hydroiodide, 2-hydroxy-ethane-sulfonate, iodide, isethionate, isobutyrate, lactate, lactobionate, malate, maleate, malonate, mandelate, metaphosphate, methanesulfonate, methylbenzoate, mono-hydrogen-phosphate, 2-naphthalenesulfonate, nicotinate, nitrate, oxalate, oleate, palmo-ate, pectinate, persulfate, phenylacetate, 3-phenylpropionate, phosphate, phosphonate, phthalate, but this does not represent a restriction. Both types of salts may be formed or interconverted preferably using ion-exchange resin techniques.

Furthermore, the base salts of the compounds of the formula I include aluminium, ammonium, calcium, copper, iron (III), iron(II), lithium, magnesium, manganese(III), manganese(II), potassium, sodium and zink salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzyl-ethylen-ediamine (benzathine), dicyclohexylamine, diethanol-amine, diethyl-amine, 2-diethyl-amino-ethanol, 2-dimethyl-amino-ethanol, ethanolamine, ethylenediamine, N-ethylmorpholine, N-ethyl-piperidine, glucamine, glucosamine, histidine, hydrabamine, isopropyl-amine, lidocaine, lysine, meglumine (N-methyl-D-glucamine), morpholine, piperazine, piperidine, polyamine resins, procaine, purines, theobromine, triethanol-amine, triethylamine, trimethylamine, tripropyl-amine and tris(hydroxy-methyl)-methylamine (tromethamine), but this is not intended to represent a restriction.

Compounds of the formula I of the present invention which contain basic N2-containing groups can be quaternised using agents such as (C1-C4)-alkyl halides, for example methyl, ethyl, isopropyl and tert-butyl chloride, bromide and iodide; di(C1-C4)alkyl sulfates, for example dimethyl, diethyl and diamyl sulfate; (C10-C18)alkyl halides, for example decyl, do-decyl, lauryl, myristyl and stearyl chloride, bromide and iodide; and aryl-(C1-C4)alkyl halides, for example benzyl chloride and phenethyl bromide. Both water- and oil-soluble compounds of the formula I can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, me-glumine, nitrate, oleate, phosphonate, pivalate, sodium phosphate, stearate, sulfate, sulfosalicylate, tartrate, thiomalate, tosylate and tro-meth-amine, but this is not intended to represent a restriction.

The acid-addition salts of basic compounds of the formula (I) are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts other-wise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanol-amine, ethylenediamine, N-methyl-D-glucamine and procaine.

The base-addition salts of acidic compounds of the formula I are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts other-wise correspond to the respective free acid forms thereof.

If a compound of the formula (I) contains more than one group which is capable of forming pharmaceutically acceptable salts of this type, the formula I also encompasses multiple salts. Typical multiple salt forms include, for example, bitartrate, diacetate, difumarate, dimeglumine, di-phosphate, disodium and trihydrochloride, but this is not intended to represent a restriction.

With regard to that stated above, it can be seen that the term "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Owing to their molecular structure, the compounds of the formula (I) can be chiral and can accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the Intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the (R) and (S) forms of tartaric acid, diacetyltartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

GENERAL METHODS

The compounds of invention have been named according to the standards used in the program AutoNom (v1.0.1.1)

The compounds according to formula (I) can be prepared from readily available starting materials by several synthetic approaches, using both solution-phase and solid-phase chemistry protocols or mixed solution and solid phase protocols. Examples of synthetic pathways are described below in the examples.

The commercially available starting materials used in the following experimental description were purchased from Aldrich, Sigma, ACROS or ABCR unless otherwise reported.

$^1$H NMR analyses were carried out using BRUKER NMR, model DPX-300 MHz FT-NMR or Bruker Avance III 400 MHz. Residual signal of deuterated solvent was used as internal reference. Chemical shifts (δ) are reported in ppm in relative to the residual solvent signal (δ=2.50 for $^1$H NMR in DMSO-d$_6$, and 7.26 in CDCl$_3$). s (singlet), d (doublet), t (triplet), q (quadruplet), br (broad), quint (quintuplet).

The MS data provided in the examples described below were obtained using either: Method A: LC/MS Waters ZMD (ESI) or Method B: a Micromass ZQ, single quadrapole LC/MS (ESCI)

HPLC analyses were obtained as followed:

Method A: Column:—Waters Xterra MS 5 µm C18, 100×4.6 mm. eluting with ACN/10 mM ammonium bicarbonate (95% ACN after 4 min.) and a flow rate of 2 mL/min.

Method B: Column:—Phenomenex Luna 5 µm C18 (2), 100×4.6 mm, eluting with ACN/water/0.1% formic acid (100% ACN after 3.5 min.) and a flow rate of 2 mL/min.

HPLC analyses were obtained as followed:

Method A: Column:—Waters Xterra MS 5 µm C18, 100×4.6 mm. eluting with ACN/10 mM ammonium bicarbonate (95% ACN after 4 min.) and a flow rate of 2 mL/min.

Method B: Column:—Phenomenex Luna 5 µm C18 (2), 100×4.6 mm, eluting with ACN/water/0.1% formic acid (100% ACN after 3.5 min.) and a flow rate of 2 mL/min. Detection of compounds was via a Micromass ZQ, single quadrapole LC-MS instrument.

Method C: Column:—Phenomenex, Gemini NX, 3 µm C18, 150×4.6 mm. eluting with ACN/10 mM ammonium bicarbonate (100% ACN after 9 min.) and a flow rate of 1 mL/min.

Method D: Column:—Supelco, Ascentis® Express C18 or Hichrom Halo C18, 2.7 µm C18, 150×4.6 mm, eluting with ACN/water/0.1% formic acid (100% ACN after 9 min.) with a flow rate of 1 mL/min.

Method E: Column:—Hichrom ACE 3 C18-AR mixed mode column, 2.7 µm C18, 100×4.6 mm, eluting with ACN/water/0.1% formic acid (100% ACN after 12 min.) with a flow rate of 1 mL/min.

Method F: Column: Waters Xbridge™ C8, (50×4.6 mm), 3.5 µm; 8 min gradient H$_2$O:CH$_3$CN:TFA from 100:0:0.1% to 0:100:0.05% with a flow rate of 2.0 mL/min.

Analytical methods (A-F) are referred to in the protocols and tables of data outlined in the document below. UV detection (maxplot) for all methods.

The mass directed preparative HPLC (MD Autoprep) purifications were performed with a mass directed autopurification Fractionlynx from Waters equipped with a Sunfire Prep C18 OBD column 19×100 mm 5 µm, unless otherwise reported. All purifications were performed with a gradient of ACN/H$_2$O or ACN/H$_2$O/HCOOH (0.1%).

Preparative HPLC:

Alternatively, compounds were purified using reverse phase HPLC using a Waters Fractionlynx preparative HPLC system (2525 pump, 2996/2998 UV/VIS detector, 2767 liquid handler). The Waters 2767 liquid handler acted as both auto-sampler and fraction collector.

The column used for the preparative purification of the compounds was a Waters Sunfire OBD Phenomenex Luna Phenyl Hexyl or Waters Xbridge Phenyl at 10 um 19×150 mm.

Appropriate focused gradients were selected based on acetonitrile and methanol solvent systems under either acidic or basic conditions. The standard gradient used was 5% ACN to 20% over 1 min, hold 1 min, to 80% ACN over 5 min, hold 4 min. Followed by 1 min 100% ACN and 1.5 min re-equilibration at initial conditions. A flow rate of 20 mL/min was used.

The microwave chemistry was performed on a single mode microwave reactor Emrys™ Optimiser or Initiator™ Sixty from Biotage.

Intermediate 1: 2-(5-Bromo-pyridin-2-yl)-5-methyl-imidazo[5,1-b][1,2,4]oxadiazole, Hydrochloride Salt

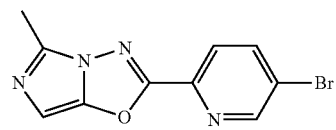

Step 1: 5-Bromo-pyridine-2-carboxylic Acid Hydrazide

5-Bromo-pyridine-2-carboxylic acid methyl ester (107 g, 495 mmol) was taken in EtOH (2 L) at 25-26° C. under nitrogen atmosphere. Hydrazine hydrate (123 mL, 2475 mmol) was added to the reaction mixture and stirred for 48 h at 25° C. (reaction completion was confirmed by TLC). The reaction mixture was concentrated to get a crude product that was precipitated as a white solid (74.6 g, 70% yield). The crude product was taken as such for the next step without further purification. $^1$H NMR (300 MHz, DMSO-d$_6$) δ 9.99 (t, J=4.3 Hz, 1H), 8.74 (dd, J=2.4, 0.7 Hz, 1H), 8.23

(dd, J=8.4, 2.4 Hz, 1H), 7.92 (dd, J=8.4, 0.7 Hz, 1H), 4.59 (d, J=4.4 Hz, 2H). LC/MS (Method A): 218.0 (M+H)⁺.

Step 2: N-{2-[N'-(5-Bromo-pyridine-2-carbonyl)-hydrazino]-2-oxoethyl}-acetamide Acetylamino-acetic acid (54.2 g, 463 mmol) was suspended in DMF (500 mL) and then di-imidazol-1-yl-methanone (82.6 g, 509 mmol) was added by portions. The mixture was reacted at room temperature until no more gas evolution was observed (1 h). A solution was obtained. It was added dropwise over 20 min to a suspension of 5-bromo-pyridine-2-carboxylic acid hydrazide (50 g, 231 mmol) in DMF (500 mL). The reaction mixture was stirred overnight at room temperature. Precipitation had occurred overnight and mixture was filtered off. The white solid was washed with MTBE (100 mL), dried under vacuum to finally obtain the pure expected intermediate (27 g, 37% yield). ¹H NMR (300 MHz, DMSO-d₆) δ 10.67 (d, J=1.4 Hz, 1H), 10.19 (d, J=1.6 Hz, 1H), 8.93 (dd, J=2.3, 0.7 Hz, 1H), 8.40 (dd, J=8.4, 2.3 Hz, 1H), 8.32 (t, J=5.8 Hz, 1H), 8.07 (dd, J=8.4, 0.7 Hz, 1H), 3.93 (d, J=5.8 Hz, 2H), 1.98 (s, 3H). LC/MS (Method A): 317.2 (M+H)⁺.

Step 3: 2-(5-Bromo-pyridin-2-yl)-5-methylimidazo[5,1-b][1,2,4]oxadiazole, Hydrochloride Salt N-{2-[N'-(5-Bromo-pyridine-2-carbonyl)-hydrazino]-2-oxo-ethyl}-acetamide (26 g, 86 mmol) was added in portions to Eaton's reagent (260 mL). Resulting viscous mixture was heated to 110° C. for 7 h after what LC/MS indicated a ~1:2 mixture of oxadiazole:imidazooxadiazole. The reaction was allowed to cool to 25° C. and was added drop-wise to a solution of K₂CO₃ 50% (800 mL). Strong gas evolution occurred upon addition. The thick mixture was diluted with water (800 mL) and was extracted with DCM (2×800 mL). Organic layers were combined, dried over MgSO₄, filtered and evaporated to dryness to obtain a mixture of the titled compound and its open form as a brown solid (16.2 g). This brown solid was taken in MeCN (320 mL). POCl₃ (5.07 mL, 55 mmol) was added drop-wise and mixture was heated to ET=90° C. The cyclization was completed within 3.5 h according to LC/MS. Reaction mixture was cooled to RT and acetonitrile (~200 mL) was evaporated. Resulting suspension was filtered. Solid was washed with EtOAc (25 mL) and then dried overnight under vacuum. Finally a purple solid was isolated as the hydrochloride salt of the expected compound (12.5 g, 46% yield). ¹H NMR (300 MHz, DMSO-d₆) δ 9.12 (dd, J=2.4, 0.7 Hz, 1H), 8.51 (dd, J=8.5, 2.3 Hz, 1H), 8.29 (dd, J=8.4, 0.8 Hz, 1H), 7.54 (s, 1H), 2.81 (s, 3H). LC/MS (Method A): 281.1 (M+H)⁺.

Intermediate 2: 3-methoxy-4-(5-methylimidazo[5,1-b][1,2,4]oxadiazol-2-yl)-phenylamine

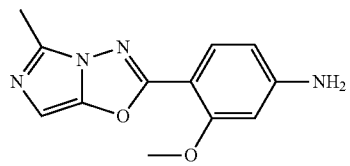 [SMILES: COc1cc(N)ccc1-c1nn2c(C)ncc2o1]

Step 1: 2-methoxy-4-nitrobenzohydrazide

To a suspension of 2-methoxy-4-nitrobenzoic acid (10 g, 50.7 mmol) in chloroform (50 mL) under nitrogen was added thionyl chloride (12 mL, 162 mmol) slowly, followed by DMF (four drops). After 16 hours at 25° C., the reaction mixture was concentrated under reduced pressure. The residue was cooled to 0° C. and diluted slowly with MeOH (50 mL), followed by hydrazine hydrate (35% aqueous solution, 13.6 mL, 152 mmol). The reaction mixture was sealed and stirred for 6 hours at 25° C. The resulting precipitate was collected by filtration, washed with water, and then dried under vacuum to afford a yellow solid as a mixture of the title compound and the methyl ester. To this solid was added MeOH (50 mL), followed by hydrazine hydrate (35% aqueous solution, 13.6 mL, 152 mmol). After 24 hours at 80° C. the resulting precipitate was collected by filtration, washed with water, and then dried under vacuum to afford the title compound (7.3 g, 69% yield). LC/MS (Method B): 212 (M+H)⁺.

Step 2: N-(2-(2-(2-methoxy-4-nitrobenzoyl)hydrazinyl)-2-oxoethyl)acetamide

To a suspension of N-acetylglycine (6.9 g, 59.8 mmol) in DMF (30 mL) was added CDI (10.1 g, 62.4 mmol) portionwise over 20 minutes. After 30 minutes a solution of 2-methoxy-4-nitrobenzohydrazide (6.3 g, 29.6 mmol) in DMF (50 mL) was added. After 16 hours at 25° C. the reaction was concentrated under reduced pressure. The residue was diluted in 2M aqueous HCl to give a precipitate, which was collected by filtration, washed with water and then dried under vacuum to afford the title compound (2.6 g, 28% yield). LC/MS (Method B): 311 (M+H)⁺.

Step 3: 2-(2-methoxy-4-nitrophenyl)-5-methylimidazo[5,1-b][1,2,4]oxadiazole

To a suspension of N-(2-(2-(2-methoxy-4-nitrobenzoyl)hydrazinyl)-2-oxoethyl)acetamide (2.9 g, 9.35 mmol) in MeCN (50 mL), was added phosphoryl chloride (8.7 mL, 93.5 mmol). After 6 hours at 90° C. the reaction was cooled to 25° C. and then concentrated under reduced pressure. The residue was quenched with ice-water, basified using saturated aqueous Na₂CO₃ solution and then extracted using EtOAc. The organic layers were combined, washed with water and brine, dried (MgSO₄) and concentrated under reduced pressure to afford the title compound (2.3 g, 90% yield). ¹H NMR (400 MHz, CHCl₃-d): δ 7.99-7.92 (m, 3H); 6.49 (s, 1H); 4.13 (s, 3H); 2.60 (s, 3H). LC/MS (Method B): 275 (M+H)⁺.

Step 4: 3-methoxy-4-(5-methylimidazo[5,1-b][1,2,4]oxadiazol-2-yl)-phenylamine A slurry was prepared of 2-(2-methoxy-4-nitrophenyl)-5-methylimidazo[5,1-b][1,2,4]oxadiazole (2.3 g, 8.4 mmol), iron powder (2.2 g, 42 mmol) and ammonium chloride (670 mg, 12.6 mmol) in THF (10 mL)/EtOH (10 mL)/water (3 mL). This reaction was sealed under nitrogen and rapidly heated to 90° C. for 1 hour. The reaction was then filtered through a celite pad, washed with MeOH (100 mL) and concentrated in vacuo. The crude product was dissolved in EtOAc, washed with dilute aqueous NaHCO₃ solution and filtered. The organic phase was then washed with water, brine and dried (MgSO₄) and concentrated under reduced pressure to give a pale yellow powder (1.4 g, 68% yield). ¹H NMR (400 MHz, DMSO-d$^6$): δ 6.39 (s, 1H); 6.34 (d, J=1.95 Hz, 1H); 6.29 (dd, J=8.57, 1.94 Hz, 1H); 6.14 (s, 2H); 3.83 (s, 3H); 2.40 (s, 3H).

Intermediate 3: 2-Methyl-4-(5-methyl-imidazo[5,1-b][1,2,4]oxadiazol-2-yl)-phenylamine

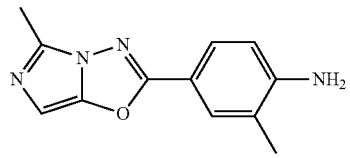 [SMILES: Cc1cc(-c2nn3c(C)ncc3o2)ccc1N]

Step 1: 3-methyl-4-nitrobenzohydrazide

To a suspension of methyl 3-methyl-4-nitrobenzoate (10 g, 51 mmol) in EtOH (100 mL), was added hydrazine hydrate (55% aqueous solution, 8.50 mL, 150 mmol) in one portion. After 48 hours at 90° C. the reaction was cooled to 0° C. The reaction mixture was diluted with water (50 mL) and stirred for a further 5 minutes. The resulting precipitate was collected by filtration, washed with water, and then dried under vacuum to afford the title compound as a white solid (7.78 g, 78% yield). 1H NMR (400 MHz, DMSO-d$^6$): δ 10.02 (s, 1H); 8.04 (d, J=8.45 Hz, 1H); 7.92 (s, 1H); 7.83 (dd, J=8.44, 1.94 Hz, 1H); 4.60 (s, 2H); 2.54 (s, 3H). LC/MS (Method B): 196 (M+H)$^+$.

Step 2: N-(2-(2-(3-methyl-4-nitrobenzoyl)hydrazinyl)-2-oxoethyl)acetamide

To a suspension of 3-methyl-4-nitrobenzohydrazide (7.78 g, 40 mmol) in DCM (100 mL) under nitrogen was added EDC-HCl (8.5 g, 44 mmol), followed by triethylamine (18.76 mL, 140 mmol). After 15 minutes N-acetylglycine (5.2 g, 44 mmol) was added and the reaction was stirred for a further 16 hours. The reaction mixture was diluted with DCM and water, and then basified with 1M aqueous NaOH and extracted using DCM. The aqueous phase was then acidified with concentrated aqueous HCl. The resulting precipitate was collected by filtration, washed with water, followed by Et$_2$O and then dried under vacuum to afford the title compound as a yellow solid (4.95 g, 42% yield). $^1$H NMR (400 MHz, DMSO-d$^6$): δ 10.61 (s, 1H); 10.09 (s, 1H); 8.22 (t, J=5.95 Hz, 1H); 8.18-8.03 (m, 1H); 7.96 (s, 1H); 7.93-7.85 (m, 1H); 3.82 (d, J=5.93 Hz, 2H); 2.51 (s, 3H); 1.88 (s, 3H). LC/MS (Method B): 295 (M+H)$^+$.

Step 3: 5-methyl-2-(3-methyl-4-nitrophenyl)imidazo[5,1-b][1,2,4]oxadiazole

To a suspension of N-(2-(2-(3-methyl-4-nitrobenzoyl)hydrazinyl)-2-oxoethyl)acetamide (0.95 g, 3.2 mmol) in MeCN (12 mL), was added phosphoryl chloride (1.5 mL, 16.1 mmol) dropwise. After 2 hours at 110° C., the reaction was cooled to 25° C. then concentrated under reduced pressure. The residue was quenched with ice-water, basified using saturated aqueous Na$_2$CO$_3$ solution and then extracted using DCM. The organic layers were combined, washed with water and brine, dried (MgSO$_4$) and concentrated under reduced pressure. The resulting crude residue was purified by chromatography (silica gel, DCM/MeOH) and the resultant solid was triturated with Et$_2$O to afford the title compound as a yellow solid (0.72 g, 86% yield). $^1$H NMR (400 MHz, DMSO-d$^6$): δ 8.18 (t, J=3.94 Hz, 2H); 8.08 (dd, J=8.54, 1.91 Hz, 1H); 6.57 (s, 1H); 2.61 (s, 3H); 2.47 (s, 3H). LC/MS (Method B): 259 (M+H)$^+$.

Step 4: 2-Methyl-4-(5-methyl-imidazo[5,1-b][1,2,4]oxadiazol-2-yl)-phenylamine

To a suspension of 5-methyl-2-(3-methyl-4-nitrophenyl)imidazo[5,1-b][1,2,4]oxadiazole (1.90 g, 7.4 mmol) in acetic acid (19 mL) and EtOH (19 mL) was added iron powder (325 mesh, 1.62 g, 29.4 mmol) portionwise (exotherm). After 3 hours the reaction had cooled to 25° C. and was filtered over celite and concentrated under reduced pressure. The residue was diluted with EtOAc and water, basified with saturated aqueous Na$_2$CO$_3$ solution and then extracted using EtOAc. The organic layers were combined, washed with water and brine, dried (MgSO$_4$) and concentrated under reduced pressure. The resulting crude residue was triturated with Et$_2$O to afford the title compound as a yellow solid (1.4 g, 83% yield). $^1$H NMR (400 MHz, DMSO-d$^6$): δ 7.61-7.54 (m, 2H); 6.73 (d, J=8.36 Hz, 1H); 6.42 (s, 1H); 5.89 (s, 2H); 2.40 (s, 3H); 2.13 (s, 3H). LC/MS (Method B): 229 (M+H)$^+$.

Intermediate 4: 4-(5-Methyl-imidazo[5,1-b][1,2,4]oxadiazol-2-yl)-phenylamine

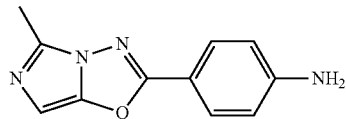 [SMILES: Cc1ncc2oc(-c3ccc(N)cc3)nn12]

Step 1: N-(2-(2-(4-nitrobenzoyl)hydrazinyl)-2-oxoethyl)acetamide

To N-acetylglycine (3.46 g, 20 mmol), 4-nitrophenylhydrazine (3.6 g, 20 mmol) and EDC-HCl (7.6 g, 40 mmol) in THF (40 mL) was added triethylamine (5.5 mL, 40 mmol). After 60 hours at 25° C., the reaction mixture was concentrated under reduced pressure and the residue was partitioned between ethyl acetate and aqueous sodium carbonate solution. The aqueous solution was acidified and the precipitate obtained was collected by filtration, washed with water and dried at 50° C. to afford the title compound as an orange powder (4.4 g, 78% yield). $^1$H NMR (400 MHz, DMSO-d d$^6$): δ 10.71 (s, 1H); 10.11 (s, 1H); 8.39-8.33 (m, 2H); 8.23 (t, J=5.94 Hz, 1H); 8.13-8.06 (m, 2H); 3.83 (d, J=5.92 Hz, 2H); 1.96-1.78 (m, 3H). LC/MS (Method B): 281.0 (M+H)$^+$.

Step 2: 5-methyl-2-(4-nitrophenyl)imidazo[5,1-b][1,2,4]oxadiazole

N-(2-(2-(4-nitrobenzoyl)hydrazinyl)-2-oxoethyl)acetamide (4.45 g, 15.8 mmol) and phosphorus oxychloride (20 mL) in acetonitrile (40 mL) were heated at reflux for 3 hours. The reaction mixture was concentrated under vacuum and the residue was treated with ice, basified with aqueous sodium hydroxide and extracted with dichloromethane. The organic layers were combined, dried (MgSO$_4$) and concentrated under reduced pressure to afford the title compound as an orange solid (2.7 g, 69% yield). $^1$H NMR (400 MHz, DMSO-d₆): δ 8.49-8.42 (m, 2H); 8.35-8.30 (m, 2H); 6.89 (s, 1H); 2.57 (s, 3H). LC/MS (Method B): 245.0 (M–H)–.

Step 3: 4-(5-Methyl-imidazo[5,1-b][1,2,4]oxadiazol-2-yl)-phenylamine 5-methyl-2-(4-nitrophenyl)imidazo[5,1-b][1,2,4]oxadiazole (500 mg, 2.05 mmol) and iron powder (1.14 g, 20.5 mmol) in acetic acid (10 mL) were stirred at 25° C. for 18 hours. The reaction mixture was filtered and washed with acetic acid. The filtrate was concentrated under reduced pressure, basified with aqueous sodium carbonate solution and extracted with chloroform. The organic layers were combined, dried (MgSO₄) and concentrated under reduced pressure to afford the title compound as a yellow solid (200 mg, 45% yield). ¹H NMR 6 (400 MHz, DMSO-d⁶): 7.68 (2H, d, J=8.52 Hz), 6.68 (2H, d, J=8.55 Hz), 6.46-6.39 (1H, s), 6.16 (2H, s), 2.40 (3H, s). LC/MS (Method B): 215.0 (M+H)⁺.

Intermediate 5: 6-(5-Methyl-imidazo[5,1-b][1,2,4]oxadiazol-2-yl)-pyridin-3-ylamine

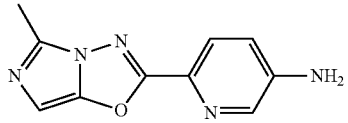 [SMILES: Cc1ncc2oc(-c3ccc(N)cn3)nn12]

Step 1: 5-Nitro-pyridine-2-carboxylic Acid Hydrazide

5-Nitro-pyridine-2-carboxylic acid methyl ester (104 g, 571 mmol) was taken in EtOH (1.0 L) at 25-26° C. under nitrogen atmosphere. Hydrazine hydrate (141 mL, 2853 mmol) was added to the reaction mixture that was stirred at 25° C. for 48 h (reaction completion was confirmed by LC/MS). An orange suspension was obtained. After filtration and drying under vacuum an orange solid was isolated as the expected title compound (110 g, 100% yield). The crude product was taken as such for the next step without further purification. ¹H NMR (300 MHz, DMSO-d₆) δ 10.28 (s, 1H), 9.34 (dd, J=2.6, 0.7 Hz, 1H), 8.74 (dd, J=8.6, 2.6 Hz, 1H), 8.22 (dd, J=8.6, 0.7 Hz, 1H), 4.76 (s, 2H). LC/MS (Method A): 183.2 (M+H)⁺.

Step 2: N-{2-[N'-(5-Nitro-pyridine-2-carbonyl)-hydrazino]-2-oxoethyl}-acetamide

N-Acetyl glycine (90 g, 768.6 mmol) was suspended in DMF (0.7 L) at 25-26° C. under vigorous stirring. Carbonyl Di-imidazole (137.1 g, 845 mmol) was added by portions to the reaction mixture. The resulting reaction was stirred at 25° C. for 0.5 h and added over a period of 30 minutes to a suspension of 5-nitro-pyridine-2-carboxylic acid hydrazide (70 g, 384 mmol) in DMF (0.7 L). The reaction was stirred for 3 hours at room temperature (reaction completion was confirmed by LC/MS). The expected compound was precipitated by addition of toluene (2.1 L, 30 vol). The resulting suspension was stirred at 25° C. overnight and the precipitate collected by filtration and washed with EtOAc (25 mL). The crude product was suspended in MeOH (2 L) overnight at 70° C. until obtaining a fine suspension and precipitated as a white solid (77 g, 71% yield). ¹H NMR (300 MHz, DMSO) δ 10.82 (s, 1H), 10.17 (s, 1H), 9.40 (dd, J=2.7, 0.7 Hz, 1H), 8.78 (dd, J=8.6, 2.6 Hz, 1H), 8.36-8.11 (m, 2H), 3.83 (d, J=5.9 Hz, 2H), 1.87 (s, 3H). LC/MS (Method A): 282.3 (M+H)⁺.

Step 3: 5-Methyl-2-(5-nitro-pyridin-2-yl)-imidazo[5,1-b][1,2,4]oxadiazole

N-{2-[N'-(5-Nitro-pyridine-2-carbonyl)-hydrazino]-2-oxo-ethyl}-acetamide (20 g, 71 mmol) was added in portions to Eaton's reagent (150 mL). Resulting viscous mixture was heated to 110° C. for 8 h after what LC/MS indicated a ~1:2 mixture of oxadiazole:imidazooxadiazole. The reaction was allowed to cool to 25° C. and was added drop-wise to a solution of K₂CO₃ 50% (800 mL). Strong gas evolution occurred upon addition. The thick mixture was diluted with water (2.0 L) and was extracted with DCM (3×700 mL). Organic layers were combined, dried over MgSO₄, filtered and evaporated to dryness to obtain a mixture of the title compound and its open form as a yellow solid (10.3 g). This material was taken in MeCN (200 mL). POCl₃ (3.75 mL, 41 mmol) was added drop-wise and mixture was heated to ET=90° C. The cyclization was completed within 3 h 30 according to LC/MS. Reaction mixture was cooled to RT and MeCN (~150 mL) was evaporated. Resulting suspension was quenched by addition of 20% aq. K₂CO₃ sol. (100 mL). Strong foaming occurred during addition. The aqueous mixture was extracted with DCM (3×100 mL). Organic layers were combined and evaporated to dryness to obtain a brown solid which was suspended in a mixture of EtOAc/toluene (20 mL/20 mL). The suspension was filtered and dried overnight under vacuum to finally obtain the title compound as a brown solid (7.3 g, 42% yield). ¹H NMR (300 MHz, DMSO-d₆) δ 9.62 (dd, J=2.6, 0.7 Hz, 1H), 8.89 (dd, J=8.7, 2.6 Hz, 1H), 8.53 (dd, J=8.7, 0.7 Hz, 1H), 7.46 (s, 1H), 2.76 (s, 3H). LC/MS (Method A): 246.1 (M+H)⁺.

Step 4: 6-(5-Methyl-imidazo[5,1-b][1,2,4]oxadiazol-2-yl)-pyridin-3-ylamine

A suspension of 5-methyl-2-(5-nitro-pyridin-2-yl)-imidazo[5,1-b][1,2,4]oxadiazole (5.2 g, 21.2 mmol) in 30% AcOH (100 mL) was degassed under nitrogen atmosphere at 25° C. 10% Palladium on activated charcoal (750 mg, 0.35 mmol) was added and the reaction hydrogenated (P=20 bars) at 25° C. for 18 hours (reaction completion was confirmed by LC/MS). The suspension was filtered over a celite pad and rinsed with 30% aq acetic acid (10 mL). The filtrate was evaporated to dryness, stripped with toluene (3×100 mL) and then dried under vacuum to afford a beige solid. The crude was suspended in MeCN (50 mL), filtered and dried to finally obtain the expected product as a beige solid (3.41 g, 75% yield). ¹H NMR (DMSO-d₆, 300 MHz) δ 8.07 (dd, J=0.7, 2.7 Hz, 1H), 7.82 (dd, J=0.7, 8.6 Hz, 1H), 7.03 (dd, J=2.7, 8.6 Hz, 1H), 6.46 (s, 1H), 6.35 (s, 2H), 2.42 (s, 3H). LC/MS (Method A): 216.0 (M+H)⁺.

Intermediate 6: 4-(5-Methyl-imidazo[5,1-b][1,2,4]oxadiazol-2-yl)-benzoic Acid Methyl Ester

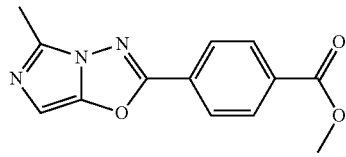 [SMILES: COC(=O)c1ccc(-c2nn3c(C)ncc3o2)cc1]

Step 1: Dimethyl Terephthalate

Terephthalic acid (20 g, 120 mmol) was taken in MeOH (200 mL) at 25-26° C. under nitrogen atmosphere. Thionyl chloride (42.9 g, 361 mmol) was added slowly over 10 minutes. The reaction mixture was heated to 80° C. for 12 h (reaction completion was confirmed by LCMS). The reaction mixture was cooled to 25-26° C. and concentrated to get the crude product as white solid (25 g). The crude product was taken up in 10% NaHCO$_3$ solution (50 mL) and stirred for 10 minutes. The precipitated solids were filtered, washed with water (50 mL) and dried to get the pure product as white solid (19 g, 82% yield). $^1$H NMR (DMSO-d$_6$, 400 MHz) δ 8.06 (s, 2H), 3.87 (s, 3H). HPLC (Method F) Rt 3.68 min (Purity: 99.5%).

Step 2: 4-Hydrazinocarbonyl-Benzoic Acid Methyl Ester

Dimethyl terephthalate (19 g, 97 mmol) was taken in EtOH (200 mL) at 25-26° C. under nitrogen atmosphere. Hydrazine hydrate (5.39 g, 0.107 mol) was added to the reaction mixture and stirred for 12 h at 90° C. (reaction completion was confirmed by TLC). The reaction mixture was cooled to 25-26° C. and concentrated to get crude product as white solid (20 g, 100% yield) The crude product was taken as such for the next step without further purification. $^1$H NMR (DMSO-d$_6$, 400 MHz) δ 9.96 (s, 1H), 8.01-7.99 (m, 2H), 7.93-7.91 (m, 2H), 4.58 (b, 2H), 3.86 (s, 3H). LC/MS (Method A): 195.3 (M+H)$^+$. HPLC (Method F) Rt 0.354 min (Purity: 70.3%).

Step 3: 4-[N'-(2-Acetylamino-acetyl)-hydrazinocarbonyl]-benzoic Acid Methyl Ester 4-Hydrazinocarbonyl-benzoic acid methyl ester (10 g, 51 mmol) was taken in DCM (100 mL) at 25-26° C. under nitrogen atmosphere. EDC-HCl (8.98 g, 56 mmol), HOBT (7.6 g, 56 mmol) and triethylamine (26.0 g, 257 mmol) were added and stirred for 15 minutes. N-acetyl glycine (6.63 g, 56 mmol) was added to the reaction mixture and stirred for 12 h (reaction completion was confirmed by TLC). The reaction mixture was quenched with ice water (50 mL) and stirred for 15 minutes. The precipitated solids were filtered and dried to get the crude product as light brown solid (12 g, 95% yield). The crude product was directly taken for next step without further purification.

Step 4: 4-(5-Methyl-imidazo[5,1-b][1,2,4]oxadiazol-2-yl)-benzoic Acid Methyl Ester 4-[N'-(2-Acetylamino-acetyl)-hydrazinocarbonyl]-benzoic acid methyl ester (12.0 g, 40 mmol) was dissolved in CH$_3$CN (120 mL) at 25-26° C. under nitrogen atmosphere. POCl$_3$ (60 mL) was added slowly over 10 minutes and the reaction mixture heated at 110° C. for 12 h (reaction completion was confirmed by TLC). The reaction mixture was cooled to 25-26° C. and concentrated to get a brown liquid residue (20 g). The residue was quenched with ice water (50 mL) and basified with solid K$_2$CO$_3$ and desired compound extracted with CH$_2$Cl$_2$ (100 mL×2). The CH$_2$Cl$_2$ layer was washed with water (100 mL), brine solution (50 mL), dried over Na$_2$SO$_4$ and concentrated to get the crude product as brown solid. The crude product was purified by column chromatography (60-120 mesh silica gel; eluent: 40% EtOAc in pet ether) to get the product as yellow solid (3.1 g, 30% yield). $^1$H NMR (DMSO-d$_6$, 400 MHz) δ 8.15 (s, 4H), 6.53 (s, 1H), 3.89 (s, 3H), 2.44 (s, 3H). LC/MS (Method A): 258.0 (M+H)$^+$. HPLC (Method F) Rt 2.35 min (Purity: 97.2%).

Intermediate 7: 3-Methoxy-4-(5-methyl-imidazo[5,1-b][1,2,4]oxadiazol-2-yl)-benzoic Acid Methyl Ester

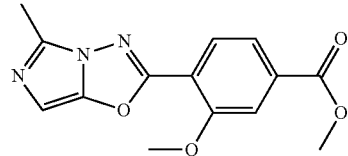 [SMILES: COC(=O)c1ccc(-c2nn3c(C)ncc3o2)c(OC)c1]

Step 1: 4-Bromo-2-methoxy-benzoic Acid Hydrazide

4-Bromo-2-methoxybenzoic acid (30 g, 122.4 mmol) was taken in MeOH (300 mL). To this solution, hydrazine hydrate (20.6 mL, 428 mmol) was added and heated 3 h at 60° C. The reaction mixture was cooled to RT and solvents removed under reduced pressure. The crude reaction mixture was quenched with water, stirred for 10 min and filtered off to afford the title compound as an off white solid (28 g, 94% yield). $^1$H NMR (DMSO-d$_6$, 400 MHz): δ 9.22 (bs, 1H), 7.57-7.55 (d, J=8.2 Hz, 1H), 7.30-7.30 (d, J=1.7 Hz, 1H), 7.22-7.19 (m, 1H), 4.52-4.51 (d, 2H), 3.86 (s, 3H).

Step 2: N-{2-[N'-(4-Bromo-2-methoxy-benzoyl)-hydrazino]-2-oxo-ethyl}-acetamide 4-Bromo-2-methoxy-benzoic acid hydrazide (28 g, 114.2 mmol), N-acetyl glycine (13.3 g, 114.2 mmol) and triethylamine (31.6 mL, 284 mmol) were introduced in a THF solution (300 mL) at 0° C. To this ice cooled solution, T3P (79.8 g, 50% in EtOAc, 125.6 mmol) was added in drops and the reaction mixture heated at 80° C. for 12 h. Upon completion, the reaction mixture was cooled down to room temperature and the solvent removed under vacuum. The crude material was quenched with ice and neutralized with sodium bicarbonate solution. The resulting mixture was stirred for 20 minutes and filtered to afford the title compound as an off white solid (32 g, 82% yield). $^1$H NMR (DMSO-d$_6$, 400 MHz): δ 10.18 (bs, 1H), 9.91 (bs, 1H), 8.17-8.14 (t, J=5.8 Hz, 1H), 7.59-7.57 (d, J=8.2 Hz, 1H), 7.36-7.35 (d, J=1.7 Hz, 1H), 7.26-7.24 (m, 1H), 3.88 (s, 3H), 3.79-3.77 (d, 2H), 1.85 (s, 3H).

Step 3: 2-(4-Bromo-2-methoxy-phenyl)-5-methyl-imidazo[5,1-b][1,2,4]oxadiazole A suspension of N-{2-[N'-(4-bromo-2-methoxy-benzoyl)-hydrazino]-2-oxo-ethyl}-acetamide (21 g, 612 mmol) and phosphorous oxychloride (27.9 mL, 306 mmol) was heated 12 hours at 80° C. in MeCN (200 mL). When the reaction was finished, it was cooled to RT and the organic solvent removed under vacuum. The residual liquid was quenched with ice and neutralized with a saturated potassium carbonate solution to pH 9 and filtered to afford the title compound as pale brown solid (16 g, 85.1% yield). $^1$H NMR (DMSO-d$_6$, 400 MHz): δ 7.82-7.80 (d, J=8.3 Hz, 1H), 7.53-7.52 (d, J=1.7 Hz, 1H), 7.37-7.35 (m, 1H) 6.48 (s, 1H), 3.95 (s, 3H) 2.42 (s, 3H).

Step 4: 3-Methoxy-4-(5-methyl-imidazo[5,1-b][1,2,4]oxadiazol-2-yl)-benzoic Acid Methyl Ester To a solution of 2-(4-bromo-2-methoxy-phenyl)-5-methyl-imidazo[5,1-b][1,2,4]oxadiazole (13 g, 0.042 mol) in MeOH (130 mL) was added triethylamine (14.6 mL, 0.1055 mol) and degassed with carbon monoxide. To this degassed mixture 1,1-Bis diphenyl phosphine ferrocene palladium (II) chloride 1:1 complex with DCM (3.44 g, 4.22 mmol) was added and heated to 60° C. for 18 h. The mixture was cooled to RT and passed through a celite bed to remove the catalyst. The solvent was removed under reduced pressure. Crude material was purified by trituration in MeOH (35 mL). The solvent was removed by filtration and product was dried under suction to afford the title compound as an off white solid (5.3 g, 43.72% yield). $^1$H NMR (DMSO-d$_6$, 400 MHz): δ 8.06-8.04 (t, J=0.9 Hz, 1H), 7.72-7.69 (t, J=7.5 Hz, 2H) 6.50 (s, 1H), 4.00 (s, 3H), 3.90 (s, 3H), 2.50-2.48 (s, 3H). LC/MS (Method A): 288 (M+H)$^+$. HPLC (Method F) Rt 2.4 min (Purity: 98.7%).

Intermediate 8: 4-(5-Ethyl-imidazo[5,1-b][1,2,4]oxadiazol-2-yl)-benzoic Acid Methyl Ester

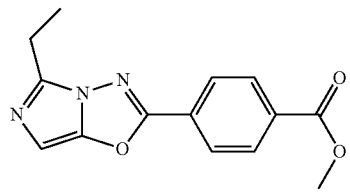 [SMILES: CCc1ncc2oc(-c3ccc(C(=O)OC)cc3)nn12]

Step 1: 4-Bromobenzoic Acid Methyl Ester

To an ice cold solution of 4-bromo benzoic acid (50 g, 248.0 mmol) in a dry mixture of DCM and MeOH (1:1, 500 mL), was added thionyl chloride (55 mL, 746.0 mmol) in drops. The reaction mixture was stirred at 0° C. for 30 min and then heated to 60° C. for 5 h. After cooling the reaction mixture to RT, the solvent was removed under reduced pressure. The residue was quenched with ice and neutralised with solid sodium bicarbonate. The product was extracted with EtOAc (3×250 mL). The combined organic layers were washed with water, brine solution and dried over sodium sulphate. The solvent was removed under vacuum to afford the title compound as an off white solid (45 g, 84% yield). $^1$H NMR (400 MHz, DMSO-d$_6$) δ 7.88-7.88 (dd, J=2.0, 2.0 Hz, 2H), 7.75-7.72 (m, 2H), 3.84 (s, 3H).

Step 2: 4-Bromo-Benzoic Acid Hydrazide

To a stirred solution of methyl 4-bromobenzoic acid methyl ester (45 g, 209.0 mmol) in MeOH (500 mL), hydrazine hydrate (39.31 g, 627.0 mmol) was added at RT and heated to 65° C. for 12 h. After cooling the reaction mixture to RT, the solvent was removed under reduced pressure. The residue was slurred with diethyl ether (300 mL). The solid was filtered off and dried under suction to afford the title compound as an off white solid (40 g, 93% yield). $^1$H NMR (400 MHz, DMSO-d$_6$) δ 9.84 (s, 1H), 7.76-7.73 (m, 2H), 7.66-7.64 (m, 2H), 4.49 (s, 2H).

Step 3: Propionylamino-Acetic Acid Tert-Butyl Ester

To an ice cold suspension of glycine tert-butyl ester hydrochloride (50 g, 298.0 mmol) in dry MeCN (500 mL) was added potassium carbonate (82.33 g, 596.6 mmol) in portions. The mixture was stirred at the same temperature for 30 min. To this mixture, propionyl chloride (41.55 g, 449.0 mmol) was added in drops and continued stirring at the same temperature for 30 min. The reaction mixture was heated to 65° C. for 12 h and then cooled to RT to be filtered off. The filtrate was removed under reduced pressure to afford the title compound as a colorless liquid (25 g). The crude product was taken as such for the next step without purification. $^1$H NMR (400 MHz, DMSO-d$_6$) δ 8.09-8.06 (t, J=5.6 Hz, 1H), 3.69-3.66 (t, 2H), 2.14-2.06 (m, 2H), 1.3 (s, 9H) 1.0-0.96 (t, 3H).

Step 4: Propionylamino-Acetic Acid

To a stirred solution of propionylamino-acetic acid tert-butyl ester (25 g, 133.0 mmol) in DCM (250 mL) was added HCl in dioxane (3M, 100 mL). It was stirred at 25° C. for 12 h. When the reaction was completed, the solvent was removed under reduced pressure to afford the title compound as an off white solid (21 g, 94% yield). The solid was carried out for next step without any purification. $^1$H NMR (400 MHz, DMSO-d$_6$) δ 8.20-8.19 (t, J=4.8 Hz, 1H), 8.08-8.06 (d, J=5.1 Hz) 3.80-3.76 (m, 2H), 2.14-2.08 (m, 2H), 1.21-1.15 (t, 3H).

Step 5: N-{2-[N'-(4-Bromo-benzoyl)-hydrazino]-2-oxo-ethyl}-propionamide

A mixture of 4-bromo-benzoic acid hydrazide (12.8 g, 59.0 mmol), propionylamino-acetic acid (10 g, 59.0 mmol) and triethylamine (20.8 mL, 149.0 mmol) in THF (150 mL) was cooled at 0° C. To this reaction mixture, T3P (41.8 mL, 50% w/w in EtOAc, 432.0 mmol) was added drop-wise and heated to 70° C. for 12 h. When the reaction was completed, the reaction mixture was cooled to RT. The solvent was removed under vacuum. The residue was quenched with ice and neutralized with solid sodium bicarbonate and extracted with EtOAc (3×100 mL). The combined organic layers were washed with water, brine solution and dried over sodium sulphate. The solvent was removed under vacuum. The residue was purified by stirring with Et$_2$O (50 mL), filtered and dried under suction to afford the title compound as an off white solid (6 g, 30% yield). $^1$H NMR (400 MHz, DMSO-d$_6$) δ 10.04 (s, 1H), 9.97 (s, 1H), 8.12-8.09 (t, J=5.9 Hz, 1H), 7.76-7.73 (m, 2H), 7.66-7.64 (m, 2H), 3.80-3.78 (d, 2H), 2.17-2.11 (t, 2H), 1.01-0.97 (t, 3H).

Step 6: 2-(4-Bromo-phenyl)-5-ethyl-imidazo[5,1-b][1,2,4]oxadiazole

To a suspension of N-{2-[N'-(4-Bromo-benzoyl)-hydrazino]-2-oxo-ethyl}-propionamide (10 g, 30.0 mmol) in MeCN (250 mL), phosphorous oxychloride (14.7 mL, 152.0 mmol) was added in drops at RT. This mixture was heated to 90° C. for 12 h. After cooling, the reaction mixture was allowed to RT and the solvent removed under reduced pressure. The residue was quenched with ice, neutralized with solid potassium carbonate and the expected compound extracted with EtOAc (3×100 mL). The combined organic layers were washed with water, brine and dried over $Na_2SO_4$ and concentrated under vacuum to get the crude material. The crude material was purified by column chromatography using silica gel (60-120 mesh) and $CHCl_3$/MeOH as eluent to afford the title compound as an off white solid (3.2 g, 35% yield). $^1$H NMR (400 MHz, DMSO-$d_6$) δ 7.97-7.95 (dd, J=6.6, 1.9 Hz, 2H), 7.84-7.82 (dd, J=6.7, 2.0 Hz, 2H), 6.52 (s, 1H), 2.79 (m, 2H), 1.30-1.24 (t, 3H).

Step 7: 4-(5-Ethyl-imidazo[5,1-b][1,2,4]oxadiazol-2-yl)-benzoic Acid Methyl Ester A solution made of 2-(4-bromo-phenyl)-5-ethyl-imidazo[5,1-b][1,2,4]oxadiazole (3.1 g, 10.6 mmol) and triethylamine (3.7 mL, 26.0 mmol) in MeOH (50 mL) was degassed with carbon monoxide. To this reaction mixture, 1,1-Bis diphenyl phosphino ferrocene palladium(II)chloride (1:1 complex with DCM (0.9 g, 1.0 mmol)) was added and heated to 60° C. for 18 h. After cooling to RT, the reaction mixture was filtered through a celite pad. The filtrate was evaporated under reduced pressure and the residue purified with Et2O (50 mL). The solid was filtered and dried under suction to afford the title compound (1.8 g, 64% yield) as an off white solid. $^1$H NMR (400 MHz, DMSO-$d_6$) δ 8.19-8.14 (m, 4H), 6.54 (s, 1H), 3.90 (s, 3H), 2.86-2.80 (m, 2H) 1.39-1.27 (t, 3H). LC/MS (Method A): 272.0 (M+H)$^+$. HPLC (Method F) Rt 2.6 min (Purity: 98.4%).

Intermediate 9: 4-(5,7-Dimethyl-imidazo[5,1-b][1,2,4]oxadiazol-2-yl)-benzoic Acid Methyl Ester

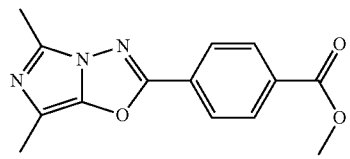 [SMILES: COC(=O)c1ccc(-c2nn3c(C)nc(C)c3o2)cc1]

Step 1: 4-Hydrazinocarbonyl-Benzoic Acid Methyl Ester

Dimethyl terephthalate (19 g, 97 mmol) was taken in EtOH (200 mL) at 25-26° C. under nitrogen atmosphere. Hydrazine hydrate (5.39 g, 107 mmol) was added to the reaction mixture and stirred for 12 h at 90° C. (reaction completion was confirmed by TLC). The reaction mixture was cooled to 25-26° C. and concentrated to get crude product as white solid (20 g, 100% yield). The crude product was taken directly for next step without further purification. $^1$H NMR (DMSO-$d_6$, 400 MHz) δ 9.96 (s, 1H), 8.01-7.99 (m, 2H), 7.93-7.91 (m, 2H), 4.58 (b, 2H), 3.86 (s, 3H). LC/MS (Method A): 195.3 (M+H)$^+$. HPLC (Method F) Rt 0.354 min (Purity: 70.3%)

Step 2: 4-[N'-(2-Acetylamino-propionyl)-hydrazinocarbonyl]-benzoic Acid Methyl Ester 4-Hydrazinocarbonyl-benzoic acid methyl ester (13 g, 66 mmol) was taken in DCM (100 mL) at 25-26° C. under nitrogen atmosphere. EDC-HCl (14.05 g, 73 mmol), HOBT (9.9 g, 73 mmol) and triethylamine (20.2 g, 0.2 mol) were added and stirred for 15 minutes. N-acetyl alanine (9.60 g, 73 mmol) was added to the reaction mixture and stirred for 12 h (reaction completion was confirmed by TLC). The reaction mixture was quenched with ice water (50 mL) and stirred for 15 minutes. The precipitated solids were filtered and dried to get the crude product as light brown solid. The crude product was directly taken for the next step without further purification (12.3 g, 90% yield).

Step 3: 4-(5,7-Dimethyl-imidazo[5,1-b][1,2,4]oxadiazol-2-yl)-benzoic Acid Methyl Ester 4-[N'-(2-Acetylamino-propionyl)-hydrazinocarbonyl]-benzoic acid methyl ester (12.0 g, 40 mmol) was dissolved in MeCN (120 mL) at 25-26° C. under nitrogen atmosphere. $POCl_3$ (60 mL) was added slowly over 10 minutes and the reaction mixture was heated to 110° C. for 12 h (reaction completion was confirmed by TLC). The reaction mixture was cooled to 25-26° C. and concentrated to get the brown liquid residue (20 g). The residue was quenched with ice water (50 mL) and basified with solid potassium carbonate and extracted with DCM (100 mL×2). The DCM layer was washed with water (100 mL), brine solution (50 mL), dried over sodium sulphate and concentrated to get crude product as brown solid. The crude product was purified by column chromatography using 60-120 mesh silica gel and 40% EtOAc in pet ether as eluent to get the product as a yellow solid (3.1 g, 30% yield). $^1$H NMR (DMSO-$d_6$, 400 MHz) δ 8.12 (s, 4H), 3.88 (s, 3H), 2.38 (s, 3H), 2.17 (s, 3H). LC/MS (Method B): 272.0 (M+H)$^+$. HPLC (Method F) Rt 2.61 min (Purity: 98.8%).

Intermediate 10: 2-(4-Bromo-phenyl)-5-methyl-imidazo[5,1-b][1,2,4]oxadiazole

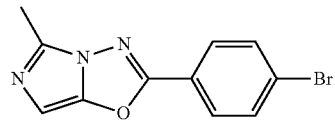 [SMILES: Cc1ncc2oc(-c3ccc(Br)cc3)nn12]

Step 1: 4-Bromobenzoic Acid Methyl Ester

4-Bromo benzoic acid (200 g, 994 mmol) was taken in $CH_3OH$ (3 L) at 25-26° C. under nitrogen atmosphere. $SOCl_2$ (591.5 g, 4.97 mol) was added slowly over a period of 30 minutes. The reaction mixture was heated to 80° C. and stirred for 12 h (reaction completion was confirmed by LC/MS). The reaction mixture was cooled to 25-26° C. and concentrated to get the crude product as white solid (250 g). The crude product was taken in 10% $NaHCO_3$ solution (1 L) and stirred for 10 minutes, the precipitated solids were filtered, washed with water (700 mL) and dried to get the pure product as white solid (194 g, 91% yield). $^1$H NMR (DMSO-$d_6$, 400 MHz) δ 7.88-7.84 (m, 2H,), 7.74-7.70 (m, 2H), 3.84 (s, 3H). HPLC (Method F) Rt 4.4 min (Purity: 99.1%).

Step 2: 4-Bromo-Benzoic Acid Hydrazide

4-Bromobenzoic acid methyl ester (200 g, 0.93 mol) was taken in EtOH (2.5 L) at 25-26° C. under nitrogen atmosphere. Hydrazine hydrate (232 g, 4.65 mol) was added to the reaction mixture and stirred for 12 h at 90° C. (reaction completion was confirmed by TLC). The reaction mixture was cooled to 25-26° C. and concentrated to get crude product as white solid (176 g, 88% yield). The crude product was taken as such for the next step without further purification. $^1$H NMR (DMSO-d$_6$, 400 MHz) δ 9.84 (s, 1H), 7.76-7.73 (m, 2H), 7.66-7.63 (m, 2H), 4.42 (b, 2H). LC/MS (Method A): 217.0 (M+H)$^+$. HPLC (Method F) Rt 2.02 min (Purity: 99.6%).

Step 3: N-{2-[N'-(4-Bromo-benzoyl)-hydrazino]-2-oxo-ethyl}-acetamide

4-Bromo-benzoic acid hydrazide (175 g, 0.81 mol) was taken in DCM (3 L) at 25-26° C. under nitrogen atmosphere. EDC-HCl (171 g, 0.89 mol), HOBt (120 g, 0.89 mol) and triethylamine (287 g, 2.83 mol) were added and stirred for 15 minutes. N-Acetyl glycine (104.27 g, 0.89 mol) was added to the reaction mixture and stirred for 12 h (reaction completion was confirmed by TLC). The reaction mixture was quenched to ice water (1 L) and stirred for 15 minutes. The precipitated solids were filtered and dried to get the product as off-white solid (150 g, 59% yield). $^1$H NMR (DMSO-d$_6$, 400 MHz) δ 10.43 (s, 1H) 9.98 (s, 1H), 8.22-8.19 (m, 1H), 7.80-7.78 (m, 2H), 7.72-7.69 (m, 2H), 3.79 (b, 2H) 1.85 (s, 3H). LC/MS (Method A): 316.0 (M+H)+. HPLC (Method F) Rt 2.09 min (Purity: 99.7%).

Step 4: 2-(4-Bromo-phenyl)-5-methyl-imidazo[5,1-b][1,2,4]oxadiazole

N-{2-[N'-(4-Bromo-benzoyl)-hydrazino]-2-oxo-ethyl}-acetamide (100 g, 0.317 mol) was dissolved in MeCN (1 L) at 25-26° C. under nitrogen atmosphere. POCl$_3$ (408 mL) was added slowly over 10 minutes and the reaction mixture was heated to 110° C. and stirred for 12 h (reaction completion was confirmed by TLC). The reaction mixture was cooled to 25-26° C. and concentrated to get the brown liquid residue (107 g). The residue was quenched to ice water (750 mL) and basified with solid potassium carbonate and extracted with DCM (1 L×2). The DCM layer was washed with water (1 L), brine solution (500 mL), dried over Na$_2$SO$_4$ and concentrated to get the crude product as brown solid. The crude product was purified by column chromatography (60-120 mesh silica gel; eluent: 40% EtOAc/pet ether) to get the product as yellow solid (47 g, 53% yield). $^1$H NMR (DMSO-d$_6$, 400 MHz) δ 7.96-7.93 (m, 2H), 7.84-7.81 (m, 2H), 6.51 (s, 1H), 2.43 (s, 3H). LC/MS (Method A): 280.0 (M+H)+. HPLC (Method F) Rt 2.77 min (Purity: 99.6%).

Intermediate 11: 5-Methylimidazo[5,1-b][1,3,4]thiadiazole-2-carboxylic Acid Ethyl Ester

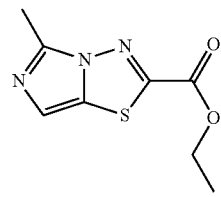

Step 1: Hydrazino Carbonylmethyl-Carbamic Acid Tert-Butyl Ester

N-(tert-butoxycarbonyl)glycine methyl ester (78.12 mL, 529 mmol) was dissolved in MeOH (200 mL) at 25° C. where upon a solution of hydrazine hydrate 100% (77.1 mL, 1586 mmol) was added to the solution. The reaction mixture was heated to 80° C. and stirred for 1 hour at this temperature (completion of the reaction was monitored by TLC). The reaction mixture was cooled down to RT and MeOH was concentrated under vacuum to yield a residue that was re-dissolved in DCM (700 mL). The organic phase was washed with water (500 mL) and a saturated NaCl solution. The expected compound was extracted with DCM (5×400 mL). Combined organics were dried with MgSO$_4$ to yield after evaporation a white solid (76 g, 76% yield). $^1$H NMR (DMSO-d$_6$, 300 MHz) δ 8.95 (s, 1H), 6.93 (t, J=6.0 Hz, 1H), 4.18 (s, 2H), 3.47 (d, J=6.2 Hz, 2H), 1.38 (s, 9H). LC/MS (Method A): 216.0 (M+H)$^+$. HPLC (Method F) Rt 1.02 min (Purity: 99.5%).

Step 2: 5-(Tert-Butoxycarbonylamino-methyl)-[1,3,4]thiadiazole-2-carboxylic Acid Ethyl Ester A suspension of hydrazino carbonylmethyl-carbamic acid tert-butyl ester (30 g, 158.6 mmol) and sodium bicarbonate (14 g, 166.5 mmol) in THF (300 mL) under inert atmosphere was cooled down to 0° C. and treated drop-wise with a solution of ethyl oxalyl chloride (18.63 mL, 166.5 mmol) in THF (60 mL) over a period of 60 minutes keeping temperature below 60° C. The reaction mixture was stirred at 0° C. for 2 hours and slowly warmed and stirred overnight at 25° C. (reaction completion was confirmed by TLC). The suspension was filtered and Lawesson's reagent (64.14 g, 159 mmol) was added to the filtrate. The resulting solution was heated at 50° C. for 4 hours until completion of the reaction. The reaction was cooled down to RT, concentrated under vacuum and filtered over alumina (fast plug) eluting with EtOAc (100%) to give a yellow solid that was used directly without further purification (29.6 g, 65% yield). $^1$H NMR (300 MHz, DMSO-d$_6$) δ 7.94 (t, J=6.0 Hz, 1H), 4.57 (d, J=6.0 Hz, 2H), 4.41 (q, J=7.1 Hz, 2H), 1.41 (s, 9H), 1.34 (t, J=7.1 Hz, 3H). LC/MS (Method A): 288.2 (M+H)$^+$.

Step 3: 5-[(acetylamino)methyl]-1,3,4-thiadiazole-2-carboxylic Acid Ethyl Ester Under nitrogen atmosphere, 5-(tert-butoxycarbonylamino-methyl)-[1,3,4]thiadiazole-2-carboxylic acid ethyl ester (29.50 g, 102.7 mmol) was taken up in AcOH (885 mL). It was heated 24 hours at 115° C. until completion of the reaction (monitored of the reaction by LC/MS). The reaction mixture was cooled to room temperature and stirred for two days. It was concentrated under vacuum and the expected compound precipitated by addition of MeCN (250 mL). After triturating at 25° C., a fine suspension was obtained and was isolated by filtration, affording the title compound as a beige solid (23.8 g, 100% yield). $^1$H NMR (300 MHz, DMSO-d$_6$) δ 8.91 (t, J=5.8 Hz, 1H), 4.67 (d, J=6.8 Hz, 2H), 4.43 (q, J=7.1 Hz, 2H), 1.88 (s, 3H), 1.32 (t, 3H).). LC/MS (Method A): 230.2 (M+H)$^+$.

Step 4: 5-methylimidazo[5,1-b][1,3,4]thiadiazole-2-carboxylic Acid Ethyl Ester 5-[(acetylamino)methyl]-1,3,4-thiadiazole-2-carboxylic acid ethyl ester (23.2 g, 101.2 mmol) was taken up in a mixture of MeCN (232 mL) and phosphorous oxychloride (27.87 mL, 303.6 mmol). The reaction mixture was heated at 80° C. for 4 hours until completion of the reaction. It was cooled to room temperature and concentrated under vacuum. The resulting residue was taken in EtOAc (300 mL) and NaHCO₃ sat added slowly until pH 8-9 (500 mL). The phases were separated. The aqueous phase was extracted with EtOAc (3×250 mL) and the combined organics washed with brine (300 mL), dried over MgSO₄, filtered and concentrated under vacuum to yield a yellow solid (20.56 g, 96% yield). ¹H NMR (300 MHz, DMSO-d₆) δ 7.05 (s, 1H), 4.45 (q, J=7.1 Hz, 2H), 2.61 (s, 3H), 1.36 (t, J=7.1 Hz, 3H). LC/MS (Method A): 212 (M+H)⁺. HPLC (Method F) Rt 1.32 min (Purity: 97.9%).

Intermediate 12: 5-Methylimidazo[5,1-b][1,3,4]thiadiazole-2-carboxylic Acid

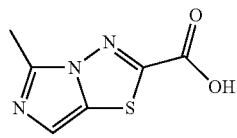

Intermediate 11 (20.5 g, 97.04 mmol) was saponified 30 minutes at room temperature in a mixture of THF (410 mL) and NaOH (194 mL, C=1.00 M, 194.1 mmol). When the reaction was completed (the reaction was monitored by LC/MS), it was concentrated under vacuum and water (150 mL) was added to the reaction mass. The aqueous phase was washed with EtOAc (100 mL) and then acidified to pH 1 (HCl 1N, 250 mL) to afford a beige solid that was filtered off as HCl salt. It was dried under vacuum to yield the title compound as off-white solid (15.3 g, 72% yield). ¹H NMR (300 MHz, DMSO-d₆) δ 12.45 (br s, 1H), 7.62 (s, 1H), 2.30 (s, 3H).

Intermediate 13: 3-methoxy-4-(5-methyl-imidazo[5,1-b][1,3,4]thiadiazol-2-yl)-phenylamine

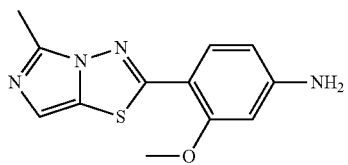 [SMILES: COc1cc(N)ccc1-c1nn2c(C)ncc2s1]

Step 1: tert-butyl 2-hydrazinyl-2-oxoethylcarbamate

To a solution of N-(tert-butoxycarbonyl)-glycine methyl ester (21 g, 110 mmol) in MeOH (100 mL), was added aqueous hydrazine hydrate (35% aqueous solution, 16 mL, 184 mmol) in one portion. After 48 hours at 25° C. the reaction was concentrated under reduced pressure. The residual solvent was evaporated with dioxane and MeOH, and dried under vacuum at 40° C. for 16 hours to afford the title compound as a white crystalline solid (21 g, 100% yield). ¹H NMR (400 MHz, DMSO-d⁶): δ 8.94 (s, 1H); 6.91 (t, J=6.17 Hz, 1H); 4.18 (s, 2H); 3.48 (d, J=6.15 Hz, 2H); 1.38 (s, 9H).

Step 2: 2-methoxy-4-nitrobenzoyl Chloride

To a stirred suspension of benzoic acid (5 g, 25 mmol) in DCM (30 mL) was added DMF (5 drops) followed by oxalyl chloride (2.3 mL, 26.6 mmol). After 18 hours stirring at 25° C. the reaction was concentrated under reduced pressure and used immediately (25 mmol 100% yield).

Step 3: tert-butyl 2-(2-(2-methoxy-4-nitrobenzoyl)hydrazinyl)-2-oxoethylcarbamate To a stirred suspension of tert-butyl 2-hydrazinyl-2-oxoethylcarbamate (4.72 g, 25 mmol) and sodium hydrogen carbonate (2.1 g, 25 mmol) in THF (40 mL) at 0° C. was added a solution of 2-methoxy-4-nitrobenzoyl chloride (25 mmol) in THF (10 mL) slowly and the reaction was allowed to warm to 25° C. After 4 hours, saturated aqueous sodium carbonate solution (50 mL) was added and the product was extracted with ethyl acetate (100 mL) and MeOH (20 mL). The combined organic layers were washed with brine (50 mL) and concentrated under reduced pressure to afford the title compound as a pale yellow crystalline solid (8.7 g, 92% yield). ¹H NMR (400 MHz, DMSO-d⁶): δ 10.22 (s, 2H); 7.93-7.87 (m, 2H); 7.81-7.72 (m, 1H); 7.05 (t, J=6.18 Hz, 1H); 3.97 (s, 3H); 3.70-3.59 (m, 2H); 1.40 (s, 9H).

Step 4: tert-butyl (5-(2-methoxy-4-nitrophenyl)-1,3,4-thiadiazol-2-yl)methylcarbamate To a stirred slurry of Lawesson's reagent (1.09 g, 2.7 mmol) in dry THF (12 mL) was added tert-butyl 2-(2-(2-methoxy-4-nitrobenzoyl)hydrazinyl)-2-oxoethylcarbamate (1 g, 2.7 mmol) under nitrogen. The reaction was sealed and heated at 60° C. for 18 hours. The mixture was then cooled and concentrated under reduced pressure. The resulting crude residue was purified by chromatography (silica gel, isohexane/ethyl acetate) to afford the title compound as a yellow solid (600 mg, 59% yield). ¹H NMR (400 MHz, CHCl₃-d): δ 8.67 (d, J=8.67 Hz, 1H); 7.99 (dd, J=8.68, 2.14 Hz, 1H); 7.91 (d, J=2.13 Hz, 1H); 5.31 (s, 1H); 4.80 (d, J=6.28 Hz, 2H); 4.13 (s, 3H); 1.49 (s, 9H).

Step 5: N-((5-(2-methoxy-4-nitrophenyl)-1,3,4-thiadiazol-2-yl)methyl)acetamide

A solution of tert-butyl (5-(2-methoxy-4-nitrophenyl)-1,3,4-thiadiazol-2-yl)methylcarbamate (600 mg, 1.6 mmol) in acetic acid (10 mL) was stirred in a sealed tube at 100° C. for 2 days. The reaction mixture was allowed to cool to 25° C. then concentrated under reduced pressure to afford the title compound as a brown solid (465 mg, 93% yield). ¹H NMR (400 MHz, DMSO-d⁶): δ 8.84 (t, J=5.95 Hz, 1H); 8.56 (d, J=8.65 Hz, 1H); 8.06-7.99 (m, 2H); 4.71 (d, J=5.92 Hz, 2H); 4.16 (s, 3H); 1.91 (s, 3H).

Step 6: 2-(2-methoxy-4-nitrophenyl)-5-methylimidazo[5,1-b][1,3,4]thiadiazole

To a stirred suspension of N-((5-(2-methoxy-4-nitrophenyl)-1,3,4-thiadiazol-2-yl)methyl)acetamide (465 mg, 1.5 mmol) in acetonitrile (10 mL) was added phosphorus oxychloride (1.07 mL, 1.76 g, 11.5 mmol) and the reaction was heated at 60° C. for 18 hours. The reaction mixture was allowed to cool to 25° C. then concentrated under reduced pressure and used without further purification (437 mg, 100% yield).

Step 7: 3-methoxy-4-(5-methyl-imidazo[5,1-b][1,3,4]thiadiazol-2-yl)-phenylamine

A slurry of nitrophenyl imidazothiadiazole (1.5 mmol) with iron powder (543 mg, 10.2 mmol) and ammonium chloride (164 mg 3.1 mmol) in THF (10 mL)/EtOH (10 mL)/water (3 mL) was prepared. This reaction was sealed under nitrogen and rapidly heated to 90° C. for 1 hour. The reaction was allowed to cool to 25° C. then filtered through a celite pad and washed with THF containing 5% MeOH. The organic phase was washed with dilute aqueous $Na_2CO_3$ solution, brine, dried ($MgSO_4$) and concentrated under reduced pressure to afford the title compound as a pale yellow powder (370 mg, 95% yield). $^1$H NMR (400 MHz, DMSO-$d^6$): δ 7.88 (d, J=9.07 Hz, 1H); 6.86 (s, 1H); 6.39-6.34 (m, 2H); 6.16 (s, 2H); 3.94 (s, 3H); 2.59 (s, 3H).

Intermediate 14: 4-(5-Methyl-imidazo[5,1-b][1,3,4]thiadiazol-2-yl)-benzoic Acid Methyl Ester

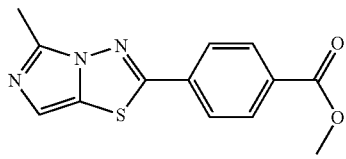 [SMILES: COC(=O)c1ccc(-c2nn3c(C)ncc3s2)cc1]

Step 1: 4-[N'-(2-tert-Butoxycarbonylamino-acetyl)-hydrazinocarbonyl]-benzoic Acid Methyl Ester 4-[N'-(2-tert-Butoxycarbonylamino-acetyl)-hydrazinocarbonyl]-benzoic acid methyl ester was prepared following the same protocol as for Intermediate 13, Steps 1 to 3, using 4-(chlorocarbonyl)benzoic acid methyl ester. $^1$H NMR (400 MHz, DMSO-$d^6$): δ 10.56 (s, 1H); 10.01 (s, 1H); 8.07 (d, J=8.14 Hz, 2H); 7.99 (d, J=8.17 Hz, 2H); 7.06 (t, J=6.16 Hz, 1H); 3.90 (s, 3H); 3.67 (d, J=6.23 Hz, 2H); 1.40 (s, 9H).

Step 2: 4-[5-(tert-Butoxycarbonylamino-methyl)-[1,3,4]thiadiazol-2-yl]-benzoic Acid Methyl Ester 4-[5-(tert-Butoxycarbonylamino-methyl)-[1,3,4]thiadiazol-2-yl]-benzoic acid methyl ester was prepared following the same protocol as for Intermediate 13, Step 4, using 4-[N'-(2-tert-Butoxycarbonylamino-acetyl)-hydrazinocarbonyl]-benzoic acid methyl ester. $^1$H NMR (400 MHz, CHCl$_3$-d): δ 8.16-8.12 (m, 2H); 8.05-8.01 (m, 2H); 5.30 (s, 1H); 4.76 (d, J=6.31 Hz, 2H); 3.96 (s, 3H); 1.49 (s, 9H).

Step 3: 4-[5-(Acetylamino-methyl)-[1,3,4]thiadiazol-2-yl]-benzoic Acid Methyl Ester 4-[5-(Acetylamino-methyl)-[1,3,4]thiadiazol-2-yl]-benzoic acid methyl ester was prepared following the same protocol as for intermediate 13, Step 5, using 4-[5-(tert-butoxycarbonylamino-methyl)-[1,3,4]thiadiazol-2-yl]-benzoic acid methyl ester. $^1$H NMR (400 MHz, DMSO-$d^6$): δ 8.88 (t, J=5.92 Hz, 1H); 8.14-8.08 (m, 4H); 4.69 (d, J=5.92 Hz, 2H); 3.90 (s, 3H); 1.92 (s, 3H).

Step 4: 4-(5-Methylimidazo[5,1-b][1,3,4]thiadiazol-2-yl)benzoic Acid Methyl Ester 4-(5-Methylimidazo[5,1-b][1,3,4]thiadiazol-2-yl)benzoic acid methyl ester was prepared following the same protocol as for intermediate 13, Step 6, using 4-[5-(acetylamino-methyl)-[1,3,4]thiadiazol-2-yl]-benzoic acid methyl ester. The crude product was purified by chromatography (silica, isohexane/ethyl acetate) to afford the title compound as a yellow solid (450 mg, 95% yield). $^1$H NMR (400 MHz, DMSO-$d^6$): δ 8.15 (d, J=8.28 Hz, 2H); 8.09 (d, J=8.28 Hz, 2H); 7.00 (s, 1H); 3.91 (s, 3H); 2.62 (s, 3H).

Intermediate 15: 4-(5-Methyl-imidazo[5,1-b][1,3,4]thiadiazol-2-yl)-phenylamine

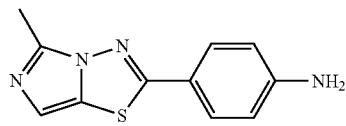 [SMILES: Cc1ncc2sc(-c3ccc(N)cc3)nn12]

Step 1: {2-[N'-(4-Nitro-benzoyl)-hydrazino]-2-oxo-ethyl}-carbamic Acid Tert-Butyl Ester {2-[N'-(4-Nitro-benzoyl)-hydrazino]-2-oxo-ethyl}-carbamic acid tert-butyl ester was prepared following the same protocol as for intermediate 13, Steps 1 to 3, using 4-nitrobenzoyl chloride. $^1$H NMR (400 MHz, DMSO-$d^6$): δ 10.74 (s, 1H); 10.10 (s, 1H); 8.34 (d, J=8.63 Hz, 2H); 8.14-8.06 (m, 2H); 7.10 (t, J=6.16 Hz, 1H); 3.67 (d, J=6.21 Hz, 2H); 1.40 (s, 9H).

Step 2: [5-(4-Nitro-phenyl)-[1,3,4]thiadiazol-2-ylmethyl]-carbamic acid tert-butyl ester

[5-(4-Nitro-phenyl)-[1,3,4]thiadiazol-2-ylmethyl]-carbamic acid tert-butyl ester was prepared following the same protocol as for intermediate 13, Step 4, using {2-[N'-(4-Nitro-benzoyl)-hydrazino]-2-oxo-ethyl}-carbamic acid tert-butyl ester. $^1$H NMR (400 MHz, CHCl$_3$-d): δ 8.38-8.30 (m, 2H); 8.16-8.12 (m, 2H); 5.40 (s, 1H); 4.80 (d, J=5.14 Hz, 2H); 1.49 (s, 9H).

Step 3: N-[5-(4-Nitro-phenyl)-[1,3,4]thiadiazol-2-ylmethyl]-acetamide

N-[5-(4-Nitro-phenyl)-[1,3,4]thiadiazol-2-ylmethyl]-acetamide was prepared following the same protocol as intermediate 13, step 5, using [5-(4-Nitro-phenyl)-[1,3,4]thiadiazol-2-ylmethyl]-carbamic acid tert-butyl ester. $^1$H NMR (400 MHz, CHCl$_3$-d): δ 8.38-8.31 (m, 2H); 8.17-8.10 (m, 2H); 6.33 (s, 1H); 4.89 (d, J=6.03 Hz, 2H); 2.09 (s, 3H).

Step 4: 4-(5-Methyl-imidazo[5,1-b][1,3,4]thiadiazol-2-yl)-phenylamine 4-(5-methylimidazo[5,1-b][1,3,4]thiadiazol-2-yl)aniline was prepared following the same protocol as intermediate 13, Steps 6 and 7, using N-[5-(4-Nitro-phenyl)-[1,3,4]thiadiazol-2-ylmethyl]-acetamide. It was isolated as a yellow solid. $^1$H NMR (400 MHz, DMSO-$d^6$): δ 7.58 (t, J=8.35 Hz, 2H); 6.88 (s, 1H); 6.71-6.64 (m, 2H); 6.05 (s, 2H); 2.54 (s, 3H).

Example 1: N-[4-(5-Methyl-imidazo[5,1-b][1,2,4]oxadiazol-2-yl)-phenyl]-2-(2-trifluoromethyl-phenyl)-acetamide

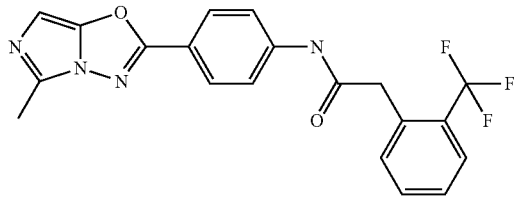 [SMILES: Cc1ncc2oc(-c3ccc(NC(=O)Cc4ccccc4C(F)(F)F)cc3)nn12]

To a solution of 2-(trifluoromethyl)phenylacetic acid (80 mg; 0.39 mmol) in DCE (8 mL) were added N,N-diisopropylethylamine (0.14 mL; 0.78 mmol) and HATU (149 mg; 0.39 mmol). The solution was stirred at room temperature for 30 minutes. Intermediate 4 (125.9 mg; 0.59 mmol) was added and the reaction was stirred at room temperature overnight. It was then diluted with DCM (20 mL) and was washed with NaHCO$_3$ sat (15 mL), water (15 mL) and brine (15 mL). Organic phase was dried over MgSO$_4$, filtered and evaporated under vacuo. The crude product was purified by flash chromatography (EtOAc/MeOH gradient from 100:0 to 80:20) then by MD Autoprep, affording the title compound as white foam (30 mg, 19% yield). $^1$H NMR (300 MHz, DMSO-d$_6$) δ 10.65 (s, 1H), 8.00 (d, J=8.8 Hz, 2H), 7.83 (d, J=8.85 Hz, 2H), 7.78-7.61 (m, 2H), 7.61-7.45 (m, 2H), 6.52 (s, 1H), 4.00 (brs, 2H), 2.44 (s, 3H). LC/MS (Method A): 401.1 (M+H)$^+$. HPLC (Method F) Rt 3.25 min (Purity: 96.7%).

Example 2: N-[4-(5-Methyl-imidazo[5,1-b][1,2,4]oxadiazol-2-yl)-phenyl]-2-m-tolyl-acetamide

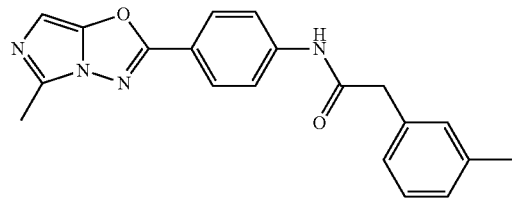 [SMILES: Cc1cccc(CC(=O)Nc2ccc(-c3nn4c(C)ncc4o3)cc2)c1]

To a solution of meta-tolylacetic acid (80 mg; 0.53 mmol) in DCE (8 mL) was added T3P solution (50% in EtOAc, 0.22 mL; 0.80 mmol) and triethylamine (0.074 mL; 0.53 mmol). The solution was stirred at 0° C. for 30 minutes. Intermediate 4 (171.2 mg; 0.80 mmol) was added and the reaction mixture was stirred at 60° C. overnight. It was then diluted with DCM (20 mL) and was washed with NaHCO$_3$ sat (15 mL), water (15 mL) and brine (15 mL). Organic phase was dried over MgSO$_4$, filtered and evaporated under vacuo. The crude product was purified by flash chromatography (EtOAc/MeOH gradient from 100:0 to 80:20) then by MD Autoprep, affording the title compound as white solid (32 mg, 17% yield). $^1$H NMR (300 MHz, DMSO-d$_6$) δ 10.59 (s, 1H), 8.00 (d, J=8.8 Hz, 2H), 7.85 (d, J=8.8 Hz, 2H), 7.27-7.01 (m, 4H), 6.5 (s, 1H), 3.66 (s, 2H), 2.44 (s, 3H), 2.30 (s, 3H). LC/MS (Method A): 347.12 (M+H)$^+$. 345.05 (M−H)$^−$. HPLC (Method F) Rt 2.81 min (Purity: 99.3%).

Example 3: N-[4-(5-Methyl-imidazo[5,1-b][1,2,4]oxadiazol-2-yl)-phenyl]-2-(3-trifluoromethyl-phenyl)-acetamide

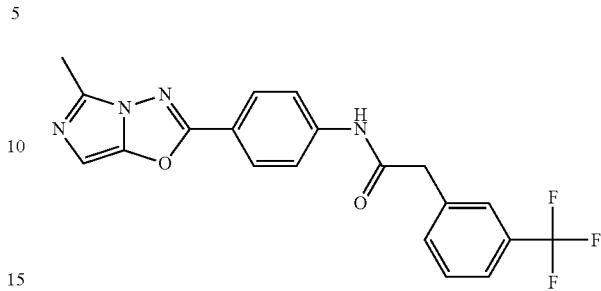

Oxalyl chloride (889 mg; 7 mmol) was added to a solution of 3-(trifluoromethyl)phenylacetic acid (428.8 mg; 2.1 mmol) and DMF (0.005 mL) in DCM (15 mL) and the resulting mixture was stirred at room temperature for 1 hour. It was concentrated in vacuo and the residue was taken up in DCM (2 mL) and added to a suspension of Intermediate 4 (150 mg; 0.70 mmol) in DMF (5 mL) and N,N-diisopropylethylamine (108.6 mg; 0.84 mmol). The reaction mixture was stirred at room temperature for 4 hours. It was then diluted with DCM (20 mL), washed with NaHCO$_3$ sat (2×15 mL), brine (15 mL), dried over Na$_2$SO$_4$ and concentrated in vacuo to give the crude product as a yellow oil. It was crystallized in hot MeCN, affording the title product as beige solid (148 mg, 53% yield). $^1$H NMR (300 MHz, DMSO-d$_6$) δ 10.65 (s, 1H), 7.99 (d, J=8.8 Hz, 2H), 7.84 (d, J=8.8 Hz, 2H), 7.72 (br s, 1H), 7.68-7.54 (m, 3H), 6.49 (s, 1H), 3.86 (s, 2H), 2.43 (s, 3H). LC/MS (Method A): 401.17 (M+H)$^+$. HPLC (Method F) Rt 3.21 min (Purity: 99.8%).

Example 4: 2-(4-Chloro-3-trifluoromethyl-phenyl)-N-[4-(5-methyl-imidazo[5,1-b][1,2,4]oxadiazol-2-yl)-phenyl]-acetamide

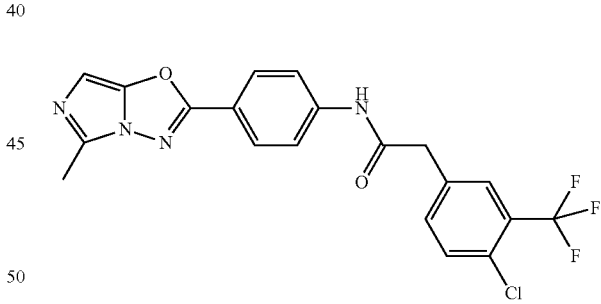

Oxalyl chloride (133 mg; 1.05 mmol) was added to a solution of 4-chloro-3-(trifluoromethyl)phenylacetic acid (50 mg; 0.21 mmol) and DMF (0.005 mL) in DCM (6 mL) at 0° C. under inert atmosphere and the resulting mixture was stirred at 0° C. for 1 hour. It was concentrated in vacuo and the residue was taken up in DCM (6 mL). N,N-diisopropylethylamine (72.23 µl; 0.42 mmol) and Intermediate 4 (67.34 mg; 0.31 mmol) were added and the mixture was stirred at room temperature overnight. It was then diluted with DCM (20 mL), washed with NaHCO$_3$ sat (2×15 mL), brine (15 mL), dried over MgSO$_4$ and concentrated in vacuo to give the crude product as white solid. It was purified by MD Autoprep affording the title compound as white solid (15 mg, 16% yield). $^1$H NMR (DMSO-d$_6$, 300 MHz) δ 10.68 (s, 1H), 8.00 (d, J=8.91 Hz, 2H), 7.84 (d, J=8.88 Hz, 2H), 7.75-7.60 (m, 3H), 6.50 (s, 1H), 3.88 (s, 2H), 2.44 (s, 3H). LC/MS (Method A): 435.02 (M+H)$^+$. 433.03 (M−H)$^−$. HPLC (Method F) Rt 3.52 min (Purity: 98.6%).

Example 5: 2-(2-Bromo-4-trifluoromethyl-phenyl)-N-[4-(5-methyl-imidazo[5,1-b][1,2,4]oxadiazol-2-yl)-phenyl]-acetamide

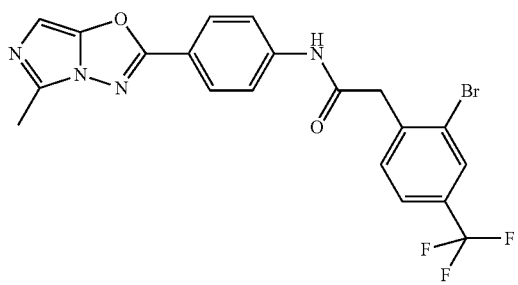 [SMILES: Cc1ncc2oc(-c3ccc(NC(=O)Cc4ccc(C(F)(F)F)cc4Br)cc3)nn12]

To a solution of 2-bromo-4-(trifluoromethyl)phenylacetic acid (126.84 mg; 0.45 mmol) in dry DMF (2 mL) in a MW vial, was added T3P (50% solution in EtOAc, 0.15 mL; 0.56 mmol) and triethylamine (0.05 mL; 0.37 mmol) at 0° C. under inert atmosphere. The solution was stirred for 1 hour at room temperature. A solution of Intermediate 4 (80 mg; 0.37 mmol) in DMF (1 mL) was then added and the resulting mixture was stirred at 100° C. overnight. The reaction mixture was cooled down to room temperature, EtOAc (20 mL) was added and the solution was washed with NaHCO$_3$ sat (15 mL), water (15 mL), brine (15 mL) and dried over MgSO$_4$. After filtration and evaporation of the solvents, yellow oil was obtained. It was purified by MD Autoprep, affording the title compound as a white solid (16 mg, 9% yield). $^1$H NMR (DMSO-d$_6$, 300 MHz) δ 10.75 (s, 1H), 8.05-7.96 (m, 3H), 7.90-7.81 (d, J=8.9 Hz, 2H), 7.80-7.75 (m, 1H), 7.68 (d, J=8.02 Hz, 1H), 6.51 (s, 1H), 4.05 (brs, 2H), 2.44 (s, 3H). LC/MS (Method A): 481.00 (M+H)$^+$. 479.02 (M−H)$^−$. HPLC (Method F) Rt 4.13 min (Purity: 97.6%).

Example 6: N-[4-(5-Methyl-imidazo[5,1-b][1,2,4]oxadiazol-2-yl)-phenyl]-2-(4-trifluoromethoxy-phenyl)-acetamide

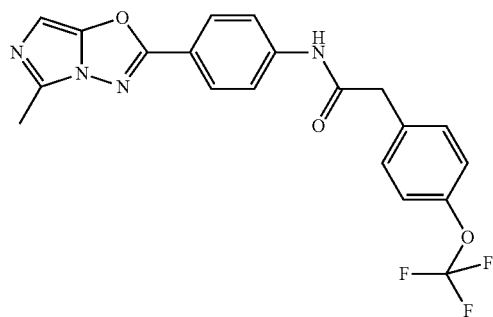 [SMILES: Cc1ncc2oc(-c3ccc(NC(=O)Cc4ccc(OC(F)(F)F)cc4)cc3)nn12]

To a solution of 4-(trifluoromethoxy)phenylacetic acid (106.88 mg; 0.49 mmol) in dry DMF (2 mL) in a MW vial, was added T3P (50% solution in EtOAc, 0.15 mL; 0.56 mmol) and triethylamine (0.05 mL; 0.37 mmol) at 0° C. under inert atmosphere. The solution was stirred for 1 hour at room temperature. A solution of Intermediate 4 (80 mg; 0.37 mmol) in DMF (1 mL) was then added and the resulting mixture was stirred at 100° C. overnight. The reaction mixture was cooled down to room temperature, EtOAc (20 mL) was added and the solution was washed with NaHCO$_3$ sat (15 mL), water (15 mL), brine (15 mL) and dried over MgSO$_4$. After filtration and evaporation of the solvents, yellow oil was obtained. It was purified by MD Autoprep, affording the title compound as a white solid (64 mg, 41% yield). $^1$H NMR (DMSO-d$_6$, 300 MHz) δ 10.64 (s, 1H), 8.00 (d, J=8.82 Hz, 2H), 7.84 (d, J=8.84 Hz, 2H), 7.47 (d, J=8.7 Hz, 2H), 7.34 (d, J=8.1 Hz, 2H), 6.50 (s, 1H), 3.77 (s, 2H), 2.44 (s, 3H). LC/MS (Method A): 417.07 (M+H)$^+$. 415.06 (M−H)$^−$. HPLC (Method F) Rt 3.34 min (Purity: 99.5%).

Example 7: 2-(4-Chloro-2,6-difluoro-phenyl)-N-[4-(5-methyl-imidazo[5,1-b][1,2,4]oxadiazol-2-yl)-phenyl]-acetamide

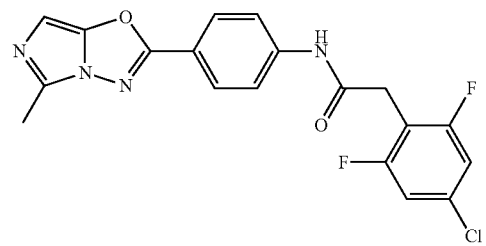 [SMILES: Cc1ncc2oc(-c3ccc(NC(=O)Cc4c(F)cc(Cl)cc4F)cc3)nn12]

The title compound was prepared following the same procedure as Example 6, starting with 4-chloro-2,6-difluorophenylacetic acid (115.71 mg; 0.56 mmol). It was isolated as white solid (32 mg, 21% yield). $^1$H NMR (DMSO-d$_6$, 300 MHz) δ 10.75 (s, 1H), 8.01 (d, J=8.85 Hz, 2H), 7.82 (d, J=8.86 Hz, 2H), 7.47-7.36 (m, 2H), 6.50 (s, 1H), 3.84 (s, 2H), 2.44 (s, 3H). LC/MS (Method A): 403.0 (M+H)$^+$. 401.0 (M−H)$^−$. HPLC (Method F) Rt 3.08 min (Purity: 97.6%).

Example 8: 2-(4-Ethoxy-phenyl)-N-[4-(5-methyl-imidazo[5,1-b][1,2,4]oxadiazol-2-yl)-phenyl]-acetamide

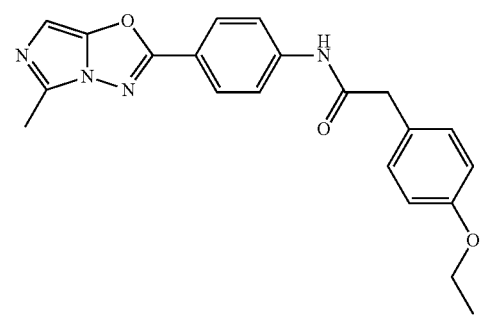 [SMILES: CCOc1ccc(CC(=O)Nc2ccc(-c3nn4c(C)ncc4o3)cc2)cc1]

The title compound was prepared following the same procedure as Example 6, starting with 4-ethoxyphenylacetic acid (100.9 mg; 0.56 mmol). It was isolated as white solid (73 mg, 52% yield). $^1$H NMR (DMSO-d$_6$, 300 MHz) δ 10.54 (s, 1H), 7.99 (d, J=8.72 Hz, 2H), 7.84 (d, J=8.66 Hz, 2H), 7.24 (d, J=8.5 Hz, 2H), 6.88 (d, J=8.5 Hz, 2H), 6.5 (s, 1H), 3.99 (q, J=7.08, 7.17 Hz, 2H), 3.62 (s, 2H), 2.44 (s, 3H), 1.31 (tr, J=6.91 Hz, 3H). LC/MS (Method A): 377.12 (M+H)⁺. 375.10 (M−H)⁻. HPLC (Method F) Rt 2.80 min (Purity: 97.4%).

Example 9: 2-(3-Bromo-phenyl)-N-[4-(5-methyl-imidazo[5,1-b][1,2,4]oxadiazol-2-yl)-phenyl]-acetamide

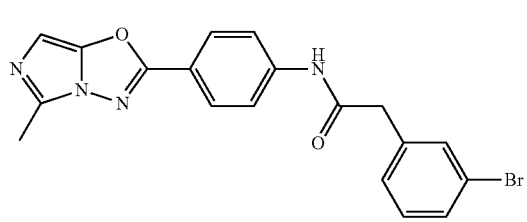 [SMILES: Cc1ncc2oc(-c3ccc(NC(=O)Cc4cccc(Br)c4)cc3)nn12]

The title compound was prepared following the same procedure as Example 6, starting with 3-bromophenylacetic acid (180.69 mg; 0.84 mmol). It was isolated as white solid (23 mg, 8% yield). ¹H NMR (DMSO-d₆, 300 MHz)) δ 10.62 (s, 1H), 8.00 (d, J=8.8 Hz, 2H), 7.84 (d, J=8.8 Hz, 2H), 7.57 (s, 1H), 7.51-7.42 (m, 1H), 7.39-7.24 (m, 2H), 6.50 (s, 1H), 3.74 (s, 2H), 2.44 (s, 3H). LC/MS (Method A): 412.97 (M+H)⁺. 411.03 (M−H)⁻. HPLC (Method F) Rt 3.63 min (Purity: 93.9%).

Representative Method A

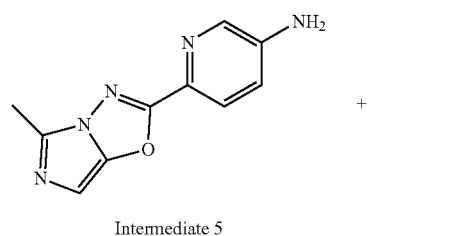

Intermediate 5

+

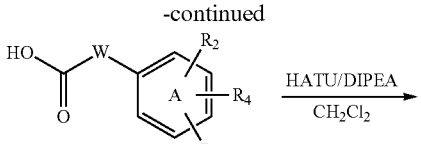

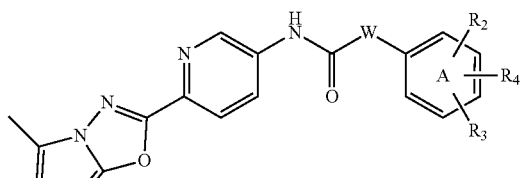

A solution of Intermediate 5 (80 mg, 0.37 mmol, 1 equiv) in dichloromethane (4 mL) and tetrahydrofuran (1 mL) was mixed with HATU (212.0 mg, 0.5579 mmol, 1.5 equiv) and the appropriate carboxylic acid of formula (V) (1.5 equiv), DIPEA (0.19 mL, 1.12 mmol, 3 equiv) was added to the reaction mixture. The reaction mixture was stirred at room temperature for about 2 days in orbital shaker. The reaction mixture was concentrated to remove the solvent, then diluted with water (20 mL) and extracted with dichloromethane (2×20 mL), combined organic layer was washed with brine solution (1×20 mL), dried over anhydrous sodium sulphate, filtered and evaporated under reduced pressure. The crude residue was purified by column chromatography using petroleum ether-ethyl acetate as eluents to get the product.

The following compounds were prepared using representative method A with intermediate 5 and an appropriate carboxylic acid of formula (V):

| Ex No | Structure (Appearance) | HPLC Rt (% Purity) | MS | NMR |
|---|---|---|---|---|
| 10 | 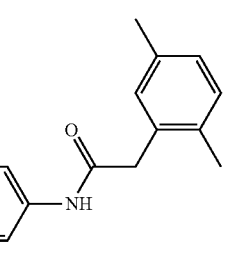<br>2-(2,5-Dimethyl-phenyl)-N-[6-(5-methyl-imidazo[5,1-b][1,2,4]oxadiazol-2-yl)-pyridin-3-yl]-acetamide (Off-white solid) | 3.37ᶠ (99.1%) | 362.0 (M + H)⁺ | ¹H NMR (400 MHz, DMSO-d⁶): δ 10.78 (s, 1H), 8.93 (d, J = 2.0 Hz, 1H), 8.32 (dd, J = 8.7, 2.5 Hz, 1H), 8.14 (d, J = 8.7 Hz, 1H), 7.06 (d, J = 4.5 Hz, 2H), 6.97 (d, J = 7.7 Hz, 1H), 6.52 (s, 1H), 3.73 (s, 2H), 2.45 (s, 3H), 2.24 (s, 6H) |

-continued

| Ex No | Structure (Appearance) | HPLC Rt (% Purity) | MS | NMR |
|---|---|---|---|---|
| 11 | N-[6-(5-Methyl-imidazo[5,1-b][1,2,4]oxadiazol-2-yl)-pyridin-3-yl]-2-(4-trifluoromethoxy-phenyl)-acetamide (Off-white solid) | 3.75$^f$ (98.4%) | 418.0 (M + H)$^+$ | $^1$H NMR (400 MHz, DMSO-d$^6$): δ 10.85 (s, 1H), 8.92-8.92 (m, 1H), 8.32 (dd, J = 8.7, 2.5 Hz, 1H), 8.14 (d, J = 8.7 Hz, 1H), 7.45-7.49 (m, 2H), 7.33-7.35 (m, 2H), 6.52 (s, 1H), 3.84 (s, 2H), 2.44 (s, 3H) |
| 12 | 2-(3,4-Dichloro-phenyl)-N-[6-(5-methyl-imidazo[5,1-b][1,2,4]oxadiazol-2-yl)-pyridin-3-yl]-acetamide (Off-white solid) | 3.66$^f$ (98.7%) | 402.0 (M + H)$^+$ | $^1$H NMR (400 MHz, DMSO-d$^6$): δ 10.83 (s, 1H), 8.92 (t, J = 2.0 Hz, 1H), 8.31 (dd, J = 8.7, 2.5 Hz, 1H), 8.14 (d, J = 8.6 Hz, 1H), 7.59-7.63 (m, 2H), 7.34 (dd, J = 8.3, 2.0 Hz, 1H), 6.52 (s, 1H), 3.80 (s, 2H), 2.44 (s, 3H) |
| 13 | N-[6-(5-Methyl-imidazo[5,1-b][1,2,4]oxadiazol-2-yl)-pyridin-3-yl]-2-naphthalen-1-yl-acetamide (Off-white solid) | 3.58$^f$ (96.9%) | 384.3 (M + H)$^+$ | $^1$H NMR (400 MHz, DMSO-d$^6$): δ 10.99 (s, 1H), 8.95 (t, J = 2.0 Hz, 1H), 8.31-8.34 (m, 1H), 8.09-8.15 (m, 2H), 7.94-7.96 (m, 1H), 7.85-7.88 (m, 1H), 7.47-7.59 (m, 4H), 6.51 (s, 1H), 4.25 (s, 2H), 2.44 (s, 3H) |
| 14 | N-[6-(5-Methyl-imidazo[5,1-b][1,2,4]oxadiazol-2-yl)-pyridin-3-yl]-2-(3-trifluoromethyl-phenyl)-acetamide (Off-white solid) | 3-59$^f$ (99.1%) | 402.0 (M + H)$^+$ | $^1$H NMR (400 MHz, DMSO-d$^6$): δ 10.87 (s, 1H), 8.92 (t, J = 0.5 Hz, 1H), 8.32 (dd, J = 8.7, 2.5 Hz, 1H), 8.14 (d, J = 8.8 Hz, 1H), 7.72 (s, 1H), 7.63-7.66 (m, 2H), 7.56-7.60 (m, 1H), 6.52 (s, 1H), 3.90 (s, 2H), 2.44 (s, 3H) |

-continued

| Ex No | Structure (Appearance) | HPLC Rt (% Purity) | MS | NMR |
|---|---|---|---|---|
| 15 | 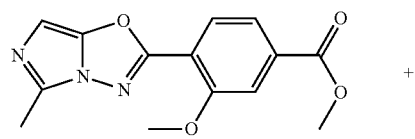<br>N-[6-(5-Methyl-imidazo[5,1-b][1,2,4]oxadiazol-2-yl)-pyridin-3-yl]-2-(3-phenoxy-phenyl)-acetamide (Yellow solid) | 3.86[f] (99.2%) | 426.2 (M + H)+ | |
| 16 | 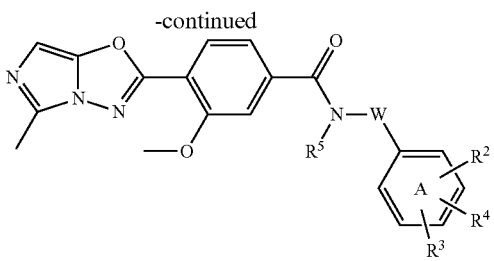<br>4-Fluoro-N-[6-(5-methyl-imidazo[5,1-b][1,2,4]oxadiazol-2-yl)-pyridin-3-yl]-3-trifluoromethoxy-benzamide (Off-white solid) | 3.76[f] (97.8%) | 422 (M + H)+ | |

[a-f]Rt refers to HPLC methods A to F

Representative Method B

Intermediate 7

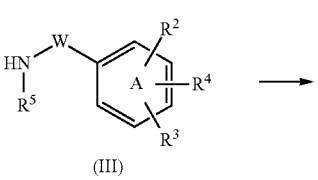

Bis(trimethylaluminum)-1,4-diazabicyclo(2.2.2)octane adduct (DABAL-Me$_3$, 267 mg, 1.04 mmol, 1.5 equiv) and appropriate amine of formula (III) (1.04 mmol, 1.5 equiv) in anhydrous THF (3 mL) were taken in 10 mL microwave vial. It was heated up to 130° C. for 20 min. Then Intermediate 7 (199 mg, 0.69 mmol, 1 equiv) was added and the reaction mixture stirred at 130° C. for another 30 min. Reaction mixture was allowed to cool to room temperature, quenched by the addition of 2M HCl. Reaction mixture was extracted with ethyl acetate. Organic layer was dried over anhydrous sodium sulphate and evaporated under reduced pressure. The crude residue was purified by column chromatography using petroleum ether-ethyl acetate as eluents to get the pure amide.

The following compounds were prepared using representative method B, with intermediate 7 and an appropriate amine of formula (III):

| Ex No | Structure (Appearance) | HPLC Rt (% Purity) | MS | NMR |
|---|---|---|---|---|
| 18 | 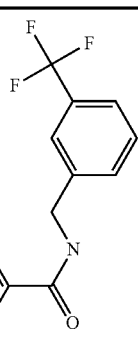<br>3-Methoxy-4-(5-methyl-imidazo[5,1-b][1,2,4]oxadiazol-2-yl)-N-(3-trifluoromethyl-benzyl)-benzamide (White solid) | 3.70$^f$ (94.9%) | 431.0 (M + H)$^+$ | $^1$H NMR (400 MHz, DMSO-d$_6$): δ 9.37 (t, J = 6.0 Hz, 1H), 8.01 (d, J = 8.1 Hz, 1H), 7.57-7.73 (m, 6H), 6.50 (s, 1H), 4.60 (d, J = 5.9 Hz, 2H), 4.00 (s, 3H), 2.45 (s, 3H) |
| 19 | 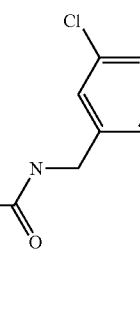<br>N-(3,4-Dichloro-benzyl)-3-methoxy-4-(5-methyl-imidazo[5,1-b][1,2,4]oxadiazol-2-yl)-benzamide (Off-white solid) | 3.77$^f$ (96.8%) | 431.0 (M + H)$^+$ | $^1$H NMR (400 MHz, DMSO-d$_6$): δ 9.33 (t, J = 5.9 Hz, 1H), 8.01 (d, J = 8.1 Hz, 1H), 7.72 (d, J = 1.3 Hz, 1H), 7.62-7.66 (m, 1H), 7.60 (d, J = 1.6 Hz, 2H), 7.34 (dd, J = 8.3, 2.0 Hz, 1H), 6.50 (s, 1H), 4.50 (d, J = 5.8 Hz, 2H), 4.00 (s, 3H), 2.45 (s, 3H) |
| 20 | 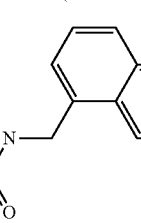<br>3-Methoxy-4-(5-methyl-imidazo[5,1-b][1,2,4]oxadiazol-2-yl)-N-naphthalen-1-ylmethyl-benzamide (Off-white solid) | 3.60$^f$ (99.1%) | 413.0 (M + H)$^+$ | $^1$H NMR (400 MHz, DMSO-d$^6$): δ 9.30 (t, J = 5.8 Hz, 1H), 8.19 (d, J = 8.2 Hz, 1H), 7.95-8.01 (m, 2H), 7.86-7.88 (m, 1H), 7.75 (d, J = 1.3 Hz, 1H), 7.67-7.69 (m, 1H), 7.51-7.60 (m, 4H), 4.99 (d, J = 5.6 Hz, 2H), 3.31 (s, 3H), 2.44 (s, 3H) |

$^{a-f}$Rt refers to HPLC methods A to F

Representative Method C

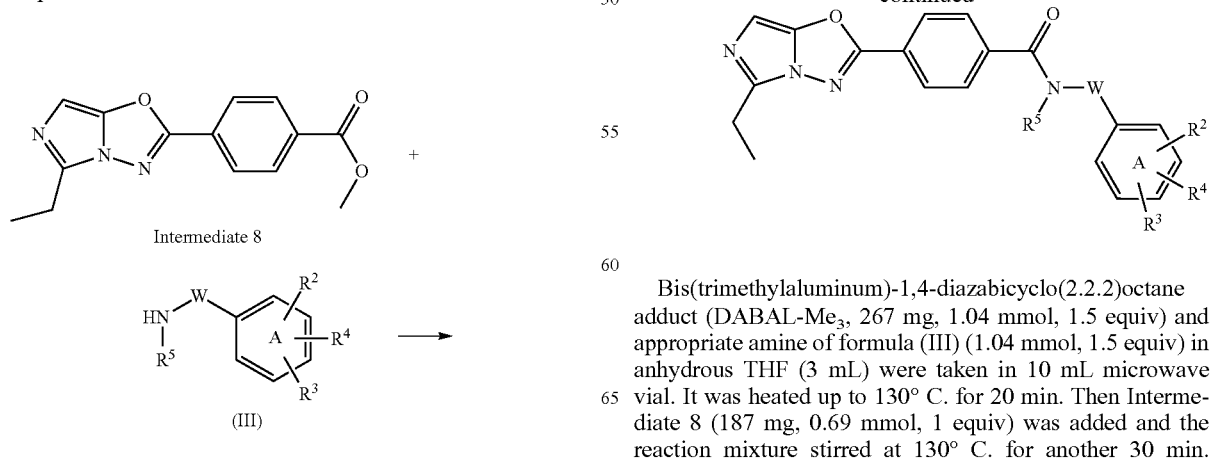

Bis(trimethylaluminum)-1,4-diazabicyclo(2.2.2)octane adduct (DABAL-Me$_3$, 267 mg, 1.04 mmol, 1.5 equiv) and appropriate amine of formula (III) (1.04 mmol, 1.5 equiv) in anhydrous THF (3 mL) were taken in 10 mL microwave vial. It was heated up to 130° C. for 20 min. Then Intermediate 8 (187 mg, 0.69 mmol, 1 equiv) was added and the reaction mixture stirred at 130° C. for another 30 min.

Reaction mixture was allowed to cool to room temperature, quenched by the addition of 2M HCl. Reaction mixture was extracted with ethyl acetate. Organic layer was dried over anhydrous sodium sulphate and evaporated under reduced pressure. The crude residue was purified by column chromatography using petroleum ether-ethyl acetate as eluents to get the pure amide.

The following compound was prepared from intermediate 8 following method C, using appropriate amine of formula (III):

| Ex No | Structure (Appearance) | HPLC Rt (% Purity) | MS | NMR |
|---|---|---|---|---|
| 21 | 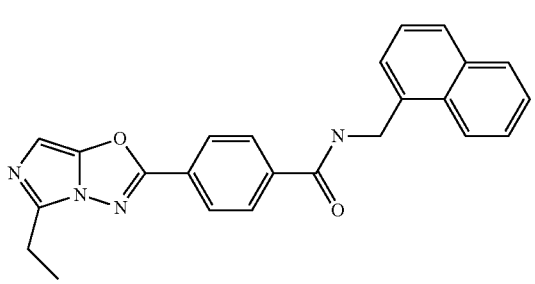 [SMILES: CCc1ncc2oc(-c3ccc(C(=O)NCc4cccc5ccccc45)cc3)nn12]<br>4-(5-Ethyl-imidazo[5,1-b][1,2,4]oxadiazol-2-yl)-N-naphthalen-1-ylmethyl-benzamide (Off-white solid) | 3.86$^f$ (99.3%) | 397.3 (M + H)$^+$ | $^1$H NMR (400 MHz, DMSO-d$^6$): δ 9.31 (t, J = 5.8 Hz, 1H), 8.20 (d, J = 1.0 Hz, 1H), 8.10-8.18 (m, 4H), 7.95-7.97 (m, 1H), 7.86 (dd, J = 7.6, 1.7 Hz, 1H), 7.47-7.60 (m, 4H), 6.54 (s, 1H), 4.98 (d, J = 5.7 Hz, 2H), 2.83 (q, J = 7.6 Hz, 2H), 1.29 (t, J = 7.6 Hz, 3H). |

$^{a\text{-}f}$Rt refers to HPLC methods A to F

Representative Method D

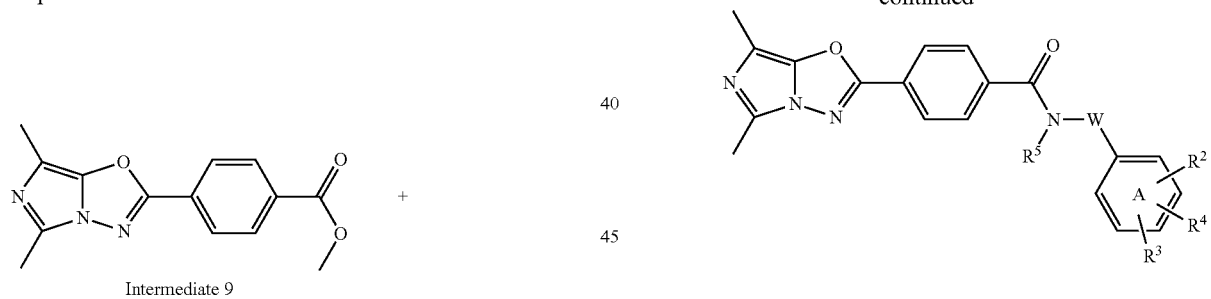

Intermediate 9

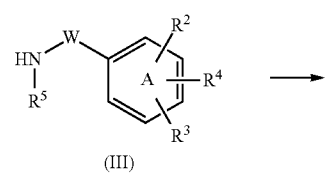

(III)

Trimethylaluminium (2M solution in THF, 0.41 mL, 0.81 mmol) was added drop-wise to a cold (0° C.) solution of amine of formula (III) (142 mg, 0.81 mmol) in DCE (10 mL). The resulting mixture was stirred at 0° C. for 30 minutes whereupon a solution of Intermediate 9 (100 mg, 0.37 mmol) in DCE (10 mL) was added. The reaction mixture was stirred at room temperature for 1 hour then 3 hours at 70° C. before being quenched with water (20 mL). The DCE phase was washed with aqueous Rochelle's salt (2×20 mL), brine (20 mL) and finally dried over sodium sulfate and concentrated in vacuo to yield a yellow oil. The crude material was purified by flash column chromatography (60-120 mesh silica gel; eluent: 40% EtOAc in DCM) affording the expected compound as a solid.

The following compounds were prepared using representative method D with intermediate 9 and an appropriate amine of formula (III):

| Ex No | Structure (Appearance) | HPLC Rt (% Purity) | MS | NMR |
|---|---|---|---|---|
| 22 | 4-(5,7-Dimethyl-imidazo[5,1-b][1,2,4]oxadiazol-2-yl)-N-naphthalen-1-ylmethyl-benzamide (White solid) | 3.62$^f$ (95.7%) | 397.1 (M + H)$^+$ | $^1$H NMR (300 MHz, DMSO-d$^6$): δ 8.14 (d, J = 7 Hz, 3H), 7.99-7.86 (m, 4H), 7.63-7.45 (m, 4H), 6.54-6.49 (m, 1H), 5.15 (d, J = 6.5 Hz, 2H), 2.65 (s, 3H), 2.40 (s, 3H) |
| 23 | 4-(5,7-Dimethyl-imidazo[5,1-b][1,2,4]oxadiazol-2-yl)-N-(2-trifluoromethyl-benzyl)-benzamide (White solid) | 3.63$^f$ (99.8%) | 415.06 (M + H)$^+$ | $^1$H NMR (300 MHz, DMSO-d$^6$): δ 8.13 (d, J = 7.5 Hz, 2H), 8.07 (d, J = 7.5 Hz, 2H), 7.65-7.60 (m, 2H), 7.54-7.47 (m, 1H), 7.47-7.41 (m, 1H), 6.98-6.91 (m, 1H), 4.86 (d, J = 6.5 Hz, 2H), 2.51 (s, 3H), 2.31 (s, 3H) |

$^{a-f}$Rt refers to HPLC methods A to F

Representative Method E

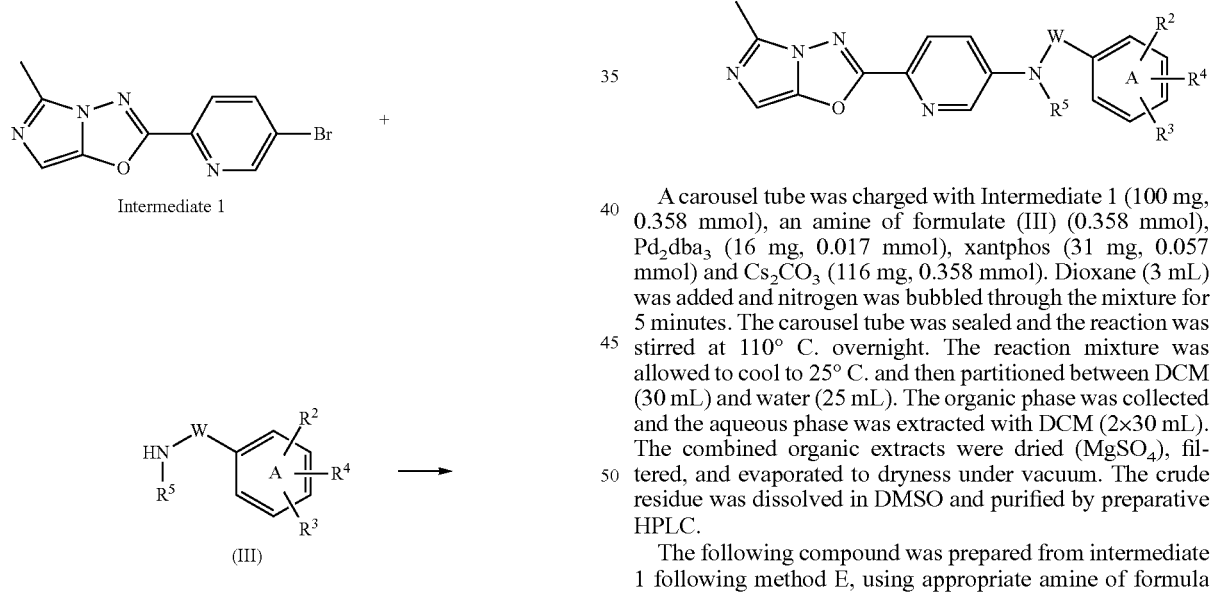

A carousel tube was charged with Intermediate 1 (100 mg, 0.358 mmol), an amine of formulate (III) (0.358 mmol), Pd$_2$dba$_3$ (16 mg, 0.017 mmol), xantphos (31 mg, 0.057 mmol) and Cs$_2$CO$_3$ (116 mg, 0.358 mmol). Dioxane (3 mL) was added and nitrogen was bubbled through the mixture for 5 minutes. The carousel tube was sealed and the reaction was stirred at 110° C. overnight. The reaction mixture was allowed to cool to 25° C. and then partitioned between DCM (30 mL) and water (25 mL). The organic phase was collected and the aqueous phase was extracted with DCM (2×30 mL). The combined organic extracts were dried (MgSO$_4$), filtered, and evaporated to dryness under vacuum. The crude residue was dissolved in DMSO and purified by preparative HPLC.

The following compound was prepared from intermediate 1 following method E, using appropriate amine of formula (III):

| Ex No | Structure (Appearance) | HPLC Rt (% Purity) | MS | NMR |
|---|---|---|---|---|
| 28 | | 2.87$^b$ (97.9%) | 374 (M + H)$^+$ | $^1$H NMR (400 MHz, DMSO-d$^6$): δ 8.18 (d, J = 2.76 Hz, 1H); 7.86 (d, J = 8.73 Hz, 1H); 7.68-7.60 (m, 2H), 7.54 (t, J = 6.18 Hz, 1H); 7.37 (dd, J = 8.28, 2.05 Hz, 1H); 7.04 (dd, J = 8.77, 2.80 Hz, 1H); 6.46 (s, 1H); |

| Ex No | Structure (Appearance) | HPLC Rt (% Purity) | MS | NMR |
|---|---|---|---|---|
| | (3,4-Dichloro-benzyl)-[6-(5-methyl-imidazo[5,1-b][1,2,4]oxadiazol-2-yl)-pyridin-3-yl]-amine (Brown solid) | | | 4.46 (d, J = 6.13 Hz, 2H); 2.42 (s, 3H). |

[a-f]Rt refers to HPLC methods A to F

Representative Method F

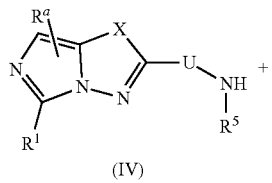

(IV)

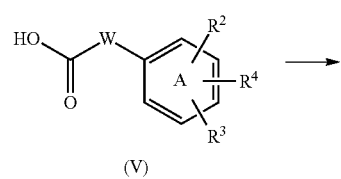

(V)

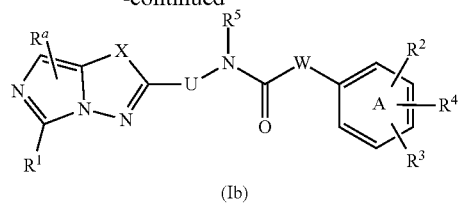

(Ib)

A carousel tube was charged with an acid of formula (V) (0.275 mmol), a solution of an amine of formula (IV) (0.25 mmol) in DMF (0.75 mL) and a solution of HATU (95 mg, 0.25 mmol) in DMF (0.5 mL). Hunig's base (43 µL, 0.25 mmol) was added and the carousel tube was sealed. After 16 hours at 25° C., the reaction mixture was purified directly by preparative HPLC.

The following compounds were prepared using representative method F with intermediate 2 and an appropriate acid of formula (V):

| Ex No | Structure (Appearance) | HPLC Rt (% Purity) | MS | NMR |
|---|---|---|---|---|
| 37 | 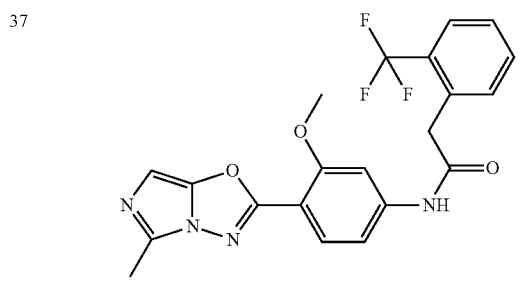<br>N-(3-methoxy-4-(5-methylimidazo[5,1-b][1,3,4]oxadiazol-2-yl)phenyl)-2-(2-(trifluoromethyl)phenyl)acetamide (Off-white solid) | 3.23[a] (97.6%) | 431 (M + H)+ | $^1$H NMR (400 MHz, DMSO-d$^6$): δ 10.65 (s, 1H); 7.86 (d, J = 8.60 Hz, 1H); 7.73 (d, J = 7.92 Hz, 1H); 7.71-7.65 (m, 2H); 7.57-7.48 (m, 2H); 7.31 (dd, J = 8.63, 1.86 Hz, 1H); 6.47 (s, 1H); 4.00 (s, 2H); 3.89 (s, 3H); 2.44 (s, 3H). |
| 36 | 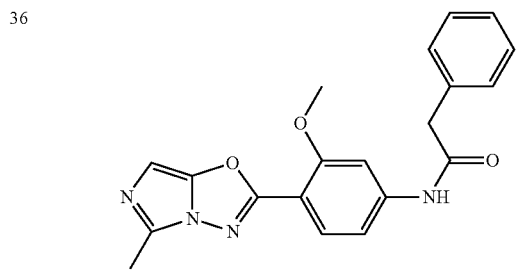<br>N-(3-methoxy-4-(5-methylimidazo[5,1-b][1,3,4]oxadiazol-2-yl)phenyl)-2-phenylacetamide (Off-white solid) | 2.96[a] (98.4%) | 363 (M + H)+ | $^1$H NMR (400 MHz, DMSO-d$^6$): δ 10.59 (s, 1H); 7.85 (d, J = 8.60 Hz, 1H); 7.67 (d, J = 1.85 Hz, 1H); 7.38-7.32 (m, 5H); 7.29-7.24 (m, 1H); 6.46 (s, 1H); 3.90 (s, 3H); 3.71 (s, 2H); 2.43 (s, 3H). |

| Ex No | Structure (Appearance) | HPLC Rt (% Purity) | MS | NMR |
|---|---|---|---|---|
| 35 | 2-(4-ethoxyphenyl)-N-(3-methoxy-4-(5-methylimidazo[5,1-b][1,3,4]oxadiazol-2-yl)phenyl)acetamide (Off-white solid) | 3.57[a] (98.8%) | 407 (M + H)+ | $^1$H NMR (400 MHz, DMSO-d$^6$): δ 10.53 (s, 1H); 7.84 (d, J = 8.60 Hz, 1H); 7.66 (d, J = 1.84 Hz, 1H); 7.35 (dd, J = 8.63, 1.86 Hz, 1H); 7.25 (d, J = 8.48 Hz, 2H); 6.91-6.87 (m, 2H); 6.46 (s, 1H); 4.00 (q, J = 6.98 Hz, 2H); 3.89 (s, 3H); 3.62 (s, 2H); 2.43 (s, 2H); 1.32 (t, J = 6.96 Hz, 3H). |
| 34 | N-(3-methoxy-4-(5-methylimidazo[5,1-b][1,3,4]oxadiazol-2-yl)phenyl)-2-(4-(trifluoromethoxy)phenyl)acetamide (Off-white solid) | 3.34[a] (98.4%) | 447 (M + H)+ | $^1$H NMR (400 MHz, DMSO-d$^6$): δ 10.63 (s, 1H); 7.85 (d, J = 8.60 Hz, 1H); 7.67 (d, J = 1.85 Hz, 1H); 7.47 (d, J = 8.49 Hz, 2H); 7.36-7.31 (m, 3H); 6.46 (s, 1H); 3.90 (s, 3H); 3.78 (s, 2H); 2.43 (s, 3H). |
| 33 | 2-(3-chlorophenyl)-N-(3-methoxy-4-(5-methylimidazo[5,1-b][1,3,4]oxadiazol-2-yl)phenyl)acetamide (Off-white solid) | 3.67[a] (98.6%) | 397 (M + H)+ | $^1$H NMR (400 MHz, DMSO-d$^6$): δ 10.61 (s, 1H); 7.86 (d, J = 8.60 Hz, 1H); 7.66 (d, J = 1.85 Hz, 1H); 7.43 (s, 1H); 7.40-7.28 (m, 4H); 6.46 (s, 1H); 3.90 (s, 3H); 3.75 (s, 2H); 2.43 (s, 3H). |
| 32 | 2-(2,6-dichloro-4-(trifluoromethyl)phenyl)-N-(3-methoxy-4-(5-methylimidazo[5,1-b][1,3,4]oxadiazol-2-yl)phenyl)acetamide (Off-white solid) | 4.08[a] (98.7%) | 499 (M + H)+ | $^1$H NMR (400 MHz, DMSO-d$^6$): δ 10.85 (s, 1H); 7.99 (s, 2H); 7.87 (d, J = 8.59 Hz, 1H); 7.67 (d, J = 1.84 Hz, 1H); 7.29 (dd, J = 8.60, 1.88 Hz, 1H); 6.47 (s, 1H); 4.21 (s, 2H); 3.89 (s, 3H); 2.44 (s, 3H). |

| Ex No | Structure (Appearance) | HPLC Rt (% Purity) | MS | NMR |
|---|---|---|---|---|
| 31 | N-(3-methoxy-4-(5-methylimidazo[5,1-b][1,3,4]oxadiazol-2-yl)phenyl)-2-(3-(trifluoromethyl)phenyl)acetamide (Off-white solid) | 3.31$^a$ (98.5%) | 431 (M + H)$^+$ | $^1$H NMR (400 MHz, DMSO-d$^6$): δ 10.65 (s, 1H); 7.86 (d, J = 8.61 Hz, 1H); 7.72 (s, 1H); 7.67 (s, 2H); 7.64 (s, 1H); 7.60 (d, J = 7.60 Hz, 1H); 7.34 (dd, J = 8.63, 1.86 Hz, 1H); 6.46 (s, 1H); 3.90 (s, 3H); 3.87 (s, 2H); 2.43 (s, 3H). |

$^{a-f}$Rt refers to HPLC methods A to F

The following compounds were prepared using representative method F with intermediate 3 and an appropriate acid of formula (V):

| Ex No | Structure (Appearance) | HPLC Rt (% Purity) | MS | NMR |
|---|---|---|---|---|
| 46 | N-(2-methyl-4-(5-methylimidazo[5,1-b][1,3,4]oxadiazol-2-yl)phenyl)-2-(3-(trifluoromethyl)phenyl)propanamide (Yellow solid) | 4.00$^a$ (99.0%) | 429 (M + H)$^+$ | $^1$H NMR (400 MHz, DMSO-d$^6$): δ 9.71 (s, 1H); 7.89 (d, J = 2.06 Hz, 1H); 7.84 (dd, J = 8.48, 2.16 Hz, 1H); 7.79 (s, 1H); 7.73 (t, J = 7.61 Hz, 2H); 7.68-7.58 (m, 2H); 6.50 (s, 1H); 4.16 (q, J = 7.01 Hz, 1H); 2.44 (s, 3H); 2.32-2.20 (m, 3H); 1.50 (d, J = 6.99 Hz, 3H). |
| 45 | N-(2-methyl-4-(5-methylimidazo[5,1-b][1,3,4]oxadiazol-2-yl)phenyl)-2-(4-(trifluoromethoxy)phenyl)acetamide (White solid) | 3.83$^a$ (97.6%) | 431 (M + H)$^+$ | $^1$H NMR (400 MHz, DMSO-d$^6$): δ 9.72 (s, 1H); 7.92 (s, 1H); 7.85 (s, 2H); 7.50 (d, J = 8.21 Hz, 2H); 7.35 (d, J = 8.16 Hz, 2H); 6.66 (s, 1H); 3.83 (s, 2H); 2.49 (s, 3H); 2.34 (s, 3H). |
| 44 | | 2.44$^b$ (96.4%) | 381 (M + H)$^+$ | $^1$H NMR (400 MHz, DMSO-d$^6$): δ 9.70 (s, 1H); 7.91 (s, 1H); 7.86-7.79 (m, 2H); 7.44-7.37 (m, 4H); 6.50 (s, 1H); 3.78 (s, 2H); 2.44 (s, 3H); 2.33 (s, 3H). |

-continued

| Ex No | Structure (Appearance) | HPLC Rt (% Purity) | MS | NMR |
|---|---|---|---|---|
| | 2-(4-chlorophenyl)-N-(2-methyl-4-(5-methylimidazo[5,1-b][1,3,4]oxadiazol-2-yl)phenyl)acetamide (Off-white solid) | | | |
| 43 | 2-(3-chlorophenyl)-N-(2-methyl-4-(5-methylimidazo[5,1-b][1,3,4]oxadiazol-2-yl)phenyl)acetamide (Off-white solid) | 10.07[c] (97.3%) | 381 (M + H)+ | $^1$H NMR (400 MHz, DMSO-d$^6$): δ 9.71 (s, 1H); 7.91 (s, 1H); 7.87-7.80 (m, 2H); 7.46 (s, 1H); 7.41-7.31 (m, 3H); 6.51 (s, 1H); 3.80 (s, 2H); 2.45 (s, 3H); 2.34 (s, 3H). |
| 42 | 2-(2,6-dichloro-4-(trifluoromethyl)phenyl)-N-(2-methyl-4-(5-methylimidazo[5,1-b][1,3,4]oxadiazol-2-yl)phenyl)acetamide (Off-white solid) | 3.33[b] (98.2%) | 483 (M + H)+ | $^1$H NMR (400 MHz, DMSO-d$^6$): δ 9.94 (s, 1H); 7.98 (s, 2H); 7.93 (s, 1H); 7.85 (dd, J = 8.52, 2.09 Hz, 1H); 7.79 (d, J = 8.50 Hz, 1H); 6.51 (s, 1H); 4.26 (s, 2H); 2.45 (s, 3H); 2.39 (s, 3H). |
| 41 | N-(2-methyl-4-(5-methylimidazo[5,1-b][1,3,4]oxadiazol-2-yl)phenyl)-2-(3-(trifluoromethyl)phenyl)acetamide (Off-white solid) | 3.71[a] (98.2%) | 415 (M + H)+ | $^1$H NMR (400 MHz, DMSO-d$^6$): δ 9.75 (s, 1H); 7.91 (s, 1H); 7.87-7.80 (m, 2H); 7.75 (s, 1H); 7.71-7.55 (m, 3H); 6.50 (s, 1H); 3.91 (s, 2H); 2.44 (s, 3H); 2.34 (s, 3H). |
| 40 | N-(2-methyl-4-(5-methylimidazo[5,1-b][1,3,4]oxadiazol-2-yl)phenyl)-2-(2-(trifluoromethyl)phenyl)acetamide (Off-white solid) | 2.95[b] (99.6%) | 415 (M + H)+ | $^1$H NMR (400 MHz, DMSO-d$^6$): δ 9.74 (s, 1H); 7.92 (s, 1H); 7.85 (dd, J = 8.54, 2.09 Hz, 1H); 7.80 (d, J = 8.50 Hz, 1H); 7.73 (d, J = 7.92 Hz, 1H); 7.67 (t, J = 7.59 Hz, 1H); 7.56 (d, J = 7.70 Hz, 1H); 7.51 (t, J = 7.68 Hz, 1H); 6.51 (s, 1H); 4.05 (s, 2H); 2.45 (s, 3H); 2.37 (s, 3H). |

-continued

| Ex No | Structure (Appareance) | HPLC Rt (% Purity) | MS | NMR |
|---|---|---|---|---|
| 39 | 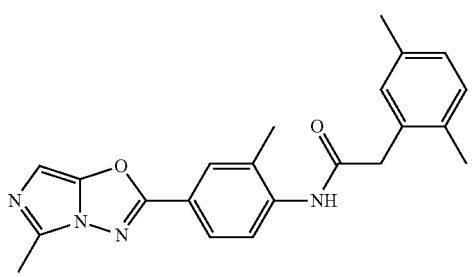<br>N-(2-methyl-4-(5-methylimidazo[5,1-b][1,3,4]oxadiazol-2-yl)phenyl)-2-(4-(trifluoromethyl)phenyl)acetamide (Off-white solid) | 3.46$^a$ (98.5%) | 415 (M + H)$^+$ | $^1$H NMR (400 MHz, DMSO-d$^6$): δ 9.76 (s, 1H); 7.91 (s, 1H); 7.88-7.79 (m, 2H); 7.72 (d, J = 8.03 Hz, 2H); 7.60 (d, J = 7.97 Hz, 2H); 6.50 (s, 1H); 3.90 (s, 2H); 2.44 (s, 3H); 2.34 (s, 3H). |
| 38 | 2-(2,5-dimethylphenyl)-N-(2-methyl-4-(5-methylimidazo[5,1-b][1,3,4]oxadiazol-2-yl)phenyl)acetamide (Off-white solid) | 3.57$^a$ (98.0%) | 375 (M + H)$^+$ | $^1$H NMR (400 MHz, DMSO-d$^6$): δ 9.59 (s, 1H); 7.91 (s, 1H); 7.84 (d, J = 1.30 Hz, 2H); 7.12-7.03 (m, 2H); 6.98 (d, J = 7.74 Hz, 1H); 6.50 (s, 1H); 3.76 (s, 2H); 2.45 (s, 3H); 2.34 (s, 3H); 2.27 (s, 3H); 2.26 (s, 3H). |

$^{a\text{-}f}$Rt refers to HPLC methods A to F

The following compounds were prepared using representative method F with intermediate 4 and an appropriate acid of formula (V):

| Ex No | Structure (Appareance) | HPLC Rt (% Purity) | MS | NMR |
|---|---|---|---|---|
| 77 | 2-(3,4-dichlorophenyl)-N-(4-(5-methylimidazo[5,1-b][1,3,4]oxadiazol-2-yl)phenyl)acetamide (Off-white solid) | 2.62$^a$ (96.1%) | 401 (M + H)$^+$ | $^1$H NMR (400 MHz, DMSO-d$^6$): δ 10.62 (s, 1H); 8.00 (d, J = 8.67 Hz, 2H); 7.84 (d, J = 8.67 Hz, 2H); 7.65-7.59 (m, 2H); 7.34 (dd, J = 8.28, 2.06 Hz, 1H); 6.50 (s, 1H); 3.77 (s, 2H); 2.44 (s, 3H). |
| 73 | 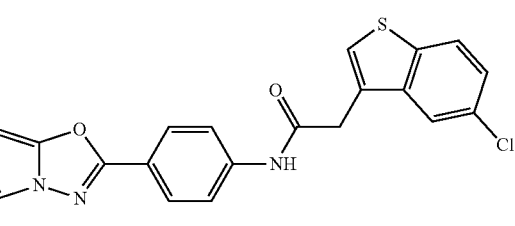<br>2-(5-chlorobenzo[b]thiophen-3-yl)-N-(4-(5-methylimidazo[5,1-b][1,3,4]oxadiazol-2-yl)phenyl)acetamide (Off-white solid) | 4.00$^a$ (95.3%) | 423 (M + H)$^+$ | $^1$H NMR (400 MHz, DMSO-d$^6$): δ 10.70 (s, 1H); 8.08-7.97 (m, 4H); 7.86 (d, J = 8.47 Hz, 2H); 7.74 (s, 1H); 7.42 (d, J = 8.65 Hz, 1H); 6.50 (s, 1H); 4.01 (s, 2H); 2.44 (s, 3H). |

| Ex No | Structure (Appearance) | HPLC Rt (% Purity) | MS | NMR |
|---|---|---|---|---|
| 71 | N-(4-(5-methylimidazo[5,1-b][1,3,4]oxadiazol-2-yl)phenyl)-2-(naphthalen-1-yl)acetamide (Off-white solid) | 3.83[a] (98.3%) | 383 (M + H)+ | $^1$H NMR (400 MHz, DMSO-d[6]): δ 10.76 (s, 1H); 8.12 (d, J = 8.29 Hz, 1H); 8.02-7.92 (m, 3H); 7.88-7.83 (m, 3H); 7.61-7.46 (m, 4H); 6.51 (s, 1H); 4.22 (s, 2H); 2.44 (s, 3H). |
| 70 | 2-(3-(benzyloxy)phenyl)-N-(4-(5-methylimidazo[5,1-b][1,3,4]oxadiazol-2-yl)phenyl)acetamide (Off-white solid) | 3.15[b] (98.1%) | 439 (M + H)+ | $^1$H NMR (400 MHz, DMSO-d[6]): δ 10.58 (s, 1H); 8.03-7.96 (m, 2H); 7.88-7.82 (m, 2H); 7.46-7.28 (m, 6H); 7.25 (t, J = 7.90 Hz, 1H); 7.02 (d, J = 2.14 Hz, 1H); 6.95-6.89 (m, 2H); 6.50 (s, 1H); 5.13-5.04 (m, 2H); 3.68 (s, 2H); 2.44 (s, 3H). |
| 69 | 2-(6-chloro-2-fluoro-3-methoxyphenyl)-N-(4-(5-methylimidazo[5,1-b][1,3,4]oxadiazol-2-yl)phenyl)acetamide (Off-white solid) | 9.85[c] (95.1%) | 415 (M + H)+ | $^1$H NMR (400 MHz, DMSO-d[6]): δ 10.72 (s, 1H); 8.03-7.97 (m, 2H); 7.86-7.80 (m, 2H); 7.29 (dd, J = 8.95, 1.75 Hz, 1H); 7.16 (t, J = 8.99 Hz, 1H); 6.51 (s, 1H); 3.94 (d, J = 2.03 Hz, 2H); 3.87 (s, 3H); 2.44 (s, 3H). |
| 68 | 2-(2,4-difluoro-3-methoxyphenyl)-N-(4-(5-methylimidazo[5,1-b][1,3,4]oxadiazol-2-yl)phenyl)acetamide (Off-white solid) | 3.38[a] (99.1%) | 399 (M + H)+ | $^1$H NMR (400 MHz, DMSO-d[6]): δ 10.64 (s, 1H); 8.02-7.98 (m, 2H); 7.87-7.81 (m, 2H); 7.17-7.08 (m, 2H); 6.50 (s, 1H); 3.92 (s, 4H); 3.80 (s, 3H); 2.44 (s, 3H). |

-continued

| Ex No | Structure (Appearance) | HPLC Rt (% Purity) | MS | NMR |
|---|---|---|---|---|
| 67 | 2-(2,6-dichloro-4-(trifluoromethyl)phenyl)-N-(4-(5-methylimidazo[5,1-b][1,3,4]oxadiazol-2-yl)phenyl)acetamide (Off-white solid) | 4.03[a] (95.7%) | 469 (M + H)+ | $^1$H NMR (400 MHz, DMSO-d$^6$): δ 10.85 (s, 1H); 8.04-7.96 (m, 4H); 7.86-7.78 (m, 2H); 6.50 (s, 1H); 4.21 (s, 2H); 2.44 (s, 3H). |
| 66 | 2-(5-fluoro-2-(trifluoromethyl)phenyl)-N-(4-(5-methylimidazo[5,1-b][1,3,4]oxadiazol-2-yl)phenyl)acetamide (White solid) | 3.88[a] (98.7%) | 419 (M + H)+ | $^1$H NMR (400 MHz, DMSO-d$^6$): δ 10.66 (s, 1H); 8.03-7.97 (m, 2H); 7.84-7.77 (m, 3H); 7.46 (dd, J = 9.81, 2.65 Hz, 1H); 7.40-7.33 (m, 1H); 6.50 (s, 1H); 4.03 (s, 2H); 2.44 (s, 3H). |
| 65 | 2-(2-chloro-4-fluorophenyl)-N-(4-(5-methylimidazo[5,1-b][1,3,4]oxadiazol-2-yl)phenyl)acetamide (Off-white solid) | 2.86[b] (99.2%) | 385 (M + H)+ | $^1$H NMR (400 MHz, DMSO-d$^6$): δ 10.66 (s, 1H); 8.03-7.97 (m, 2H); 7.87-7.81 (m, 2H); 7.53-7.43 (m, 2H); 7.23 (td, J = 8.52, 2.71 Hz, 1H); 6.52 (s, 1H); 3.91 (s, 2H); 2.45 (s, 3H). |
| 64 | 2-(3-cyanophenyl)-N-(4-(5-methylimidazo[5,1-b][1,3,4]oxadiazol-2-yl)phenyl)acetamide (Off-white solid) | 3.33[a] (99.4%) | 358 (M + H)+ | $^1$H NMR (400 MHz, DMSO-d$^6$): δ 10.65 (s, 1H); 8.02-7.98 (m, 2H); 7.89-7.79 (m, 3H); 7.76 (dt, J = 7.69, 1.44 Hz, 1H); 7.70 (d, J = 7.90 Hz, 1H); 7.57 (t, J = 7.73 Hz, 1H); 6.50 (s, 1H); 3.83 (s, 2H); 2.44 (s, 3H). |
| 63 | 2-(3-chlorophenyl)-N-(4-(5-methylimidazo[5,1-b][1,3,4]oxadiazol-2-yl)phenyl)acetamide (Off-white solid) | 10.0[c] (97.9%) | 367 (M + H)+ | $^1$H NMR (400 MHz, DMSO-d$^6$): δ 10.61 (s, 1H); 8.03-7.96 (m, 2H); 7.87-7.80 (m, 2H); 7.43 (s, 1H); 7.41-7.29 (m, 3H); 6.51 (s, 1H); 3.75 (s, 2H); 2.44 (s, 3H). |

-continued

| Ex No | Structure (Appareance) | HPLC Rt (% Purity) | MS | NMR |
|---|---|---|---|---|
| 62 | 2-(2,4-dichlorophenyl)-N-(4-(5-methylimidazo[5,1-b][1,3,4]oxadiazol-2-yl)phenyl)acetamide (Off-white solid) | 3.01[b] (98.8%) | 401 (M + H)+ | $^1$H NMR (400 MHz, DMSO-d$^6$): δ 10.67 (s, 1H); 8.04-7.98 (m, 2H); 7.87-7.81 (m, 2H); 7.63 (d, J = 2.12 Hz, 1H); 7.49 (d, J = 8.29 Hz, 1H); 7.44 (dd, J = 8.25, 2.14 Hz, 1H); 6.50 (s, 1H); 3.92 (s, 2H); 2.44 (s, 3H). |
| 61 | N-(4-(5-methylimidazo[5,1-b][1,3,4]oxadiazol-2-yl)phenyl)-2-(2,3,5-trifluorophenyl)acetamide (White solid) | 3.75[a] (98.3%) | 387 (M + H)+ | $^1$H NMR (400 MHz, DMSO-d$^6$): δ 10.70 (s, 1H); 8.05-7.97 (m, 2H); 7.87-7.79 (m, 2H); 7.51-7.42 (m, 1H); 7.22-7.17 (m, 1H); 6.50 (s, 1H); 3.90 (s, 2H); 2.44 (s, 3H). |
| 60 | N-[4-(5-Methyl-imidazo[5,1-b][1,2,4]oxadiazol-2-yl)-phenyl]-2-o-tolyl-acetamide (Off-white solid) | 2.31[b] (99.5%) | 347 (M + H)+ | $^1$H NMR (400 MHz, DMSO-d$^6$): δ 10.58 (s, 1H); 8.04-7.96 (m, 2H); 7.89-7.83 (m, 2H); 7.28-7.22 (m, 1H); 7.21-7.12 (m, 3H); 6.50 (s, 1H); 3.75 (s, 2H); 2.44 (s, 3H); 2.30 (s, 3H). |
| 57 | 2-(4-tert-Butyl-phenyl)-N-[4-(5-methyl-imidazo[5,1-b][1,2,4]oxadiazol-2-yl)-phenyl]-acetamide (Off-white solid) | 2.74[b] (99.3%) | 389 (M + H)+ | $^1$H NMR (400 MHz, DMSO-d$^6$): δ 10.57 (s, 1H); 8.01-7.96 (m, 2H); 7.88-7.82 (m, 2H); 7.38-7.33 (m, 2H); 7.27 (d, J = 8.16 Hz, 2H); 6.50 (s, 1H); 3.66 (s, 2H); 2.44 (s, 3H); 1.27 (s, 9H). |
| 56 | | 3.15[b] (91.2%) | 409 (M + H)+ | $^1$H NMR (400 MHz, DMSO-d$^6$): δ 10.69 (s, 1H); 8.00 (d, J = 8.48 Hz, 2H); 7.87 (d, J = 8.53 Hz, 2H); 7.65 (t, J = 7.91 Hz, 4H); 7.50-7.42 (m, 4H); 7.36 (t, J = 7.42 Hz, 1H); 6.50 (s, 1H); 3.76 (s, 3H); 2.44 (s, 4H). |

| Ex No | Structure (Appearance) | HPLC Rt (% Purity) | MS | NMR |
|---|---|---|---|---|
| | 2-Biphenyl-4-yl-N-[4-(5-methyl-imidazo[5,1-b][1,2,4]oxadiazol-2-yl)-phenyl]-acetamide (Off-white solid) | | | |
| 55 | N-(4-(5-methylimidazo[5,1-b][1,3,4]oxadiazol-2-yl)phenyl)-2-(3-(trifluoromethyl)phenyl)propanamide (Off-white solid) | 2.73[b] (98.9) | 415 (M + H)+ | 1H NMR (400 MHz, DMSO-d6): 10.57 (1H, s), 8.01-7.95 (2H, m), 7.87-7.81 (2H, m), 7.77-7.66 (2H, m), 7.67-7.56 (2H, m), 6.49 (1H, s), 4.02 (1H, q, J = 6.99 Hz), 2.44 (3H, s), 1.49 (3H, d, J = 6.97 Hz). |
| 53 | 2-(2-Methoxy-phenyl)-N-[4-(5-methyl-imidazo[5,1-b][1,2,4]oxadiazol-2-yl)-phenyl]-acetamide (White solid) | 3.10[a] (98.3%) | 363 (M + H)+ | 1H NMR (400 MHz, DMSO-d6): δ 10.50 (s, 1H); 8.01-7.96 (m, 2H); 7.89-7.82 (m, 2H); 7.28-7.21 (m, 2H); 6.99 (d, J = 8.16 Hz, 1H); 6.92 (td, J = 7.41, 1.12 Hz, 1H); 6.50 (s, 1H); 3.77 (s, 3H); 3.70 (s, 2H); 2.44 (s, 2H). |
| 51 | 2-(3,5-Dimethyl-phenyl)-N-[4-(5-methyl-imidazo[5,1-b][1,2,4]oxadiazol-2-yl)-phenyl]-acetamide (White solid) | 2.49[b] (98.9%) | 361 (M + H)+ | 1H NMR (400 MHz, DMSO-d6): δ 10.59 (s, 1H); 8.02 (d, J = 8.63 Hz, 2H); 7.87 (d, J = 8.65 Hz, 2H); 6.95 (s, 2H); 6.89 (s, 1H); 6.72 (s, 1H); 3.62 (s, 2H); 2.26 (s, 6H). |
| 50 | 2-(2,5-Dimethyl-phenyl)-N-[4-(5-methyl-imidazo[5,1-b][1,2,4]oxadiazol-2-yl)-phenyl]-acetamide (White solid) | 2.95[b] (99.2%) | 361 (M + H)+ | 1H NMR (400 MHz, DMSO-d6): δ 10.58 (s, 1H); 8.03-7.96 (m, 2H); 7.90-7.82 (m, 2H); 7.06 (d, J = 5.91 Hz, 1H); 7.00-6.94 (m, 1H); 6.55 (s, 1H); 3.71 (s, 2H); 2.25 (s, 6H). |

| Ex No | Structure (Appareance) | HPLC Rt (% Purity) | MS | NMR |
|---|---|---|---|---|
| 49 | 2-(4-Cyano-phenyl)-N-[4-(5-methyl-imidazo[5,1-b][1,2,4]oxadiazol-2-yl)-phenyl]-acetamide (Off-white solid) | 9.58$^c$ (97.2%) | 358 (M + H)$^+$ | $^1$H NMR (400 MHz, DMSO-d$^6$): δ 10.67 (s, 1H); 8.04-7.96 (m, 2H); 7.87-7.79 (m, 4H); 7.55 (d, J = 8.06 Hz, 2H); 6.50 (s, 1H); 3.86 (s, 2H); 2.44 (s, 3H). |
| 48 | N-[4-(5-Methyl-imidazo[5,1-b][1,2,4]oxadiazol-2-yl)-phenyl]-2-(4-trifluoromethyl-phenyl)-acetamide (Off-white solid) | 3.9$^a$ (96.9%) | 401 (M + H)$^+$ | $^1$H NMR (400 MHz, DMSO-d$^6$): δ 10.66 (s, 1H); 8.02-7.97 (m, 2H); 7.87-7.81 (m, 2H); 7.72 (d, J = 8.06 Hz, 2H); 7.58 (d, J = 8.01 Hz, 2H); 6.50 (s, 1H); 3.85 (s, 2H); 2.44 (s, 3H). |
| 47 | 2-(4-Chloro-phenyl)-N-[4-(5-methyl-imidazo[5,1-b][1,2,4]oxadiazol-2-yl)-phenyl]-acetamide (Off-white solid) | 3.8$^a$ (98.25%) | 367 (M + H)$^+$ | $^1$H NMR (400 MHz, DMSO-d$^6$): δ 10.60 (s, 1H); 8.04-7.96 (m, 2H); 7.88-7.80 (m, 2H); 7.43-7.35 (m, 4H); 6.50 (s, 1H); 3.73 (s, 2H); 2.44 (s, 3H). |

$^{a-f}$Rt refers to HPLC methods A to F

Representative Method G

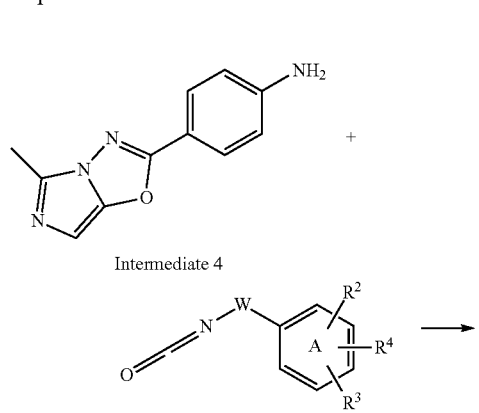

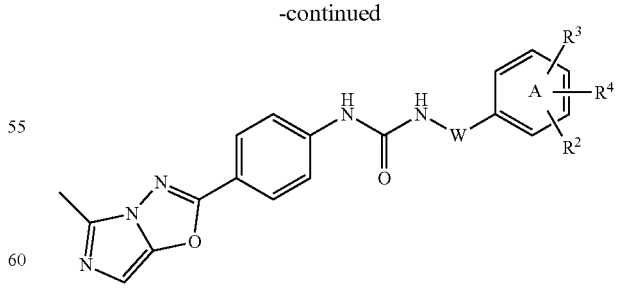

A carousel tube was charged with a solution of Intermediate 4 (0.23 mmol) in dichloromethane (4 mL) and the appropriate isocyanate (0.27 mmol) was added. After 18 hours at 60° C., the reaction mixture was concentrated in vacuo and purified by preparative HPLC.

The following compounds were prepared using representative method G with intermediate 4 and an appropriate isocyanate:

afford the 2- and 4-substituted aminopyrimidine products. As Examples: N-benzyl-4-chloropyrimidin-2-amine $^1$H NMR (400 MHz, DMSO-d$^6$): δ 8.26-8.18 (m, 2H); 7.35-

| Ex No | Structure (Appearance) | HPLC Rt (% Purity) | MS | NMR |
|---|---|---|---|---|
| 52 | 1-[4-(5-Methyl-imidazo[5,1-b][1,2,4]oxadiazol-2-yl)-phenyl]-3-(3-trifluoromethyl-phenyl)-urea (Yellow solid) | 3.00$^b$ (98.9%) | 402 (M + H)$^+$ | $^1$H NMR (400 MHz, DMSO-d$^6$): δ 9.32 (s, 1H); 9.22 (s, 1H); 8.04 (s, 1H); 7.98 (d, J = 8.51 Hz, 2H); 7.73 (d, J = 8.52 Hz, 2H); 7.61 (d, J = 8.29 Hz, 1H); 7.54 (t, J = 7.88 Hz, 1H); 7.36 (d, J = 7.58 Hz, 1H); 6.50 (s, 1H); 2.45 (s, 3H). |
| 54 | 1-(2-Chloro-benzyl)-3-[4-(5-methyl-imidazo[5,1-b][1,2,4]oxadiazol-2-yl)-phenyl]-urea (Orange solid) | 2.74$^b$ (94.1%) | 382 (M + H)$^+$ | $^1$H NMR (400 MHz, DMSO- d$^6$): δ 9.22 (s, 1H); 7.92 (d, J = 8.53 Hz, 2H); 7.65 (d, J = 8.55 Hz, 2H); 7.44 (dd, J = 17.20, 7.56 Hz, 2H); 7.39-7.27 (m, 2H); 6.89 (t, J = 6.05 Hz, 1H); 6.48 (s, 1H); 4.40 (d, J = 5.90 Hz, 2H); 2.43 (s, 3H). |
| 58 | 1-[4-(5-Methyl-imidazo[5,1-b][1,2,4]oxadiazol-2-yl)-phenyl]-3-(2-trifluoromethyl-phenyl)-urea (Orange solid) | 2.88$^b$ (97.4%) | 402 (M + H)$^+$ | $^1$H NMR (400 MHz, DMSO-d$^6$): δ 7.98 (d, J = 8.66 Hz, 2H); 7.93 (d, J = 8.31 Hz, 1H); 7.74-7.68 (m, 3H); 7.66 (t, J = 8.05 Hz, 1H); 7.36-7.28 (m, 2H); 6.50 (s, 1H); 2.44 (s, 3H). |
| 59 | 1-[4-(5-Methyl-imidazo[5,1-b][1,2,4]oxadiazol-2-yl)-phenyl]-3-(4-trifluoromethoxy-phenyl)-urea (Orange solid) | 3.08$^b$ (98.7%) | 418 (M + H)$^+$ | $^1$H NMR (400 MHz, DMSO- d$^6$): δ 9.60 (s, 1H); 9.41 (s, 1H); 8.01-7.93 (m, 2H); 7.77-7.69 (m, 2H); 7.63-7.58 (m, 2H); 7.31 (d, J = 8.61 Hz, 2H); 6.50 (s, 1H); 2.45 (s, 3H). |

$^{a-f}$Rt refers to HPLC methods A to F

Representative Method H
Step 1:

To a suspension of amine (3.35 mmol) in EtOH (5 mL) was added 2,4-dichloropyrimidine (500 mg, 3.35 mmol) and DIPEA (0.58 mL, 3.35 mmol). The reaction mixture was sonicated for 30 seconds then stirred at 25° C. After 16 hours the reaction mixture was concentrated under reduced pressure onto silica gel. The crude product was purified by chromatography (silica gel, isohexane/ethyl acetate) to 7.28 (m, 4H); 7.25-7.20 (m, 1H); 6.69 (d, J=5.15 Hz, 1H); 4.49 (s, 2H). 2-chloro-N-(2-(trifluoromethyl)benzyl)pyrimidin-4-amine $^1$H NMR (400 MHz, DMSO-d$^6$): δ 8.43 (s, 1H); 7.99 (d, J=6.04 Hz, 1H); 7.76 (d, J=7.82 Hz, 1H); 7.68 (t, J=7.65 Hz, 1H); 7.56-7.47 (m, 2H); 6.60 (d, J=5.98 Hz, 1H); 4.69 (s, 2H).
Step 2:

A carousel tube was charged with a suspension of chloropyrimidine amine (0.45 mmol) in DMF (1 mL) and a solution of Intermediate 4 (0.45 mmol) in DMF (1 mL). The reaction was gently heated until a solution formed, then p-toluenesulfonic acid (172 mg, 0.9 mmol) was added, the reaction tube was sealed and heated at 60° C. After 11 hours the reaction was cooled to 25° C. then cautiously diluted with saturated Na$_2$CO$_3$ aqueous solution. The reaction was extracted using EtOAc, the organic phases were combined and concentrated under reduced pressure. The crude product was dissolved in DMF and purified by preparative HPLC.

The following compounds were prepared using representative method H with intermediate 4 and an appropriate chloropyrimidine:

| Ex No | Structure (Appearance) | HPLC Rt (% Purity) | MS | NMR |
|---|---|---|---|---|
| 72 | 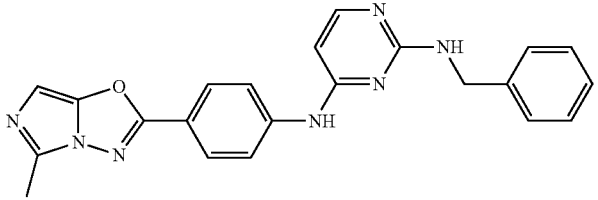<br>N2-benzyl-N4-(4-(5-methylimidazo[5,1-b][1,3,4]oxadiazol-2-yl)phenyl)pyrimidine-2,4-diamine<br>(Off-white solid) | 2.27[b] (91.4%) | 398 (M + H)+ | $^1$H NMR (400 MHz, DMSO-d$^6$): δ 9.67 (s, 1 H); 7.96 (d, J = 5.63 Hz, 1 H); 7.86 (s, 4 H); 7.56 (s, 1 H); 7.39-7.29 (m, 4 H); 7.22 (t, J = 7.11 Hz, 1 H); 6.53-6.47 (m, 1 H); 6.10 (d, J = 5.65 Hz, 1 H); 4.52 (d, J = 6.26 Hz, 2 H); 2.45 (s, 3 H). |
| 74 | 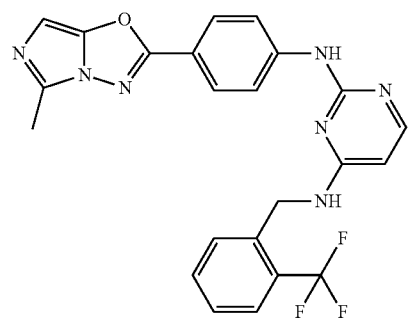<br>N2-(4-(5-methylimidazo[5,1-b][1,3,4]oxadiazol-2-yl)phenyl)-N4-(2-(trifluoromethyl)benzyl)pyrimidine-2,4-diamine<br>(Off-white solid) | 7.06[d] (93.9%) | 466 (M + H)+ | $^1$H NMR (400 MHz, DMSO-d$^6$): δ 9.61 (s, 1 H); 7.96 (d, J = 5.78 Hz, 1 H); 7.93-7.68 (m, 5 H); 7.71-7.62 (m, 1 H); 7.56 (d, J = 7.86 Hz, 1 H); 6.51-6.47 (m, 1 H); 6.22 (s, 1 H); 4.80 (s, 2 H); 2.43 (s, 3 H). |
| 75 | 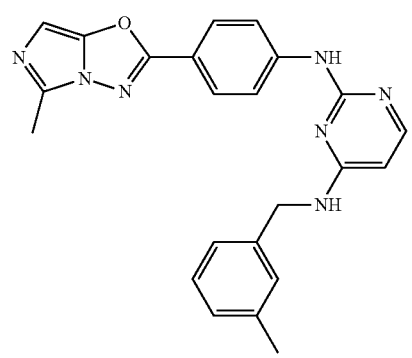<br>N4-(3-methylbenzyl)-N2-(4-(5-methylimidazo[5,1-b][1,3,4]oxadiazol-2-yl)phenyl)pyrimidine-2,4-diamine<br>(Off-white solid) | 6.97[d] (96.4%) | 412 (M + H)+ | $^1$H NMR (400 MHz, DMSO-d$^6$): δ 9.58 (s, 1 H); 7.98-7.87 (m, 6 H); 7.27-7.12 (m, 3 H); 7.07 (d, J = 7.49 Hz, 1 H); 6.48 (s, 1 H); 6.12 (s, 1 H); 4.55 (s, 2 H); 2.44 (s, 3 H); 2.31 (s, 3 H). |

| Ex No | Structure (Appareance) | HPLC Rt (% Purity) | MS | NMR |
|---|---|---|---|---|
| 76 | N2-(4-(5-methylimidazo[5,1-b][1,3,4]oxadiazol-2-yl)phenyl)-N4-(3-(trifluoromethyl)benzyl)pyrimidine-2,4-diamine (Off-white solid) | 3.36[a] (94.4%) | 466 (M + H)+ | 1H NMR (400 MHz, DMSO-d6): δ 9.60 (s, 1 H); 7.99-7.87 (m, 4 H); 7.84 (d, J = 8.54 Hz, 2 H); 7.73 (s, 1 H); 7.69 (d, J = 7.19 Hz, 1 H); 7.65-7.57 (m, 2 H); 6.48 (s, 1 H); 6.15 (d, J = 5.96 Hz, 1 H); 4.68 (s, 2 H); 2.44 (s, 3 H). |

[a-f]Rt refers to HPLC methods A to F

The following compounds were prepared using representative method F with intermediate 5 and an appropriate acid of formula (V):

| Ex No | Structure (Appareance) | HPLC Rt (% Purity) | MS | NMR |
|---|---|---|---|---|
| 78 | N-[6-(5-Methyl-imidazo[5,1-b][1,2,4]oxadiazol-2-yl)-pyridin-3-yl]-2-(4-phenoxy-phenyl)-acetamide (Off-white solid) | 3.73[a] (99.3%) | 426 (M + H)+ | 1H NMR (400 MHz, DMSO-d6): δ 10.83 (s, 1 H); 8.95 (d, J = 2.45 Hz, 1 H); 8.35 (dd, J = 8.71, 2.49 Hz, 1 H); 8.16 (d, J = 8.69 Hz, 1 H); 7.43-7.35 (m, 4 H); 7.17-7.11 (m, 1 H); 7.02-6.97 (m, 4 H); 6.53 (s, 1 H); 3.75 (s, 2 H); 2.46 (s, 3 H). |
| 79 | 2-(2,3-Difluoro-phenyl)-N-[6-(5-methyl-imidazo[5,1-b][1,2,4]oxadiazol-2-yl)-pyridin-3-yl]-acetamide (Off-white solid) | 2.63[b] (97.8%) | 370 (M + H)+ | 1H NMR (400 MHz, DMSO-d6): δ 10.92 (s, 1 H); 8.94 (d, J = 2.48 Hz, 1 H); 8.32 (dd, J = 8.70, 2.51 Hz, 1 H); 8.16 (d, J = 8.69 Hz, 1 H); 7.41-7.33 (m, 1 H); 7.28-7.16 (m, 2 H); 6.53 (s, 1 H); 3.93 (s, 2 H); 2.46 (s, 3 H). |

| Ex No | Structure (Appearance) | HPLC Rt (% Purity) | MS | NMR |
|---|---|---|---|---|
| 80 | 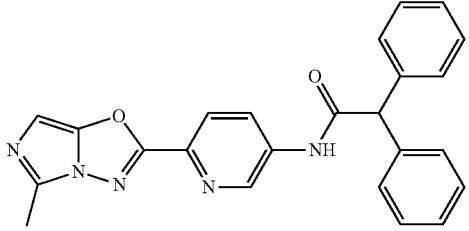<br>N-[6-(5-Methyl-imidazo[5,1-b][1,2,4]oxadiazol-2-yl)-pyridin-3-yl]-2,2-diphenyl-acetamide<br>(Off-white solid) | 3.75[a] (98.3%) | 410 (M + H)+ | 1H NMR (400 MHz, DMSO-d6): δ 11.06 (s, 1 H); 8.95 (d, J = 2.46 Hz, 1 H); 8.38 (dd, J = 8.71, 2.50 Hz, 1 H); 8.15 (d, J = 8.70 Hz, 1 H); 7.40-7.24 (m, 10 H); 6.53 (s, 1 H); 5.26 (s, 1 H); 2.46 (s, 3 H). |
| 81 | 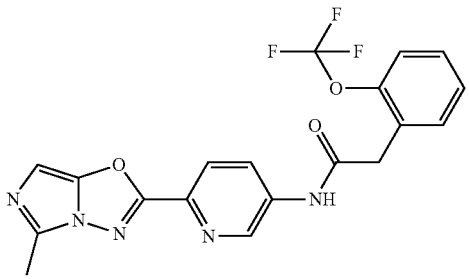<br>N-[6-(5-Methyl-imidazo[5,1-b][1,2,4]oxadiazol-2-yl)-pyridin-3-yl]-2-(2-trifluoromethoxy-phenyl)-acetamide<br>(Off-white solid) | 2.78[b] (99.4%) | 418 (M + H)+ | 1H NMR (400 MHz, DMSO-d6): δ 10.89 (s, 1 H); 8.93 (d, J = 2.45 Hz, 1 H); 8.32 (dd, J = 8.70, 2.48 Hz, 1 H); 8.16 (d, J = 8.69 Hz, 1 H); 7.54-7.49 (m, 1 H); 7.48-7.36 (m, 3 H); 6.53 (s, 1 H); 3.90 (s, 2 H); 2.46 (s, 3 H). |
| 82 | 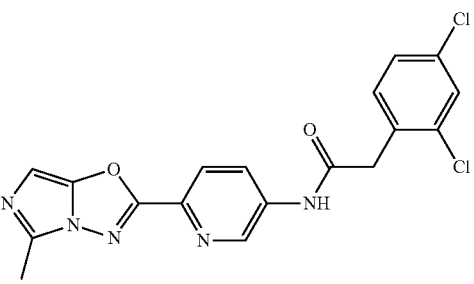<br>2-(2,4-Dichloro-phenyl)-N-[6-(5-methyl-imidazo[5,1-b][1,2,4]oxadiazol-2-yl)-pyridin-3-yl]-acetamide<br>(Off-white solid) | 2.85[b] (98.9%) | 402 (M + H)+ | 1H NMR (400 MHz, DMSO-d6): δ 10.89 (s, 1 H); 8.93 (d, J = 2.45 Hz, 1 H); 8.32 (dd, J = 8.70, 2.48 Hz, 1 H); 8.16 (d, J = 8.69 Hz, 1 H); 7.54-7.49 (m, 1 H); 7.48-7.36 (m, 2 H); 6.53 (s, 1 H); 3.90 (s, 2 H); 2.46 (s, 3 H). |
| 83 | 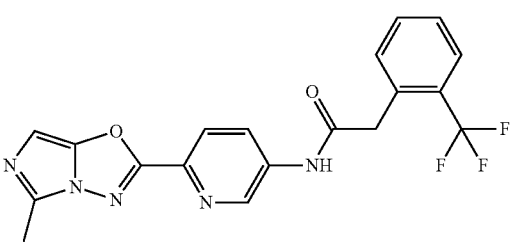<br>N-[6-(5-Methyl-imidazo[5,1-b][1,2,4]oxadiazol-2-yl)-pyridin-3-yl]-2-(2-trifluoromethyl-phenyl)-acetamide<br>(White solid) | 3.45[a] (99.6%) | 402 (M + H)+ | 1H NMR (400 MHz, DMSO-d6): δ 10.88 (s, 1 H); 8.94 (d, J = 2.45 Hz, 1 H); 8.30 (dd, J = 8.71, 2.49 Hz, 1 H); 8.16 (d, J = 8.69 Hz, 1 H); 7.74 (d, J = 7.87 Hz, 1 H); 7.68 (t, J = 7.60 Hz, 1 H); 7.59-7.49 (m, 2 H); 6.53 (s, 1 H); 4.04 (s, 2 H); 2.46 (s, 3 H). |

| Ex No | Structure (Appearance) | HPLC Rt (% Purity) | MS | NMR |
|---|---|---|---|---|
| 84 | 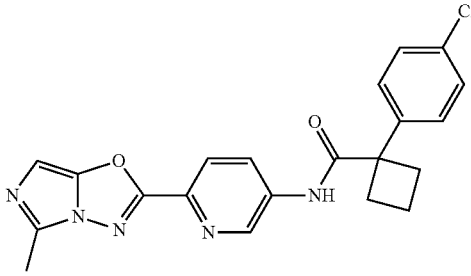<br>1-(4-Chloro-phenyl)-cyclobutanecarboxylic acid [6-(5-methyl-imidazo[5,1-b][1,2,4]oxadiazol-2-yl)-pyridin-3-yl]amide<br>(Brown solid) | 10.2[e] (96.3%) | 408 (M + H)[+] | $^1$H NMR (400 MHz, DMSO-d$^6$): δ 10.07 (s, 1 H); 8.97 (d, J = 2.44 Hz, 1 H); 8.36 (dd, J = 8.73, 2.49 Hz, 1 H); 8.13 (d, J = 8.73 Hz, 1 H); 7.53-7.41 (m, 4 H); 6.52 (s, 1 H); 2.88 (dt, J = 11.49, 7.70 Hz, 2 H); 2.57-2.42 (m, 2 H); 2.45 (s, 3 H); 1.93-1.80 (m, 2 H). |
| 85 | 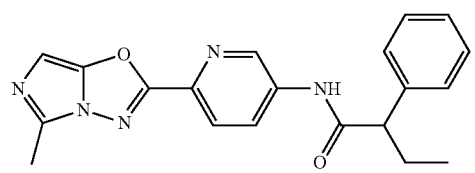<br>N-[6-(5-Methyl-imidazo[5,1-b][1,2,4]oxadiazol-2-yl)-pyridin-3-yl]-2-phenyl-butyramide<br>(White solid) | 3.17[a] (99.0)% | 362 (M + H)[+] | $^1$H NMR (400 MHz, DMSO-d$^6$): δ 10.74 (s, 1 H); 8.92 (d, J = 2.48 Hz, 1 H); 8.36 (dd, J = 8.71, 2.51 Hz, 1 H); 8.14 (d, J = 8.70 Hz, 1 H); 7.44-7.37 (m, 2 H); 7.36 (t, J = 7.50 Hz, 2 H); 7.29-7.24 (m, 1 H); 6.52 (s, 1 H); 3.65 (t, J = 7.55 Hz, 1 H); 2.12-2.06 (m, 1 H); 1.79-1.73 (m, 1 H); 0.88 (t, J = 7.29 Hz, 3 H). |

[a-f]Rt refers to HPLC methods A to F

Representative Method I

To a suspension of bis(trimethylaluminum)-1,4-diazabicyclo(2.2.2)octane adduct (DABAL-Me$_3$, 115 mg, 0.45 mmol) in THF (3 mL) in a carousel tube, was added an appropriate amine of formula (III) (0.45 mmol), the reaction was heated at 40° C. for 45 minutes. Ester derivative (0.3 mmol) was added and the reaction was flushed with nitrogen, sealed and heated to 70° C. After 16 hours the reaction was cooled to 25° C., quenched with dilute aqueous HCl solution (2 mL) and then stirred for 20 minutes. The organic phase was collected and the aqueous phase was extracted with EtOAc. The organic fractions were dried (MgSO$_4$), filtered over silica and concentrated under reduced pressure. The residue was dissolved in DMSO and purified by reverse phase preparative HPLC.

The following compounds were prepared using representative method I with intermediate 6 and an appropriate amine of formula (III).

| Ex No | Structure (Appearance) | HPLC Rt (% Purity) | MS | NMR |
|---|---|---|---|---|
| 86 | 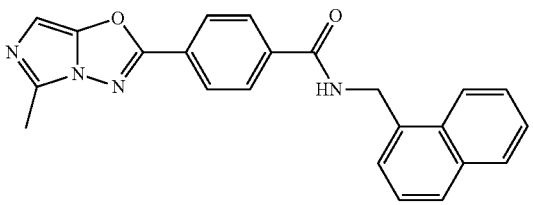<br>4-(5-methylimidazo[5,1-b][1,2,4]oxadiazol-2-yl)-N-(naphthalen-1-ylmethyl)benzamide<br>(Yellow solid) | 3.72[a] (97.3%) | 383 (M + H)[+] | $^1$H NMR (400 MHz, DMSO-d$^6$): δ 9.33 (t, J = 5.70 Hz, 1 H); 8.22-8.10 (m, 5 H); 8.00-7.94 (m, 1 H); 7.88 (d, J = 7.70 Hz, 1 H); 7.64-7.48 (m, 4 H); 6.55 (s, 1 H); 4.99 (d, J = 5.64 Hz, 2 H); 2.47 (s, 3 H). |

| Ex No | Structure (Appearance) | HPLC Rt (% Purity) | MS | NMR |
|---|---|---|---|---|
| 87 | 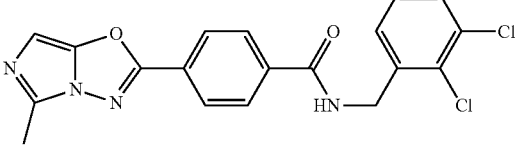<br>N-(2,3-dichlorobenzyl)-4-(5-methylimidazol[5,1-b][1,3,4]oxadiazol-2-yl)benzamide<br>(Off-white solid) | 3.02$^b$ (97.3%) | 401 (M + H)$^+$ | $^1$H NMR (400 MHz, DMSO-d$^6$): δ 9.35 (t, J = 5.74 Hz, 1 H); 8.22-8.10 (m, 4 H); 7.62-7.56 (m, 1 H); 7.40-7.34 (m, 2 H); 6.56 (s, 1 H); 4.61 (d, J = 5.68 Hz, 2 H); 2.48 (s, 3 H). |
| 88 | 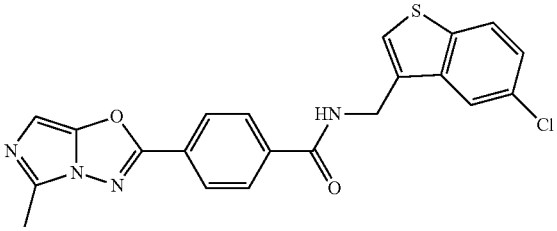<br>N-((5-chlorobenzo[b]thiophen-3-yl)methyl)-4-(5-methylimidazo[5,1-b][1,3,4]oxadiazol-2-yl)benzamide<br>(Yellow solid) | 8.25$^d$ (94.7%) | 423 (M + H)$^+$ | $^1$H NMR (400 MHz, DMSO-d$^6$): δ 9.34 (t, J = 5.80 Hz, 1 H); 8.18-8.01 (m, 6 H); 7.75 (s, 1 H); 7.42 (dd, J = 8.57, 2.10 Hz, 1 H); 6.55 (s, 1 H); 4.73 (d, J = 5.74 Hz, 2 H); 2.47 (s, 3 H). |

$^{a-f}$Rt refers to HPLC methods A to F

The following compounds were prepared using representative method E with intermediate 10 and an appropriate amine of formula (III).

| Ex No | Structure (Appearance) | HPLC Rt (% Purity) | MS | NMR |
|---|---|---|---|---|
| 29 | 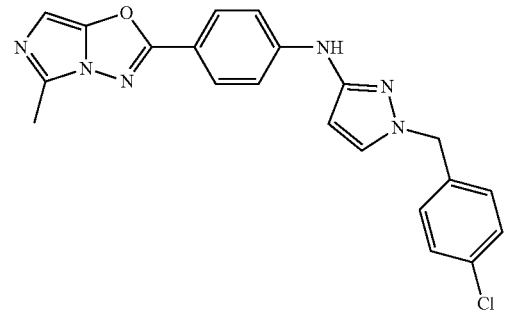<br>[1-(4-Chloro-benzyl)-1H-pyrazol-3-yl]-[4-(5-methyl-imidazo[5,1-b][1,2,4]oxadiazol-2-yl)-phenyl]-amine<br>(Yellow solid) | 2.98$^b$ (97.9%) | 405 (M + H)$^+$ | $^1$H NMR (400 MHz, DMSO-d$^6$): δ 9.27 (s, 1 H); 7.85 (d, J = 8.74 Hz, 2 H); 7.78 (d, J = 2.31 Hz, 1 H); 7.50-7.39 (m, 4 H); 7.28 (d, J = 8.28 Hz, 2 H); 6.46 (s, 1 H); 5.97 (d, J = 2.31 Hz, 1 H); 5.27 (s, 2 H); 2.43 (s, 3 H). |

| Ex No | Structure (Appareance) | HPLC Rt (% Purity) | MS | NMR |
|---|---|---|---|---|
| 30 | 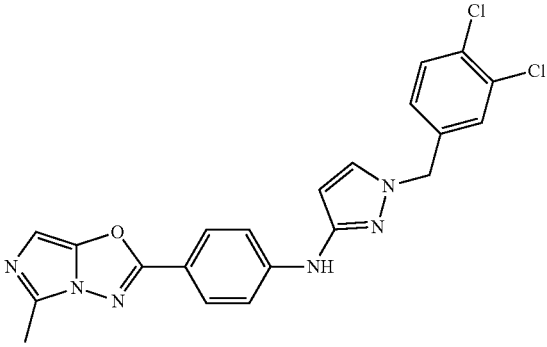[1-(3,4-Dichloro-benzyl)-1H-pyrazol-3-yl]-[4-(5-methyl-imidazo[5,1-b][1,2,4]oxadiazol-2-yl)-phenyl]-amine (Yellow solid) | 3.13[b] (98.5%) | 439 (M + H)[+] | $^1$H NMR (400 MHz, DMSO-d$^6$): δ 9.29 (s, 1 H); 7.87-7.78 (m, 3 H); 7.67-7.60 (m, 1 H); 7.55-7.44 (m, 3 H); 7.24 (dd, J = 8.30, 2.08 Hz, 1 H); 6.46 (s, 1 H); 5.99 (d, J = 2.33 Hz, 1 H); 5.29 (s, 2 H); 2.43 (s, 3 H). |

[a-f]Rt refers to HPLC methods A to F

Representative Method J

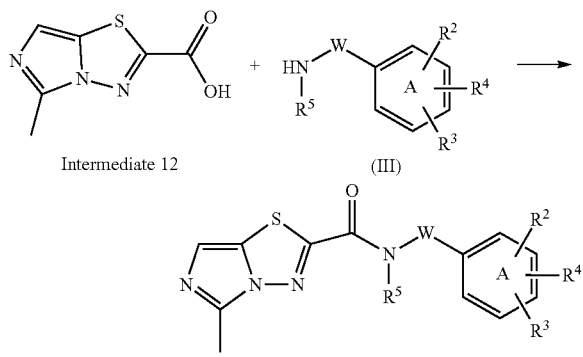

An appropriate amine of formula (III) (0.4 mmol) was dissolved in DCM (3 mL) and diisopropylethylamine (0.174 mL, 1 mmol). Intermediate 12, hydrochloride salt (80 mg, 0.36 mmol) was added and the reaction was left to stir for approximately 15 minutes until all the reagents were in solution. HATU (152 mg, 0.4 mmol) was added and the reaction was left to stir at 25° C. for 6 h. The DCM solution was then extracted with saturated aqueous sodium bicarbonate solution, dried (MgSO$_4$), filtered and concentrated in vacuo. The crude residue was then purified by reverse-phase preparative HPLC.

The following compounds were prepared using representative method J with intermediate 12 and an appropriate amine of formula (III):

| Ex No | Structure (Appareance) | HPLC Rt (% Purity) | MS | NMR |
|---|---|---|---|---|
| 105 | 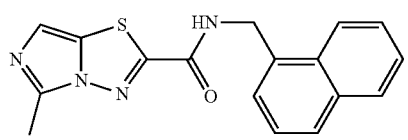5-methyl-N-(naphthalen-1-ylmethyl)imidazo[5,1-b][1,3,4]thiadiazole-2-carboxamide (Yellow solid) | 3.07[b] (98.8%) | 323 (M + H)[+] | $^1$H NMR (400 MHz, CHCl$_3$-d): δ 8.06 (d, J = 8.28 Hz, 1 H); 7.95-7.86 (m, 2 H); 7.63-7.53 (m, 3 H); 7.53-7.47 (m, 1 H); 7.17 (s, 1 H); 6.96 (s, 1 H); 5.13 (d, J = 5.65 Hz, 2 H); 2.59 (s, 3 H). |

-continued

| Ex No | Structure (Appearance) | HPLC Rt (% Purity) | MS | NMR |
|---|---|---|---|---|
| 106 | 5-Methyl-imidazo[5,1-b][1,3,4]thiadiazole-2-carboxylic acid 4-(4-fluoro-phenoxy)-benzylamide (Yellow solid) | 3.37[b] (98.7%) | 383 (M + H)+ | $^1$H NMR (400 MHz, DMSO-$d^6$): δ 9.78 (t, J = 6.21 Hz, 1 H); 7.35 (d, J = 8.41 Hz, 2 H); 7.23-7.16 (m, 2 H); 7.07-6.93 (m, 4 H); 4.43 (d, J = 6.21 Hz, 2 H); 2.59 (s, 3 H). |
| 107 | 5-Methyl-imidazo[5,1-b][1,3,4]thiadiazole-2-carboxylic acid 4-phenoxy-benzylamide (Yellow solid) | 3.39[a] (96.3%) | 365 (M + H)+ | $^1$H NMR (400 MHz, DMSO-$d^6$): δ 9.77 (t, J = 6.20 Hz, 1 H); 7.37 (t, J = 8.11 Hz, 4 H); 7.13-7.08 (m, 1 H); 7.01-6.95 (m, 5 H); 4.44 (d, J = 6.21 Hz, 2 H); 2.58 (s, 3 H). |
| 108 | (5-Methyl-imidazo[5,1-b][1,3,4]thiadiazol-2-yl)-(2-phenyl-piperidin-1-yl)-methanone (Yellow oil) | 3.39[a] (99.7%) | 327 (M + H)+ | $^1$H NMR (400 MHz, DMSO-$d^6$): δ 7.42 (t, J = 7.54 Hz, 2 H); 7.36-7.25 (m, 3 H); 7.00 (d, J = 19.64 Hz, 1 H); 6.05 (s, 0.39 H); 5.81 (s, 0.61 H); 4.67 (d, J = 13.67 Hz, 0.61 H); 4.42 (s, 0.39 H); 3.27-3.00 (m, 1 H); 2.81 (s, 1 H); 2.70-2.30 (m, 3 H); 2.18-1.86 (m, 2 H); 1.84-1.34 (m, 3 H). |
| 109 | [3-(4-Fluoro-phenyl)-piperidin-1-yl]-(5-methyl-imidazo[5,1-b][1,3,4]thiadiazol-2-yl)-methanone (Brown solid) | 3.35[a] (97.2%) | 345 (M + H)+ | $^1$H NMR (400 MHz, DMSO-$d^6$): δ 8.19 (s, 1 H); 7.43 (dd, J = 8.36, 5.51 Hz, 2 H); 7.23 (td, J = 8.77, 2.72 Hz, 2 H); 7.01 (d, J = 7.38 Hz, 1 H); 4.85 (d, J = 13.18 Hz, 0.5 H); 4.51 (dd, J = 26.74, 12.52 Hz, 0.5 H); 3.11-2.96 (m, 2 H); 2.63 (s, 0.5 H); 2.57-2.54 (m, 2, 5H); 2.04-1.85 (m, 3 H). |

-continued

| Ex No | Structure (Appearance) | HPLC Rt (% Purity) | MS | NMR |
|---|---|---|---|---|
| 110 | 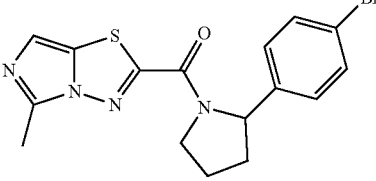<br>[2-(4-Bromo-phenyl)-pyrrolidin-1-yl]-(5-methyl-imidazo[5,1-b][1,3,4]thiadiazol-2-yl)-methanone<br>(Yellow solid) | 3.25[b]<br>(99.8%) | 391<br>(M + H)+ | $^1$H NMR (400 MHz, DMSO-d$^6$): δ 7.56-7.46 (m, 2 H); 7.23 (dd, J = 12.02, 8.33 Hz, 2 H); 7.07 (s, 0.58 H); 6.95 (s, 0.42 H); 5.87 (d, J = 7.93 Hz, 0.42 H); 5.21 (dd, J = 7.89, 4.46 Hz, 0.58 H); 4.34-4.16 (m, 1 H); 3.97-3.89 (m, 0.42 H); 3.82-3.71 (m, 0.58 H); 2.65 (s, 1.74 H); 2.55-2.22 (m, 1.76 H); 2.04-1.74 (m, 2.5 H). |
| 111 | 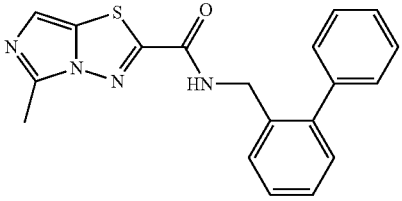<br>5-Methyl-imidazo[5,1-b][1,3,4]thiadiazole-2-carboxylic acid (biphenyl-2-ylmethyl)-amide<br>(Yellow solid) | 2.79[a]<br>(94.4%) | 349<br>(M + H)+ | $^1$H NMR (400 MHz, DMSO-d$^6$): δ 9.65 (t, J = 6.00 Hz, 1 H); 7.47-7.30 (m, 8 H); 7.22 (dd, J = 7.16, 1.85 Hz, 1 H); 6.96 (s, 1 H); 4.42 (d, J = 5.97 Hz, 2 H); 2.58 (s, 3 H). |
| 112 | 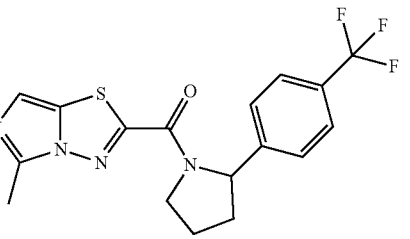<br>(5-Methyl-imidazo[5,1-b][1,3,4]thiadiazol-2-yl)-[2-(4-trifluoromethyl-phenyl)-pyrrolidin-1-yl]-methanone<br>(Yellow solid) | 8.53[d]<br>(98.5%) | 381<br>(M + H)+ | $^1$H NMR (400 MHz, CHCl$_3$-d): δ 7.61 (dd, J = 8.02, 4.65 Hz, 2 H); 7.34 (dd, J = 21.64, 8.06 Hz, 2 H); 6.97 (s, 0.54 H); 6.90-6.85 (m, 0.46 H); 6.04 (d, J = 8.04 Hz, 0.46 H); 5.41 (dd, J = 8.06, 4.36 Hz, 0.54 H); 4.46-4.29 (m, 1 H); 4.11-4.03 (m, 0.5 H); 3.95 (ddd, J = 12.90, 9.86, 7.30 Hz, 0.5 H); 2.73 (s, 1.62 H); 2.60-2.41 (m, 0.5 H); 2.40 (s, 1.38 H); 2.26-1.93 (m, 2.5 H). Restricted rotation |
| 113 | 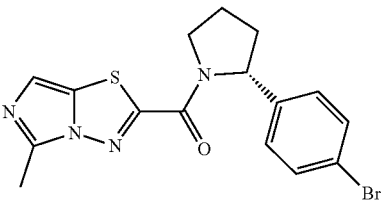<br>(R)-(2-(4-bromophenyl)pyrrolidin-1-yl)(5-methylimidazo[5,1-b][1,3,4]thiadiazol-2-yl)methanone<br>(Yellow solid) | 3.80[a]<br>(99.7%) | 391<br>(M + H)+ | $^1$H NMR (400 MHz, CHCl$_3$-d): δ 7.44 (t, J = 8.75 Hz, 2 H); 7.12 (d, J = 8.16 Hz, 1 H); 7.04 (d, J = 8.14 Hz, 1 H); 6.94 (s, 0.5 H); 6.85 (s, 0.5 H); 5.93 (d, J = 7.84 Hz, 0.5 H); 5.30 (dd, J = 7.93, 4.30 Hz, 0.5 H); 4.38-4.25 (m, 1 H); 4.06-3.98 (m, 0.5 H); 3.93-3.86 (m, 0.5 H); 2.71 (s, 1.5 H); 2.54-2.30 (m, 2 H); 2.18-1.89 (m, 2.5 H). Presence of rotamers |

-continued

| Ex No | Structure (Appearance) | HPLC Rt (% Purity) | MS | NMR |
|---|---|---|---|---|
| 114 | 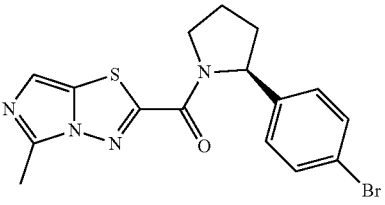<br>(S)-(2-(4-bromophenyl)pyrrolidin-1-yl)(5-methylimidazo[5,1-b][1,3,4]thiadiazol-2-yl)methanone<br>(Yellow solid) | 3.82$^a$ (99.7%) | 391 (M + H)$^+$ | $^1$H NMR (400 MHz, CHCl$_3$-d): δ 7.44 (t, J = 8.75 Hz, 2 H); 7.12 (d, J = 8.16 Hz, 1 H); 7.04 (d, J = 8.14 Hz, 1 H); 6.94 (s, 0.5 H); 6.85 (s, 0.5 H); 5.93 (d, J = 7.84 Hz, 0.5 H); 5.30 (dd, J = 7.93, 4.30 Hz, 0.5 H); 4.38-4.25 (m, 1 H); 4.06-3.98 (m, 0.5 H); 3.93-3.86 (m, 0.5 H); 2.71 (s, 1.5 H); 2.54-2.30 (m, 2 H); 2.18-1.89 (m, 2.5 H). Presence of rotamers |
| 115 | 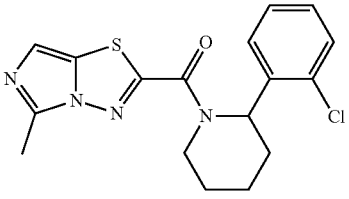<br>[2-(2-Chloro-phenyl)-piperidin-1-yl]-(5-methyl-imidazo[5,1-b][1,3,4]thiadiazol-2-yl)-methanone<br>(Yellow oil) | 3.66$^a$ (98.3%) | 361 (M + H)$^+$ | $^1$H NMR (400 MHz, DMSO-d$^6$): δ 7.50-7.40 (m, 2 H); 7.36-7.25 (m, 2 H); 6.88 (s, 1 H); 6.10 (s, 0.5 H); 5.63-5.53 (m, 0.5 H); 4.74 (s, 0.5 H); 4.53 (s, 0.5 H); 3.75 (s, 1 H); 2.39 (s, 2 H); 2.10 (s, 1 H); 1.99-1.42 (m, 5 H); |
| 116 | 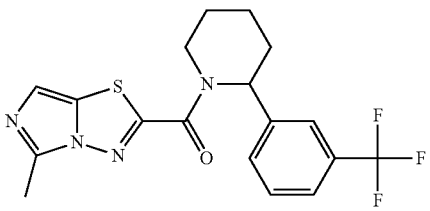<br>(5-Methyl-imidazo[5,1-b][1,3,4]thiadiazol-2-yl)-[2-(3-trifluoromethyl-phenyl)-piperidin-1-yl]-methanone<br>(Yellow oil) | 3.65$^a$ (99.0%) | 395 (M + H)$^+$ | $^1$H NMR (400 MHz, DMSO-d$^6$): δ 7.65 (s, 4 H); 6.97 (s, 0.5 H); 6.51 (s, 0.5 H); 6.05 (s, 0.5 H); 5.82 (s, 0.5 H); 4.68 (s, 0.5 H); 4.43 (s, 0.5 H); 3.10 (s, 0.5 H); 2.81 (s, 0.5 H); 2.57 (s, 2 H); 2.32 (s, 1 H); 1.99 (s, 1 H); 1.83-1.27 (m, 4 H). |
| 117 | 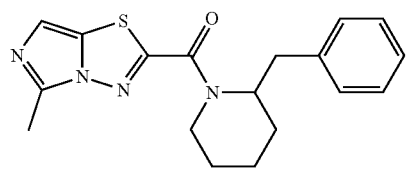<br>(2-Benzyl-piperidin-1-yl)-(5-methyl-imidazo[5,1-b][1,3,4]thiadiazol-2-yl)-methanone<br>(Yellow oil) | 3.12$^b$ (98.9%) | 341 (M + H)$^+$ | $^1$H NMR (400 MHz, DMSO-d$^6$): δ 7.39-7.09 (m, 5 H); 6.90 (d, J = 9.28 Hz, 1 H); 5.20 (s, 0.63 H); 4.84 (s, 0.37 H); 4.48 (d, J = 13.64 Hz, 0.37 H); 4.35 (d, J = 13.42 Hz, 0.63 H); 3.17 (d, J = 18.18 Hz, 2 H); 2.97 (dd, J = 13.35, 7.55 Hz, 1H); 2.57 (s, 2 H); 2.53 (s, 1 H); 1.90-1.39 (m, 5 H). |

| Ex No | Structure (Appearance) | HPLC Rt (% Purity) | MS | NMR |
|---|---|---|---|---|
| 118 | 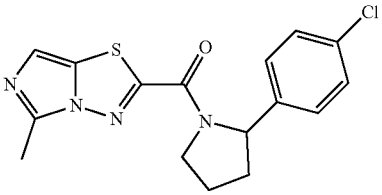<br>[2-(4-Chloro-phenyl)-pyrrolidin-1-yl]-(5-methyl-imidazo[5,1-b][1,3,4]thiadiazol-2-yl)-methanone<br>(Yellow solid) | 3.13[b]<br>(99.9%) | 347<br>(M + H)+ | $^1$H NMR (400 MHz, CHCl$_3$-d): δ 7.34-7.22 (m, 2 H); 7.17 (d, J = 8.27 Hz, 1 H); 7.10 (d, J = 8.24 Hz, 1 H); 6.94 (s, 0.5H H); 6.85 (s, 0.5 H); 5.95 (d, J = 7.81 Hz, 0.5 H); 5.32 (dd, J = 7.93, 4.29 Hz, 0.5 H); 4.41-4.25 (m, 0.5 H); 4.06-3.98 (m, 0.5 H); 3.94-3.85 (m, 0.5 H); 2.71 (s, 1.5 H); 2.54-2.29 (m, 2 H); 2.20-1.89 (m, 2.5 H).<br>Restricted rotation |
| 119 | 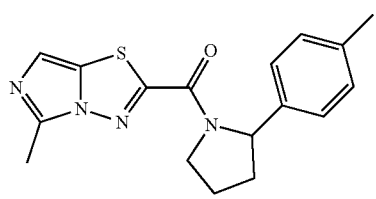<br>(5-Methyl-imidazo[5,1-b][1,3,4]thiadiazol-2-yl)-(2-p-tolyl-pyrrolidin-1-yl)-methanone<br>(Yellow solid) | 3.08[a]<br>(98.1%) | 327<br>(M + H)+ | $^1$H NMR (400 MHz, CHCl$_3$-d): δ 7.19-6.99 (m, 4 H); 6.93 (s, 0.5 H); 6.88-6.80 (m, 0.5 H); 5.95 (d, J = 7.89 Hz, 0.5 H); 5.33 (dd, J = 7.91, 4.10 Hz, 0.5 H); 4.40-4.23 (m, 0.5 H); 4.07-3.99 (m, 0.5 H); 3.93-3.83 (m, 0.5 H); 2.71 (s, 1.5 H); 2.47 (s, 1.5 H); 2.52-2.28 (m, 1.5 H); 2.32 (s, 1.5 H); 2.29 (s, 1.5 H); 2.32-2.12 (m, 0.5 H); 2.11-1.92 (m, 2.5 H). |
| 120 | 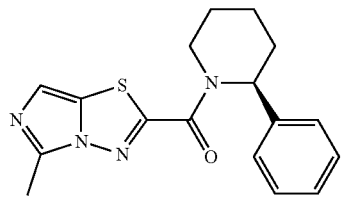<br>(5-Methyl-imidazo[5,1-b][1,3,4]thiadiazol-2-yl)-((S)-2-phenyl-piperidin-1-yl)-methanone<br>(Green oil) | 3.82[a]<br>(99.9%) | 327<br>(M + H)+ | $^1$H NMR (400 MHz, CHCl$_3$-d): 7.44 (2 H, t, J = 8.75 Hz), 7.12 (1 H, d, J = 8.16 Hz), 7.04 (1 H, d, J = 8.14 Hz), 6.94 (0.5 H, s), 6.85 (0.5 H, s), 5.93 (0.5 H, d, J = 7.84 Hz), 5.30 (0.5 H, dd, J = 7.93, 4.30 Hz), 4.38-4.25 (1 H, m), 3.93-3.86 (1 H, m), 2.71 (1.5 H, s), 2.54-2.30 (2.5 H, m), 2.18-1.89 (3 H, m). |
| 121 | 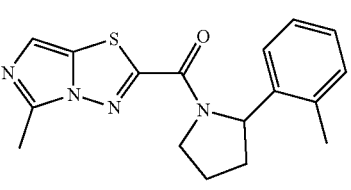<br>(5-Methyl-imidazo[5,1-b][1,3,4]thiadiazol-2-yl)-(2-o-tolyl-pyrrolidin-1-yl)-methanone<br>(Yellow solid) | 3.00[b]<br>(97.9%) | 327<br>(M + H)+ | $^1$H NMR (400 MHz, CHCl$_3$-d): δ 7.21-7.09 (m, 3 H); 7.04 (dd, J = 8.73, 5.04 Hz, 0.32 H); 6.97-6.93 (m, 1 H); 6.84 (s, 0.68 H); 6.07 (d, J = 8.01 Hz, 0.68 H); 5.55 (dd, J = 8.05, 3.86 Hz, 0.32 H); 4.47 (ddd, J = 11.92, 7.80, 4.83 Hz, 0.32 H); 4.35-4.28 (m, 0.32 H); 4.16-4.08 (m, 0.68 H); 3.96-3.86 (m, 0.68 H); 2.72 (s, 1 H); 2.50-2.38 (m, 5.5 H); 2.14-1.94 (m, 2.5 H). |

| Ex No | Structure (Appearance) | HPLC Rt (% Purity) | MS | NMR |
|---|---|---|---|---|
| 122 | 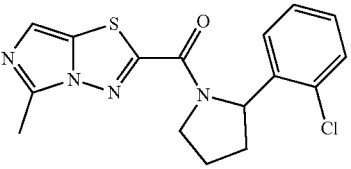<br>[2-(2-Chloro-phenyl)-pyrrolidin-1-yl]-(5-methyl-imidazo[5,1-b][1,3,4]thiadiazol-2-yl)-methanone<br>(Yellow solid) | 3.13[b]<br>(97.9%) | 347<br>(M + H)+ | $^1$H NMR (400 MHz, CHCl$_3$-d): δ 7.45-7.39 (m, 1 H); 7.32-7.10 (m, 2 H); 7.14-7.10 (m, 0.77 H); 7.09-7.01 (m, 1 H); 6.97 (s, 0.23 H); 6.86 (s, 0.77 H); 6.26 (d, J = 8.06 Hz, 0.77 H); 5.70 (dd, J = 8.11, 3.90 Hz, 0.23 H); 4.46 (dd, J = 12.03, 6.13 Hz, 0.23 H); 4.33-4.28 (m, 0.23 H); 4.15-4.06 (m, 0.77 H); 3.93 (ddd, J = 12.92, 10.29, 7.32 Hz, 0.77 H); 2.72 (s, 0.7H) 2.64-2.37 (m, 2.8 H); 2.16-1.89 (m, 2.5 H). |
| 123 | 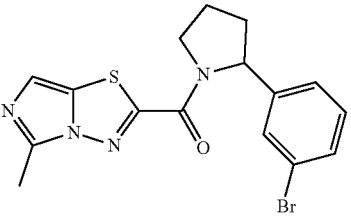<br>[2-(3-Bromo-phenyl)-pyrrolidin-1-yl]-(5-methyl-imidazo[5,1-b][1,3,4]thiadiazol-2-yl)-methanone<br>(Yellow solid) | 3.43[a]<br>(97.7%) | 391<br>(M + H)+ | $^1$H NMR (400 MHz, CHCl$_3$-d): δ 7.41 (dd, J = 7.74, 1.46 Hz, 0.5 H); 7.37 (d, J = 7.16 Hz, 2 H); 7.21 (dt, J = 13.03, 7.66 Hz, 2 H); 7.10 (d, J = 7.78 Hz, 0.5 H); 6.97 (s, 0.5 H); 6.87 (s, 0.5 H); 5.92 (d, J = 7.92 Hz, 0.5 H); 5.33 (dd, J = 7.92, 4.12 Hz, 0.5 H); 4.42-4.36 (m, 0.5 H); 4.35-4.29 (m, 0.5 H); 4.06 (dd, J = 13.22, 6.50 Hz, 0.5 H); 3.98-3.90 (m, 0.5 H); 2.73 (s, 1.5 H); 2.56-2.36 (m, 2 H); 2.22-1.94 (m, 2.5 H). |
| 124 | 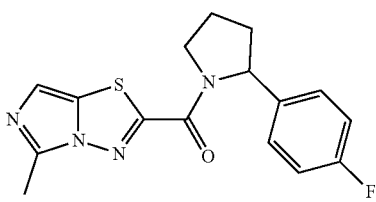<br>[2-(4-Fluoro-phenyl)-pyrrolidin-1-yl]-(5-methyl-imidazo[5,1-b][1,3,4]thiadiazol-2-yl)-methanone<br>(Yellow solid) | 7.93[d]<br>(98.6%) | 331<br>(M + H)+ | $^1$H NMR (400 MHz, CHCl$_3$-d): δ 7.27-7.19 (m, 1 H); 7.19-7.11 (m, 1 H); 7.09-6.97 (m, 2 H); 6.97 (s, 0.5 H); 6.88 (s, 0.5 H); 5.97 (d, J = 7.79 Hz, 0.5 H); 5.36 (dd, J = 7.88, 4.25 Hz, 0.5 H); 4.43-4.27 (m, 1 H); 4.08-4.00 (m, 0.5 H); 3.96-3.87 (m, 0.5 H); 2.73 (s, 1.5 H); 2.54-2.31 (m, 2 H); 2.25-1.93 (m, 3 H). |

[a-f]Rt refers to HPLC methods A to F

The following compounds were prepared using representative method F with intermediate 13 and an appropriate carboxylic acid of formula (V).

| Ex No | Structure (Appareance) | HPLC Rt (% Purity) | MS | NMR |
|---|---|---|---|---|
| 125 | 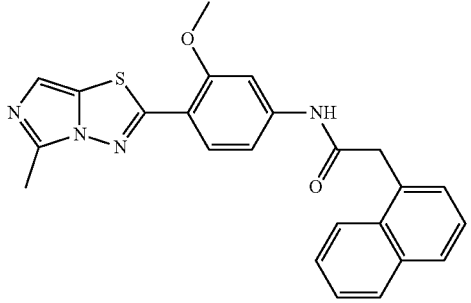<br>N-[3-Methoxy-4-(5-methyl-imidazo[5,1-b][1,3,4]thiadiazol-2-yl)-phenyl]-2-naphthalen-1-yl-acetamide<br>(Yellow solid) | 3.16[b] (97.4%) | 429 $(M + H)^+$ | $^1$H NMR (400 MHz, DMSO-$d^6$): δ 10.77 (s, 1 H); 8.12 (t, J = 7.95 Hz, 2 H); 7.98-7.93 (m, 1 H); 7.89-7.84 (m, 1 H); 7.74 (d, J = 1.92 Hz, 1 H); 7.62-7.48 (m, 4 H); 7.33 (dd, J = 8.72, 1.93 Hz, 1 H); 6.88 (s, 1 H); 4.22 (s, 2 H); 3.94 (s, 3 H); 2.58 (s, 3 H). |
| 126 | 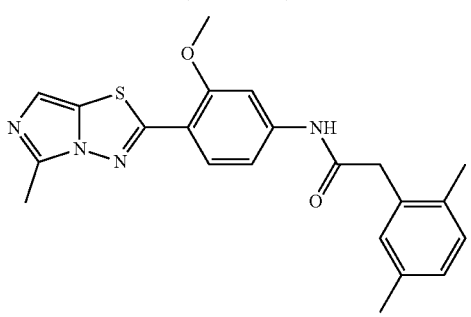<br>2-(2,5-Dimethyl-phenyl)-N-[3-methoxy-4-(5-methyl-imidazo[5,1-b][1,3,4]thiadiazol-2-yl)-phenyl]-acetamide<br>(Yellow solid) | 3.18[b] (96.3%) | 407 $(M + H)^+$ | $^1$H NMR (400 MHz, DMSO-$d^6$): δ 10.56 (s, 1 H); 8.11 (d, J = 8.68 Hz, 1 H); 7.73 (d, J = 1.91 Hz, 1 H); 7.32 (dd, J = 8.71, 1.93 Hz, 1 H); 7.09-7.05 (m, 2 H); 6.98 (dd, J = 7.67, 1.84 Hz, 1 H); 6.89 (s, 1 H); 3.96 (s, 3 H); 3.70 (s, 2 H); 2.63-2.39 (m, 3 H); 2.26 (s, 6 H). |

[a-f]Rt refers to HPLC methods A to F

The following compound was prepared using representative method I with intermediate 14 and an appropriate amine of formula (III).

| Ex No | Structure (Appareance) | HPLC Rt (% Purity) | MS | NMR |
|---|---|---|---|---|
| 127 | 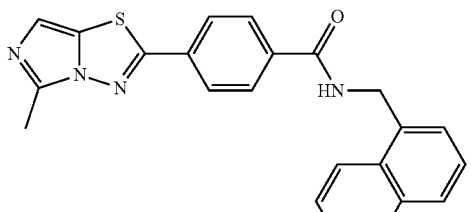<br>4-(5-Methyl-imidazo[5,1-b][1,3,4]thiadiazol-2-yl)-N-naphthalen-1-ylmethyl-benzamide<br>(Yellow solid) | 3.19[b] (98.7%) | 399 $(M + H)^+$ | $^1$H NMR (400 MHz, DMSO-$d^6$): δ 9.28 (t, J = 5.72 Hz, 1 H); 8.18 (d, J = 8.14 Hz, 1 H); 8.09 (d, J = 8.27 Hz, 2 H); 8.02 (d, J = 8.26 Hz, 2 H); 7.97-7.93 (m, 1 H); 7.88-7.83 (m, 1 H); 7.61-7.47 (m, 4 H); 6.97 (s, 1 H); 4.97 (d, J = 5.64 Hz, 2 H); 2.60 (s, 3 H). |

[a-f]Rt refers to HPLC methods A to F

The following compounds were prepared using representative method F with intermediate 15 and an appropriate carboxylic acid of formula (V):

| Ex No | Structure (Appearance) | HPLC Rt (% Purity) | MS | NMR |
|---|---|---|---|---|
| 128 | 2-(3,4-Dichloro-phenyl)-N-[4-(5-methyl-imidazo[5,1-b][1,3,4]thiadiazol-2-yl)-phenyl]-acetamide (Yellow solid) | 3.07[b] (98.6%) | 417 (M + H)+ | $^1$H NMR (400 MHz, DMSO-d$^6$): δ 10.58 (s, 1 H); 7.90-7.84 (m, 2 H); 7.82-7.76 (m, 2 H); 7.62-7.57 (m, 2 H); 7.32 (dd, J = 8.28, 2.06 Hz, 1 H); 6.93 (s, 1 H); 3.74 (s, 2 H); 2.56 (s, 3 H). |
| 100 | N-[4-(5-Methyl-imidazo[5,1-b][1,3,4]thiadiazol-2-yl)-phenyl]-2-(3-trifluoromethyl-phenyl)-acetamide (Yellow solid) | 3.69[a] (98.5%) | 417 (M + H)+ | $^1$H NMR (400 MHz, DMSO-d$^6$): δ 10.60 (s, 1 H); 7.90-7.84 (m, 2 H); 7.83-7.77 (m, 2 H); 7.70 (s, 1 H); 7.65-7.60 (m, 2 H); 7.60-7.53 (m, 1 H); 6.93 (s, 1 H); 3.83 (s, 2 H); 2.56 (s, 3 H). |

[a-f]Rt refers to HPLC methods A to F

Representative Method K

Step 1: 2-(4-isothiocyanatophenyl)-5-methylimidazo[5,1-b][1,3,4]oxadiazole

To a suspension of 4-(5-methylimidazo[5,1-b][1,3,4]oxadiazol-2-yl)aniline (1 g, 4.67 mmol) in DCM (50 mL) was added thiocarbonyl pyridine (1.05 g, 4.54 mmol). After 18 hours at 25° C. the reaction mixture was concentrated under reduced pressure to afford the title compound. No further purification was carried out. LC-MS 257 (M+H)+.

Step 2: 1-(4-(5-methylimidazo[5,1-b][1,3,4]oxadiazol-2-yl)phenyl)thiourea 2-(4-isothiocyanatophenyl)-5-methylimidazo[5,1-b][1,3,4]oxadiazole (assumed 4.67 mmol) was cooled to 0° C., ammonia in MeOH (2.0 M, 25 mL) was added to the reaction and stirring was continued for 1 hour. The resulting precipitate was collected by filtration and washed with MeOH to afford the title compound as a yellow solid (1.13 g, 4.15 mmol, 89% yield). LC-MS 274 (M+H)+. $^1$H NMR (400 MHz, DMSO-d$^6$): δ 10.10 (s, 1H); 7.97 (d, J=8.44 Hz, 2H); 7.80 (d, J=8.44 Hz, 2H); 6.51 (s, 1H); 2.45 (s, 3H).

Step 3: methyl (4-(5-methylimidazo[5,1-b][1,3,4]oxadiazol-2-yl)phenyl)carbamimidothioate Hydroiodide To a suspension of 1-(4-(5-methylimidazo[5,1-b][1,3,4]oxadiazol-2-yl)phenyl)thiourea (1.13 g, 4.15 mmol) in EtOH (32 mL) was added iodomethane (0.26 mL, 4.15 mmol). After 2 hours at 60° C. the reaction was concentrated under reduced pressure to afford the title compound as an orange solid (1.68 g, assume 4.15 mmol, 100% yield). LC-MS 288 (M+H)+.

Step 4: 5-chloro-2-(4-fluorophenyl)pentanoic Acid

To a solution of 2-(4-fluorophenyl)acetic acid (1.54 g, 10 mmol) in anhydrous THF (20 mL) under nitrogen and cooled to 0° C. was added NaHMDS (1.0M, 20 mL, 20 mmol) dropwise. After 20 minutes at 0° C. 1-chloro-3-iodopropane (1.05 mL, 10 mmol) was added and the reaction was allowed to warm to 25° C. After 16 hours, water (4 mL) was added to the reaction dropwise, which was then concentrated under reduced pressure. The residue was diluted with aqueous NaOH solution (1.0 M) and extracted with Et$_2$O. The aqueous phase was acidified with dilute aqueous HCl solution to pH 5 then extracted with Et$_2$O. The organic phase was washed with sodium sulfite solution and brine, dried (MgSO$_4$) and concentrated under reduced pressure. The residue was purified by chromatography (silica, petroleum ether/EtOAc) to afford the title compound as a solid (1.36 g, 5.91 mmol, 59% yield) LC-MS 229 (M–H)–. $^1$H NMR (400 MHz, DMSO-d$^6$): δ 12.38 (s, 1H); 7.27 (t, J=6.72 Hz, 2H); 7.09 (t, J=8.62 Hz, 2H); 3.59-3.48 (m, 3H); 2.03-1.91 (m, 1H); 1.76-1.43 (m, 3H).

Step 5: (Z)-methyl N'-(5-chloro-2-(4-fluorophenyl)pentanoyl)-N-(4-(5-methylimidazo[5,1-b][1,3,4]oxadiazol-2-yl)phenyl)carbamimidothioate To a suspension of 5-chloro-2-(4-fluorophenyl)pentanoic acid (0.26 g, 1.14 mmol), methyl (4-(5-methylimidazo[5,1-b][1,3,4]oxadiazol-2-yl)phenyl)carbamimidothioate hydroiodide (0.43 g, 1.04 mmol), EDCI (0.4 g, 2.08 mmol) and HOPO (0.23 g, 2.08 mmol) in DMF (5 mL) under N$_2$ was added DIPEA (0.45 mL, 2.6 mmol). After 16 hours the reaction was diluted with water and extracted using EtOAc. The organic phase was washed with brine, dried (MgSO$_4$) and concentrated under reduced pressure. The residue was purified by chromatography (silica gel, EtOAc) to afford the title compound as a solid (0.29 g, 0.58 mmol, 56% yield). LC-MS 500 (M+H)$^+$.

Step 6: 5-(4-chloro-1-(4-fluorophenyl)butyl)-N-(4-(5-methylimidazo[5,1-b][1,3,4]oxadiazol-2-yl)phenyl)-1H-1,2,4-triazol-3-amine To a suspension of (Z)-methyl N'-(5-chloro-2-(4-fluorophenyl)pentanoyl)-N-(4-(5-methylimidazo[5,1-b][1,3,4]oxadiazol-2-yl)phenyl)carbamimidothioate (0.29 g, 0.58 mmol) in EtOH (8 mL) was added hydrazine hydrate (55% aqueous solution, 0.2 mL, 2.32 mmol). After 1 hour at 70° C. the reaction was cooled to 25° C. and degassed with nitrogen for 30 minutes. The reaction was diluted with water and extracted using EtOAc. The organic phase was washed with water then brine, dried (MgSO$_4$) and concentrated under reduced pressure to afford the title compound as a yellow solid (0.17 g, 0.37 mmol, 64% yield). This was progressed without further purification. LC-MS 466 (M+H)+. $^1$H NMR (400 MHz, DMSO-d$^6$): δ 13.26 (s, 1H); 9.90 (s, 1H); 7.90 (d, J=8.50 Hz, 2H); 7.74-7.66 (m, 2H); 7.42 (dd, J=8.37, 5.40 Hz, 2H); 7.18 (t, J=8.79 Hz, 2H); 6.47 (s, 1H); 4.17 (d, J=8.84 Hz, 1H); 3.66 (t, J=6.52 Hz, 2H); 2.43 (s, 3H); 2.28-2.17 (m, 1H); 2.21-1.92 (m, 1H); 1.75-1.61 (m, 2H).

Step 7: 8-(4-fluorophenyl)-N-(4-(5-methylimidazo[5,1-b][1,3,4]oxadiazol-2-yl)phenyl)-5,6,7,8-tetrahydro-[1,2,4]triazolo[1,5-a]pyridin-2-amine To a suspension of 5-(4-chloro-1-(4-fluorophenyl)butyl)-N-(4-(5-methylimidazo[5,1-b][1,3,4]oxadiazol-2-yl)phenyl)-1H-1,2,4-triazol-3-amine (0.17 g, 0.37 mmol) in acetone (3.5 mL) was added NaI (0.28 g, 1.85 mmol), followed by DIPEA (0.065 mL, 0.37 mmol). After 48 hours at 80° C. the reaction was concentrated under reduced pressure. The residue was diluted with water and EtOAc. The water was decanted off and resulting suspension was concentrated under reduced pressure. The residue was dissolved in DMSO and purified by preparative HPLC. The resultant solid was triturated with EtOH to afford the title compound as a yellow solid.

The following compounds were prepared using representative method K and intermediate 4.

| Ex No | Structure (Appearance) | HPLC Rt (% Purity) | MS | NMR |
|---|---|---|---|---|
| 24 | 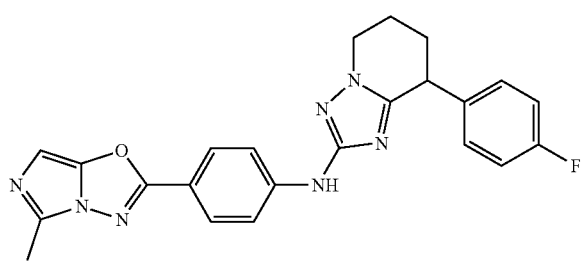<br>8-(4-fluorophenyl)-N-(4-(5-methylimidazo[5,1-b][1,3,4]oxadiazol-2-yl)phenyl)-5,6,7,8-tetrahydro-[1,2,4]triazolo[1,5-a]pyridin-2-amine (Off-white solid) | 9.58$^e$ (98.2%) | 430 (M + H)$^+$ | $^1$H NMR (400 MHz, DMSO-d$^6$): δ 9.86 (s, 1 H); 7.85 (d, J = 8.74 Hz, 2 H); 7.62 (d, J = 8.70 Hz, 2 H); 7.30-7.22 (m, 2 H); 7.16-7.06 (m, 2 H); 6.42 (s, 1 H); 4.23 (dd, J = 8.97, 5.60 Hz, 1 H); 4.14 (t, J = 5.75 Hz, 2 H); 2.39 (s, 3 H); 2.23-2.15 (m, 1 H); 2.10-1.88 (m, 3 H). |

| Ex No | Structure (Appareance) | HPLC Rt (% Purity) | MS | NMR |
|---|---|---|---|---|
| 25 | 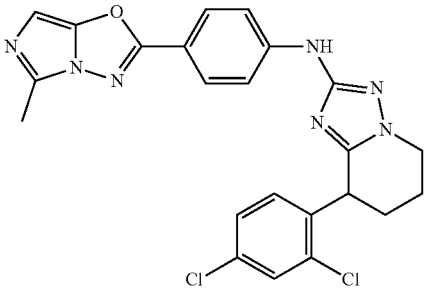 [8-(2,4-Dichloro-phenyl)-5,6,7,8-tetrahydro-[1,2,4]triazolo[1,5-a]pyridin-2-yl]-[4-(5-methyl-imidazo[5,1-b][1,2,4]oxadiazol-2-yl)-phenyl]-amine (White solid) | 3.19[b] (99.6%) | 480 $(M+H)^+$ | $^1$H NMR (400 MHz, DMSO-$d^6$): δ 9.88 (s, 1 H); 7.88 (d, J = 8.75 Hz, 2 H); 7.67-7.61 (m, 3 H); 7.39 (dd, J = 8.39, 2.23 Hz, 1 H); 7.26 (d, J = 8.39 Hz, 1 H); 6.45 (s, 1 H); 4.57 (dd, J = 9.19, 5.84 Hz, 1 H); 4.21-4.10 (m, 2 H); 2.41 (s, 3 H); 2.26-2.17 (m, 1 H); 2.11 (s, 3 H). |

[a-f]Rt refers to HPLC methods A to F

Representative Method L

Step 1: 2-bromo-6-phenylcyclohexanone

To a solution of phenyl cyclohexanone (2 g, 11.4 mmol) in chloroform (10 mL) cooled to −10° C. was added a solution of bromine (1.91 g, 12 mmol) in chloroform dropwise. On completion of the addition the reaction mixture was allowed to warm to 0° C. and stir for 2 h. The solvent was then evaporated under reduced pressure, the residue was dissolved in methanol and cooled to 0° C. and stirred for thirty minutes. The solid obtained was collected by filtration, washed with methanol and dried to give the title compound (255 mg, 1 mmol, 8% yield). $^1$H NMR (400 MHz, CHCl$_3$-d): δ 7.37-7.24 (m, 3H); 7.17-7.12 (m, 2H); 4.80 (ddd, J=13.06, 5.96, 1.12 Hz, 1H); 3.71 (dd, J=12.62, 5.32 Hz, 1H); 2.81-2.70 (m, 1H); 2.40-2.16 (m, 2H); 2.11-1.88 (m, 3H).

Step 2: 4-phenyl-4,5,6,7-tetrahydrobenzo[d]thiazol-2-amine

2-Bromo-6-phenylcyclohexanone (250 mg, 0.98 mmol) and thiourea (75 mg 0.98 mmol) in ethanol (10 mL) were heated at reflux for 18 h. The solvent was evaporated under reduced pressure. The residue was triturated with ether to give a solid. The solid was partitioned between ethyl acetate and aqueous sodium carbonate solution. The ethyl acetate extracts were combined, dried over magnesium sulphate, filtered and evaporated under reduced pressure to give the title compound as a solid (210 mg, 0.91 mmol, 91% yield). LC-MS (M+H)+231. $^1$H NMR (400 MHz, CHCl$_3$-d): δ 7.31-7.25 (m, 3H); 7.21-7.15 (m, 1H); 7.12-7.07 (m, 2H); 4.78 (s, 2H); 3.96 (t, J=5.66 Hz, 1H); 2.74-2.58 (m, 2H); 2.19-2.08 (m, 1H); 1.91-1.68 (m, 5H).

Step 3: N-(4-(5-methylimidazo[5,1-b][1,3,4]oxadiazol-2-yl)phenyl)-4-phenyl-4,5,6,7-tetrahydrobenzo[d]thiazol-2-amine 2-(4-Bromophenyl)-5-methylimidazo[5,1-b][1,3,4]oxadiazole (134.8 mg, 0.485 mmol), 4-phenyl-4,5,6,7-tetrahydrobenzo[d]thiazol-2-amine (111.5 mg, 0.485 mmol), Pd$_2$dba$_3$ (17.7 mg, 4 mol %) BINAP (12 mg, 4 mol %) and sodium t-butoxide (65 mg, 0.67) were placed in a carousel tube. 1,4-Dioxan was added and the reaction mixture was degassed for a further ten minutes. The reaction mixture was sealed and heated at 80° C. for 18 h. The reaction mixture was poured into aqueous sodium carbonate solution and extracted with ethyl acetate. The ethyl acetate extracts were combined, washed with brine, dried over magnesium sulphate, filtered and evaporated under reduced pressure to give an oil. The oil was purified by preparative HPLC to give the title compound (36.4 mg, 0.085 mmol, 17.5% yield).

The following compounds were prepared using representative method L and intermediate 4.

| Ex No | Structure (Appearance) | HPLC Rt (% Purity) | MS | NMR |
|---|---|---|---|---|
| 26 | 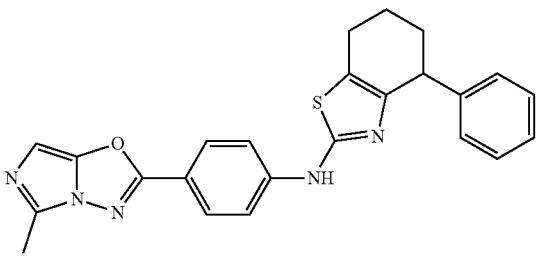<br>[4-(5-Methyl-imidazo[5,1-b][1,2,4]oxadiazol-2-yl)-phenyl]-(4-phenyl-4,5,6,7-tetrahydro-benzothiazol-2-yl)-amine<br>(Off-white solid) | 11.43$^c$ (97.1%) | 428 (M + H)$^+$ | $^1$H NMR (400 MHz, CHCl$_3$-d): δ 7.96-7.88 (m, 2 H); 7.51 (s, 1 H); 7.37-7.18 (m, 4 H); 7.17-7.11 (m, 2 H); 6.43 (s, 1 H); 4.09 (t, J = 5.94 Hz, 1 H); 2.87-2.70 (m, 2 H); 2.54 (s, 3 H); 2.28-2.18 (m, 1 H); 1.98-1.78 (m, 2 H). |
| 27 | 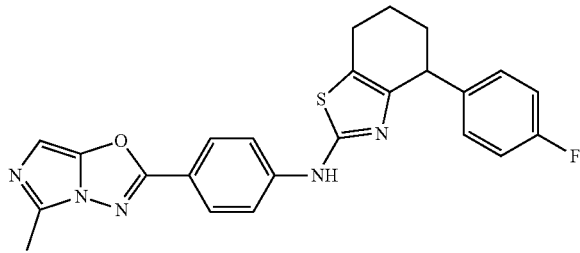<br>[4-(4-Fluoro-phenyl)-4,5,6,7-tetrahydro-benzothiazol-2-yl]-[4-(5-methyl-imidazo[5,1-b][1,2,4]oxadiazol-2-yl)-phenyl]-amine<br>(Off-white solid) | 3.43$^b$ (96.9%) | 446 (M + H)$^+$ | $^1$H NMR (400 MHz, CHCl$_3$-d): δ 7.97-7.89 (m, 2 H); 7.49 (s, 1 H); 7.39-7.31 (m, 2 H); 7.13-7.07 (m, 2 H); 7.03-6.94 (m, 2 H); 6.44 (s, 1 H); 4.07 (t, J = 5.41 Hz, 1 H); 2.83-2.74 (m, 2 H); 2.54 (s, 3 H); 2.25-2.17 (m, 1 H); 1.93-1.81 (m, 2 H). |

$^{a-f}$Rt refers to HPLC methods A to F

Representative Method E

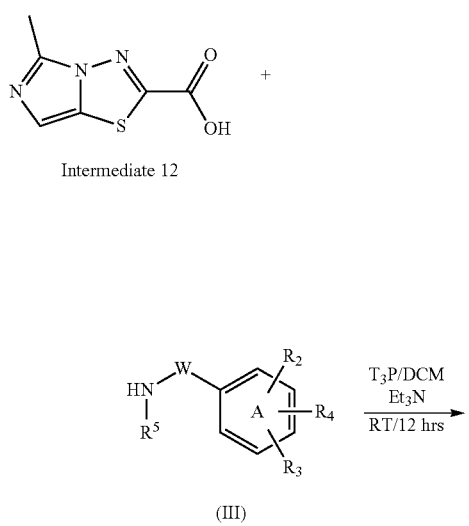

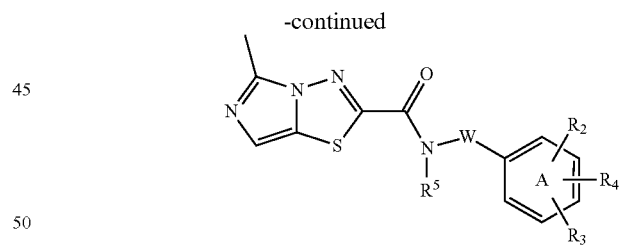

In an 8 mL vial, a solution of Intermediate 12 (58.6 mg, 0.32 mmol) in 3 mL dichloromethane was mixed with amine (III) (0.39 mmol) and Et$_3$N (1.6 mmol). The reaction mixture was then cooled down to 0° C. and T$_3$P (0.98 mmol) was added. After the addition, the vial was placed in the orbital shaker for about 12 hrs. Upon consumption of starting material (monitored by TLC and LC-MS), reaction mass was concentrated under vacuo to remove the solvent. The crude residue was dissolved in dichloromethane (4 mL) and washed with water (2 mL). The organic layer was evaporated under vacuo and the residue was passed through SPE-NH$_2$ column (2 g, 6 mL) to get the pure amide. The solvents used for elution were pet ether/dichloromethane/methanol.

The following compound was prepared from intermediate 12 and an appropriate amine of formula (III):

| Ex No | Structure (Appearance) | HPLC Rt (% Purity) | MS |
|---|---|---|---|
| 94 | 5-Methyl-imidazo[5,1-b][1,3,4]thiadiazole-2-carboxylic acid [2-(1H-indol-3-yl)-ethyl]-amide (Yellow solid) | 2.9$^f$ (98.7%) | 326 (M + H)$^+$ |
| 95 | 5-Methyl-imidazo[5,1-b][1,3,4]thiadiazole-2-carboxylic acid (3-chloro-benzyl)-methyl-amide (Yellow solid) | 3.26$^f$ (99.0%) | 321 (M + H)$^+$ |
| 96 | 5-Methyl-imidazo[5,1-b][1,3,4]thiadiazole-2-carboxylic acid 2-ethoxy-benzylamide (Yellow solid) | 3.17$^f$ (98.2%) | 317 (M + H)$^+$ |
| 97 | 5-Methyl-imidazo[5,1-b][1,3,4]thiadiazole-2-carboxylic acid methyl-phenethyl-amide (Yellow solid) | 2.92$^f$ (99.5%) | 301 (M + H)$^+$ |
| 98 | 5-Methyl-imidazo[5,1-b][1,3,4]thiadiazole-2-carboxylic acid benzyl-methyl-amide (Yellow gum) | 2.8$^f$ (98.5%) | 287 (M + H)$^+$ |
| 99 | 5-Methyl-imidazo[5,1-b][1,3,4]thiadiazole-2-carboxylic acid benzyl-ethyl-amide (Yellow gum) | 3.14$^f$ (99.6%) | 301 (M + H)$^+$ |
| 101 | 5-Methyl-imidazo[5,1-b][1,3,4]thiadiazole-2-carboxylic acid methyl-(3-trifluoromethyl-benzyl)-amide (Yellow gum) | 3.54$^f$ (97.8%) | 355 (M + H)$^+$ |

$^{a\text{-}f}$Rt refers to HPLC methods A to F

Example 89: 5-Methyl-imidazo[5,1-b][1,3,4]thiadiazole-2-carboxylic Acid Benzyl-Isobutyl-Amide Intermediate 12 (50 mg, 0.23 mmol) was preactivated with HATU (112 mg, 0.30 mmol) in a mixture of DCM (4.00 mL) and triethylamine (95.0 µL, 0.68 mmol) before adding benzyl-isobutyl-amine (56 mg, 0.34 mmol). The resulting reaction mixture was stirred at room temperature for 2 hours and upon completion quenched with water. It was then diluted with DCM (20 mL) and washed with NH$_4$Cl sat (15 mL) and brine (15 mL). The organic phase was dried with magnesium sulfate and evaporated to yield a crude product purified by flash chromatography (60-120 mesh silica gel, eluent: 50% EtOAc in Petroleum ether) affording the expected compound as a yellow solid (73 mg, 94% yield). $^1$H NMR (DMSO-d$_6$, 300 MHz) δ 9.43 (d, J=8.6 Hz, 1H), 7.36 (dd, J=7.6, 1.6 Hz, 1H), 7.32-7.14 (m, 1H), 7.09-6.85 (m, 3H), 5.10-5.05 (m, 1H), 4.80-4.78 (m, 1H), 3.85-3.82 (m, 2H), 2.63 (s, 3H), 2.10-1.95 (m, 1H), 0.90 (d, J=6.9 Hz, 6H). LC/MS (Method A): 329.4 (M+H)$^+$. HPLC (Method F) Rt 3.26 min (Purity. 96.1%).

Example 90: 5-Methyl-imidazo[5,1-b][1,3,4]thiadiazole-2-carboxylic Acid [1-(2-ethoxy-phenyl)-ethyl]-amide

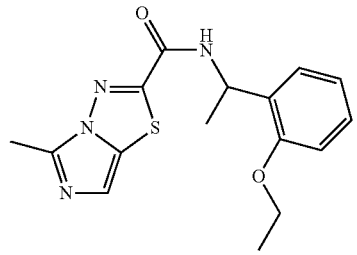 [SMILES: CCOc1ccccc1C(C)NC(=O)c1nn2c(C)ncc2s1]

The title compound was prepared following the same procedure as Example 89, using 1-(2-ethoxy-phenyl)-ethylamine as amine. The resulting crude product was purified by preparative HPLC. The title compound was obtained as a yellow solid (15 mg, 20% yield). $^1$H NMR (DMSO-d$_6$, 300 MHz) δ 9.43 (d, J=8.6 Hz, 1H), 7.37 (dd, J=7.6, 1.6 Hz, 1H), 7.30-7.17 (m, 1H), 7.06-6.86 (m, 3H), 5.52-5.36 (m, 1H), 4.18-4.01 (m, 2H), 2.63 (s, 3H), 1.46 (d, J=7.0 Hz, 3H), 1.39 (t, J=6.9 Hz, 3H). LC/MS (Method A): 331.3 (M+H)$^+$. HPLC (Method F) Rt 3.05 min (Purity: 97.9%).

Example 91: 5-Methyl-imidazo[5,1-b][1,3,4]thiadiazole-2-carboxylic Acid [(4-chloro-phenyl)-cyclopropyl-methyl]-amide

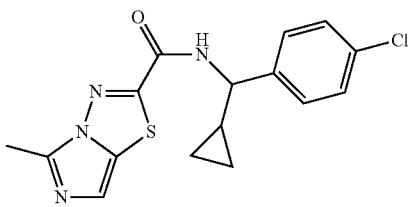 [SMILES: Cc1ncc2sc(C(=O)NC(c3ccc(Cl)cc3)C3CC3)nn12]

Intermediate 12 (50 mg, 0.23 mmol) was preactivated with a T3P solution (80% in EtOAc, 0.27 mL, 0.46 mmol; 2.00 equiv) in a mixture of DCM (4 mL) and Hünig's base (0.12 mL, 0.68 mmol) before introducing C-(4-Chlorophenyl)-C-cyclopropyl-methylamine hydrochloride (59.6 mg, 0.27 mmol). The resulting reaction mixture was stirred at room temperature for 3 hours and upon completion quenched with water. It was then diluted with DCM (20 mL) and washed with NH$_4$Cl sat (15 mL) and brine (15 mL). The organic phase was dried with magnesium sulfate and evaporated to yield a crude product purified by preparative HPLC affording the expected compound as a yellow solid (60 mg, 73% yield). $^1$H NMR (DMSO-d$_6$, 300 MHz) δ 9.93 (d, J=8.2 Hz, 1H), 7.61-7.47 (m, 2H), 7.46-7.37 (m, 2H), 6.96 (d, J=7.2 Hz, 1H), 4.31-4.18 (m, 1H), 4.11 (q, J=5.2 Hz, 1H), 3.17 (d, J=5.2 Hz, 1H), 2.62 (d, J=6.7 Hz, 3H), 1.60-1.40 (m, 1H), 0.70-0.28 (m, 4H). LC/MS (Method A): 347.3 (M+H)$^+$. HPLC (Method F) Rt 3.29 min (Purity: 97.9%).

Example 92: 5-Methyl-imidazo[5,1-b][1,3,4]thiadiazole-2-carboxylic Acid 2-(2,2,2-trifluoro-ethoxy)-benzylamide

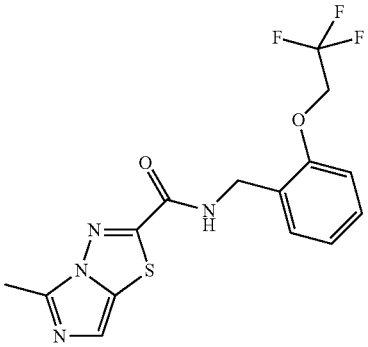 [SMILES: Cc1ncc2sc(C(=O)NCc3ccccc3OCC(F)(F)F)nn12]

The title compound was prepared following the same procedure as Example 91, using 2-(2,2,2-Trifluoro-ethoxy)-benzylamine as amine. The resulting crude product was purified by flash chromatography (60-120 mesh silica gel, eluent: 50% EtOAc in Petroleum ether) affording the expected compound as a yellow solid (52 mg, 60% yield). $^1$H NMR (DMSO-d$_6$, 300 MHz) δ 9.58 (t, J=6.0 Hz, 1H), 7.34-7.24 (m, 2H), 7.13 (d, J=7.7 Hz, 1H), 7.07-7.00 (m, 1H), 6.99 (s, 1H), 4.82 (q, J=8.9 Hz, 2H), 4.49 (d, J=6.0 Hz, 2H), 2.60 (s, 3H). LC/MS (Method A): 371.3 (M+H)$^+$. HPLC (Method F) Rt 2.95 min (Purity: 97.7).

Example 93: (5-Methyl-imidazo[5,1-b][1,3,4]thiadiazol-2-yl)-(2-phenyl-pyrrolidin-1-yl)-methanone

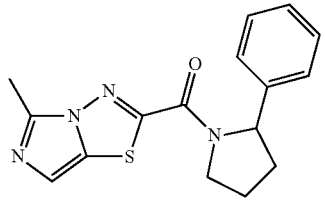 [SMILES: Cc1ncc2sc(C(=O)N3CCCC3c3ccccc3)nn12]

Intermediate 12 (100 mg, 0.46 mmol) was dissolved in a mixture of DCM (10.00 mL) and diisopropylethylamine (309.7 µl, 1.82 mmol) at room temperature and preactivated 5 minutes with T3P solution (80% in EtOAc, 0.54 mL; 0.91 mmol). 2-Phenyl-pyrrolidine (71 mg, 0.48 mmol) was then added and the reaction mixture stirred at 25° C. overnight. The solution was quenched with water and the DCM phase washed with a saturated sodium bicarbonate solution (pH=10) and finally with brine. The organic layer was dried with magnesium sulphate and concentrated under vacuum affording an orange residue that was purified on silica gel using 50% EtOAc in pet ether as eluent. The expected compound (140 mg, 98% yield) was obtained as a colorless oil. $^1$H NMR (DMSO-d$_6$, 300 MHz) δ 7.32-7.10 (m, 5H), 6.89-6.78 (m, 1H), 5.94 (s, 1H), 4.39-3.79 (brm, 2H), 2.67-1.91 (brm, 7H). LC/MS (Method A): 313.3 (M+H)$^+$. HPLC (Method F) Rt 2.52 min (Purity: 99.1%).

Example 102: (3,4-Dichloro-benzyl)-[5-(5-methyl-imidazo[5,1-b][1,3,4]thiadiazol-2-yl)-[1,3,4]oxadiazol-2-yl]-amine

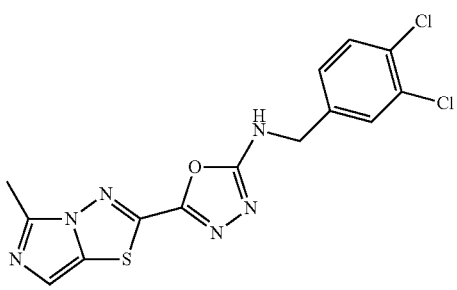 [SMILES: Cc1ncc2sc(-c3nnc(NCc4ccc(Cl)c(Cl)c4)o3)nn12]

Step 1: 5-Methyl-imidazo[5,1-b][1,3,4]thiadiazole-2-carboxylic Acid Hydrazide

Intermediate 11 (200 mg, 0.95 mmol) was heated 1 hour at 60° C. in a mixture of hydrazine hydrate solution (24-26% in water, 1.72 mL, 9.5 mmol) and THF (5 mL). Upon completion of the reaction, the reaction mixture was evaporated to dryness and the resulting product triturated with ethanol, filtered and dried under vacuum affording the title compound as a yellow solid (150 mg, 80% yield). LC/MS (Method A): 198.2 (M+H)$^+$. HPLC (Method F) Rt 3.03 min (Purity: 100%).

Step 2: (3,4-Dichloro-benzyl)-[5-(5-methyl-imidazo[5,1-b][1,3,4]thiadiazol-2-yl)-[1,3,4]oxadiazol-2-yl]-amine A mixture of 5-methyl-imidazo[5,1-b][1,3,4]thiadiazole-2-carboxylic acid hydrazide (75 mg, 0.38 mmol) obtained in Step 1 and 1,2-dichloro-4-isocyanatomethyl-benzene (84.5 mg, 0.42 mmol) were stirred 2 hours in THF (50 mL). The resulting yellow precipitate obtained was isolated by filtration and rinsed twice with Et$_2$O. It was then heated in THF (5 mL) at 80° C. for 18 hours in a mixture of tetrachloromethane (0.11 mL, 1.14 mmol), NEt$_3$ (0.15 mL, 1.14 mmol) and polymer bound triphenylphosphine (100-200 M, loading=1.6 mmol/g, 398 mg, 1.14 mmol). The reaction mixture was cooled down and the resin filtered off, washed twice with DCM and the organic solvents evaporated to dryness. The resulting crude product was purified by flash chromatography on silica gel using EtOAc/MeOH (98/2) as eluent affording the title compound as a white solid (160 mg; 91% yield). $^1$H NMR (DMSO-d$_6$, 300 MHz) δ 7.54-7.46 (m, 2H), 7.29-7.25 (m, 1H), 6.99 (s, 1H), 5.78-5.70 (m, 1H), 4.66 (d, J=7 Hz, 2H), 2.72 (s, 3H). LC/MS (Method A): 382.2 (M+H)$^+$. HPLC (Method F) Rt 3.07 min (Purity: 99.3%).

Example 103: (4-Fluoro-benzyl)-[5-(5-methyl-imidazo[5,1-b][1,3,4]thiadiazol-2-yl)-[1,3,4]oxadiazol-2-yl]-amine

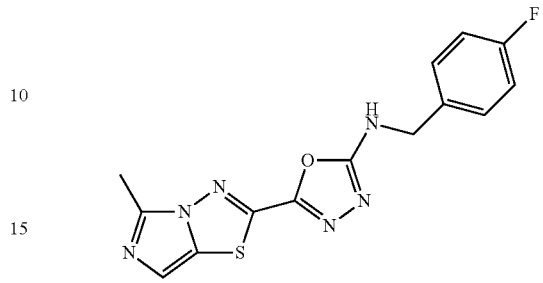

A mixture of 5-methyl-imidazo[5,1-b][1,3,4]thiadiazole-2-carboxylic acid hydrazide (100 mg, 0.51 mmol), prepared as for Example 102 (Step 1) and 1-fluoro-4-isocyanatomethyl-benzene (0.07 mL, 0.56 mmol) were stirred in THF (50 mL) for 2 hours. The resulting yellow precipitate obtained was isolated by filtration and rinsed with Et$_2$O. It was then heated in THF (5 mL) at 80° C. for 18 hours in a mixture of tetrachloromethane (0.11 mL, 1.14 mmol), NEt$_3$ (0.15 mL, 1.14 mmol) and polymer bound triphenylphosphine (100-200 M, loading=1.6 mmol/g, 398 mg, 1.14 mmol). The reaction mixture was cooled down and the resin filtered off, washed twice with DCM and the organic solvents evaporated to dryness. The resulting crude product was purified by flash chromatography on silica gel using EtOAc/MeOH (98/2) as eluent affording the title compound as a white solid (150 mg, 85% yield). $^1$H NMR (DMSO-d$_6$, 300 MHz) δ 7.44-7.37 (m, 2H), 7.13-7.05 (m, 2H), 6.95 (s, 1H), 5.95-5.83 (m, 1H), 4.67 (d, J=7 Hz, 2H), 2.72 (s, 3H). LC/MS (Method A): 331.1 (M+H)$^+$. HPLC (Method F) Rt 2.30 min (Purity: 98.2%).

Example 104: (2-Fluoro-benzyl)-[5-(5-methyl-imidazo[5,1-b][1,3,4]thiadiazol-2-yl)-[1,3,4]oxadiazol-2-yl]-amine

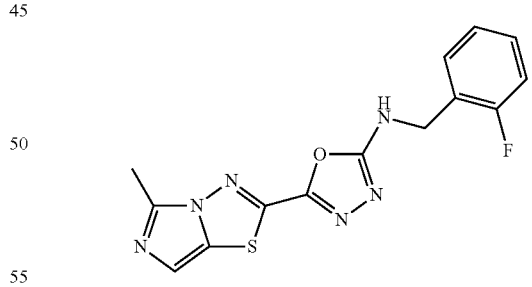

A mixture of 5-methyl-imidazo[5,1-b][1,3,4]thiadiazole-2-carboxylic acid hydrazide (100 mg, 0.51 mmol) prepared as for Example 102 (Step 1) and 1-fluoro-2-isocyanatomethyl-benzene (0.07 mL, 0.56 mmol) were stirred at RT for 2 hours in THF (50 mL). The resulting yellow precipitate obtained was isolated by filtration and rinsed with Et$_2$O. It was then heated in THF (5 mL) at 80° C. for 18 hours in a mixture of tetrachloromethane (0.11 mL, 1.14 mmol), NEt$_3$ (0.15 mL, 1.14 mmol) and polymer bound triphenylphosphine (100-200 M, loading=1.6 mmol/g, 398 mg, 1.14 mmol). The reaction mixture was cooled down and the resin filtered off, washed twice with DCM and the organic solvents evaporated to dryness. The resulting crude product was purified by flash chromatography on silica gel using EtOAc/MeOH (98/2) as eluent affording the title compound as a white solid (150 mg, 85% yield). $^1$H NMR (DMSO-$d_6$, 300 MHz) δ 7.53-7.46 (m, 1H), 7.41-7.34 (m, 1H), 7.22-7.11 (m, 2H), 7.05-6.88 (m, 1H), 5.67-5.54 (m, 1H), 4.75 (d, J=7 Hz, 2H), 2.74 (s, 3H). LC/MS (Method A): 331.1 (M+H)$^+$. HPLC (Method F) Rt 2.23 min (Purity: 98.6%).

Example 129: In Vitro Assays

Amyloid-β Peptide Release (Aβ42 & AβTotal) Assay to Determine IC$_{50}$ Values.

Amyloid-β peptide release (Aβ42 & AβTotal) assays are performed in 384 well microtiter plates (Perkin Elmer AlphaPlate #6008350) in a final volume of 20 µl, using supernatant derived from HEK cells overexpressing APP (HEK-APP) exposed to test compounds. Compounds are dissolved in and diluted in 100% DMSO and incubated with HEK-APP cells for 24 h at 37° C. in 5% CO$_2$. The supernatant from HEK-APP cells are mixed with antibodies: for Aβ42 detection: AlphaLISA Amyloid-β 1-42 Kit (Perkin Elmer AL203L) Anti-Amyloid β1-42-specific antibody acceptor beads, biotinylated anti-Amyloid-"β1-42" antibody and streptavidin (SA) donor beads diluted in AlphaLISA buffer (to the instructions of the supplier). For Aβ total detection: Custom Anti-Amyloid-βtotal acceptor beads (6E10 acceptor beads), biotinylated anti-Amyloid "β1-42" antibody (Perkin Elmer AL203L) and streptavidin (SA) donor beads diluted in AlphaLISA buffer (to the instructions of the supplier). After addition of supernatant to the antibody mix, the assay is incubated for 4.5 h. Amyloid-β peptide release (Aβ42 & AβTotal) is measured with a Pherastar FS (BMG) multimode reader using the alphascreen module.

Cell Viability Assay to Determine IC$_{50}$ Values.

Cell viability assays are performed in 384 well microtiter plates (Corning #3712) in a final volume of 30 µl, using plates containing HEK-APP cells exposed to test compounds for 24 h. After addition of equal volume of CellTiter-Glo (Promega) to the cells, the assay is incubated for 10 min. Cell viability is measured with a Pherastar FS (BMG) multimode reader using the Luminescence plus module.

Results are given in the following table:

| Ex. No | Structure | Ab42 IC50 Ranges | Abtot/Ab42 selectivity ranges |
|---|---|---|---|
| 1 | 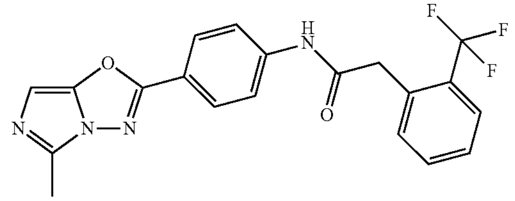 [SMILES: Cc1ncc2oc(-c3ccc(NC(=O)Cc4ccccc4C(F)(F)F)cc3)nn12] | c | b |
| 2 | 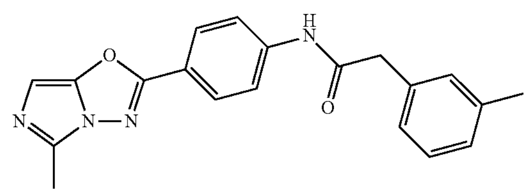 [SMILES: Cc1cccc(CC(=O)Nc2ccc(-c3nn4c(C)ncc4o3)cc2)c1] | d | c |
| 3 | 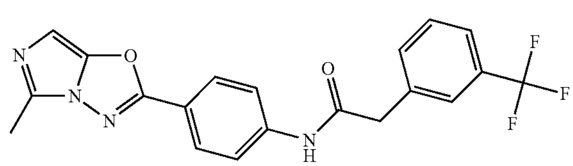 [SMILES: Cc1ncc2oc(-c3ccc(NC(=O)Cc4cccc(C(F)(F)F)c4)cc3)nn12] | d | c |
| 4 | 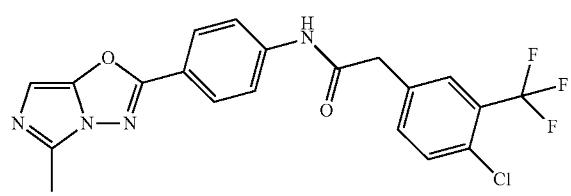 [SMILES: Cc1ncc2oc(-c3ccc(NC(=O)Cc4ccc(Cl)c(C(F)(F)F)c4)cc3)nn12] | d | c |
| 5 | 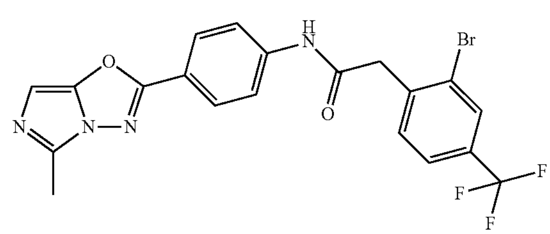 [SMILES: Cc1ncc2oc(-c3ccc(NC(=O)Cc4ccc(C(F)(F)F)cc4Br)cc3)nn12] | c | c |

-continued

| Ex. No | Structure | Ab42 IC50 Ranges | Abtot/Ab42 selectivity ranges |
|---|---|---|---|
| 6 | 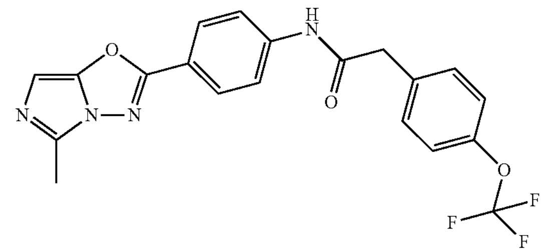 [SMILES: Cc1ncc2oc(-c3ccc(NC(=O)Cc4ccc(OC(F)(F)F)cc4)cc3)nn12] | c | c |
| 7 | 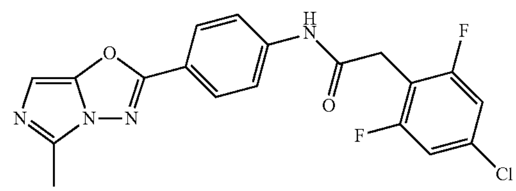 [SMILES: Cc1ncc2oc(-c3ccc(NC(=O)Cc4c(F)cc(Cl)cc4F)cc3)nn12] | c | b |
| 8 | 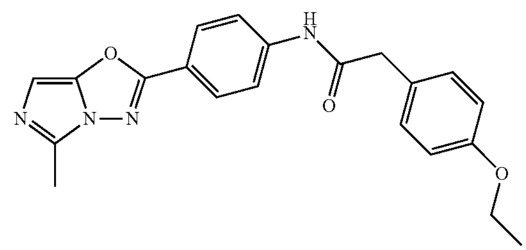 [SMILES: CCOc1ccc(CC(=O)Nc2ccc(-c3nn4c(C)ncc4o3)cc2)cc1] | d | c |
| 9 | 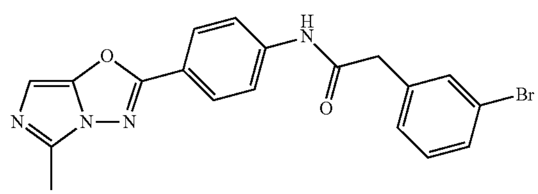 [SMILES: Cc1ncc2oc(-c3ccc(NC(=O)Cc4cccc(Br)c4)cc3)nn12] | c | c |
| 10 | 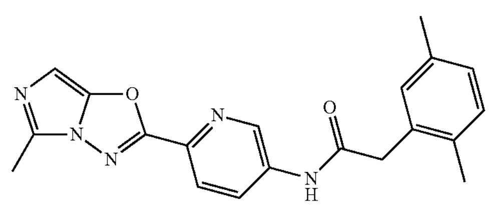 [SMILES: Cc1ccc(C)c(CC(=O)Nc2ccc(-c3nn4c(C)ncc4o3)nc2)c1] | d | c |
| 11 | 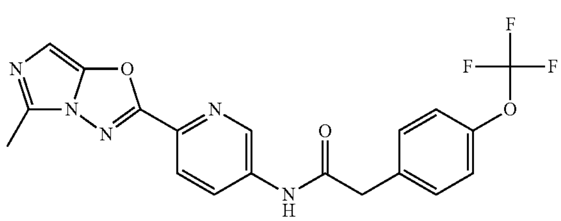 [SMILES: Cc1ncc2oc(-c3ccc(NC(=O)Cc4ccc(OC(F)(F)F)cc4)cn3)nn12] | b | b |
| 12 | 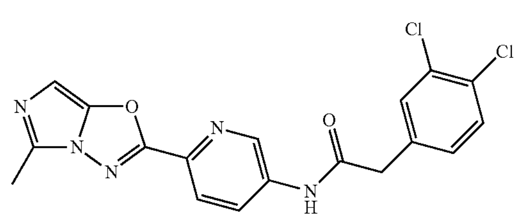 [SMILES: Cc1ncc2oc(-c3ccc(NC(=O)Cc4ccc(Cl)c(Cl)c4)cn3)nn12] | c | c |

| Ex. No | Structure | Ab42 IC50 Ranges | Abtot/Ab42 selectivity ranges |
|---|---|---|---|
| 13 | 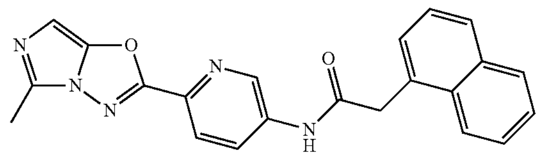 [SMILES: Cc1ncc2oc(-c3ccc(NC(=O)Cc4cccc5ccccc45)cn3)nn12] | d | c |
| 14 | 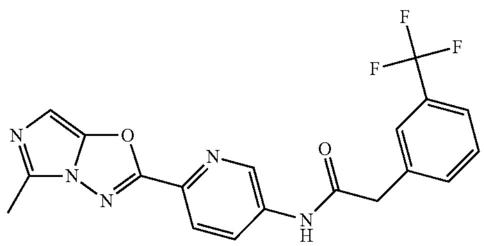 [SMILES: Cc1ncc2oc(-c3ccc(NC(=O)Cc4cccc(C(F)(F)F)c4)cn3)nn12] | d | c |
| 15 | 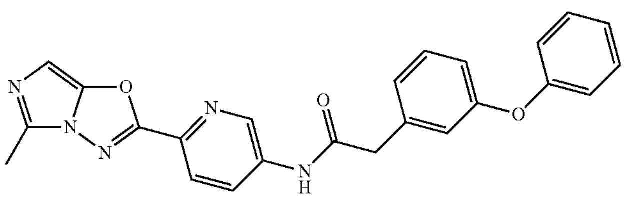 [SMILES: Cc1ncc2oc(-c3ccc(NC(=O)Cc4cccc(Oc5ccccc5)c4)cn3)nn12] | c | b |
| 16 | 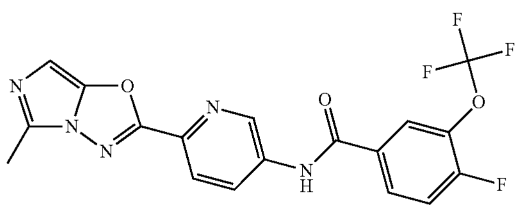 [SMILES: Cc1ncc2oc(-c3ccc(NC(=O)c4ccc(F)c(OC(F)(F)F)c4)cn3)nn12] | d | d |
| 18 | 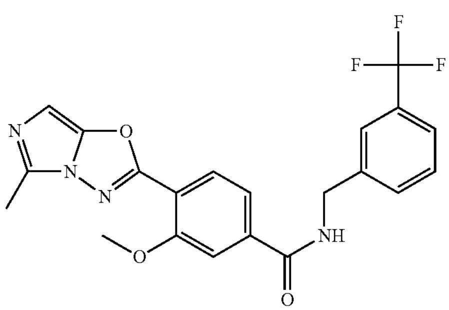 [SMILES: COc1cc(C(=O)NCc2cccc(C(F)(F)F)c2)ccc1-c1nn2c(C)ncc2o1] | d | c |
| 19 | 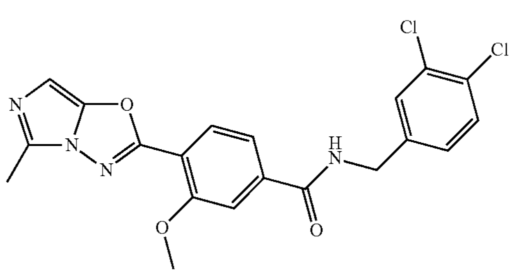 [SMILES: COc1cc(C(=O)NCc2ccc(Cl)c(Cl)c2)ccc1-c1nn2c(C)ncc2o1] | d | c |

-continued

| Ex. No | Structure | Ab42 IC50 Ranges | Abtot/Ab42 selectivity ranges |
|---|---|---|---|
| 20 | 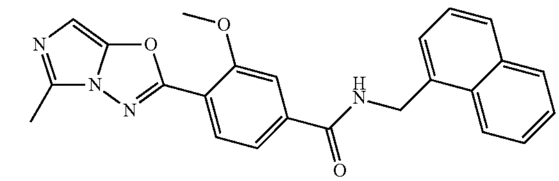 [SMILES: COc1cc(C(=O)NCc2cccc3ccccc23)ccc1-c1nn2c(C)ncc2o1] | d | c |
| 21 | 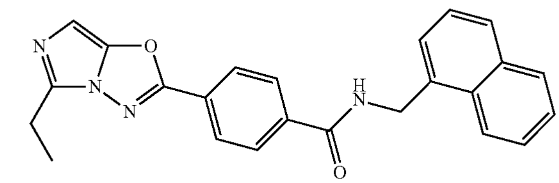 [SMILES: CCc1ncc2oc(-c3ccc(C(=O)NCc4cccc5ccccc45)cc3)nn12] | d | c |
| 22 | 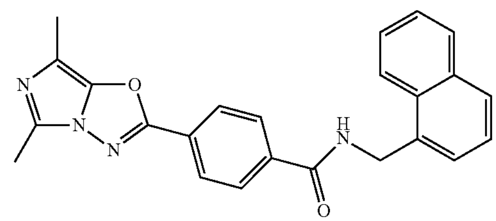 [SMILES: Cc1nc(C)n2nc(-c3ccc(C(=O)NCc4cccc5ccccc45)cc3)oc12] | c | c |
| 23 | 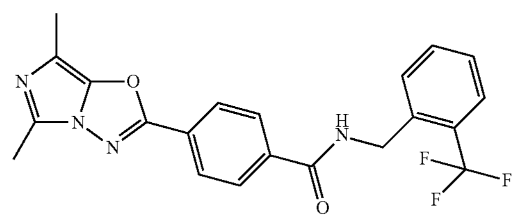 [SMILES: Cc1nc(C)n2nc(-c3ccc(C(=O)NCc4ccccc4C(F)(F)F)cc3)oc12] | d | c |
| 24 | 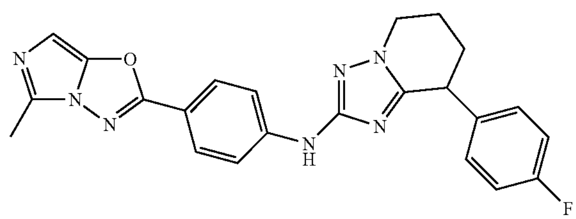 [SMILES: Cc1ncc2oc(-c3ccc(Nc4nc5n(n4)CCCC5c4ccc(F)cc4)cc3)nn12] | c | c |
| 25 | 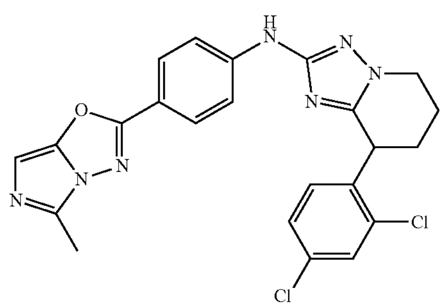 [SMILES: Cc1ncc2oc(-c3ccc(Nc4nc5n(n4)CCCC5c4ccc(Cl)cc4Cl)cc3)nn12] | c | c |
| 26 | 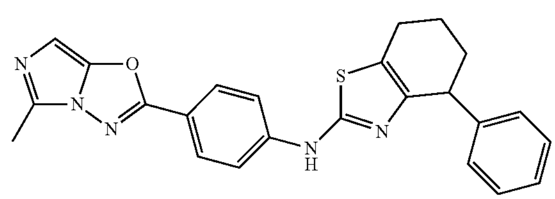 [SMILES: Cc1ncc2oc(-c3ccc(Nc4nc5c(s4)CCCC5c4ccccc4)cc3)nn12] | d | c |

-continued

| Ex. No | Structure | Ab42 IC50 Ranges | Abtot/Ab42 selectivity ranges |
|---|---|---|---|
| 27 | 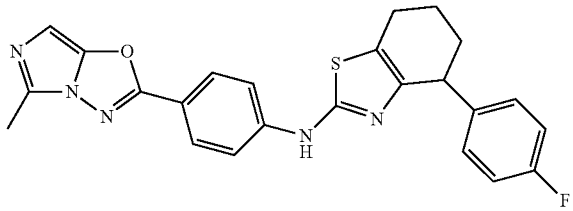 [SMILES: Cc1ncc2oc(-c3ccc(Nc4nc5c(s4)CCCC5c4ccc(F)cc4)cc3)nn12] | d | d |
| 28 | 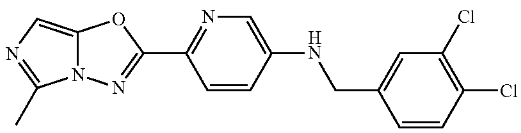 [SMILES: Cc1ncc2oc(-c3ccc(NCc4ccc(Cl)c(Cl)c4)cn3)nn12] | b | d |
| 29 | 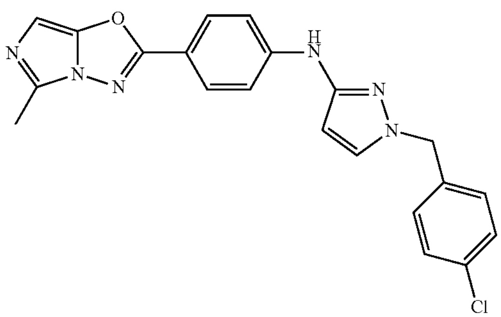 [SMILES: Cc1ncc2oc(-c3ccc(Nc4ccn(Cc5ccc(Cl)cc5)n4)cc3)nn12] | d | d |
| 30 | 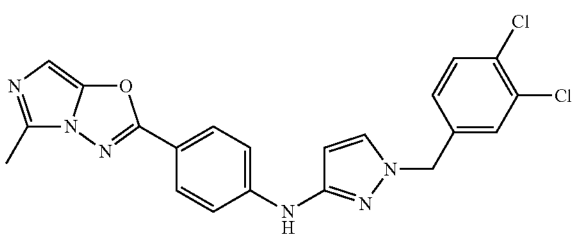 [SMILES: Cc1ncc2oc(-c3ccc(Nc4ccn(Cc5ccc(Cl)c(Cl)c5)n4)cc3)nn12] | d | c |
| 31 | 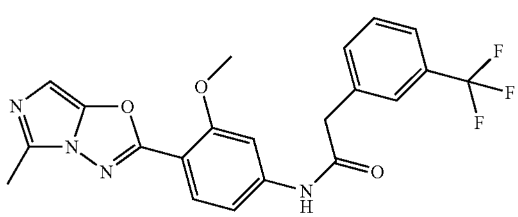 [SMILES: COc1cc(NC(=O)Cc2cccc(C(F)(F)F)c2)ccc1-c1nn2c(C)ncc2o1] | b | a |
| 32 | 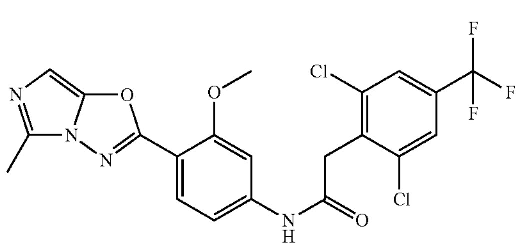 [SMILES: COc1cc(NC(=O)Cc2c(Cl)cc(C(F)(F)F)cc2Cl)ccc1-c1nn2c(C)ncc2o1] | b | a |

-continued

| Ex. No | Structure | Ab42 IC50 Ranges | Abtot/Ab42 selectivity ranges |
|---|---|---|---|
| 33 | 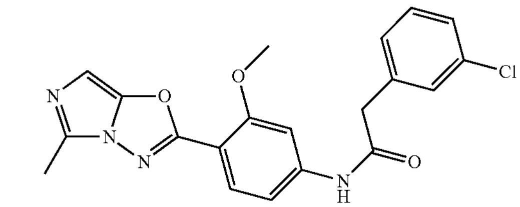 [SMILES: COc1cc(NC(=O)Cc2cccc(Cl)c2)ccc1-c1nn2c(C)ncc2o1] | c | b |
| 34 | 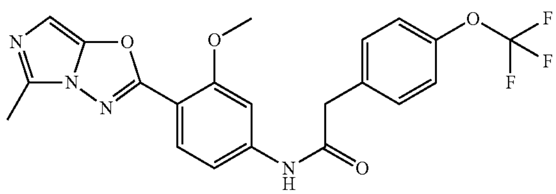 [SMILES: COc1cc(NC(=O)Cc2ccc(OC(F)(F)F)cc2)ccc1-c1nn2c(C)ncc2o1] | c | b |
| 35 | 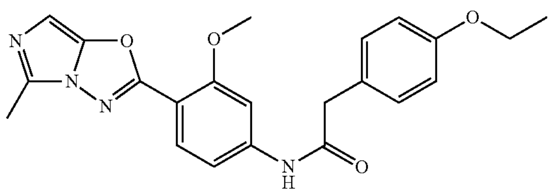 [SMILES: CCOc1ccc(CC(=O)Nc2ccc(-c3nn4c(C)ncc4o3)c(OC)c2)cc1] | c | b |
| 36 | 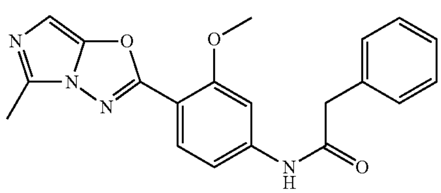 [SMILES: COc1cc(NC(=O)Cc2ccccc2)ccc1-c1nn2c(C)ncc2o1] | d | c |
| 37 | 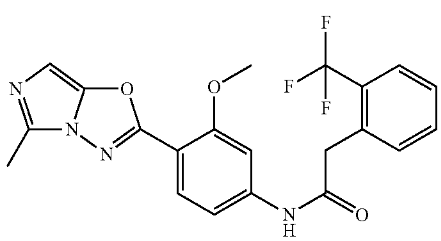 [SMILES: COc1cc(NC(=O)Cc2ccccc2C(F)(F)F)ccc1-c1nn2c(C)ncc2o1] | d | c |
| 38 | 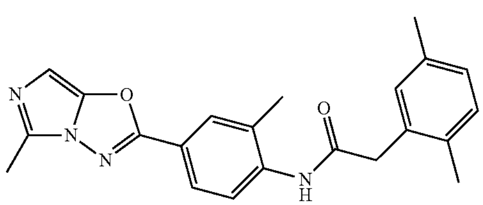 [SMILES: Cc1ccc(C)c(CC(=O)Nc2ccc(-c3nn4c(C)ncc4o3)cc2C)c1] | b | a |
| 39 | 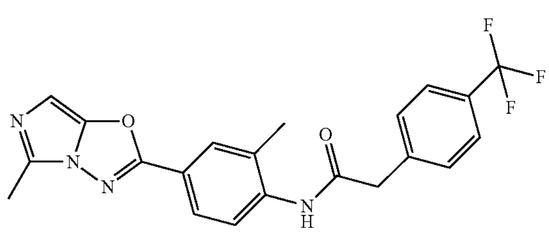 [SMILES: Cc1cc(-c2nn3c(C)ncc3o2)ccc1NC(=O)Cc1ccc(C(F)(F)F)cc1] | c | b |

-continued
| Ex. No | Structure | Ab42 IC50 Ranges | Abtot/Ab42 selectivity ranges |
|---|---|---|---|
| 40 | 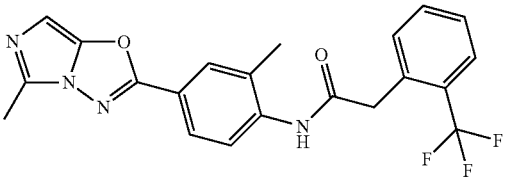 [SMILES: Cc1cc(-c2nn3c(C)ncc3o2)ccc1NC(=O)Cc1ccccc1C(F)(F)F] | c | b |
| 41 | 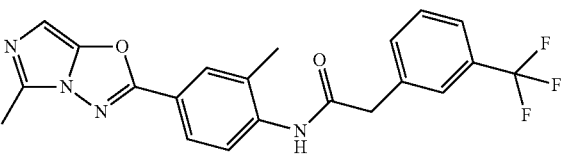 [SMILES: Cc1cc(-c2nn3c(C)ncc3o2)ccc1NC(=O)Cc1cccc(C(F)(F)F)c1] | c | b |
| 42 | 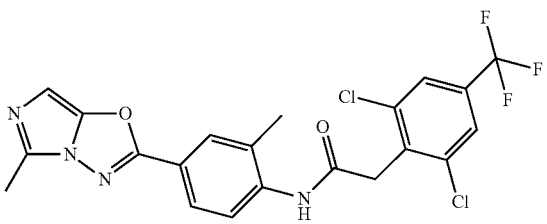 [SMILES: Cc1cc(-c2nn3c(C)ncc3o2)ccc1NC(=O)Cc1c(Cl)cc(C(F)(F)F)cc1Cl] | c | b |
| 43 | 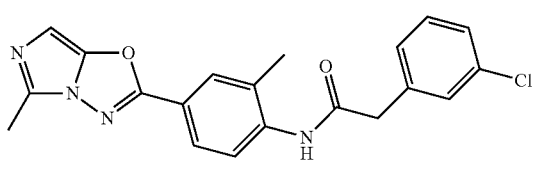 [SMILES: Cc1cc(-c2nn3c(C)ncc3o2)ccc1NC(=O)Cc1cccc(Cl)c1] | d | c |
| 44 | 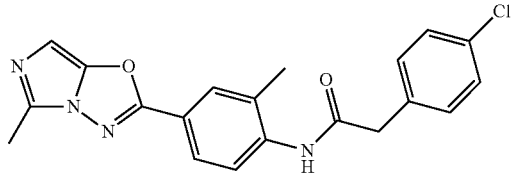 [SMILES: Cc1cc(-c2nn3c(C)ncc3o2)ccc1NC(=O)Cc1ccc(Cl)cc1] | c | b |
| 45 | 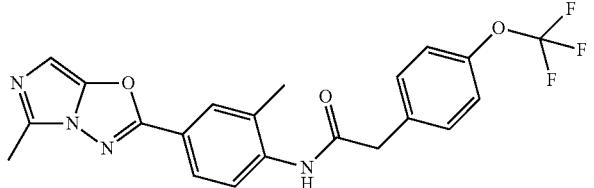 [SMILES: Cc1cc(-c2nn3c(C)ncc3o2)ccc1NC(=O)Cc1ccc(OC(F)(F)F)cc1] | c | b |
| 46 | 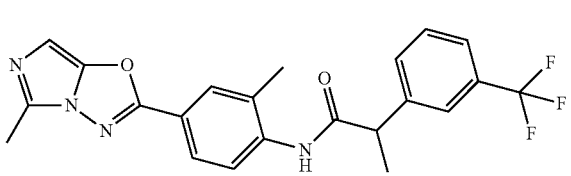 [SMILES: Cc1cc(-c2nn3c(C)ncc3o2)ccc1NC(=O)C(C)c1cccc(C(F)(F)F)c1] | c | b |
| 47 | 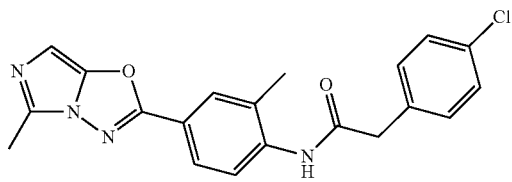 [SMILES: Cc1cc(-c2nn3c(C)ncc3o2)ccc1NC(=O)Cc1ccc(Cl)cc1] | c | c |

-continued
| Ex. No | Structure | Ab42 IC50 Ranges | Abtot/Ab42 selectivity ranges |
|---|---|---|---|
| 48 | 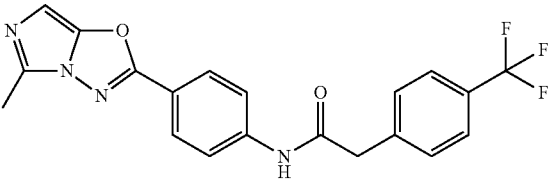 [SMILES: Cc1ncc2oc(-c3ccc(NC(=O)Cc4ccc(C(F)(F)F)cc4)cc3)nn12] | d | c |
| 49 | 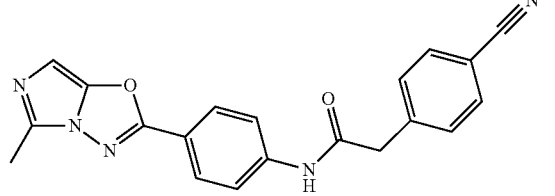 | d | c |
| 50 | 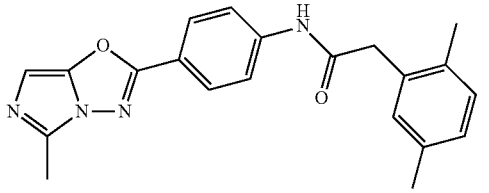 [SMILES: Cc1ccc(C)c(CC(=O)Nc2ccc(-c3nn4c(C)ncc4o3)cc2)c1] | c | c |
| 51 | 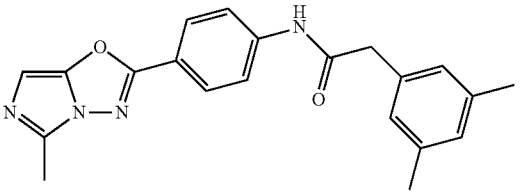 [SMILES: Cc1cc(C)cc(CC(=O)Nc2ccc(-c3nn4c(C)ncc4o3)cc2)c1] | c | c |
| 52 | 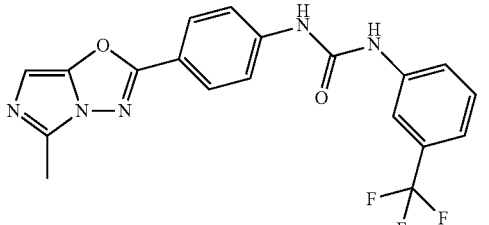 | d | d |
| 53 | 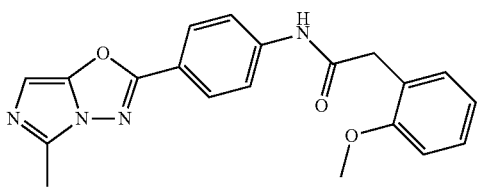 [SMILES: COc1ccccc1CC(=O)Nc1ccc(-c2nn3c(C)ncc3o2)cc1] | d | d |
| 54 | 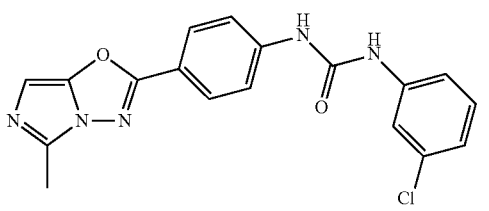 [SMILES: Cc1ncc2oc(-c3ccc(NC(=O)Nc4cccc(Cl)c4)cc3)nn12] | d | c |

-continued

| Ex. No | Structure | Ab42 IC50 Ranges | Abtot/Ab42 selectivity ranges |
|---|---|---|---|
| 55 | 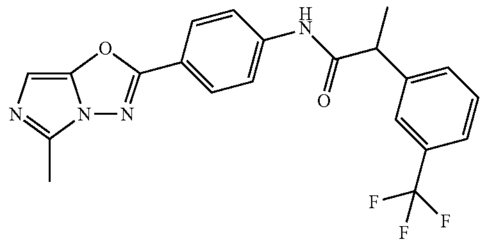 [SMILES: Cc1ncc2oc(-c3ccc(NC(=O)C(C)c4cccc(C(F)(F)F)c4)cc3)nn12] | d | c |
| 56 | 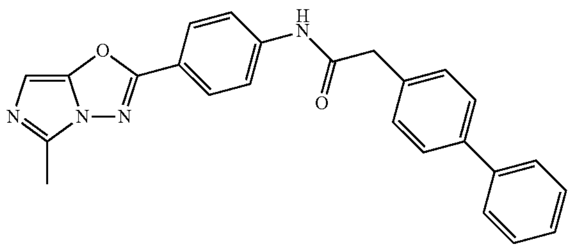 [SMILES: Cc1ncc2oc(-c3ccc(NC(=O)Cc4ccc(-c5ccccc5)cc4)cc3)nn12] | b | a |
| 57 | 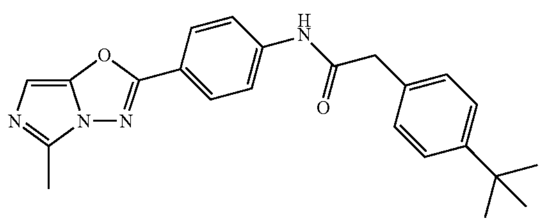 [SMILES: Cc1ncc2oc(-c3ccc(NC(=O)Cc4ccc(C(C)(C)C)cc4)cc3)nn12] | c | b |
| 58 | 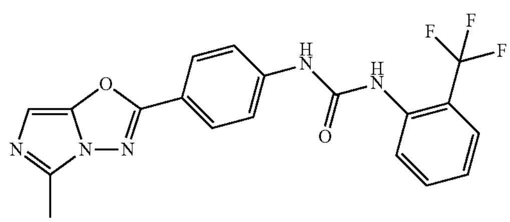 [SMILES: Cc1ncc2oc(-c3ccc(NC(=O)Nc4ccccc4C(F)(F)F)cc3)nn12] | c | d |
| 59 | 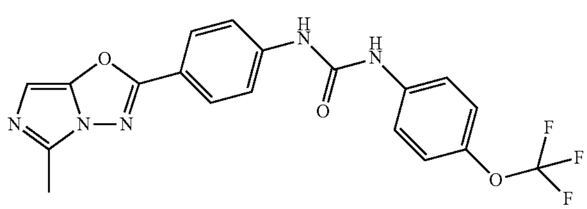 [SMILES: Cc1ncc2oc(-c3ccc(NC(=O)Nc4ccc(OC(F)(F)F)cc4)cc3)nn12] | d | c |
| 60 | 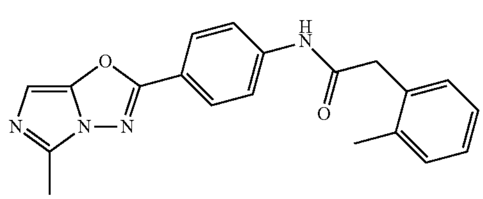 [SMILES: Cc1ccccc1CC(=O)Nc1ccc(-c2nn3c(C)ncc3o2)cc1] | d | c |
| 61 | 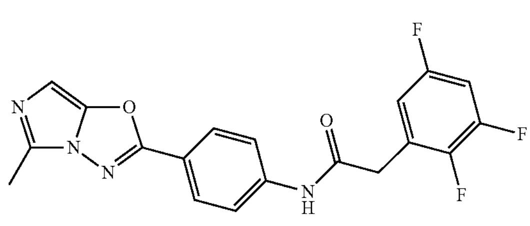 [SMILES: Cc1ncc2oc(-c3ccc(NC(=O)Cc4cc(F)cc(F)c4F)cc3)nn12] | c | b |

-continued

| Ex. No | Structure | Ab42 IC50 Ranges | Abtot/Ab42 selectivity ranges |
|---|---|---|---|
| 62 | 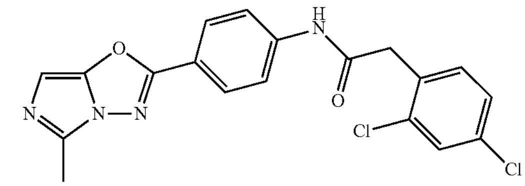 [SMILES: Cc1ncc2oc(-c3ccc(NC(=O)Cc4ccc(Cl)cc4Cl)cc3)nn12] | c | b |
| 63 | 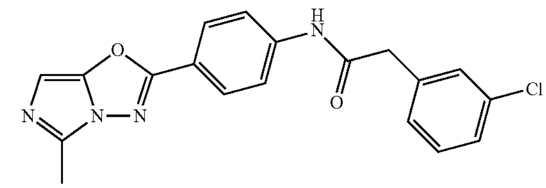 [SMILES: Cc1ncc2oc(-c3ccc(NC(=O)Cc4cccc(Cl)c4)cc3)nn12] | c | b |
| 64 | 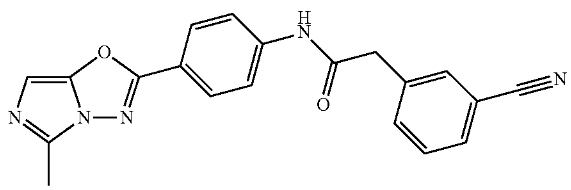 [SMILES: Cc1ncc2oc(-c3ccc(NC(=O)Cc4cccc(C#N)c4)cc3)nn12] | c | b |
| 65 | 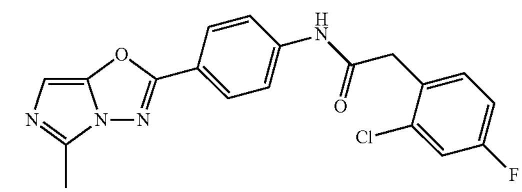 [SMILES: Cc1ncc2oc(-c3ccc(NC(=O)Cc4ccc(F)cc4Cl)cc3)nn12] | d | c |
| 66 | 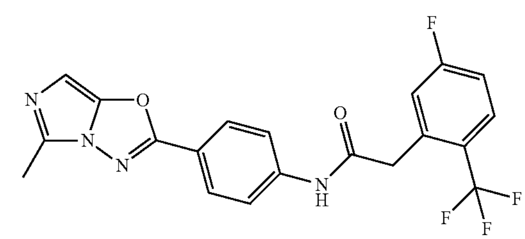 [SMILES: Cc1ncc2oc(-c3ccc(NC(=O)Cc4cc(F)ccc4C(F)(F)F)cc3)nn12] | d | c |
| 67 | 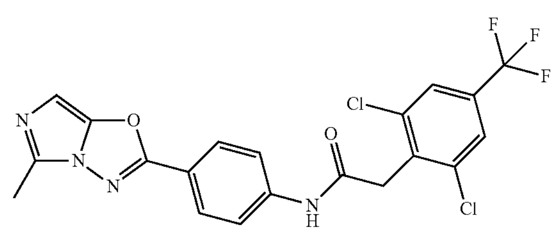 [SMILES: Cc1ncc2oc(-c3ccc(NC(=O)Cc4c(Cl)cc(C(F)(F)F)cc4Cl)cc3)nn12] | d | c |
| 68 | 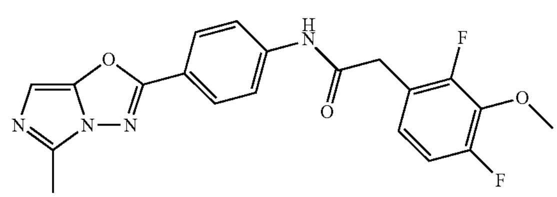 [SMILES: COc1c(F)ccc(CC(=O)Nc2ccc(-c3nn4c(C)ncc4o3)cc2)c1F] | c | b |

-continued

| Ex. No | Structure | Ab42 IC50 Ranges | Abtot/Ab42 selectivity ranges |
|---|---|---|---|
| 69 | 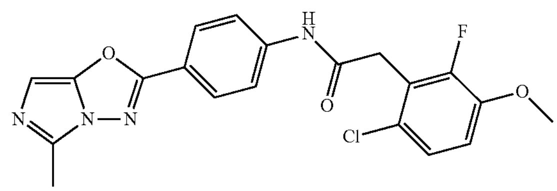 [SMILES: COc1ccc(Cl)c(CC(=O)Nc2ccc(-c3nn4c(C)ncc4o3)cc2)c1F] | c | b |
| 70 | 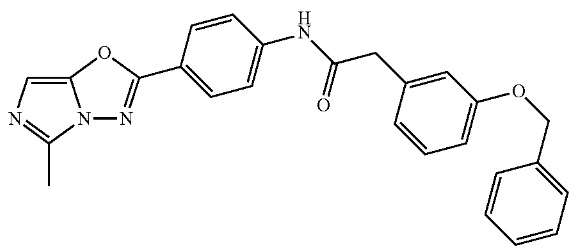 [SMILES: Cc1ncc2oc(-c3ccc(NC(=O)Cc4cccc(OCc5ccccc5)c4)cc3)nn12] | d | c |
| 71 | 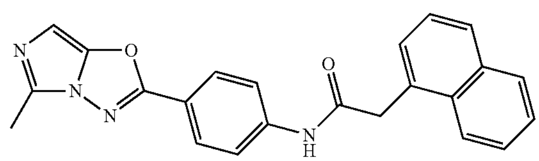 [SMILES: Cc1ncc2oc(-c3ccc(NC(=O)Cc4cccc5ccccc45)cc3)nn12] | c | b |
| 72 | 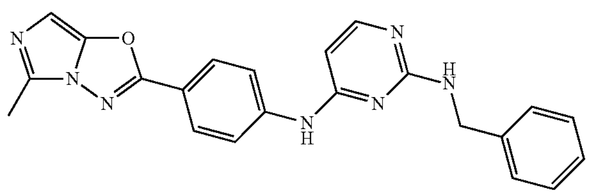 [SMILES: Cc1ncc2oc(-c3ccc(Nc4ccnc(NCc5ccccc5)n4)cc3)nn12] | d | d |
| 73 | 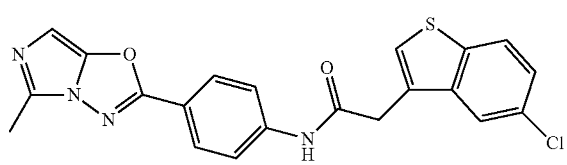 [SMILES: Cc1ncc2oc(-c3ccc(NC(=O)Cc4csc5ccc(Cl)cc45)cc3)nn12] | d | c |
| 74 | 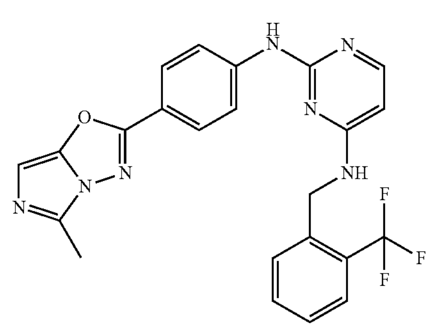 [SMILES: Cc1ncc2oc(-c3ccc(Nc4nccc(NCc5ccccc5C(F)(F)F)n4)cc3)nn12] | d | d |

-continued

| Ex. No | Structure | Ab42 IC50 Ranges | Abtot/Ab42 selectivity ranges |
|---|---|---|---|
| 75 | 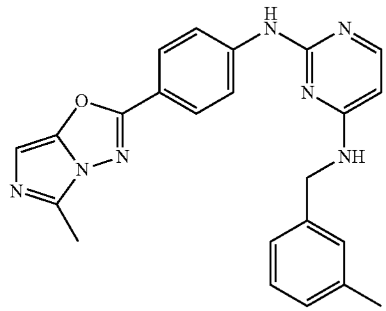 [SMILES: Cc1cccc(CNc2ccnc(Nc3ccc(-c4nn5c(C)ncc5o4)cc3)n2)c1] | d | d |
| 76 | 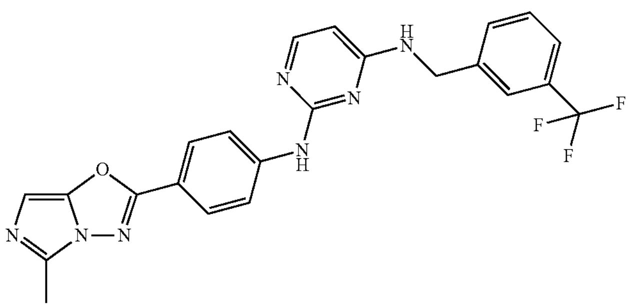 [SMILES: Cc1ncc2oc(-c3ccc(Nc4nccc(NCc5cccc(C(F)(F)F)c5)n4)cc3)nn12] | d | d |
| 77 | 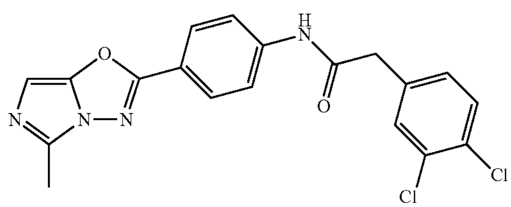 [SMILES: Cc1ncc2oc(-c3ccc(NC(=O)Cc4ccc(Cl)c(Cl)c4)cc3)nn12] | b | a |
| 78 | 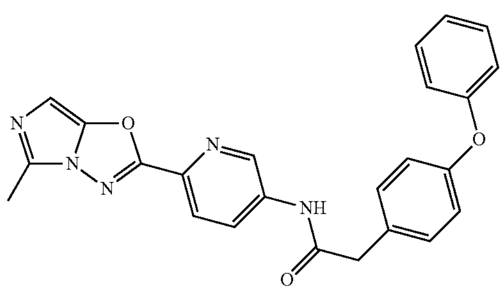 [SMILES: Cc1ncc2oc(-c3ccc(NC(=O)Cc4ccc(Oc5ccccc5)cc4)cn3)nn12] | d | c |
| 79 | 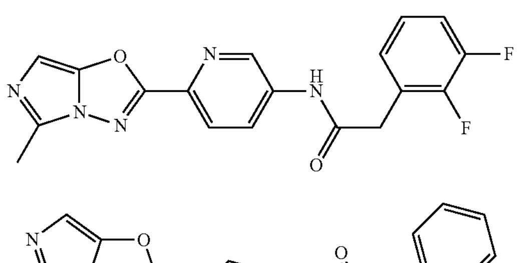 | d | c |
| 80 | 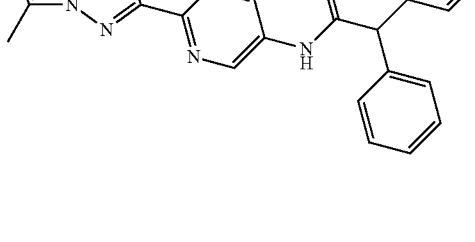 | c | c |

-continued
| Ex. No | Structure | Ab42 IC50 Ranges | Abtot/Ab42 selectivity ranges |
|---|---|---|---|
| 81 | 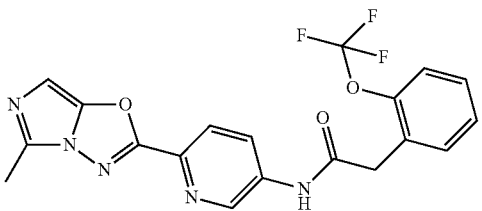 [SMILES: Cc1ncc2oc(-c3ccc(NC(=O)Cc4ccccc4OC(F)(F)F)cn3)nn12] | d | c |
| 82 | 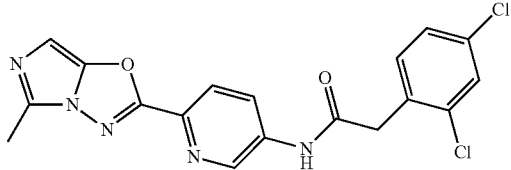 [SMILES: Cc1ncc2oc(-c3ccc(NC(=O)Cc4ccc(Cl)cc4Cl)cn3)nn12] | d | c |
| 83 | 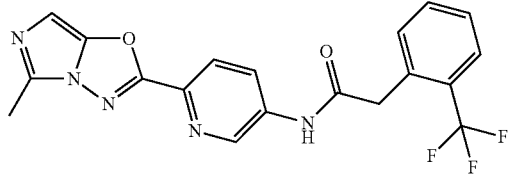 | d | c |
| 84 | 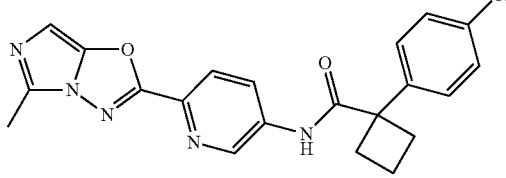 | c | c |
| 85 | 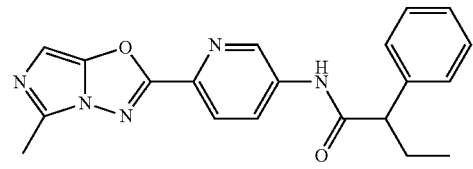 [SMILES: CCC(C(=O)Nc1ccc(-c2nn3c(C)ncc3o2)nc1)c1ccccc1] | d | c |
| 86 | 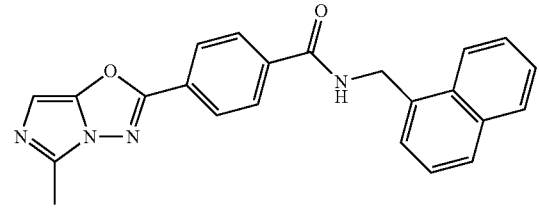 [SMILES: Cc1ncc2oc(-c3ccc(C(=O)NCc4cccc5ccccc45)cc3)nn12] | c | b |
| 87 | 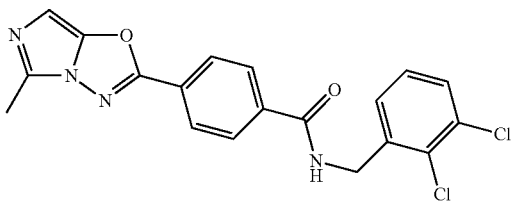 [SMILES: Cc1ncc2oc(-c3ccc(C(=O)NCc4cccc(Cl)c4Cl)cc3)nn12] | d | c |

-continued

| Ex. No | Structure | Ab42 IC50 Ranges | Abtot/Ab42 selectivity ranges |
|---|---|---|---|
| 88 | 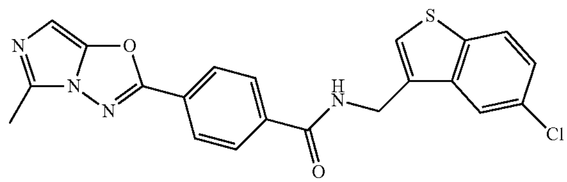 [SMILES: Cc1ncc2oc(-c3ccc(C(=O)NCc4csc5ccc(Cl)cc45)cc3)nn12] | d | c |
| 89 | 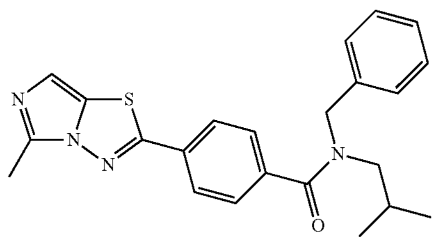 [SMILES: Cc1ncc2sc(-c3ccc(C(=O)N(Cc4ccccc4)CC(C)C)cc3)nn12] | b | d |
| 90 | 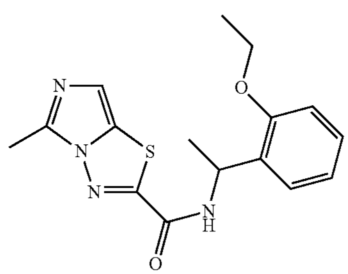 [SMILES: CCOc1ccccc1C(C)NC(=O)c1nn2c(C)ncc2s1] | c | d |
| 91 | 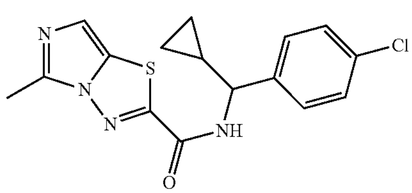 [SMILES: Cc1ncc2sc(C(=O)NC(c3ccc(Cl)cc3)C3CC3)nn12] | d | d |
| 92 | 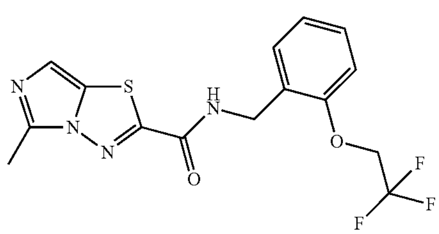 [SMILES: Cc1ncc2sc(C(=O)NCc3ccccc3OCC(F)(F)F)nn12] | a | d |
| 93 | 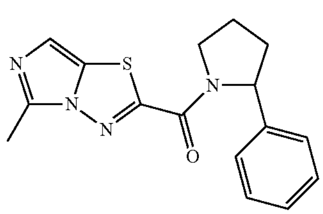 [SMILES: Cc1ncc2sc(C(=O)N3CCCC3c3ccccc3)nn12] | b | d |

-continued
| Ex. No | Structure | Ab42 IC50 Ranges | Abtot/Ab42 selectivity ranges |
|---|---|---|---|
| 94 | 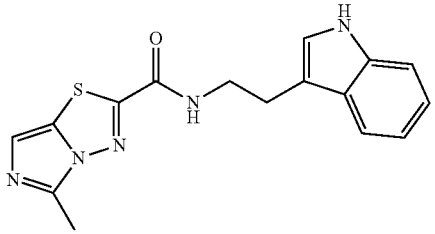 [SMILES: Cc1ncc2sc(C(=O)NCCc3c[nH]c4ccccc34)nn12] | c | d |
| 95 | 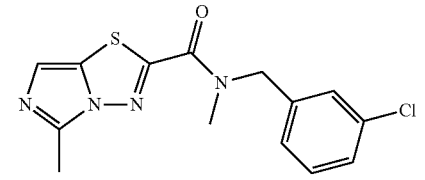 [SMILES: Cc1ncc2sc(C(=O)N(C)Cc3cccc(Cl)c3)nn12] | c | d |
| 96 | 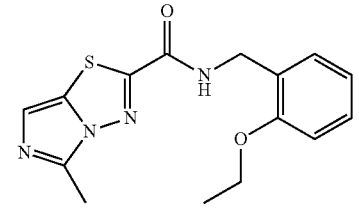 [SMILES: CCOc1ccccc1CNC(=O)c1nn2c(C)ncc2s1] | c | d |
| 97 | 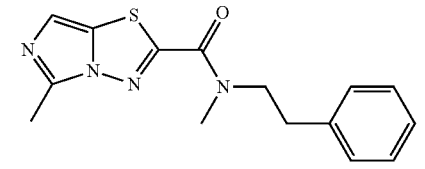 [SMILES: Cc1ncc2sc(C(=O)N(C)CCc3ccccc3)nn12] | c | d |
| 98 | 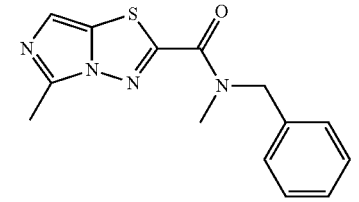 [SMILES: Cc1ncc2sc(C(=O)N(C)Cc3ccccc3)nn12] | d | d |
| 99 | 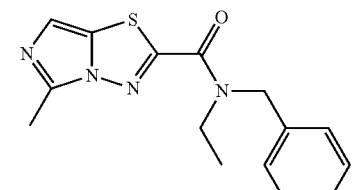 | d | d |
| 100 | 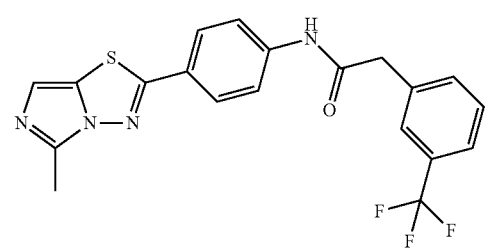 [SMILES: Cc1ncc2sc(-c3ccc(NC(=O)Cc4cccc(C(F)(F)F)c4)cc3)nn12] | b | b |

-continued
| Ex. No | Structure | Ab42 IC50 Ranges | Abtot/Ab42 selectivity ranges |
|---|---|---|---|
| 101 | 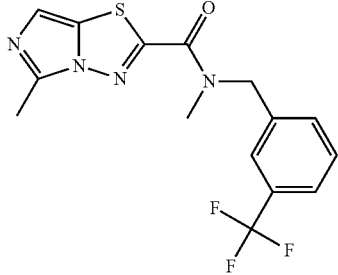 [SMILES: Cc1ncc2sc(C(=O)N(C)Cc3cccc(C(F)(F)F)c3)nn12] | c | d |
| 102 | 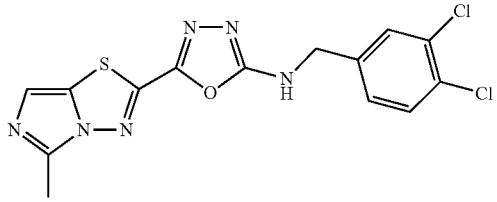 [SMILES: Cc1ncc2sc(-c3nnc(NCc4ccc(Cl)c(Cl)c4)o3)nn12] | b | d |
| 103 | 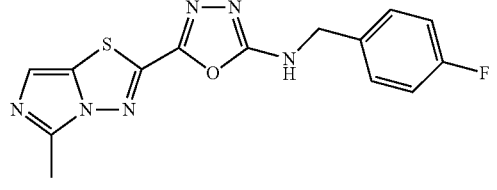 [SMILES: Cc1ncc2sc(-c3nnc(NCc4ccc(F)cc4)o3)nn12] | c | d |
| 104 | 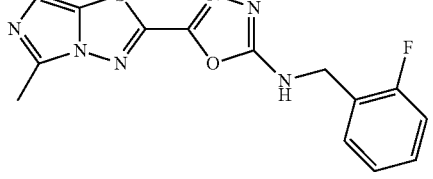 | d | d |
| 105 | 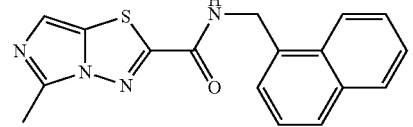 | c | d |
| 106 | 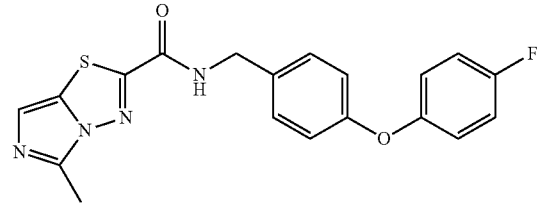 [SMILES: Cc1ncc2sc(C(=O)NCc3ccc(Oc4ccc(F)cc4)cc3)nn12] | b | b |
| 107 | 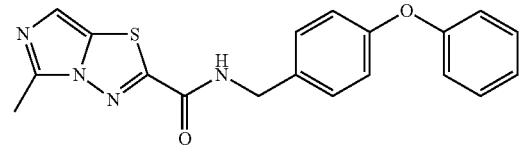 [SMILES: Cc1ncc2sc(C(=O)NCc3ccc(Oc4ccccc4)cc3)nn12] | b | c |

-continued

| Ex. No | Structure | Ab42 IC50 Ranges | Abtot/Ab42 selectivity ranges |
|---|---|---|---|
| 108 | 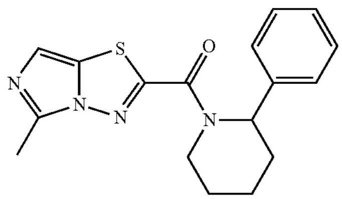 [SMILES: Cc1ncc2sc(C(=O)N3CCCCC3c3ccccc3)nn12] | c | d |
| 109 | 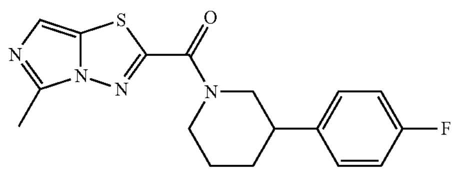 [SMILES: Cc1ncc2sc(C(=O)N3CCCC(c4ccc(F)cc4)C3)nn12] | d | d |
| 110 | 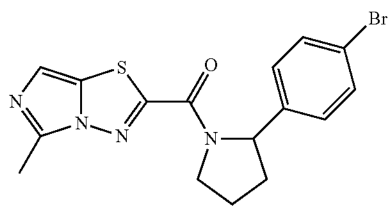 [SMILES: Cc1ncc2sc(C(=O)N3CCCC3c3ccc(Br)cc3)nn12] | a | d |
| 111 | 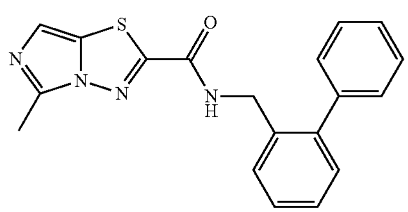 [SMILES: Cc1ncc2sc(C(=O)NCc3ccccc3-c3ccccc3)nn12] | d | d |
| 112 | 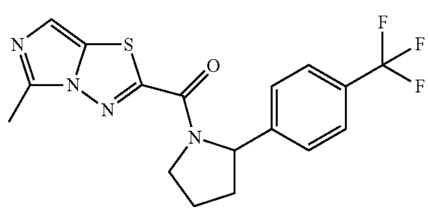 [SMILES: Cc1ncc2sc(C(=O)N3CCCC3c3ccc(C(F)(F)F)cc3)nn12] | b | d |
| 113 | 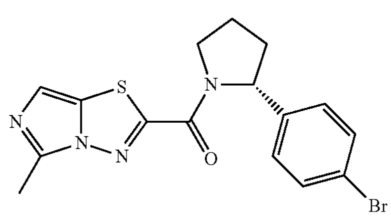 [SMILES: Cc1ncc2sc(C(=O)N3CCC[C@@H]3c3ccc(Br)cc3)nn12] | a | d |
| 114 | 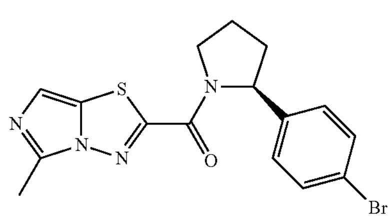 [SMILES: Cc1ncc2sc(C(=O)N3CCC[C@H]3c3ccc(Br)cc3)nn12] | d | d |

-continued

| Ex. No | Structure | Ab42 IC50 Ranges | Abtot/Ab42 selectivity ranges |
|---|---|---|---|
| 115 | 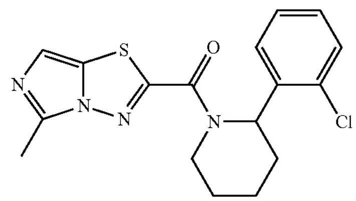 [SMILES: Cc1ncc2sc(C(=O)N3CCCCC3c3ccccc3Cl)nn12] | c | d |
| 116 | 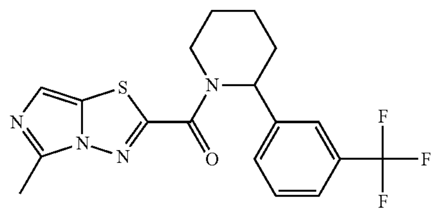 [SMILES: Cc1ncc2sc(C(=O)N3CCCCC3c3cccc(C(F)(F)F)c3)nn12] | d | d |
| 117 | 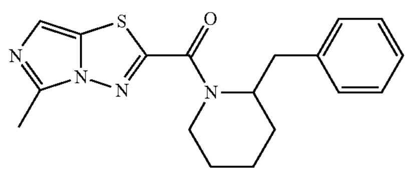 [SMILES: Cc1ncc2sc(C(=O)N3CCCCC3Cc3ccccc3)nn12] | d | d |
| 118 | 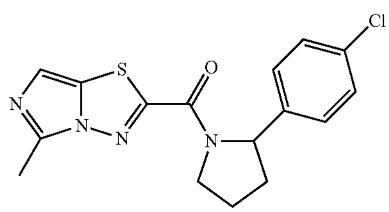 [SMILES: Cc1ncc2sc(C(=O)N3CCCC3c3ccc(Cl)cc3)nn12] | b | d |
| 119 | 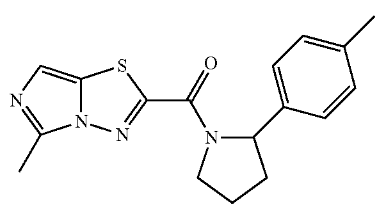 [SMILES: Cc1ccc(C2CCCN2C(=O)c2nn3c(C)ncc3s2)cc1] | b | d |
| 120 | 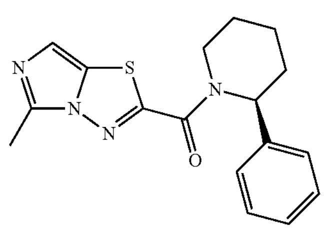 [SMILES: Cc1ncc2sc(C(=O)N3CCCC[C@H]3c3ccccc3)nn12] | c | d |
| 121 | 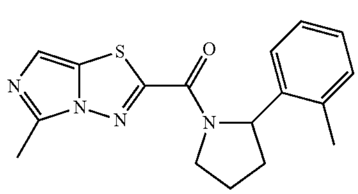 [SMILES: Cc1ccccc1C1CCCN1C(=O)c1nn2c(C)ncc2s1] | c | d |

-continued

| Ex. No | Structure | Ab42 IC50 Ranges | Abtot/Ab42 selectivity ranges |
|---|---|---|---|
| 122 | 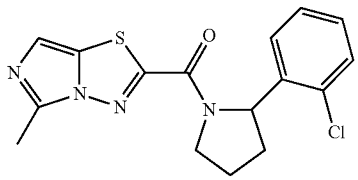 | d | d |
| 123 | 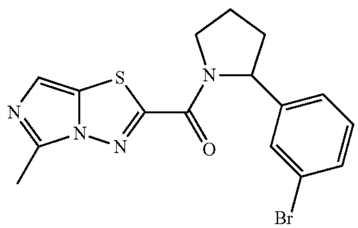 [SMILES: Cc1ncc2sc(C(=O)N3CCCC3c3cccc(Br)c3)nn12] | d | d |
| 124 | 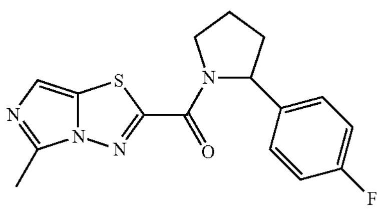 [SMILES: Cc1ncc2sc(C(=O)N3CCCC3c3ccc(F)cc3)nn12] | b | d |
| 125 | 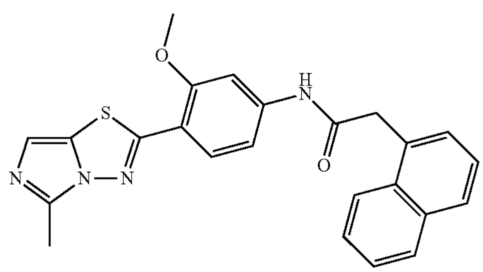 [SMILES: COc1cc(NC(=O)Cc2cccc3ccccc23)ccc1-c1nn2c(C)ncc2s1] | b | c |
| 126 | 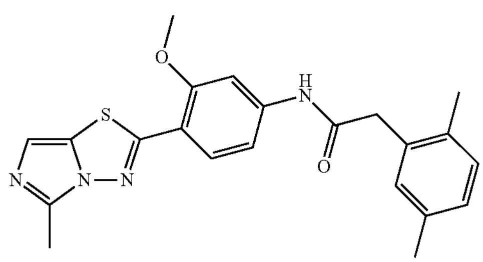 [SMILES: COc1cc(NC(=O)Cc2cc(C)ccc2C)ccc1-c1nn2c(C)ncc2s1] | c | d |
| 127 | 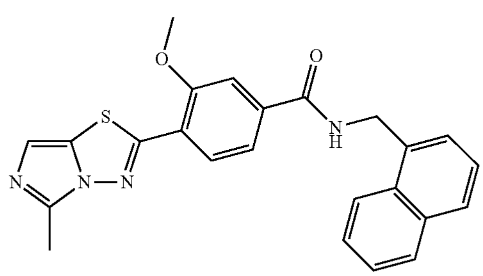 [SMILES: COc1cc(C(=O)NCc2cccc3ccccc23)ccc1-c1nn2c(C)ncc2s1] | c | b |

| Ex. No | Structure | Ab42 IC50 Ranges | Abtot/Ab42 selectivity ranges |
|---|---|---|---|
| 128 | 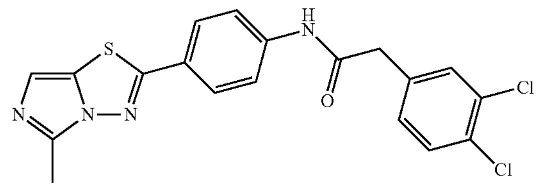 [SMILES: Cc1ncc2sc(-c3ccc(NC(=O)Cc4ccc(Cl)c(Cl)c4)cc3)nn12] | c | c |

Activity
a: IC50 ≤ 100 nM
b: 100 nM < IC50 ≤ 500 nM
c: 500 nM < IC50 ≤ 1000 nM
d: 1000 nM < IC50 ≤ 2200 nM
Selectivity
a: selectivity ≥ 100 fold
b: 100 fold > selectivity ≥ 50 fold
c: 50 fold > selectivity ≥ 10 fold
d: 10 fold > selectivity Pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medica-ment after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be for-mulated by dispersion of the compounds in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula (I) and salts, solvates and physiologically functional derivatives thereof and the other active ingredients can also be administered in the form of liposome delivery systems, such as, for exam-ple, small unilamellar vesicles, large unilamellar vesicles and multilamellar vesicles. Liposomes can be formed from various phospholipids, such as, for example, cholesterol, stearylamine or phosphatidylcholines.

The compounds of the formula (I) and the salts, solvates and physiologically functional derivatives thereof and the other active ingredients can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropyl-methacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, poly-orthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base.

Alternatively, the active ingredient can be formulated to give a cream with an oil-in-water cream base or a water-in-oil base.

Pharmaceutical formulations adapted for topical application to the eye include eye drops, in which the active ingredient is dissolved or sus-pended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insuf-flators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

Formulation 1—Tablets:

A compound of formula (I) is admixed as a dry powder with a dry gelatin binder in an approximate 1:2 weight ratio. A minor amount of magnesium stearate is added as a lubricant. The mixture is formed into 240-270 mg tablets (80-90 mg of active compound according to the invention per tablet) in a tablet press.

Formulation 2—Capsules:

A compound of formula (I) is admixed as a dry powder with a starch diluent in an approximate 1:1 weight ratio. The mixture is filled into 250 mg capsules (125 mg of active compound according to the invention per capsule).

Formulation 3—Liquid:

A compound of formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets:

A compound of formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active compound according to the invention) in a tablet press.

Formulation 5—Injection:

A compound of formula (I) is dissolved in a buffered sterile saline injectable aqueous medium to a concentration of approximately 5 mg/mL.

The invention claimed is:

1. A compound of Formula (I)

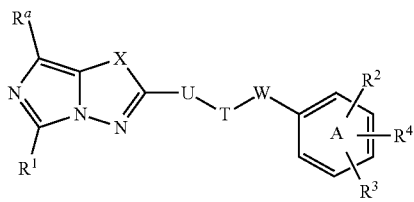

(I)

wherein

X denotes S,

U is selected from
  (i) a phenyl ring which may be substituted by 1 or 2 groups independently selected from $C_1$-$C_6$-alkoxy, $C_1$-$C_6$-alkyl, halogen, and CN; and
  (ii) a single bond;

T denotes —NR$^5$CO—, —CONR$^5$, or —CO—;

W is selected from:

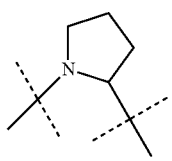 , 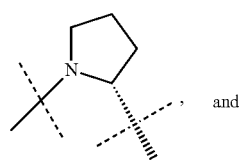 , and

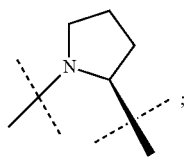 ;

each R$^5$ is independently H or a linear or branched $C_1$-$C_6$-alkyl,

R$^1$ denotes a linear or branched alkyl having 1 to 6 carbon atoms;

R$^a$ denotes H, CN, halogen, a linear or branched alkyl having 1 to 6 carbon atoms, wherein 1 to 3 H atoms may be replaced by halogens, or linear or branched alkoxy having 1 to 6 carbon atoms, wherein 1 to 3 H atoms may be replaced by halogens, R$^2$, R$^3$, R$^4$ are each independently selected from CN, halogen, a linear or branched alkyl having 1 to 6 carbon atoms, wherein 1 to 3 H atoms may be replaced by halogens, and linear or branched alkoxy having 1 to 6 carbon atoms, wherein 1 to 3 H atoms may be replaced by halogens, and a pharmaceutically acceptable salt, stereoisomer, or mixture thereof, in all ratios.

2. The compound according to claim 1 wherein U is a single bond or one of the following groups:

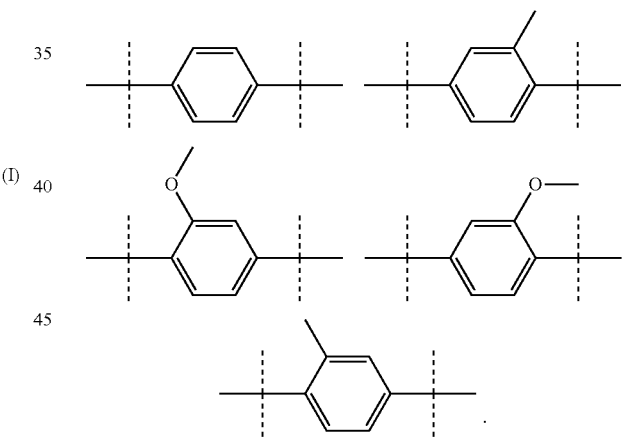

3. The compound according to claim 1 wherein the compound is selected from:

| Ex. No | Structure |
|---|---|
| 93 | 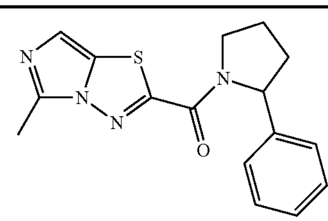 |

-continued

| Ex. No | Structure |
|---|---|
| 110 | (imidazo-thiadiazole)-C(O)-N-pyrrolidinyl-(4-bromophenyl) |
| 112 | (imidazo-thiadiazole)-C(O)-N-pyrrolidinyl-(4-trifluoromethylphenyl) |
| 113 | (imidazo-thiadiazole)-C(O)-N-pyrrolidinyl-(4-bromophenyl) |
| 114 | (imidazo-thiadiazole)-C(O)-N-pyrrolidinyl-(4-bromophenyl) |
| 118 | (imidazo-thiadiazole)-C(O)-N-pyrrolidinyl-(4-chlorophenyl) |

-continued

| Ex. No | Structure |
|---|---|
| 119 | (imidazo-thiadiazole)-C(O)-N-pyrrolidinyl-(4-methylphenyl) |
| 121 | (imidazo-thiadiazole)-C(O)-N-pyrrolidinyl-(2-methylphenyl) |
| 122 | (imidazo-thiadiazole)-C(O)-N-pyrrolidinyl-(2-chlorophenyl) |
| 123 | (imidazo-thiadiazole)-C(O)-N-pyrrolidinyl-(3-bromophenyl) |
| 124 | (imidazo-thiadiazole)-C(O)-N-pyrrolidinyl-(4-fluorophenyl) |

4. A pharmaceutical composition comprising at least one compound according to claim 1 and a pharmaceutically acceptable excipient.

* * * * *